United States Patent
Kagan et al.

(10) Patent No.: US 9,060,844 B2
(45) Date of Patent: Jun. 23, 2015

(54) APPARATUS AND METHODS FOR TREATMENT OF MORBID OBESITY

(75) Inventors: Jonathan Kagan, Hopkins, MN (US); James Balliro, Jackson, WY (US); David Carr-Locke, Chestnut Hill, MA (US); Mitchell Dann, Wilson, WY (US); Lee Guterman, Amherst, NY (US); Sayeed Ikramuddin, Eden Prairie, MN (US); James Leary, Granite Bay, CA (US); Richard Thomas, Lincoln, MA (US)

(73) Assignee: ValenTx, Inc., Maple Grove, MN (US)

( * ) Notice: Subject to any disclaimer, the term of this patent is extended or adjusted under 35 U.S.C. 154(b) by 383 days.

(21) Appl. No.: 10/698,148

(22) Filed: Oct. 31, 2003

(65) Prior Publication Data
US 2004/0092892 A1 May 13, 2004

Related U.S. Application Data

(60) Provisional application No. 60/422,987, filed on Nov. 1, 2002, provisional application No. 60/430,857, filed on Dec. 3, 2002, provisional application No. 60/437,513, filed on Dec. 30, 2002, provisional (Continued)

(51) Int. Cl.
*A61M 25/00* (2006.01)
*A61F 5/00* (2006.01)
*A61F 2/04* (2013.01)

(52) U.S. Cl.
CPC .................. *A61F 5/0079* (2013.01); *A61F 2/04* (2013.01); *A61F 5/0086* (2013.01)

(58) Field of Classification Search
CPC ........... A61B 17/0401; A61B 17/0469; A61B 17/064; A61B 17/068; A61B 17/072; A61F 5/0079; A61F 5/0086

USPC ............... 604/264, 514, 516, 500; 623/23.65, 623/23.6; 606/153
See application file for complete search history.

(56) References Cited

U.S. PATENT DOCUMENTS

| 3,357,432 | A | 12/1967 | Sparks |
| 4,006,747 | A | 2/1977 | Kronenthal et al. |

(Continued)

FOREIGN PATENT DOCUMENTS

| EP | 0817598 | 2/1996 |
| EP | 1237501 | 9/2000 |

(Continued)

OTHER PUBLICATIONS

Antireflux operations at flexible endoscopy using endoluminal stitching techniques: an experimental study, Sritharan S. Kadirkamanathan et al., *Gastrointestinal Endoscopy*, vol. 44, No. 2, 1995 pp. 133-143.

(Continued)

*Primary Examiner* — Phillip Gray
(74) *Attorney, Agent, or Firm* — Knobbe, Martens, Olson & Bear, LLP

(57) ABSTRACT

Apparatus and methods are described for treatment of morbid obesity using minimally invasive techniques. The apparatus includes a system of components that may be used separately or in combination for effectively reducing stomach volume, bypassing a portion of the stomach and/or small intestines, reducing nutrient absorption in the stomach and/or small intestines and/or depositing minimally or undigested food farther than normal into the intestines, thereby stimulating intestinal responses. The components described include an artificial stoma device, a gastric sleeve device, an intestinal sleeve device, a combined gastrointestinal sleeve device and permanent and detachable attachment systems. Also described are devices for delivering and deploying the components of the system.

12 Claims, 64 Drawing Sheets

Related U.S. Application Data application No. 60/448,817, filed on Feb. 21, 2003, provisional application No. 60/480,485, filed on Jun. 21, 2003, provisional application No. 60/428,483, filed on Nov. 22, 2002.

(56) References Cited

U.S. PATENT DOCUMENTS

| | | | |
|---|---|---|---|
| 4,043,345 A | 8/1977 | Kramann et al. | |
| 4,134,405 A | 1/1979 | Smit | |
| 4,217,664 A | 8/1980 | Faso | |
| 4,235,238 A | 11/1980 | Ogiu et al. | |
| 4,252,131 A | 2/1981 | Hon et al. | |
| 4,315,509 A | 2/1982 | Smit | |
| 4,329,995 A | 5/1982 | Anthracite | |
| 4,501,264 A | 2/1985 | Rockey | |
| 4,532,926 A | 8/1985 | O'Holla | |
| 4,630,609 A | 12/1986 | Chin | |
| 4,641,653 A | 2/1987 | Rockey | |
| 4,719,916 A | 1/1988 | Ravo | |
| 4,763,653 A | 8/1988 | Rockey | |
| 4,846,836 A | 7/1989 | Reich | |
| 4,905,693 A | 3/1990 | Ravo | |
| 4,946,440 A | 8/1990 | Hall | |
| 5,085,661 A | 2/1992 | Moss | |
| RE34,021 E | 8/1992 | Mueller et al. | |
| 5,171,305 A | 12/1992 | Schickling et al. | |
| 5,236,423 A | 8/1993 | Mix et al. | |
| 5,306,300 A | 4/1994 | Berry | |
| 5,314,473 A | 5/1994 | Godin | |
| 5,411,508 A | 5/1995 | Bessler et al. | |
| 5,431,666 A | 7/1995 | Sauer et al. | |
| 5,458,573 A | 10/1995 | Summers | |
| 5,470,337 A * | 11/1995 | Moss | 606/139 |
| 5,582,616 A | 12/1996 | Bolduc et al. | |
| 5,645,568 A | 7/1997 | Chervitz et al. | |
| 5,785,684 A | 7/1998 | Zimmon | |
| 5,820,584 A | 10/1998 | Crabb | |
| 5,824,008 A | 10/1998 | Bolduc et al. | |
| 5,843,164 A | 12/1998 | Frantzen et al. | |
| 5,861,036 A | 1/1999 | Godin | |
| 5,887,594 A | 3/1999 | LoCicero, III | |
| 5,957,940 A | 9/1999 | Tanner et al. | |
| 5,972,023 A | 10/1999 | Tanner et al. | |
| 5,997,556 A | 12/1999 | Tanner | |
| 6,113,609 A * | 9/2000 | Adams | 606/139 |
| 6,193,733 B1 | 2/2001 | Adams | |
| 6,254,642 B1 * | 7/2001 | Taylor | 623/23.64 |
| 6,264,700 B1 | 7/2001 | Kilcoyne et al. | |
| 6,285,897 B1 | 9/2001 | Kilcoyne et al. | |
| 6,312,437 B1 | 11/2001 | Kortenbach | |
| 6,338,345 B1 | 1/2002 | Johnson et al. | |
| 6,387,104 B1 * | 5/2002 | Pugsley et al. | 606/139 |
| 6,409,656 B1 | 6/2002 | Sangouard et al. | |
| 6,447,533 B1 | 9/2002 | Adams | |
| 6,494,888 B1 | 12/2002 | Laufer et al. | |
| 6,520,974 B2 | 2/2003 | Tanner et al. | |
| 6,535,764 B2 | 3/2003 | Imran et al. | |
| 6,544,291 B2 | 4/2003 | Taylor | |
| 6,558,400 B2 | 5/2003 | Deem et al. | |
| 6,558,429 B2 | 5/2003 | Taylor | |
| 6,592,596 B1 | 7/2003 | Geitz | |
| 6,595,911 B2 | 7/2003 | LoVuolo | |
| 6,626,916 B1 | 9/2003 | Yeung et al. | |
| 6,626,919 B1 | 9/2003 | Swanstrom | |
| 6,675,809 B2 | 1/2004 | Stack et al. | |
| 6,699,263 B2 | 3/2004 | Cope | |
| 6,702,735 B2 | 3/2004 | Kelly | |
| 6,736,828 B1 | 5/2004 | Adams et al. | |
| 6,740,121 B2 | 5/2004 | Geitz | |
| 6,746,489 B2 | 6/2004 | Dua et al. | |
| 6,764,518 B2 | 7/2004 | Godin | |
| 6,773,452 B2 | 8/2004 | Shaker | |
| 6,790,237 B2 | 9/2004 | Stinson | |
| 6,845,776 B2 | 1/2005 | Stack et al. | |
| 7,037,344 B2 | 5/2006 | Kagan et al. | |
| 7,120,498 B2 | 10/2006 | Imran et al. | |
| 7,121,283 B2 | 10/2006 | Stack et al. | |
| 7,152,607 B2 | 12/2006 | Stack et al. | |
| 7,175,669 B2 | 2/2007 | Geitz | |
| 7,220,284 B2 | 5/2007 | Kagan et al. | |
| 7,267,694 B2 | 9/2007 | Levine et al. | |
| 7,288,099 B2 | 10/2007 | Deem et al. | |
| 7,306,614 B2 | 12/2007 | Weller et al. | |
| 7,309,341 B2 | 12/2007 | Ortiz et al. | |
| 7,314,489 B2 | 1/2008 | McKenna et al. | |
| 7,329,285 B2 | 2/2008 | Levine et al. | |
| 7,347,875 B2 | 3/2008 | Levine et al. | |
| 7,354,454 B2 | 4/2008 | Stack et al. | |
| 7,371,215 B2 | 5/2008 | Colliou et al. | |
| 2001/0016748 A1 | 8/2001 | Tanner et al. | |
| 2001/0020189 A1 | 9/2001 | Taylor | |
| 2001/0020190 A1 | 9/2001 | Taylor | |
| 2001/0044595 A1 | 11/2001 | Reydel et al. | |
| 2001/0056282 A1 | 12/2001 | Sonnenschein et al. | |
| 2002/0016607 A1 | 2/2002 | Bonadio et al. | |
| 2002/0026214 A1 | 2/2002 | Tanner et al. | |
| 2002/0035370 A1 | 3/2002 | Kortenbach | |
| 2002/0040226 A1 | 4/2002 | Laufer et al. | |
| 2002/0082621 A1 | 6/2002 | Schurr et al. | |
| 2002/0165589 A1 | 11/2002 | Imaran et al. | |
| 2002/0183768 A1 | 12/2002 | Deem et al. | |
| 2002/0188354 A1 | 12/2002 | Peghini | |
| 2003/0014064 A1 | 1/2003 | Blatter | |
| 2003/0018358 A1 | 1/2003 | Saadat | |
| 2003/0040804 A1 | 2/2003 | Stack et al. | |
| 2003/0040808 A1 | 2/2003 | Stack et al. | |
| 2003/0055313 A1 | 3/2003 | Anderson et al. | |
| 2003/0055442 A1 | 3/2003 | Laufer et al. | |
| 2003/0065340 A1 | 4/2003 | Geitz | |
| 2003/0065359 A1 | 4/2003 | Weller et al. | |
| 2003/0093117 A1 | 5/2003 | Saadat | |
| 2003/0109892 A1 | 6/2003 | Deem et al. | |
| 2003/0109931 A1 | 6/2003 | Geitz | |
| 2003/0120285 A1 | 6/2003 | Kortenbach | |
| 2003/0130560 A1 | 7/2003 | Suzuki et al. | |
| 2003/0130561 A1 | 7/2003 | Suzuki et al. | |
| 2003/0139752 A1 | 7/2003 | Pasricha et al. | |
| 2003/0171775 A1 | 9/2003 | Belson | |
| 2003/0181929 A1 | 9/2003 | Geitz | |
| 2003/0191497 A1 | 10/2003 | Cope | |
| 2003/0199989 A1 | 10/2003 | Stack et al. | |
| 2003/0199990 A1 | 10/2003 | Stack et al. | |
| 2003/0199991 A1 | 10/2003 | Stack et al. | |
| 2003/0208209 A1 | 11/2003 | Gambale et al. | |
| 2004/0002734 A1 | 1/2004 | Fallin et al. | |
| 2004/0024427 A1 | 2/2004 | Imran et al. | |
| 2004/0039452 A1 * | 2/2004 | Bessler | 623/23.65 |
| 2004/0044364 A1 | 3/2004 | DeVries et al. | |
| 2004/0059349 A1 | 3/2004 | Sixto, Jr. et al. | |
| 2004/0059354 A1 | 3/2004 | Smith | |
| 2004/0082963 A1 * | 4/2004 | Gannoe et al. | 606/153 |
| 2004/0087976 A1 | 5/2004 | DeVries et al. | |
| 2004/0087977 A1 | 5/2004 | Nolan et al. | |
| 2004/0089313 A1 | 5/2004 | Utley et al. | |
| 2004/0092892 A1 | 5/2004 | Kagan et al. | |
| 2004/0092974 A1 | 5/2004 | Gannoe et al. | |
| 2004/0093065 A1 | 5/2004 | Yachia et al. | |
| 2004/0097986 A1 | 5/2004 | Adams | |
| 2004/0097987 A1 | 5/2004 | Pugsley et al. | |
| 2004/0102855 A1 | 5/2004 | Shank | |
| 2004/0107004 A1 | 6/2004 | Levine et al. | |
| 2004/0116949 A1 | 6/2004 | Ewers et al. | |
| 2004/0117031 A1 | 6/2004 | Stack et al. | |
| 2004/0122453 A1 | 6/2004 | Deem et al. | |
| 2004/0122456 A1 | 6/2004 | Saadat et al. | |
| 2004/0122473 A1 | 6/2004 | Ewers et al. | |
| 2004/0133089 A1 | 7/2004 | Kilcoyne et al. | |
| 2004/0133147 A1 | 7/2004 | Woo | |
| 2004/0133219 A1 | 7/2004 | Forsell | |
| 2004/0133238 A1 | 7/2004 | Cerier | |
| 2004/0138525 A1 | 7/2004 | Saadat et al. | |
| 2004/0138529 A1 | 7/2004 | Wiltshire et al. | |
| 2004/0138761 A1 | 7/2004 | Stack et al. | |

(56) References Cited

U.S. PATENT DOCUMENTS

| | | |
|---|---|---|
| 2004/0143342 A1 | 7/2004 | Stack et al. |
| 2004/0147858 A1 | 7/2004 | Lee |
| 2004/0147958 A1 | 7/2004 | Lam et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162567 A9 | 8/2004 | Adams |
| 2004/0162568 A1 | 8/2004 | Saadat et al. |
| 2004/0167546 A1 | 8/2004 | Saadat et al. |
| 2004/0181242 A1 | 9/2004 | Stack et al. |
| 2004/0186514 A1 | 9/2004 | Swain et al. |
| 2004/0193190 A1 | 9/2004 | Luddicoat et al. |
| 2004/0199189 A1 | 10/2004 | Gifford et al. |
| 2004/0204768 A1 | 10/2004 | Geitz |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0243195 A1 | 12/2004 | Imran et al. |
| 2004/0249362 A1 | 12/2004 | Levine et al. |
| 2004/0249367 A1 | 12/2004 | Saadat et al. |
| 2005/0033240 A1 | 2/2005 | Oishi et al. |
| 2005/0033331 A1 | 2/2005 | Burnett et al. |
| 2005/0033332 A1 | 2/2005 | Burnett et al. |
| 2005/0049718 A1 | 3/2005 | Dann et al. |
| 2005/0065401 A1 | 3/2005 | Saadat et al. |
| 2005/0075653 A1 | 4/2005 | Saadat et al. |
| 2005/0075654 A1 | 4/2005 | Kelleher |
| 2005/0080431 A1 | 4/2005 | Levine et al. |
| 2005/0080444 A1 | 4/2005 | Kraemer et al. |
| 2005/0085787 A1 | 4/2005 | Laufer |
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0101977 A1 | 5/2005 | Gannoe et al. |
| 2005/0125020 A1 | 6/2005 | Meade et al. |
| 2005/0125075 A1 | 6/2005 | Meade et al. |
| 2005/0143784 A1 | 6/2005 | Imran |
| 2005/0177181 A1 | 8/2005 | Kagan et al. |
| 2005/0187567 A1 | 8/2005 | Baker et al. |
| 2005/0192629 A1 | 9/2005 | Jaadat et al. |
| 2005/0197714 A1 | 9/2005 | Sayet |
| 2005/0197715 A1 | 9/2005 | Kugler et al. |
| 2005/0203547 A1 | 9/2005 | Weller et al. |
| 2005/0222592 A1 | 10/2005 | Gannoe et al. |
| 2005/0247320 A1 | 11/2005 | Stack et al. |
| 2005/0256587 A1 | 11/2005 | Egan |
| 2005/0261549 A1 | 11/2005 | Hewit et al. |
| 2005/0261712 A1 | 11/2005 | Balbierz et al. |
| 2005/0267499 A1 | 12/2005 | Stack et al. |
| 2006/0009858 A1 | 1/2006 | Levine et al. |
| 2006/0020164 A1 | 1/2006 | Butler et al. |
| 2006/0020247 A1 | 1/2006 | Kagan et al. |
| 2006/0020277 A1 | 1/2006 | Gostout et al. |
| 2006/0020278 A1 | 1/2006 | Burnett et al. |
| 2006/0025819 A1 | 2/2006 | Nobis et al. |
| 2006/0047289 A1 | 3/2006 | Fogel |
| 2006/0064120 A1 | 3/2006 | Levine et al. |
| 2006/0074458 A1 | 4/2006 | Imran |
| 2006/0155312 A1 | 7/2006 | Levine et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0173422 A1 | 8/2006 | Reydel et al. |
| 2006/0206063 A1 | 9/2006 | Kagan et al. |
| 2006/0206064 A1 | 9/2006 | Kagan et al. |
| 2006/0287734 A1 | 12/2006 | Stack et al. |
| 2006/0293742 A1 | 12/2006 | Dann et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0027548 A1 | 2/2007 | Levine et al. |
| 2007/0027549 A1 | 2/2007 | Godin |
| 2007/0032879 A1 | 2/2007 | Levine et al. |
| 2007/0083271 A1 | 4/2007 | Levine et al. |
| 2007/0106313 A1 | 5/2007 | Golden et al. |
| 2007/0225555 A1 | 9/2007 | Stefanchik |
| 2007/0233162 A1 | 10/2007 | Gannoe et al. |
| 2008/0004606 A1 | 1/2008 | Swain et al. |
| 2008/0033574 A1 | 2/2008 | Bessler et al. |
| 2008/0103604 A1 | 5/2008 | Levine et al. |
| 2008/0208356 A1 | 8/2008 | Stack et al. |
| 2008/0269797 A1 | 10/2008 | Stack et al. |

FOREIGN PATENT DOCUMENTS

| | | |
|---|---|---|
| WO | WO 80/00007 | 1/1980 |
| WO | WO 91/01117 | 2/1991 |
| WO | WO 96/29954 | 10/1996 |
| WO | WO 98/56440 A1 | 12/1998 |
| WO | WO 99/60931 A1 | 12/1999 |
| WO | WO 00/12027 | 3/2000 |
| WO | WO 01/35834 A1 | 5/2001 |
| WO | WO 01/43663 | 6/2001 |
| WO | WO 01/85034 A1 | 11/2001 |
| WO | WO 02/094132 A1 | 11/2002 |
| WO | WO 02/102227 A2 | 12/2002 |
| WO | WO 03/017882 A2 | 3/2003 |
| WO | WO 03/086246 A1 | 10/2003 |
| WO | WO 03/086247 A1 | 10/2003 |
| WO | WO 03/094785 A1 | 11/2003 |
| WO | WO 2004/017863 A2 | 3/2004 |
| WO | WO 2004/021894 A1 | 3/2004 |
| WO | WO2004/041119 A2 | 5/2004 |
| WO | WO 2004/047686 | 6/2004 |
| WO | WO 2004/049982 A2 | 6/2004 |
| WO | WO 2004/064680 A1 | 8/2004 |
| WO | WO 2004/064685 A1 | 8/2004 |
| WO | WO 2004/080336 A2 | 9/2004 |
| WO | WO 2004/087014 A2 | 10/2004 |
| WO | WO 2004/087233 A2 | 10/2004 |
| WO | WO 2004/086984 A1 | 11/2004 |
| WO | WO 2004/103214 A1 | 12/2004 |
| WO | WO 2004/103430 A2 | 12/2004 |
| WO | WO 2004/105643 | 12/2004 |
| WO | WO 2005/011463 A2 | 2/2005 |
| WO | WO 2005/011519 | 2/2005 |
| WO | WO 2005/011519 A2 | 2/2005 |
| WO | WO 2005/032422 | 4/2005 |
| WO | WO 2005/037152 A1 | 4/2005 |
| WO | WO 2005/060869 A1 | 7/2005 |
| WO | WO 2005/060882 A1 | 7/2005 |
| WO | WO 2006/044640 A1 | 4/2006 |

OTHER PUBLICATIONS

Endoscopic suturing, C. Paul Swain MD, *Balliere's Clinical Gastroenterology*, vol. 13, No. 1. pp. 97-108, 1999.

Antireflux operations at flexible endoscopy using endoluminal stitching techniques: an experimental study, Sritharan S. Kadirkamanathan et al., *Gastrointestinal Endoscoov*, vol. 44, No. 2, 1995 pp. 133-143.

Progression rate of self-propelled feeding tubes in critically ill patients, Mette M. Berger et al., *Intensive Care Med* Oct. 29, 2002, pp. 1768-1774.

Iatrogenic Intussusception: a Complication of Long Intestinal Tubes, Patricia Redmond, M.D., et al., *American Jounal of Gastroenterology*, vol. 77, No. 1, 1982, pp. 39-42.

Design and Testing of a New, Small Diameter, Single Stitch Endoscopic Sewing Machine, C.P. Swain et al., *Abstracts Submitted to A/S/G/E/* 1990, Vo. 36, No. 2, 1990, pp. 213, 214.

Endoscopic Suturing of a Novel Gastroesophageal Antireflux Device (GARD) A Prelinary Report, N.J. Godin et al., *Gastrointestinal Endoscopy*, vol. 43, No. 4, 1996.

An endoscopic stapling device: the development of new flexible endoscopically controlled device for placing multiple transmural staples in gastrointestinal tissue, C. Paul Swain, MD et al., *Gastrointestinal Endoscopy*, vol. 35, No. 4, 1989 pp. 338-339.

An endoscopically deliverable tissue-transfixing device for securing biosensors in the gastrointestinal tract, C. Paul Swain, MD et al. *Gastrointestinal Endoscopy*, 1994.

(56) References Cited

OTHER PUBLICATIONS

Development of a gastroplasty with variable diameter. Experimental study using artificial sphincters, M. Merlini et al., 1992 Abstract.

Synthetic Biodegradable Polymers as Medical Devices, John C. Middleton et al., *Medical Plastics and Biomaterials Magazine MPS Article Index*, Mar. 1998.

*Experimental study on in situ tissue engineering of the stomach by an acellular collagen sponge scaffold graft*, Hori Y. Nakamura et al., Abstract, May 2001.

*Repair of Full-Thickness Defects in Alimentary Tract Wall with Patches of Expanded Polytetrafluoroethylene*, Daniel S. Oh, MD et al., Annals of Surgery 2002; 235:708-712.

*Stents in the small intestine*, Singh S, Gagneja HK, Abstract, Oct. 2002.

Endoscopic vertical band gastroplasty with an endoscopic sewing machine, Amjad N. Awan MD et al., *Gastrointestinal Endoscopy*, vol. 55, No. 2, 2002, pp. 254-256.

A through-the-scope device of suturing and tissue approximation under EUS control, Annette Fritscher-Ravens, MD, et al., *Gastrointestinal Endoscopy*, vol. 56, No. 5, 2002, pp. 737-742.

*Evaluation of porcine-derived small intestine submucosa as a biodegradable graft for gastrointestinal healing*, SG del la Fuente et al., Abstract, J. Gastrointest Surg Jan. 2003.

Bard EndoCinch: the device, the technique and pre-clinical studies, Paul Swain, M.D. et al., *Gastrointestinal Endoscopy Clinics of North America*, 13, 2003 pp. 75-88.

Endoscopic suturing for gastroesophageal reflux disease: clinical outcome with the Bard Endocinch, Richard I. Rothstein, MD et al., *Gastrointestinal Endoscopy Clinics of North America*13 (2003) pp. 89-101.

Wilson-Cook sewing device: the device, technique, and preclinical studies, Michael Rosen MD, et al., *Gastrointestinal Endoscopy Clinics of North America*, 13 (2003) pp. 103-108.

Endoscopic full-thickness plication: the device, technique, pre-clinical and early clinical experience, Ram Chuttani, MD, *Gastrointestinal Endoscopy Clinics of North America*, 13 (2003) pp. 109-116.

Microvasive gastric stapler: the device, technique, and preclinical results, Tom R. De Meester MD, *Gastrointestinal Endoscopy Clinics of North America*, 13 (2003) pp. 117-133.

Endoscopic Gastropexy and Crural Repair for Gastro-Esophageal Reflux: Transgastric Surgery Under Endoscopic Ultrasound Control II, Anette Fritscher-Ravens et al. *Digestive Disease Week* 2003 Abstract.

Endoscopic suturing for treatment of GERD, m. Brian Fennerty, MD, *Gastrointestinal Endoscopy*, vol. 57, No. 3, 2003 pp. 390-395.

Transgastric gastropexy and hiatal hernia repair for GERD under EUS control: a porcine model, Annette Fritscher-Ravens, MD et al., *Gastrointestinal Endoscopy*, vol. 59, No. 1, 2004, pp. 89-95.

Effect of Duodenal-Jejunal Exclusion of a Non-obese Animal Model of Type 2 Diabetes, Francesco Rubino, MD et al., *Annals of Surgery*, vol. 239, No. 1, Jan. 2004, pp.

*The LAP-BAND Solution*, BioEnterics Corporation, Brochurehttp://www.bioenterics.com/.

*Successful Uses in Approximation Ligation & Fixation using the QUIK-STITCH, Endoscopic Suturing System*, PARÉSurgical, Inc. Brochure 2001.

*Obesity Treatment*, Medical Innovation Developpement, Brochure.

*The Remote Controlle Sedish Band, The method of choice in modern treatment of morbid obesity*, OBTECH Medical AG, Brochure.

*The Bard EndoCinch Procedure*, Introducing Endoscopic Technology for the Treatment of GERD.

*Microvasive WALLSTENT® Colonic and Duodenal Endoprosthesis*, Boston Scientific website, www.bostonscientific.com, Sep. 20, 2002.

*COOK® Wilson-Cook Medical GI Endoscopy*, Wilson Cook: Biliary/Pancreatic Stents, www.cookgroup.com, Sep. 20, 2002.

ross.com, *Abbott Laboratories Online*, Product Handbook, T-Fastener Set.

*T=Anchor Introducer Gun™ Details*, Moss™ Tubes Brochure.

Bioabsorable Polymers, William B. Gleason, *University of Minnesota*, 1998.

*Cope Gastrointestinal Suture Anchor Set*, www.cookgroup.com, Cook Diagnostic and Interventional Products Advertisement 2000.

*LSI Solutions®*, SEW-RIGHT® SR 5, Advertisement received at ASBS Conference 2002.

SEW-RIGHT® SR 5™ & SR 10™, Ti-KNOT® TK 5™ Advertisement received at ASBS Conference 2002.

PCT International Search Report, PCT/US2003/34822 mailed Feb. 4, 2004.

PCT International Search Report, PCT/US2004/44049 mailed May 30, 2007.

A new method of enteroscopy—The double-balloon method, Yamamoto et al., *Can J. Gastroenterol*, vol. 17, No. 4 Apr. 2003, pp. 273-274.

Radiocontrolled Movement of a Robot Endoscope in the Human Gastrointestinal Tract, Paul Swain et al., Abstract—*Gastrointestinal Endoscopy*, vol. 61, No. 5 DDW Abstract Issue: Apr. 2005.

Techniques for Advancing Guide Wires and Devices in the Lumen of the Gastrointestinal Tract, Long et al., *Gastrointestial Endoscopy*, vol. 57, No. 5 Apr. 2003 Abstract, 2003 ASGE Meeting, May 18-21, Orlando Florida.

U.S. Appl. No. 11/431,040, filed May 2006, Kagan et al.

U.S. Appl. No. 11/548,605, filed Oct. 2006, Dann.

Three-dimensional manometric imaging of the lower esophageal sphincter, Hubert J. Stein, MD. *Surgery*, 1995 vol. 117 No. 6 pp. 692-698.

PCT International Search Report for PCT/US07/08882, mailed Dec. 26, 2007.

PCT International Search Report for PCT/US2005/15795 mailed Nov. 14, 2005.

\* cited by examiner

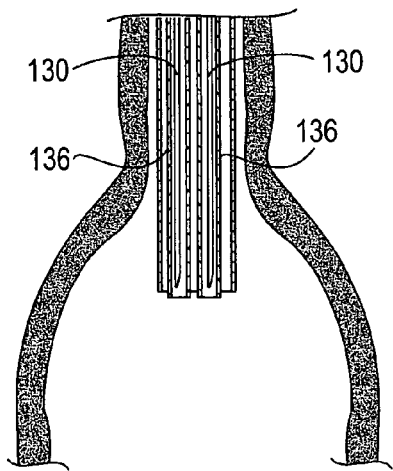
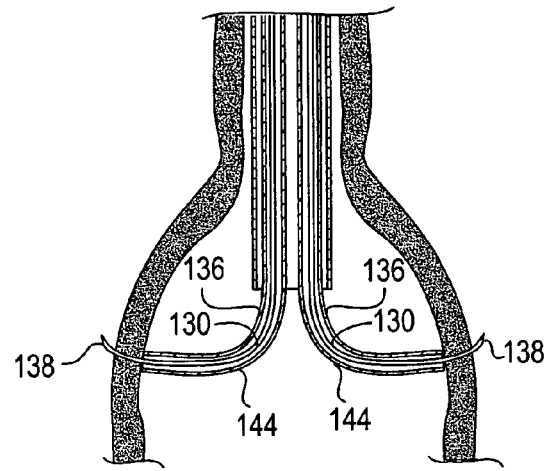
FIG 6A       FIG 6B
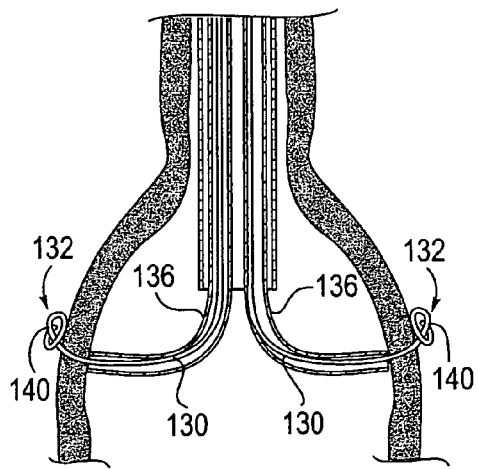
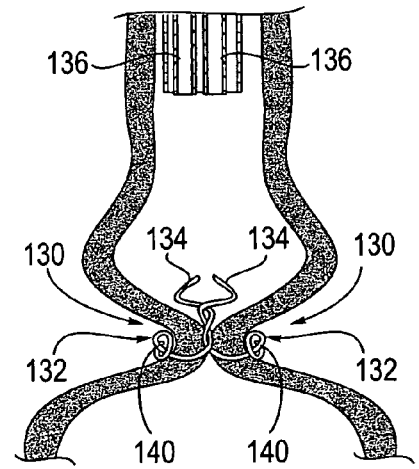
FIG 6C       FIG 6D

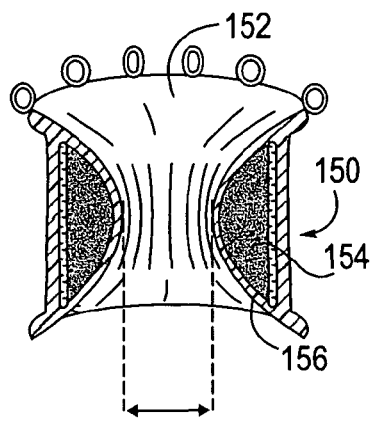
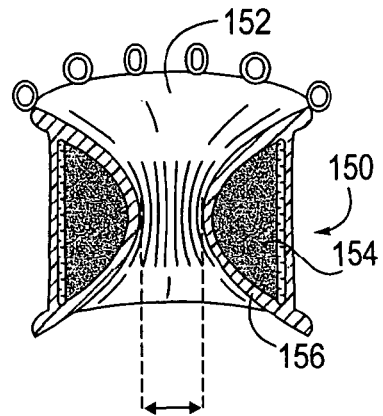
FIG 7A             FIG 7B
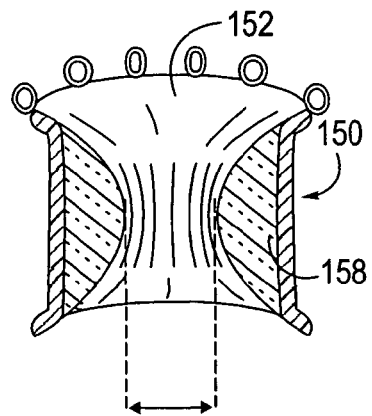
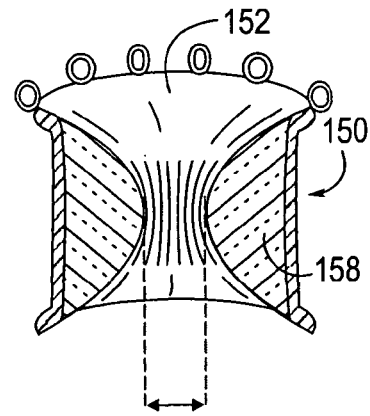
FIG 8A             FIG 8B
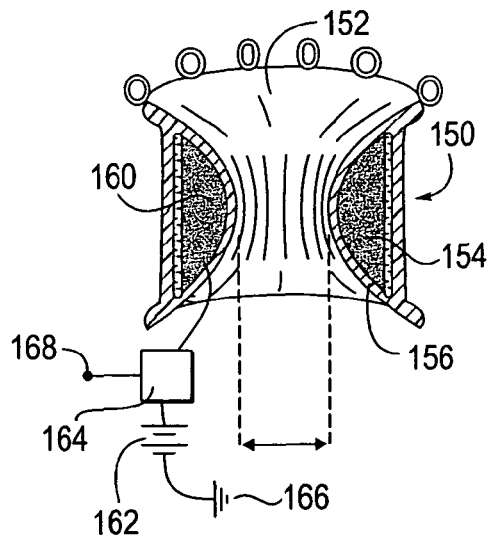
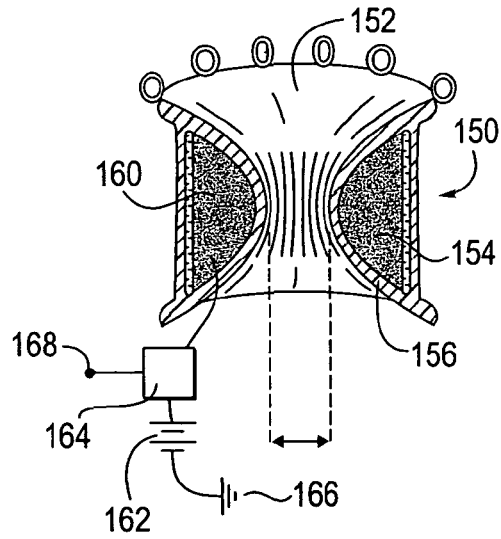
FIG 9A             FIG 9B

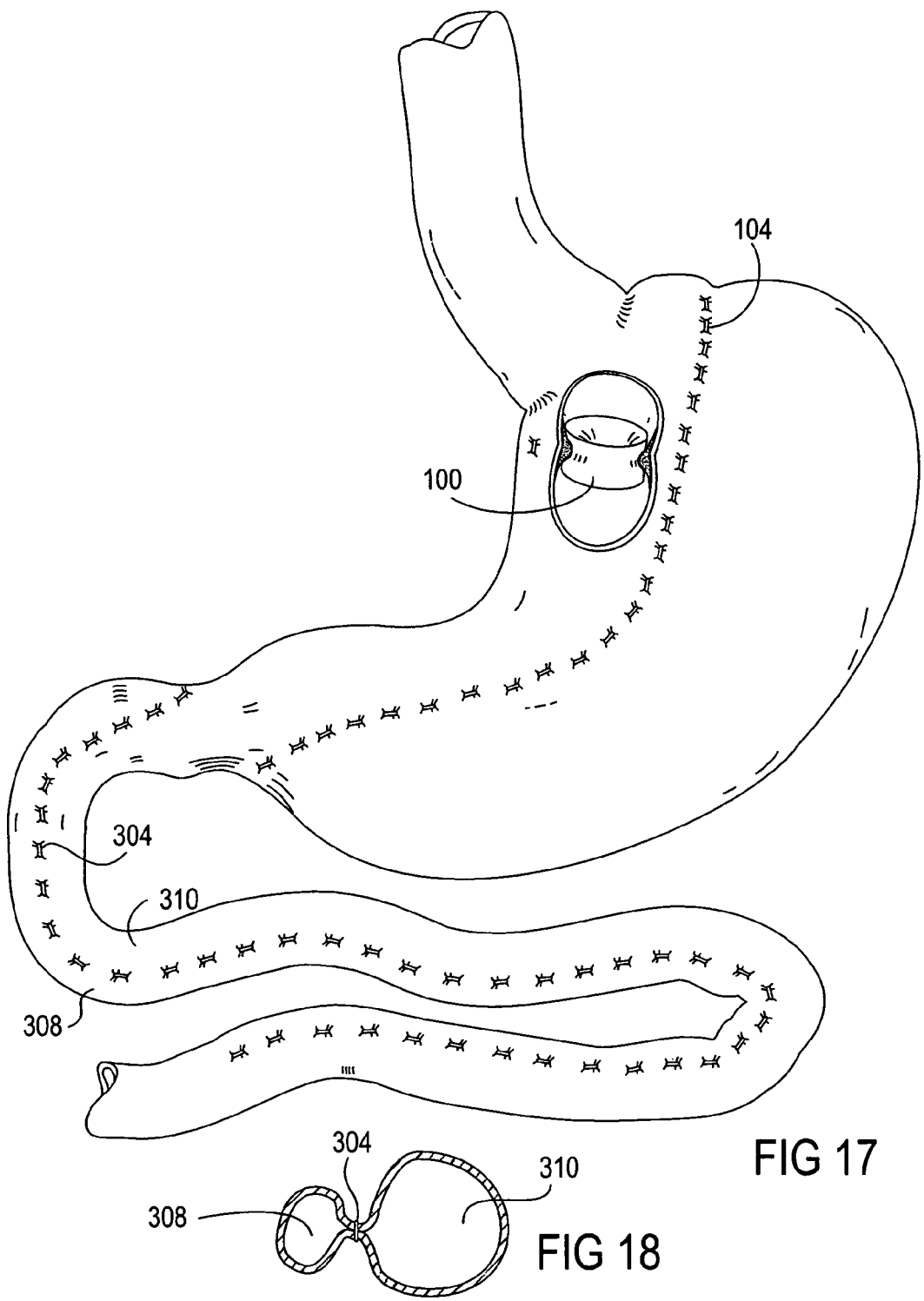

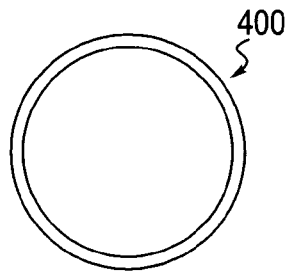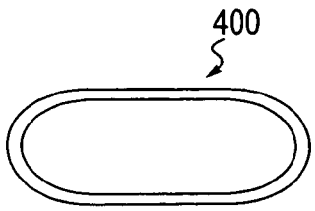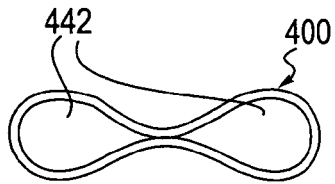
FIG 26A  FIG 26B  FIG 26C
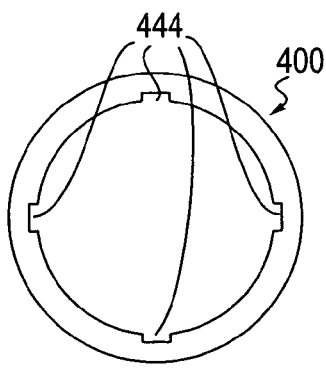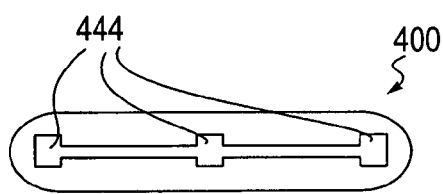
FIG 27A  FIG 27B
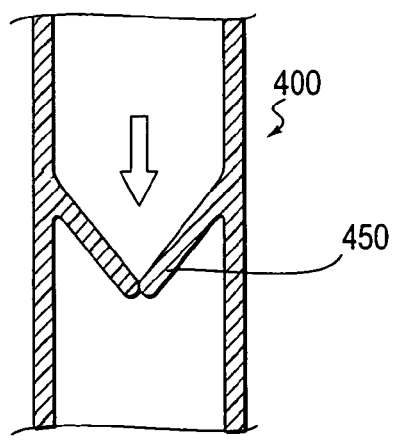
FIG 28

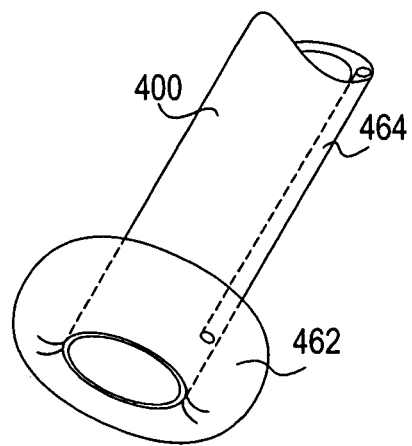
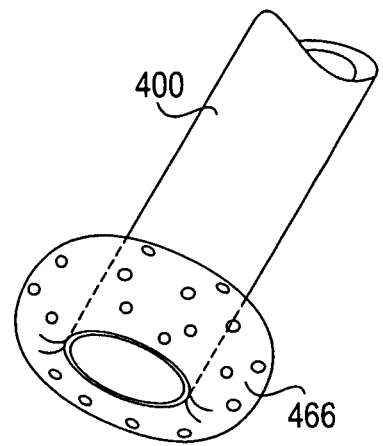
FIG 32A          FIG 32B
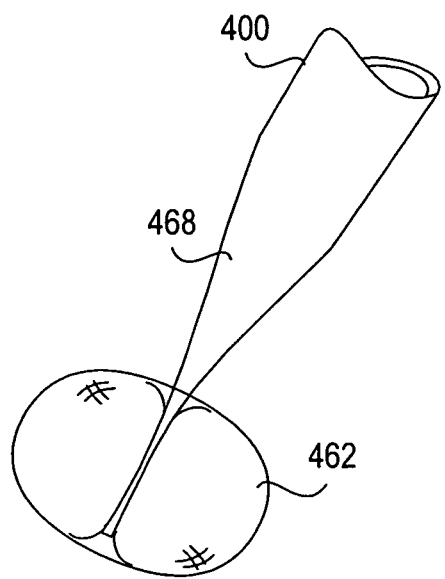
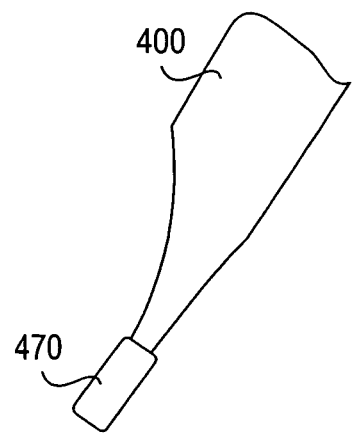
FIG 32C          FIG 32D

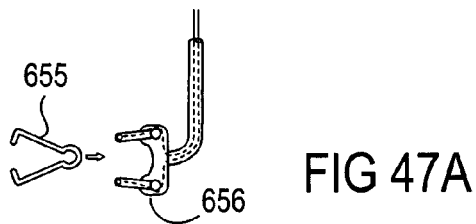
FIG 47A
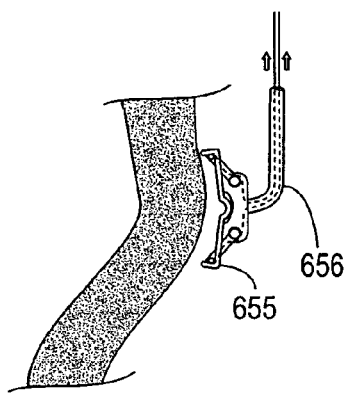
FIG 47B
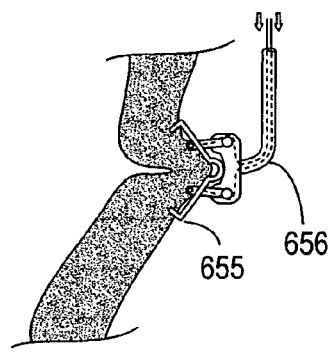
FIG 47C
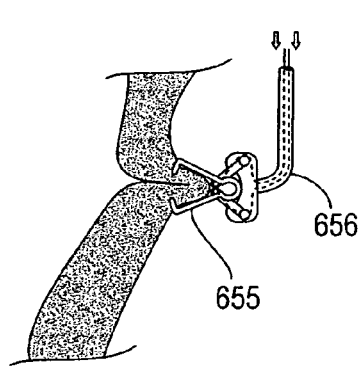
FIG 47D
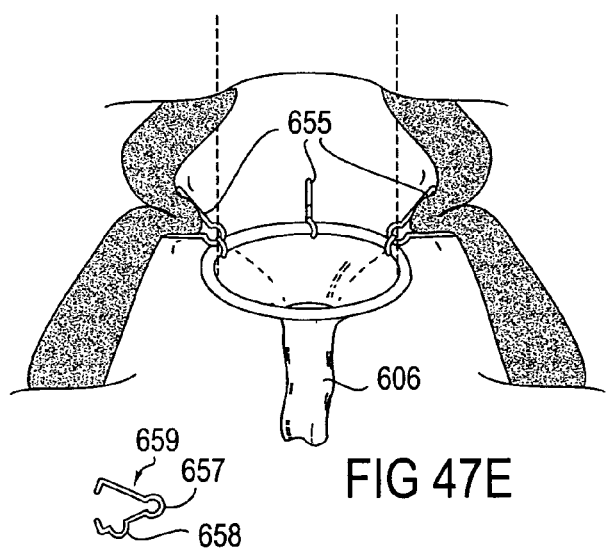
FIG 47E
FIG 47F

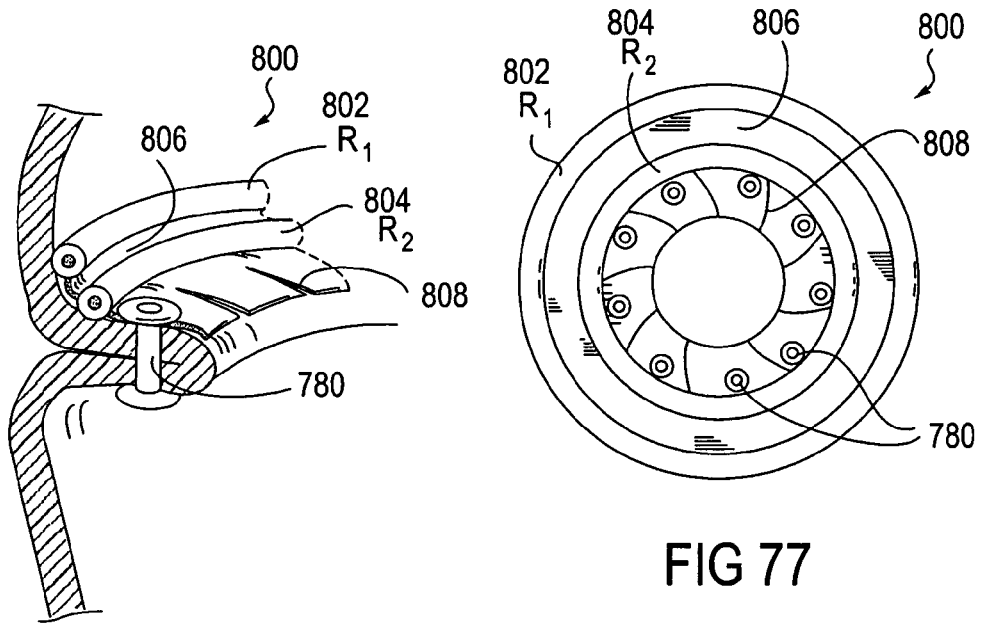
FIG 77
FIG 78
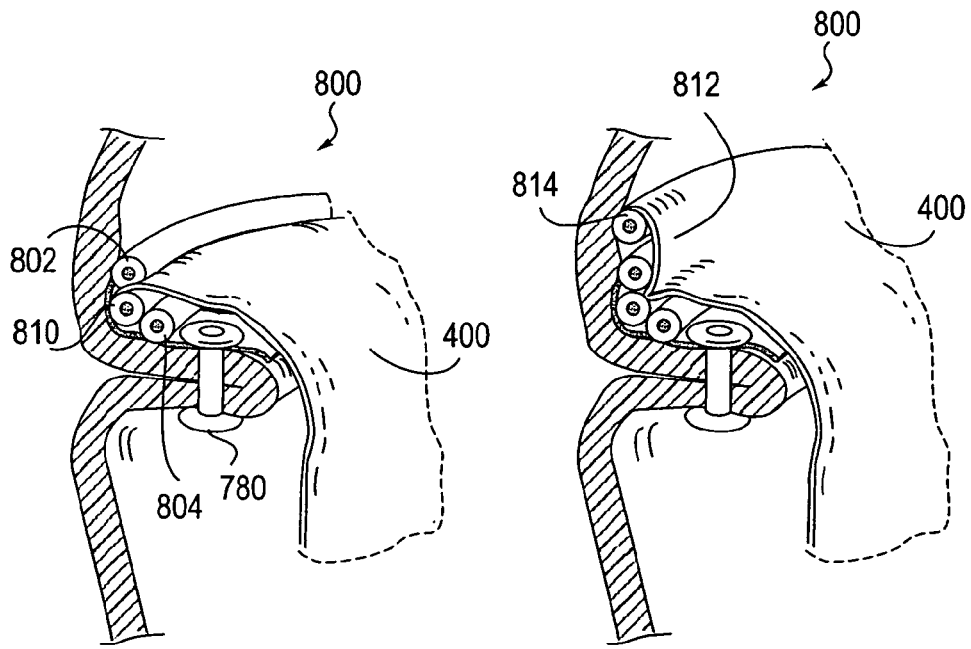
FIG 79
FIG 80

APPARATUS AND METHODS FOR TREATMENT OF MORBID OBESITY

CROSS-REFERENCE TO OTHER APPLICATIONS

The present application claims priority of U.S. Provisional Patent Applications No. 60/422,987, filed on Nov. 1, 2002, for Apparatus and Methods for Treatment of Morbid Obesity; No. 60/430,857, filed on Dec. 3, 2002, for Biliopancreatic Diverter Tube for Treatment of Morbid Obesity; No. 60/437,513, filed on Dec. 30, 2002, for Apparatus and Methods for Gastric Surgery, No. 60/448,817, filed on Feb. 21, 2003, for Surgical Fastener System and Method for Attachment within a Hollow Organ, and No. 60/480,485, filed on Jun. 21, 2003 for Gastrointestinal Sleeve Device and Method of Use. The present application is also related to the subject matter of U.S. Provisional Patent Application No. 60/428,483, filed on Nov. 22, 2002, for Gastroplasty Clamp. These and all other patents and patent applications referred to herein are hereby incorporated by reference in their entirety.

BACKGROUND OF THE INVENTION

Bariatrics is the field of medicine encompassing the study of overweight, its causes, prevention and treatment. Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found in U.S. Provisional Patent Application No. 60/422,987 Apparatus and Methods for Treatment of Morbid Obesity and also on the website of the American Society for Bariatric Surgery at http://www.asbs.org.

Medical sleeve devices for placement in a patient's stomach are described by Rockey in U.S. Pat. Nos. 4,501,264, 4,641,653 and 4,763,653. The medical sleeve described in these patents are said to reduce the surface area available for absorption in the stomach, however it is not configured to effectively reduce the volume of the stomach nor will the device described isolate ingested food from stomach secretions. The medical sleeve is not configured to be deployed in a patient's small intestine.

Other sleeve devices for placement in a patient's intestines are described in U.S. Pat. No. 4,134,405 (Smit), U.S. Pat. No. 4,315,509 (Smit), U.S. Pat. No. 5,306,300 (Berry), and U.S. Pat. No. 5,820,584 (Crabb). The sleeve devices described in these patents are said to be placed at the lower end of the stomach and therefore do not serve to isolate ingested food from the digestive secretions of the stomach. These sleeve devices are not configured to be deployed in a patient's stomach or to effectively reduce the volume of the patient's stomach or small intestine.

In U.S. patent application Ser. No. 2003/0040804, Stack et al. describe a satiation device to aid in weight loss by controlling feelings of hunger. The patent application describes an antral tube that expands into the antrum of the stomach to create a feeling of satiation. The devices described are not configured to isolate ingested food and liquids from digestive secretions in the stomach or the intestines.

In U.S. patent application Ser. No. 2003/0040808, Stack et al. describe a satiation device for inducing weight loss in a patient includes a tubular prosthesis positionable at the gastro-esophageal junction region, preferably below the z-line. The prosthesis is placed such that an opening at its proximal end receives masticated food from the esophagus, and such that the masticated food passes through the pouch and into the stomach via an opening in its distal end.

In U.S. patent application Ser. No. 2003/0093117, Sadaat describes an implantable artificial partition that includes a plurality of anchors adapted for intraluminal penetration into a wall of the gastro-intestinal lumen to prevent migration or dislodgement of the apparatus, and a partition, which may include a drawstring or a toroidal balloon, coupled to the plurality of anchors to provide a local reduction in the cross-sectional area of the gastro-intestinal lumen.

In U.S. patent application Ser. No. 2003/0120265, Deem et al. describe various obesity treatment tools and methods for reducing the size of the stomach pouch to limit the caloric intake as well as to provide an earlier feeling of satiety. The smaller pouches may be made using individual anchoring devices, rotating probes, or volume reduction devices applied directly from the interior of the stomach. A pyloroplasty procedure to render the pyloric sphincter incompetent and a gastric bypass procedure using atraumatic magnetic anastomosis devices are also described.

In U.S. patent application Ser. No. 2003/0144708, Starkebaum describes methods and systems for treating patients suffering from eating disorders and obesity using electrical stimulation directly or indirectly to the pylorus of a patient to substantially close the pylorus lumen to inhibit emptying of the stomach.

The present invention also relates to apparatus and methods for performing gastric and esophageal surgery that can be applied using minimally invasive techniques for creating a stoma or restriction in a patient's stomach or esophagus. The apparatus and methods are useful for treatment of morbid obesity and for treatment of gastroesophageal reflux disease (GERD). Surgical treatments for gastroesophageal reflux disease include fundoplasty and fundoplication, which can be performed using open surgical techniques or laparoscopic surgical techniques. These procedures create a valve-like structure at the gastroesophageal junction to prevent reflux of the stomach contents. Although methods have been proposed for performing fundoplication using peroral endoscopic techniques, these methods have not been widely adopted. Examples of instruments and methods for performing fundoplication can be found in the following patents: WO0185034 Devices and related methods for securing a tissue fold, U.S. Pat. No. 6,312,437 Flexible endoscopic surgical instrument for invagination and fundoplication.

1. Field of the Invention

The present invention relates generally to apparatus and methods for treatment of obesity, and particularly morbid obesity. In particular, it relates to apparatus and methods that can be applied using minimally invasive techniques for effectively reducing stomach volume, bypassing a portion of the stomach and/or small intestines and/or reducing nutrient absorption in the stomach and/or small intestines 2. Description of the Related Art

*

SUMMARY OF THE INVENTION

In keeping with the foregoing discussion, the present invention provides apparatus and methods that can be applied using minimally invasive techniques for treatment of obesity, and particularly morbid obesity. The apparatus takes the form of a system of components that may be used separately or in combination for effectively reducing stomach volume, bypassing a portion of the stomach and/or small intestines, reducing nutrient absorption in the stomach and/or small intestines and/or depositing minimally or undigested food farther than normal into the intestines (thereby stimulating intestinal responses).

In one aspect of the invention, the system may include an artificial stoma device located in the stomach or lower esophagus that can reduce the flow of food into the stomach (when located in the stomach) or back from the stomach into the esophagus (when located in the esophagus or at the gastroesophageal junction). Alternatively, the system may utilize a surgically created artificial stoma. Stomas that prevent flow of gastric contents into the esophagus can be used in the treatment of GERD. The stoma is introduced transesophageally and implanted under visualization with a flexible endoscope. The stoma may be anchored to the esophageal or stomach wall using sutures, staples or clips. Alternatively, the stoma may be anchored with a sutureless attachment that does not penetrate the esophageal or stomach wall. Optionally, multiple stomas can be installed, e.g. one for GERD and one for restriction of food passage. Optionally, the stoma may be used in conjunction with gastric suturing, stapling or banding to create a narrow passage for installation of the stoma and/or for reduction of gastric volume. The gastric stapling or banding may be applied using transesophageal or laparoscopic techniques. Optionally the stoma may be in multiple parts where the parts may be individually placed, replaced or exchanged. Optionally, the stoma may have an adjustable opening to vary the flow of food through the stoma and/or allow the passage of diagnostic or therapeutic devices such as endoscopes. The adjustable stoma may be adjusted at the time of implantation or it may be adjustable remotely after implantation without invasive procedures. Alternatively, the stoma may be a self-adjusting "smart stoma" that opens and/or closes in response to stomach conditions.

In another aspect, the system may include an internal gastric sleeve that may be used separately or used with, attached to or integrated with the artificial stoma component. The gastric sleeve may have a funnel-shaped entry with a reinforced anchoring segment or other anchoring mechanism for attachment in the stomach at or near the gastroesophageal junction. Optionally, the artificial stoma component may be positioned a clinically significant distance distal to the sleeve attachment. When placed in the stomach, the entry portion of the sleeve proximate to the stoma effectively reduces the volume of the stomach because the flow of solid food is limited to the lumen of the sleeve. When combined with a restrictive stoma, the sleeve functions as the pouch in a gastric bypass or vertical banded (or other) gastroplasty. The sleeve can be designed and placed to maximize the amount of stomach wall included by the sleeve opening and therefore included in the pouch thereby formed. This will enable a maximum number of stretch receptors and other stimulating mechanisms in the stomach to transmit satiety (fullness) signals to help reduce food intake.

The entire gastric sleeve or a portion of it can be porous or semipermeable to allow the flow of digestive secretions into the sleeve and to allow the flow of nutrients and/or fluids out through the wall of the gastric sleeve. Valves may be provided in the wall of the gastric sleeve to allow digestive secretions to enter the sleeve, but to prevent solid food and/or nutrients from flowing out through the wall of the sleeve. Alternatively, the entire gastric sleeve or a portion of it can be nonporous or impermeable to act as an internal gastric bypass. In certain embodiments, the wall of the gastric sleeve is flexible to allow the peristaltic motions of the stomach to effect movement of food through the gastric sleeve. The wall of the sleeve may be reinforced with rings or a spiral made of wire and/or plastic. Alternatively, the gastric sleeve may be attached to an artificial stoma component that includes its own anchoring mechanism. Optionally, the distal end of the gastric sleeve may be anchored in the region of the pylorus. Optionally the distal end of the gastric sleeve can incorporate an enlarged reservoir portion proximal to the pylorus. Optionally the sleeve can include coatings on its interior and/or exterior to enhance the surface properties of the sleeve in clinically relevant manners.

In conjunction with the stoma and/or gastric sleeve, the volume of the stomach can be reduced by suturing, stapling using open, transesophageal or laparoscopic techniques. Alternatively or in addition, a gastric balloon or other volume displacement device may be used in conjunction with the gastric sleeve to provide a feeling of satiety. These adjunctive techniques have the effect of further reducing nutrient intake (in the case of a stomach reduction and pouch formation upstream of a stoma) and enhancing the effect of peristaltic motions of the stomach for moving food through the gastric sleeve intake (in the case of a stomach reduction downstream of a stoma where there is a gastric sleeve). A gastric sleeve that extends beyond the pylorus, with or without an intestinal sleeve, can allow use of the pylorus as a natural stoma by configuring the sleeve to close by the pylorus and then open to allow passage of food when the muscles of the pylorus relax.

One advantage of using an internal gastric sleeve over prior art gastric volume reduction techniques is that volume reduction can be better defined in that the patient cannot deliberately or inadvertently increase the volume of the sleeve over time by overeating as occurs when the stomach wall stretches. Another advantage of an internal sleeve over prior art banding techniques is that stomach wall is not trapped between an external structure and ingested food whereby the stomach wall is subject to compression due to overeating.

In another aspect, the system may include an internal intestinal sleeve that may be used separately or used with, attached to or integrated with the internal gastric sleeve and/or artificial stoma component. The entire intestinal sleeve or a portion of it can be porous or semipermeable to allow the flow of digestive secretions into the sleeve and to allow the flow of nutrients and/or fluids out through the wall of the sleeve. Valves may be provided in the wall of the intestinal sleeve to allow digestive secretions to enter the sleeve, but to prevent solid food and/or nutrients from flowing out through the wall of the sleeve. Alternatively, the entire intestinal sleeve or a portion of it can be nonporous or impermeable to act as an internal intestinal bypass. In certain embodiments, the wall of the intestinal sleeve is flexible to allow the peristaltic motions of the intestinal wall to effect movement of food through the intestinal sleeve. The wall of the sleeve may be reinforced with rings or a spiral made of wire and/or plastic. Optionally these components can include radiopaque materials for visualization of the device when it is in the body. Optionally the sleeve can include coatings on its interior and/or exterior to enhance the surface properties of the sleeve in clinically relevant manners.

In one aspect of the present invention, there is provided a method of treating a patient. The method includes the steps of providing a gastrointestinal sleeve having a proximal end, a distal end and a length of at least about 50 cm. The sleeve is positioned with the proximal end adjacent an attachment site in the vicinity of the lower esophageal sphincter, with the distal end extending transluminally at least as far as the jejunum. At least one plication is formed at the attachment site, and the sleeve is attached to the plication. Two or three or four of five or more plications may alternatively be formed, for direct or indirect attachment to the sleeve. The distal end of the sleeve may extend into the intestine at least as far as the ligament of Treitz. The providing step may comprise providing a sleeve having a substantially constant diameter throughout its length.

Optionally, the intestinal sleeve may have a proximal end with a reinforced anchoring segment or other anchoring mechanism for attachment in the region of the pylorus. Alternatively, the intestinal sleeve may be attached to or continuous with the internal gastric sleeve. Optionally, the distal end of the intestinal sleeve may include an anchoring mechanism.

Optionally, the above system components can include means of separately installing, replacing and/or removing single components. This would include means of reversibly attaching and connecting components. This would allow a therapeutic device to be assembled over multiple operations or in a single procedure. Alternatively, the above components can be preassembled with a specific combination of desired features for an individual patient and thereby installed and removed in a single operation. Preferably, each component of the system includes one or more radiopaque and/or sonoreflective markers for enhanced imaging by X-ray, fluoroscopy and/or ultrasonic imaging.

Certain implementations of the invention will achieve some or all of the following advantages:
1. Minimally invasive, peroral/transesophageal implantation, with optional surgical and/or laparoscopic assist
2. Customizable to each patient and revisable in-situ based upon the results of the intervention
3. Completely reversible using minimally invasive techniques
4. Lower morbidity, mortality
5. When used with a gastric and/or intestinal sleeve, does not allow an appreciable amount of digestion to occur until the food exits the sleeve into the intestine by keeping food separate from gastric and/or intestinal secretions. This delivers undigested food to the jejunum where a dumping syndrome reaction and/or other results of overstimulation of the intestine may occur depending upon the clinical situation and the food ingested.

The system optionally includes a biliopancreatic diverter tube for effectively reducing nutrient absorption in the small intestines by diverting the release of digestive salts and enzymes from the gallbladder and pancreas into the small intestine downstream in the gastrointestinal tract, resulting in a reduction in the location and the amount of intestine exposed to digestible nutrients, and thus reducing the digestion and absorption of fat and other sources of calories.

The system optionally includes a surgical fastener system for removably or reversibly attaching a surgical appliance within a hollow organ in a patient's body. The surgical fastener system can be configured for many different surgical applications within a patient's body. In many applications, it is desirable to removably or reversibly attach a surgical appliance within a hollow organ such that it can be removed or revised at a later date. Examples of applications where the surgical fastener system of the present invention can be used include: attachment of an artificial stoma device or gastrointestinal sleeve device within a patient's stomach or intestines for treatment of morbid obesity, attachment of a valve or restriction in a patient's esophagus for treatment of gastroesophageal reflux disease, attachment of a filter device within a patient's vena cava for treatment of thromboembolic disease, and attachment of a valve or other device within a patient's aorta or urethra.

With these broader applications in mind, the surgical fastener system will be described in relation to a particular application for reversibly attaching a surgical appliance within a patient's stomach or esophagus for treatment of conditions including morbid obesity and gastroesophageal reflux disease. Morbid obesity can be surgically treated by creating a restriction in a patient's stomach to limit the amount of food that can enter the stomach. Alternatively or in addition, the patient's stomach and/or intestines can be partially bypassed, for example using an internal gastrointestinal sleeve device, to reduce the amount of nutrients that are absorbed from the food as it passes through the gastrointestinal system. GERD can be treated by attachment of a valve or restriction in a patient's esophagus at the gastroseophageal junction to prevent food and digestive juices from refluxing into the esophagus.

Certain embodiments of the fastener system utilize folding or plication of the stomach and/or esophageal wall or other hollow organ to create a reinforced attachment point for the fasteners. Various devices and methods have been previously described utilizing fundoplication to create a restriction or a valve-like structure at the gastroesophageal junction for treatment of gastroesophageal reflux disease. For example, see patents: U.S. Pat. Nos. 5,897,562, 6,312,437, Ser. No. 20020035370A1, WO00185034, WO00228289 and WO09922649, which are hereby incorporated by reference. By contrast, in certain embodiments of the present invention, the fastener system preferably attaches to the stomach or other hollow organ with a minimum of stress and deformation. One way of accomplishing this is by utilizing a multiplicity of independent fasteners attached around the inner periphery of the organ without causing any narrowing or restriction in the organ. Alternatively, the fastener system may utilize a continuous ring structure that is sized to fit closely with the inner diameter of the organ without significant deformation of the organ. In the alternative, when a stoma or restriction is desired at the point of attachment system, the fastener system and methods of the present invention can be modified to create a narrowing, restriction or a valve-like structure in the hollow organ simultaneously with providing a removable attachment for a surgical appliance or the like.

Alternatively or in addition, the system may optionally include a surgical instrument for creating a stoma or restriction in a patient's stomach or esophagus using minimally invasive surgical techniques. This apparatus can also be used to create a plication or fold in the stomach or esophagus and furthermore can then be used to attach other devices to the fold thereby created. In addition, the system may optionally include a stomal ring clip device implantable within the patient's stomach for forming and maintaining the stoma or restriction. The surgical instruments and the implantable stomal ring clip devices may be used separately or in combination depending on the needs of the individual patient. Methods are described using the surgical instruments and the implantable stomal ring clip devices separately and in combination for creating a stoma or restriction in a patient's stomach or esophagus. The apparatus and methods are useful for treatment of morbid obesity and can be combined with other surgical techniques or devices as part of a complete treatment regimen. The apparatus and methods are useful for treatment of GERD by creating a restriction or a valve-like structure at the gastroesophageal junction to prevent reflux of the stomach contents.

T-tag fasteners can be used to facilitate endoscopic attachment of the various components of the system to the tissues in or around the patient's gastrointestinal tract. In addition, T-pledgets can be used in situations where reinforcement of the tissue to be attached is desired. For example, such fasteners can be used for fastening a stoma device, a sleeve device or an attachment ring to the gastric wall. Optionally, the gastric wall may be folded into a single or double plication for attachment of the system components with the fasteners. Alternatively or in addition, where it is appropriate, laparoscopic assistance may be used for forming the plications or applying the fasteners. Expandable T-tags and T-pledgets and other structures to reduce tissue erosion are also described.

Apparatus and methods are described for performing an endoscopic gastropexy attachment procedure for anchoring the gastric wall to the patient's diaphragm to provide greater support for the components of the system. A component of the system, such as a stoma device, a sleeve device or an attachment ring, can be attached simultaneously or in a subsequent step with the gastropexy attachment. T-tag fasteners or the like can be used to facilitate gastropexy attachment procedure.

BRIEF DESCRIPTION OF THE DRAWINGS

FIGS. 6A-6D show wire fasteners useful for attaching the stoma device and forming a gastroplasty pouch.

FIGS. 7A-7B show an enlarged view of a smart stoma device with a stoma aperture that varies its diameter in response to conditions in the patient's stomach.

FIG. 8A-8B show another embodiment of a smart stoma device with a stoma aperture that varies its diameter in response to conditions in the patient's stomach.

FIGS. 9A-9B show an enlarged view of a smart stoma device with a closed loop controlled variable diameter stoma aperture.

FIG. 17 shows an artificial stoma device implanted within a patient's stomach with a line of gastroplasty sutures or staples to reduce the gastric volume. Also shown is a line of sutures or staples longitudinally dividing the small intestine to create a biliopancreatic channel separate from the intestinal lumen.

FIG. 18 shows a cross section of the patient's small intestine showing the biliopancreatic channel.

FIGS. 26A, 26B and 26C show a cross section of the gastrointestinal sleeve device with optional features intended to keep the lumen of the sleeve open even if the sleeve collapses.

FIGS. 27A and 27B show a cross section of the gastrointestinal sleeve device with optional internal channels intended to keep the lumen of the sleeve open even if the sleeve collapses.

FIG. 28 illustrates an optional one-way valve feature of the gastrointestinal sleeve device.

FIGS. 32A-32D illustrate optional features to assist in the deployment of the gastrointestinal sleeve device within a patient's gastrointestinal tract.

FIG. 47A shows a clip that can be used to plicate tissue, and also provide a platform for attaching another device or hanger. The clip is shown being used with one embodiment for a plication tool.

FIGS. 47B-47D show the sequence of steps used to deliver the clip of FIG. 47A. This process may be repeated to collectively form a support structure for another device.

FIG. 47E shows another device that is positioned to hang from several clips positioned within a passageway.

FIG. 47F shows an alternative clip embodiment having two separate attachment platforms.

FIG. 77 shows a top view of an attachment ring device for attaching a gastrointestinal sleeve device within a patient's stomach.

FIG. 78 shows a cross section of the attachment ring device of FIG. 77.

FIG. 79 shows a cross section of the attachment ring device of FIG. 77 with a gastrointestinal sleeve device installed.

FIG. 80 shows a cross section of the attachment ring device and the gastrointestinal sleeve device of FIG. 79 with an optional leak shield installed.

DETAILED DESCRIPTION OF THE PREFERRED EMBODIMENT

The present invention provides apparatus and methods for treatment of obesity, and particularly morbid obesity. The apparatus takes the form of a system of components that may be used separately or in combination for effectively reducing stomach volume, bypassing a portion of the stomach and/or small intestines and reducing nutrient absorption in the stomach and/or small intestines. Each of the components can be implanted using minimally invasive techniques, preferably using a transesophageal approach under visualization with a flexible endoscope. Optionally, laparoscopic surgical techniques may be used to assist in the implantation of the components and/or for adjunctive therapies in the digestive tract.

In the following, the word endoscope (and endoscopic) will refer to an instrument for visually examining the interior of a bodily canal or a hollow organ. For procedures performed via a peroral route, a flexible endoscope, such as a gastroscope, is generally preferred. The word laparoscope (laparoscopic) will refer to rigid endoscopes generally passed through surgically created portals. Also in the following the terms biodegradable and bioresorbable will be used interchangeably. Also in the following the term stoma will be used to refer to an opening formed in a hollow organ which may or may not be configured to restrict flow of food and/or digestive juices. Endoscopic overtube and orogastric tube sleeve are also used interchangeably.

Figure 1:
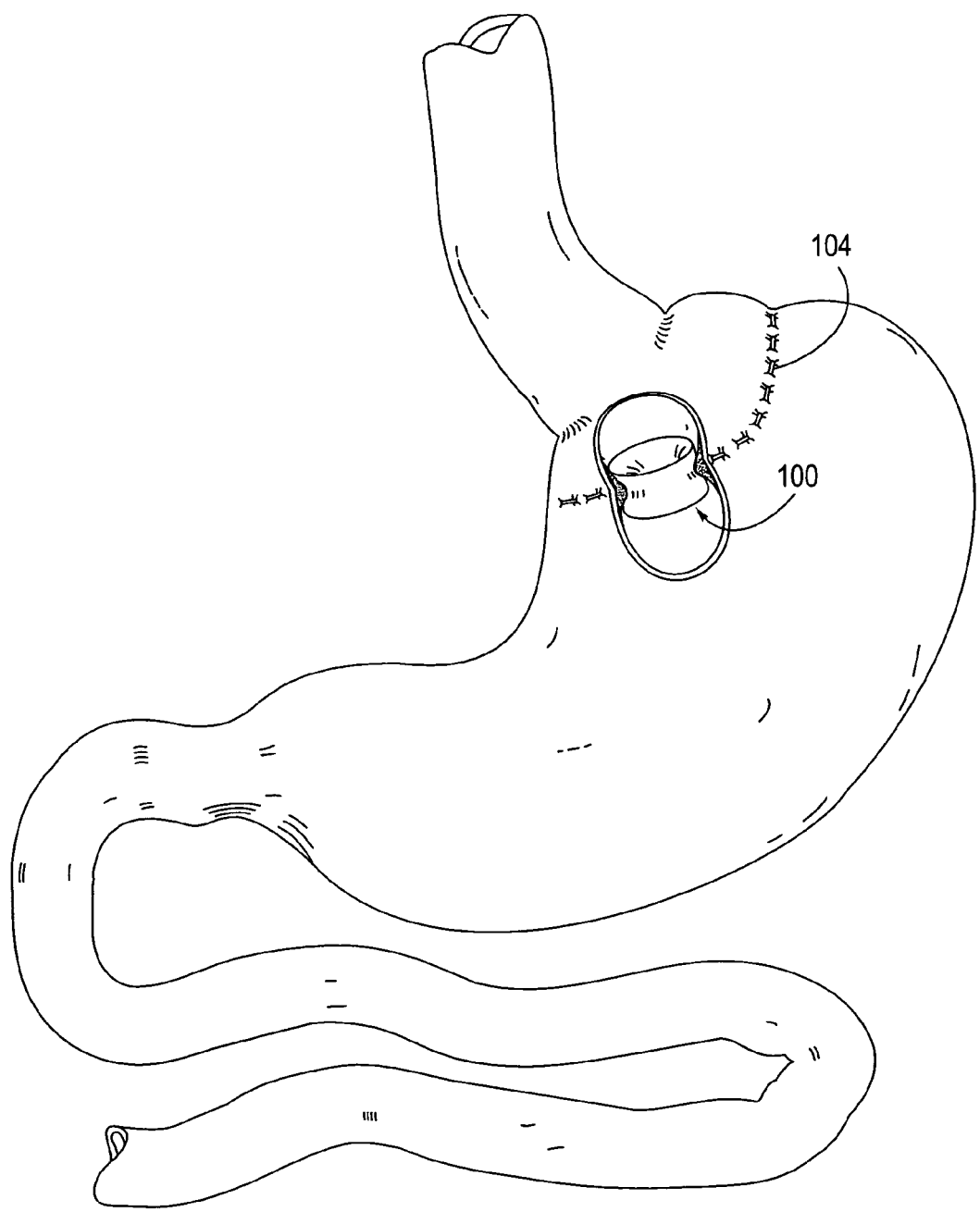
FIG. 1 shows an artificial stoma device implanted within a patient's stomach with a line of gastroplasty sutures or staples to create a narrow passage.

In one aspect of the invention, the system may include an artificial stoma 100 located in the stomach or lower esophagus that can optionally reduce the flow of food into the stomach. FIG. 1 shows an artificial stoma device 100 implanted within a patient's stomach. The stoma device 100 is introduced transesophageally and implanted under visualization with a flexible endoscope. The stoma may be optionally restrictive or non-restrictive of food flow. The stoma may be anchored to the esophageal or stomach wall using sutures, staples, clips or other anchoring mechanisms as described herein. Optionally, the stoma 100 may be used in conjunction with gastric suturing, stapling or banding to create a narrow passage for installation of the stoma and/or for reduction of gastric volume. The gastric suturing, stapling or banding may be applied using open, transesophageal or laparoscopic techniques. In the example shown in FIG. 1, a line of gastroplasty sutures or staples 104 has been used to create a small gastroplasty pouch with a narrow passage for installation of the stoma 100. The gastroplasty sutures or staples 104 may be applied using open, transesophageal or laparoscopic techniques.

The artificial stoma 100 may include a fabric cuff on the outer circumference to facilitate ingrowth of tissue to secure the stoma device 100 in place. In-growth can be further facilitated by partial transection of the gastric wall through the mucosa. This will put the fabric cuff in contact with muscularis. Alternatively or in addition, a number of suture attachment points can be included on the outer circumference of the stoma device. The suture attachment points may take the form of suture attachment loops attached to the outer circumference of the stoma device or a ring with suture attachment holes formed in it.

In certain embodiments, the outer circumference of the stoma 100 is flexible and elastic with properties to minimize the resistance of the stoma 100 to motion of the stomach at the stomal attachment points. This also serves to minimize the forces that can lead to tissue erosion.

Figure 2A:
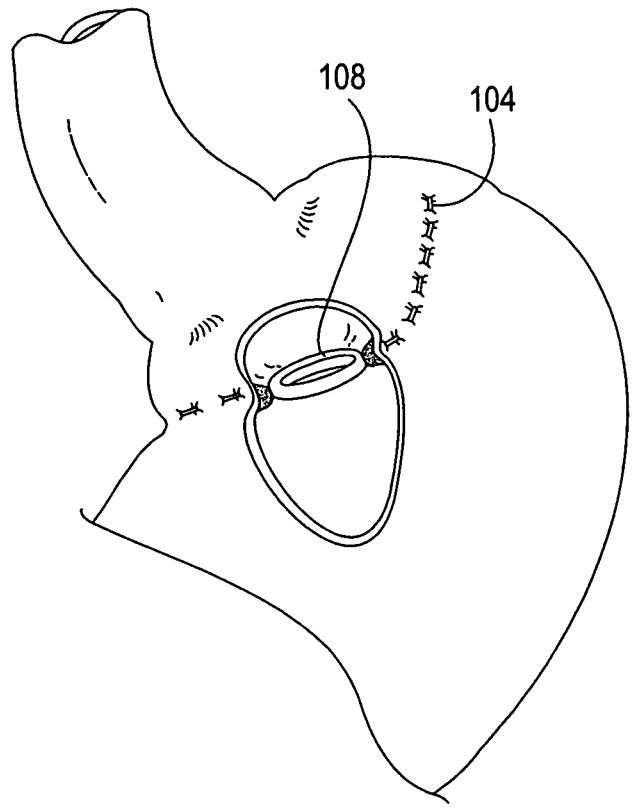
FIGS. 2A-2B shows a stoma device with a separate anchoring device in the form of an anchoring ring.
Figure 2B:
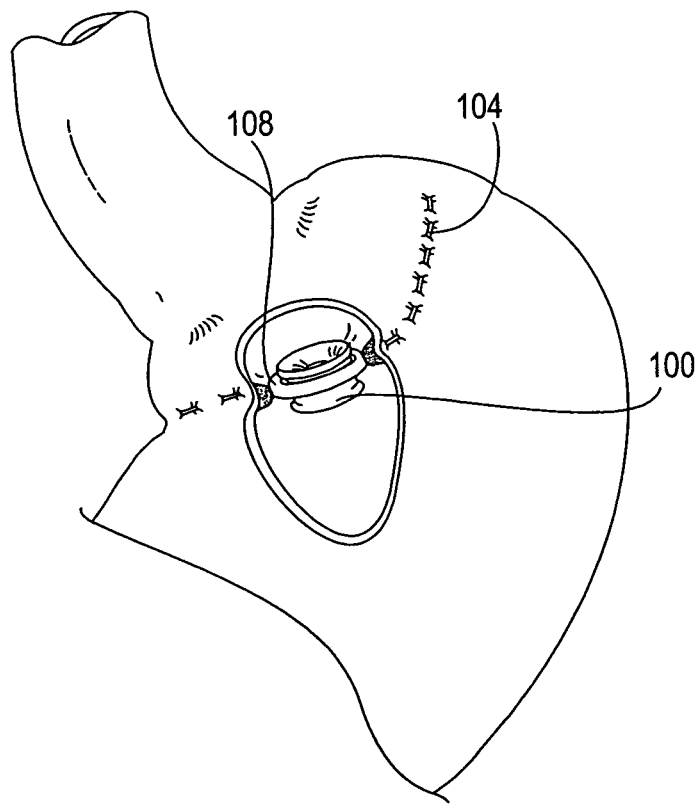

In an alternative embodiment, the artificial stoma device may include a separate anchoring device that may be in the form of an anchoring ring or a series of anchoring points for attachment to the gastric or esophageal wall. FIGS. 2A-2B shows a stoma device 100 with a separate anchoring device in the form of an anchoring ring 108. The anchoring ring 108 may include a sutureless anchoring mechanism and/or a fabric cuff or other attachment points for sutures, staples, clips or other anchoring mechanisms. The anchoring device 108 is initially implanted in the stomach or lower esophagus, as shown in FIG. 2A. Preferably, the tissue is allowed to heal for a number of weeks before the artificial stoma 100 is installed by attaching it to the anchoring device 108 in a subsequent procedure, as shown in FIG. 2B.

Figure 3:
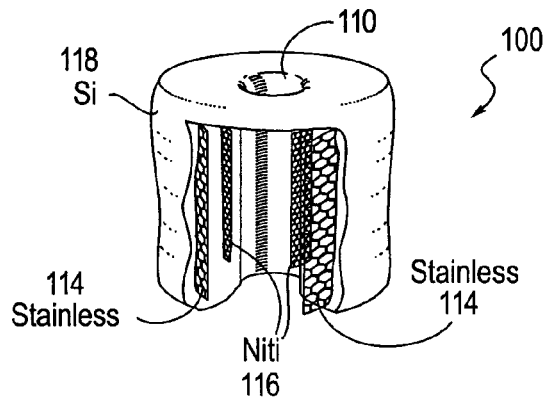
FIG. 3 shows an enlarged view of an artificial stoma device with a variable diameter stoma aperture.

Optionally, the stoma 100 may have an adjustable opening 110 to vary the flow of food through the stoma. FIG. 3 shows an enlarged view of an artificial stoma device 100 a variable diameter stoma aperture 110. The adjustable stoma 100 may be adjusted at the time of implantation and/or it may be adjustable remotely after implantation without invasive procedures.

The adjustable stoma 100 may be formed as a cylinder that can be collapsed for insertion, and then expanded when in place. Preferably, the outer diameter will maintain a set, but somewhat elastic, diameter to facilitate fixation in the body. The outer circumference may be supported by a metal lattice 114 that is deformed permanently by the initial deployment. Possible materials for the metal lattice 114 include 304 and 316 stainless steel. Deployment can be by a coaxial balloon catheter.

In certain embodiments, the inner circumference of the adjustable stoma is supported by a metal lattice 116 made of a NiTi alloy where the deformation needed to deploy the device and set the size of the inner diameter can be reversed by the application of heat. Heat could be applied by a balloon catheter with circulating heated fluid, RF energy or other known means. The NiTi lattice 116 can then be expanded and deformed to the desired diameter by a balloon catheter inflated in the stoma aperture 110. Alternatively, the lattice 116 may be made of a material that is plastically deformable, such as stainless steel, to adjust the stoma aperture 110 larger using a dilator, such as an inflatable balloon.

In the example of FIG. 3, the entire adjustable stoma 100 is covered by a biocompatible material 118, such as an elastomer, to prevent ingress of fluids into the interior of the adjustable stoma 100. Examples of suitable materials include silicone (e.g. Dow Silastic or similar material from Nusil Technology) and polyurethane (e.g. Dow Pellethane). The stoma could alternately be constructed from or coated with a fluoropolymer such as a PFA, FEP or PTFE (e.g. Dupont Teflon). The outer circumference is adapted for accepting sutures or staples for attachment within the body.

Figure 4A:
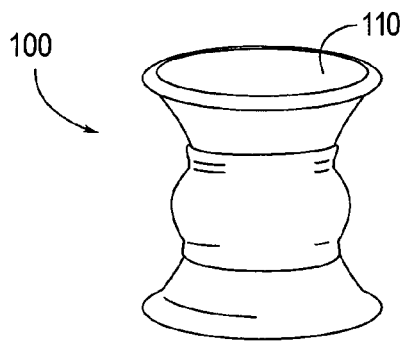
FIGS. 4A-4B shows an alternate embodiment of an artificial stoma device with a variable diameter stoma aperture.
Figure 4B:
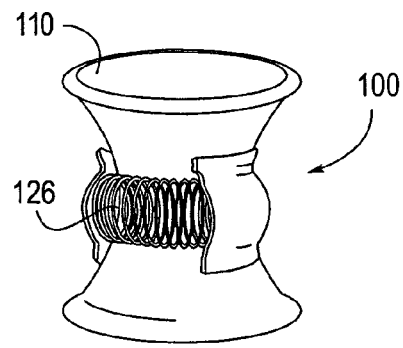

FIGS. 4A-4B shows an alternate embodiment of an artificial stoma device 100 with a variable diameter stoma aperture 110. The inner circumference of the adjustable stoma is supported by a wire coil 126 that helps to maintain the adjustable stoma aperture 110. In certain embodiments, the wire coil 126 is made of a shape-memory NiTi alloy, so that the stoma aperture 110 can be adjusted larger or smaller using the method described below. Alternatively, the wire coil 126 may be made of a material that is plastically deformable, such as stainless steel, to adjust the stoma aperture 110 larger using a dilator, such as an inflatable balloon. Alternatively or in addition, a lattice or other easily deformable structure may be used in place of the wire coil 126. The wire coil 126 may be Stomas of this type are preferably inserted in a collapsed state to facilitate passage through the esophagus. This type of stoma and other collapsible stomas can utilize a removable sleeve or other means for temporarily holding the stoma in the collapsed state.

Any of the restrictive stoma devices described herein can be placed in the lower esophagus or near the GEJ to prevent reflux. Esophageal or anti-relux stomas will preferably be configured to allow one-way flow and seal against or resist retrograde flow. This could be accomplished with a smart type stoma as described herein, preferably one that closes in response to gastric secretions, or a one-way valve, such as a duckbill or flap type valve.

In one embodiment, the stoma device 100 may be implanted and adjusted according to the following method:
Stoma Placement
1) place oral-gastric tube into the patient's stomach, the oral-gastric tube can optionally include a separable sleeve;
2) insert a guidewire through the oral-gastric tube into the stomach;
3) remove the oral-gastric tube, optionally, the sleeve may be left in place to protect the esophagus;
4) position the adjustable stoma over the balloon on a primary dilatation catheter;
5) insert the dilatation catheter and the adjustable stoma over the guidewire into the stomach;
6) inflate the balloon on the dilatation catheter to expand the adjustable stoma;
7) exchange the dilatation catheter and repeat if necessary to achieve the proper outer diameter;
8) suture or staple the stomach wall to approximate a gastric pouch, this can be done with open surgery, laparoscopically or, preferably, transesophageally;
9) reinflate the balloon on the dilatation catheter to grip the adjustable stoma;
10) withdraw the dilatation catheter until the adjustable stoma is positioned within the suture line in the desired stoma position;
11) secure the adjustable stoma in place and suture, staple and/or glue to seal the adjustable stoma to the gastric pouch;
12) withdraw the dilatation catheter;
13) insert the heat application means over the guidewire and position it within the stoma aperture;
14) apply heat to shrink the inner diameter of the adjustable stoma;
15) withdraw the heat application means;
16) if necessary, insert a dilatation catheter and inflate the balloon to dilate the stoma aperture to the desired diameter;
17) withdraw the dilatation catheter, guidewire and orogastric tube sleeve (if used)

This method can be modified for installation of a fixed diameter stoma device or a smart stoma device that does not require heating and/or dilatation to adjust the inner diameter of the stoma aperture. The method can also be modified for installation of a stoma device with a self-expanding metal lattice on the outer circumference, obviating the need for the primary dilatation catheter. The order of the method can also be modified, for example the pouch can be created first or the artificial stoma can be placed in a pre-existing pouch where the surgically created stoma has become enlarged. Other methods of attachment described herein may also be used for placement of a stoma device.

The adjustable stoma device may be initially implanted with the stoma aperture larger than clinically useful. This would allow food to pass easily through the stoma aperture and minimizes the stress on the attachment points for the stoma device and the sutures or staples forming the gastric pouch. This will allow the stomach wall to heal before the stoma aperture is reduced to a clinically significant diameter, which will naturally place more stress on the tissue and the attachment points.

Figure 5A:
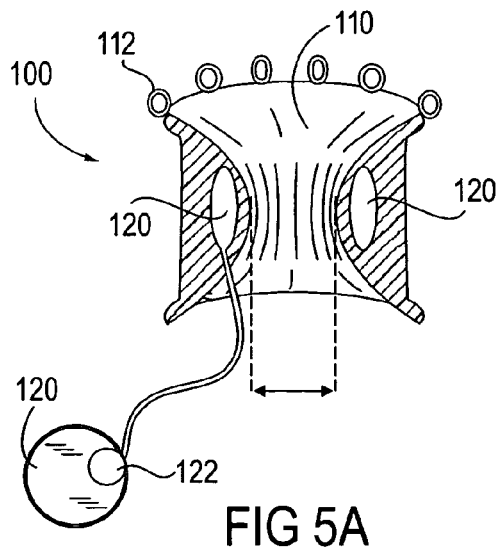
FIGS. 5A-5B show an adjustable stoma with an inflatable bladder, pump and reservoir and with optional suture anchors.
Figure 5B:
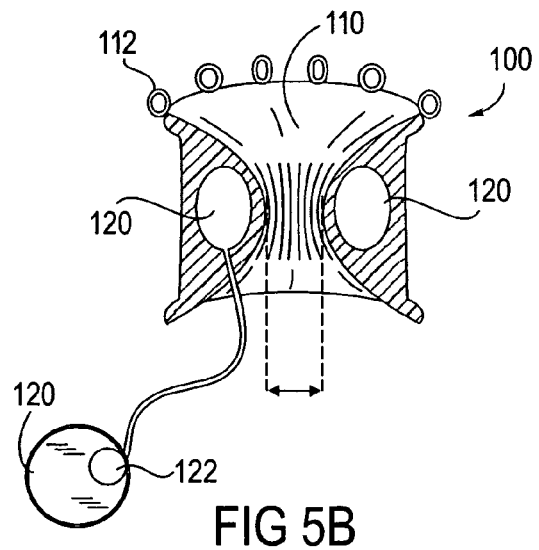

Alternatively, the adjustable stoma 100 may be configured such that the inner diameter 110 is adjusted by inflation by transferring fluid from a reservoir into the annulus between the inner and outer circumference. FIGS. 5A-5B show an adjustable stoma 100 with an inflatable bladder 120, pump 122 and reservoir 124 and with optional suture anchors 112.

Stapling or suturing for placement of the adjustable stoma device 100 is preferably accomplished transesophageally with the use of a flexible endoscope. Sutures may be placed into the muscularis, through the muscularis and/or full thickness through the muscularis and serosa based upon the clinical situation. One method for accomplishing this involves the use of wire fasteners 130 that are formed with a "button" end 132 and a "twist tie" end 134, which are shown in FIGS. 6A-6D. In certain embodiments, the wire fasteners 130 are formed from a superelastic NiTi alloy so that the fasteners can be straightened out and passed through a delivery cannula 136, as shown in FIG. 6A. The distal tip 138 of the wire can be sharpened so that it will penetrate tissue. A portion of the distal end of the wire is formed so that it will assume a circular or spirally curled "button" shape 132 after it has passed through the tissue, as shown in FIG. 6B. The "button" shape 132 attaches the fastener to the stomach wall and prevents it from being pulled out through the tissue. The curl of the "button" 132 can be shaped so that it protects the sharpened distal tip 138 of the wire and prevents it from damaging the stomach wall or surrounding tissues after the fastener is deployed. There is an approximately 90 degree bend 140 in the wire just proximal to the "button" portion 132. A portion of the proximal end of the wire is formed to create the "twist tie" 134, which reforms when the wire fastener 130 is pushed out of the delivery cannula 136, as shown in FIG. 6C. The "twist tie" 134 can be a helical curl or other shape that will entangle and interlock with a mating fastener when the two are approximated to one another, as shown in FIG. 6D. Alternately, the proximal end 134 of the wire fastener 130 can form a loop for attachment of standard suture materials.

The delivery cannula 136, which may be configured with a torquable shaft with a fixed or variable curve 144 at the distal end, is used to deliver the wire fasteners 130 to the desired location. The distal end of the delivery cannula 136 is advanced until it contacts the stomach wall, then a pusher wire or the like is used to advance the wire fastener 130 through the delivery cannula 136, as shown in FIG. 6A. As the wire fastener 130 exits the delivery cannula 136, the sharpened distal tip 138 penetrates the stomach wall. The "button" portion 132 of the wire assumes its curved configuration distal to the stomach wall as the fastener 130 is advanced farther out of the delivery cannula 136, as shown in FIG. 6B. These steps are repeated to place a second wire fastener 130 in the opposite wall of the stomach. Then, the two delivery cannulas 136 are withdrawn while continuing to advance the wires out of the delivery cannulas to allow the "twist tie" portions to assume their helical curled shape proximal to the stomach wall and the two fasteners are approximated to one another so that the two "twist tie" portions intertwist with one another as they exit the delivery cannulas to attach the two walls of the stomach together, as shown in FIG. 6D. Alternatively, the wire fasteners 130 can employ a loop, rather than a "twist tie" to enable approximation using a secondary means such as sutures. A line of fasteners 130 can be thus deployed to create a gastroplasty pouch or band.

In an alternate embodiment, the wire fasteners may be configured to have a "button" portion 132 on both ends of the wire. These fasteners can be deployed laparoscopically to penetrate both walls of the stomach with a "button" 132 placed on each side of the stomach to attach the walls together. Such fasteners can be combined with buttressing reinforcements such as pledgets made from Teflon, bovine or porcine tissue or other know materials. "T-tag" type fasteners could be applied to this use and type of application.

T-tag fasteners can be used to attach many of the structured described herein. A T-tag is basically a cross member or "T" that is attached to an elongated member or tail at or near the mid-point of the T. A "stem" may be a structure at the joining point of the T and tail. T-tag fasteners are generally configured to flex at the juncture of the T and tail to allow delivery along the axis of the T through a minimal puncture diameter. T-tag fasteners can be configured with an extended tail that may extend out the mouth and optionally be used to parachute devices for attachment into position in vivo. Other T-tag configurations can include, crimp, snap, screw or other means of securing the T-tag tail when appropriate. One embodiment of a T-tag fastener could include a dual tail. Such a dual tail could be combined with extended tails that could then be tied out side the body with the ensuing knots then tightened within the body. Such a dual tail could be constructed of one of a number of non-biodegradable suture materials known in the art including polypropylene, nylon, braided Dacron or silk. In some clinical situations biodegradable tails could be indicated and could be constructed using materials described herein.

Figure 93A:
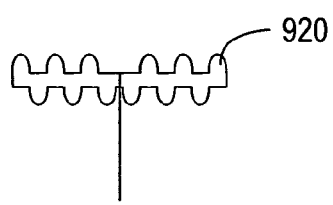
FIGS. 93A-93D illustrate examples of expanding T-tag fasteners.
Figure 94A:
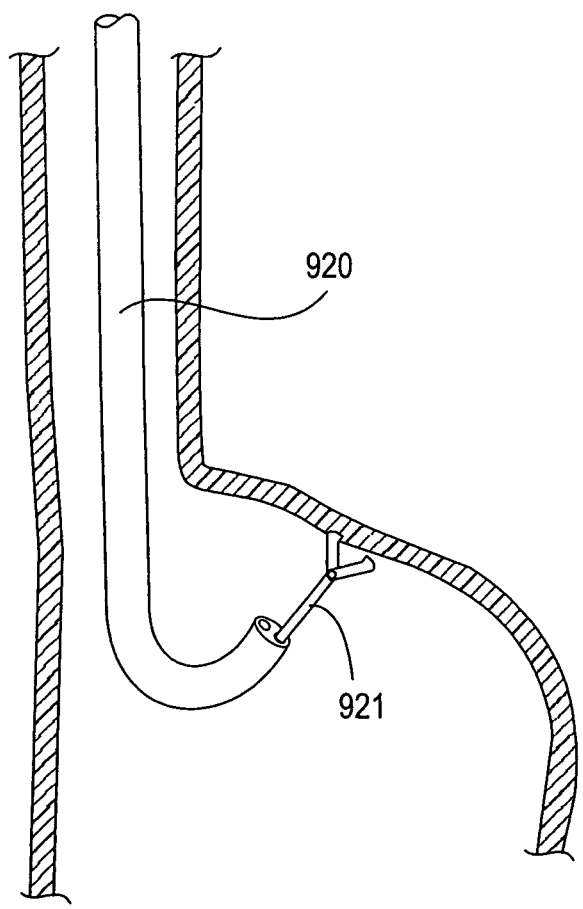
FIGS. 94A-94C illustrate placement of T-tag fasteners.
Figure 94B:
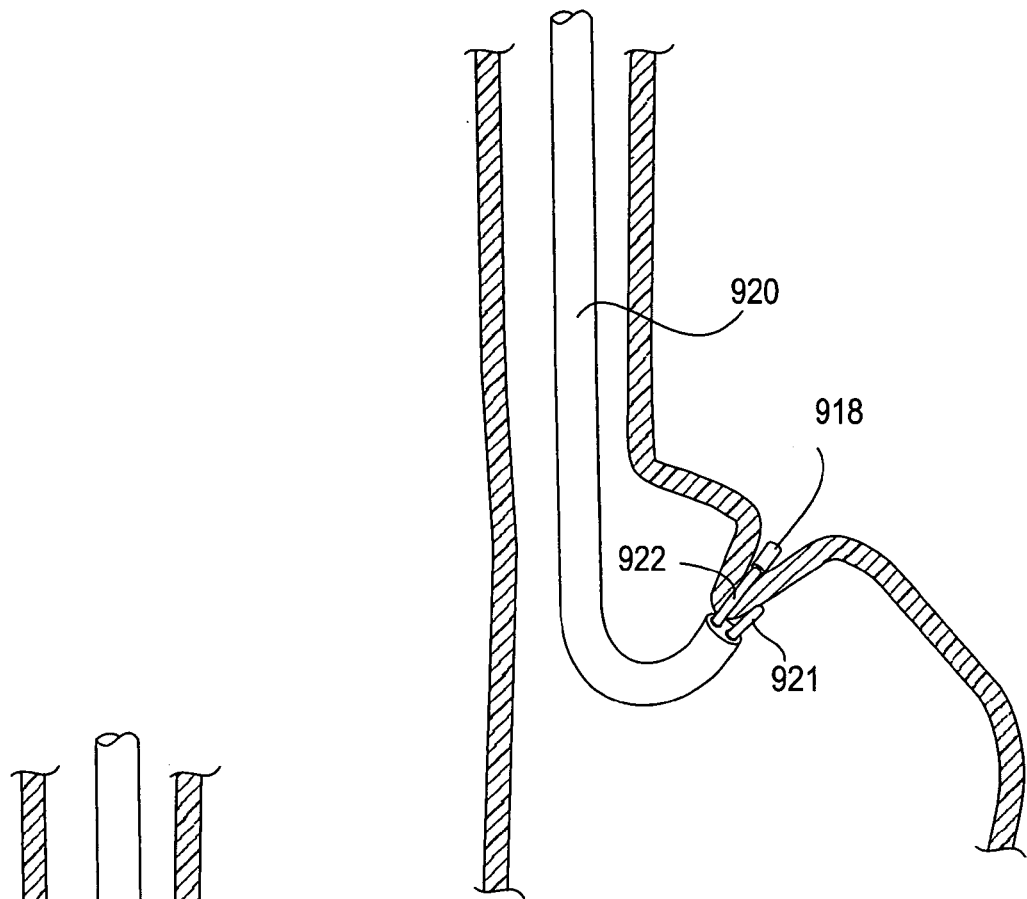
Figure 94C:
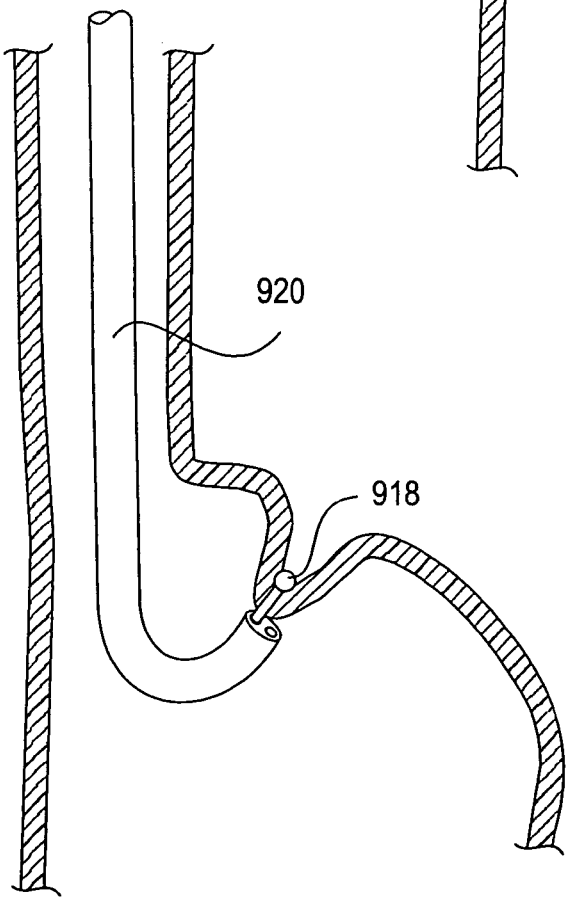

FIGS. 94A-94C illustrate a method of placing T-tag fasteners 918 through the gastric wall that prevents accidental damage to other structures. One method of accomplishing this end could involve the use of an endoscope 920 with two (2) working channels. One channel could be used to deliver a grasping means 921 that would grasp the gastric wall (as illustrated in FIG. 93A) and invaginate it to displace the area grasped away from adjoining structures (e.g. spleen). The second working channel can then be used to deliver a T-tag fastener 918 through, for example, a hollow needle type delivery system 922 (e.g. T-ANCHOR INTRODUCER GUN (Moss Tubes)) that has been redesigned so it can be passed through the working channel of an endoscope and then rotate 90 degrees into position (as illustrated in FIGS. 94B and 94C). Laparoscopic or other extragastric means could also be applied to the end of preventing damage to adjoining structures.

For each subsequent T-tag fastener 918, the previously placed fastener(s) may be used to grip and invaginate the gastric wall. The fasteners may be used to assist in forming of a plication or in retracting and positioning the gastric wall for fastening another component, such as a stoma, sleeve or attachment ring. Similarly, other gripping means, such as vacuum, transmural hooks and the like, may be used to facilitate placement of fasteners to assist in forming of a plication or in retracting and positioning the gastric wall for fastening another component of the system.

An example of a method of use of one configuration (dual tail T-tag) of the structures described above when used to attach an attachment ring as in FIG. 77 could be as follows:
1. Position endoscope overtube
2. Insert endoscope (2-channel) and, using grasper and T-tag delivery device, deploy a T-tag and position the T-tag tails externally (Repeat 6 times)
3. Pre-thread T-tag tails through an attachment ring matching each pair of the 2-tailed T-tags to capture a predetermined portion of the attachment ring material
4. Prepare to parachute the attachment ring through over tube and pass the ring through overtube.
5. Snug T-tag tails to position attachment ring and ready for final attachment
6. Using appropriate instruments partially tie the knots externally and advance the partial knots into position to be secured and trimmed (Repeat 6 times)
7. Remove all instrumentation The final result is now illustrated as FIG. 91A. This attachment method can be modified by the use of multiple rows of T-tag fasteners as described herein.

Peroral extra-gastric buttress reinforcement—Buttresses are preferably placed in locations subject to forces to which there will be clinical benefit to distributing forces. The buttressing material is generally configured perpendicular to the axis of the attachment means (e.g. suture, rivet or staple) and therefore best distribute forces along the axis of the attachment means. When a device is attached to the intragastric wall such forces can be directed inward from the gastric wall. Therefore, if the buttress is attached to the intragastric wall, the buttress may not be along the axis best suited to resist the applied force.

Many of the apparatus and methods described herein use a plication to redirect these forces to allow intragastric buttresses to distribute these forces in a beneficial, i.e. more perpendicular, direction. Other apparatus and methods described use other structural means to distribute forces on the extragastric wall in which case inwardly directed forces would be in a beneficially perpendicular direction. The following describes an exemplary apparatus and method to embody and deliver extragastric buttresses.

Use of a curved needle to deliver a buttress that, in one configuration is a teflon pledget, to a location on the extra gastric wall from the inside of the stomach. This pledget would be captured in an invaginating (into the stomach) plication that could then be secured by sutures, staples, rivets et al. The buttress could be a tubular shapes segment of expanded teflon similar to a small diameter vascular graft. This could be delivered on the outside of a curved needle, which, upon withdrawal retrograde from the direction of delivery, would leave the pledget in position outside the stomach. The plication would be preferably secured prior to the removal of the needle. The buttresses could be delivered in a similar manner through the lumen of a hollow needle. In this case it may be preferred to partially withdraw the needle and deploy the buttress prior to securing the plication.

This system, as can others described herein, could use 4-10 or more primary fixations to resist tension and optionally use intermediate sutures, rivets, etc. if appropriate to resist leaks.

Fastener (T-tag) buttress (T-pledget) method and structure—An alternate method of delivering these buttresses would be using a T-fastener (T-tag) where the "T" portion was constructed of a material with properties that would be useful as a buttressing material. This would be a T-tag buttress or a T-tag pledget. Hereinafter T-pledget. These T-tags could be delivered through a hollow needle type delivery system (e.g. T-ANCHOR INTRODUCER GUN (Moss, Moss Tubes)) that has been redesigned/modified so it can be passed through the working channel of an endoscope. One advantage of the use of T-pledget is that a T-tag can be designed with an elongated tail that can extent out through the mouth and be used to parachute structures into place in-vivo. T-pledget tails could include preloaded needles. Needles could be curved or straight.

The suture, staple, rivet or other fastener used to secure the sleeve attachment ring or other device into place could, based upon the clinical situation, capture the pledget portion of the T-pledget to fix it in place in relation to the attachment means.

A method of use of one configuration of the T-pledget structures described above when used to attach an attachment ring could be as follows:
1. Position endoscope overtube
2. Insert endoscope (2-channel) and using grasper and T-pledget, deploy T-pledget and position tails externally 3. Pre-thread T-pledget tails through attachment ring
4. Prepare to parachute attachment ring through over tube and pass the ring through overtube
5. Snug T-pledget tails to position the ring and ready for final attachment
6. Using tails, guide the PLICATOR (NDO Surgical Inc.) into position and fire the PLICATOR to form a plication over the T-pledget
7. Trim tails and remove all instrumentation The final result is now illustrated as FIG. 91B (showing a dual attachment face ring as described below).

T-pledgets can be structured using a variety of means. A portion of standard Teflon pledget material can have a suture tied or otherwise attached, at or near its mid point. This can be structured or otherwise prepared for delivery by means such as rolling and/or compressing to facilitate passage through tissue with a minimum disruption of the tissue layer. Ideally the T-pledget would have a minimum diameter when passing through tissue. Depending upon the clinical situation varying deployed diameters/areas could be preferred. A hollow needle or other hollow tube can be used to facilitate passage through tissue. Structure and/or material selection to enhance axial rigidity along the axis of delivery will be beneficial is some clinical situations. A piercing point on the leading edge of the "T" may be useful with some deliver mechanisms.

Many of the features described above can be achieved with construction using a single piece of Polypropylene, Nylon, or other polymeric material well known in the art for use in construction sutures, which forms the "T" and tail as a single unit. Alternately 2 different materials can be combined, for example by insert molding, to achieve different properties of the "T" and tail. In another embodiment this could be combined with a "T" portion that is coated with a material selected for specific clinical properties such as encouraging or discouraging either in-growth or adhesion. The "T" portion may also be surrounded by another material such as Teflon pledget material or Dacron graft material. "T" diameter will vary according to the material used for example ranging from 0.5 mm to 3.0 mm in diameter for nylon or polypropylene with the typical "T" having a diameter of 1-2 mm. A tail could be the dimension of a standard suture and could generally vary from 5-0 to 0 (P standard classification) though smaller or larger sizes may be appropriate in certain clinical situations.

In one configuration that could have advantages in certain clinical situations the "T" and/or tail portions of the T-pledget could be constructed in part or in toto of a biodegradable material as described herein. In one such configuration the "T" portion would be constructed of a flexible buttress material that is not biodegradable. In some embodiments this could have a tubular configuration. This would include a core of a more rigid material that is biodegradable. The tail in this situation could be optionally biodegradable. This combination T-pledget can have advantages in that its "T" portion will 1) have increased rigidity for insertion; 2) maintain its ridgidity during the time period while the tissue goes through its healing period and ideally until it regains its strength; and 3) become softer and more flexible to minimize the potential for erosion over the length of time the pledget is in position. Various buttress materials, both biodegradable and not, are described herein.

In an alternative embodiment a porous buttress material could be impregnated with a biodegradable material to achieve a similar result. Similarly a biodegradable material could coat a buttress material. The rigidity of both the permanent buttress material and the biodegradable material may be selected and modified to suit specific clinical situations. In some situations the biodegradable material may be of a lesser rigidity compared to the buttress material. Embodiments that include a biodegradable tail portion could have an advantage in certain clinical situations, as this would eliminate the tail as a focus for a leak after it has degraded. Bioresorbable materials such as polyglecaprone (Monocryl, Ethicon), polyglactin (Vycril, Ethicon) or other as well know in the art can be appropriate for use in these applications.

Bio-stable, solvent dissolvable pledget material—In other situations the pledget material could be made from a material that is stable in the body but could dissolve in the presence of a biocompatible solvent, or a biocompatible solution including a chemical or catalyst that will initiate the pledget's dissolution. This would allow simplified removal of the pledget material via lavage of the peritoneum if the stomach attachment means were to be released through an endoscopic procedure or were otherwise desirable based upon the clinical circumstances.

Figure 91A:
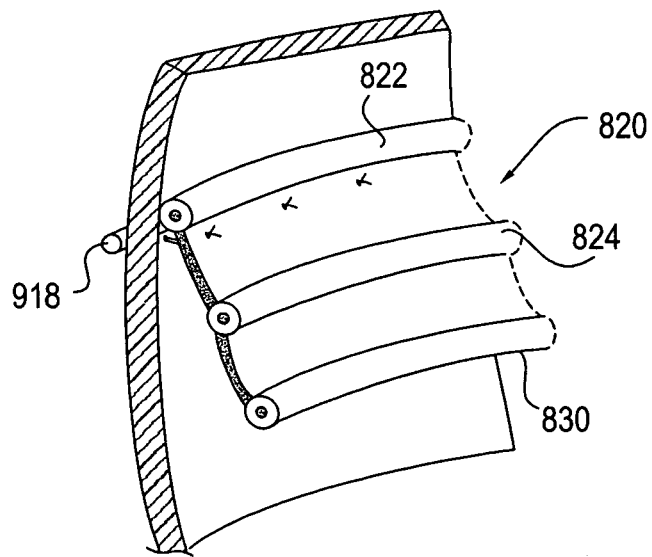
FIGS. 91A and 91B illustrate T-tag and T-pledget ring attachment.
Figure 91B:
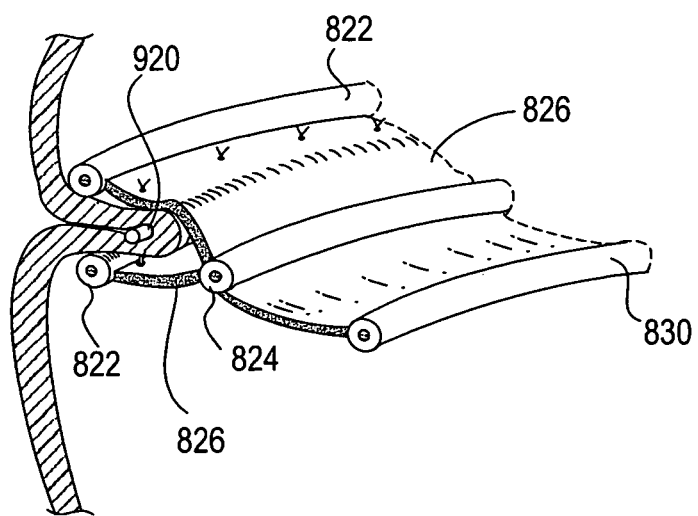

Dual attachment faces and T-tag or T-pledget extra-gastric buttress reinforcement—As illustrated in FIG. 91B, in one embodiment of attachment to a plication, the structure of the device being attached can include attachment faces that capture both sides of the plication thereby forming a buttressing means for the means used to secure the plication.

As discussed herein, forces can be applied inwardly by devices attached to the intragastric wall. Other forces are applied to the gastric wall due to the natural muscular action of the gastric wall. These forces can serve to be applied in the plane of a gastric wall and, in this case, can serve to apply tension to separate a plication. Use of a T-pledget as an extragastric buttress in combination with a device that includes attachment faces that capture both sides of the plication as shown in FIG. 91B can be particularly beneficial in resisting these forces.

Dual attachment faces 926 can be integrated with the ring, or other attachment means, used to secure other devices, e.g. a sleeve, to the stomach or they could be separable to facilitate delivery, attachment and/or removal. If separate, the ring can optionally include structures such as holes or other guide means that would facilitate parachuting the device into position. These attachment faces can be made of materials that either encourage or discourage in-growth and/or epithelialization as dictated by the clinical situation. Dual attachment can also be used without extragastric buttressing.

Use of attachment face materials and buttress materials that discourage in-growth along with securing means that initiate minimal scar formation could enhance the reversibility of the procedure if and when the securing means were to be released and removed. Attachment faces, along with any structures attached to or incorporated within, could then be sloughed and passed naturally and/or removed via a transoral route as indicated by the device and the clinical situation. Use of an overtube to protect the esophagus during transoral removal of certain devices can be clinically indicated based upon the size and shape of the device being removed.

The concept of using attachment faces that capture both sides of a plication can be applied to other attachment means described herein. The concept of using one or more separable attachment faces as a means to capture other devices can optionally be applied to other attachment means described herein.

A method of use of one configuration of the structures described above could be as follows:
1. Position endoscope overtube
2. Insert endoscope (2-channel) and using grasper and T-pledget device, deploy T-pledget and position tails externally (Repeat 6 times)

3. Pre-thread T-pledget tails through attachment face material (and, if used, thread through separate sleeve ring)—Note that the tails are passed through the attachment face material at a location that will provide for an appropriate amount of attachment face material on either side of the plication as indicated by the clinical situation.
4. Prepare to parachute devices through over tube and pass device(s) through overtube
5. Snug T-pledget tails to position device(s) and ready for final attachment
6. Using tails, guide the PLICATOR (NDO Surgical Inc.) into position and fire the PLICATOR to form a plication over the T-pledget (Repeat 6 times)
7. Trim tails and remove all instrumentation In an alternate example of the above-described method using a dual tail T-tag or a T-tag device with securing structure, step 6 can be replaced with tying or otherwise securing each T-tag as the final attachment.

In a similar manner to a T-pledget, a pledget can be delivered to the extragastric surface using an expanding tip configuration similar to a 2-wing Malecot catheter. The expandable Malecot tip would be detachable from its delivery cannula.

In this case the Malecot pledget could include:
1. a pointed distal tip for penetration through the gastric wall (note in some embodiments this tip may be dissolvable to reduce the potential for long term tissue irritation)
2. a suture-like tail attached to distal tip (to retract and expand the tip)
3. a method that would include applying tension to the suture tail to expand the tip after it has been positioned beyond the extragastric surface
4. a delivery cannula that can support the proximal portion of the pledget (support to translate suture retraction into pledget tip expansion)

Retraction of the delivery cannula/pusher would leave the expanded Malecot pledget on the extragastric surface.

In-line pledget (alternative to curved needle delivery)—In this case the pledget material would be in line and coaxial with the suture. The pledget would include at least one tapered end for passage through tissue and may be expandable over time (to allow a small hole or passage through the tissue and a greater buttress area). The needle on the end of the suture would be passed through the gastric wall twice (first inside-to-outside and then, approximately a pledget's length apart, outside-to-inside). This could be accomplished with laparoscopic assistance; a large radius curved needle or other means. The suture would be advanced until the pledget is in position and excess suture would be trimmed. The suture could be biodegradable.

T-tag 918 and T-pledget 920 embodiments designed for expandability—A T-tag or T-fastener can be used to provide knot free means to apply tension to a suture and an associated anatomic structure. A further advantage of a T-tag is that the forces applied to the suture tail of the "T" are distributed over a larger area than a single stitch. This is accomplished by using a "T" dimensioned with a width wider than the diameter of the suture and a length longer than a typical bite or stitch. A disadvantage of a T-tag is that insertion of a T-tag through tissue requires a hole many times, for example 5-15 times, the diameter of the suture tail.

Figure 93B:
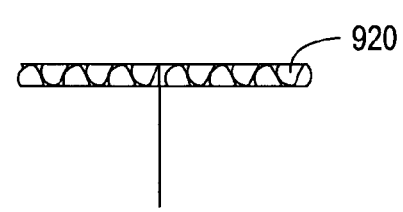
Figure 93C:
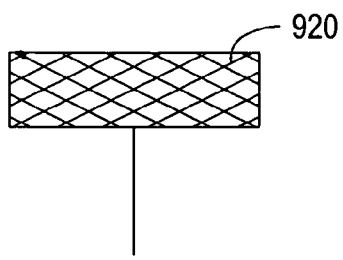
Figure 93D:
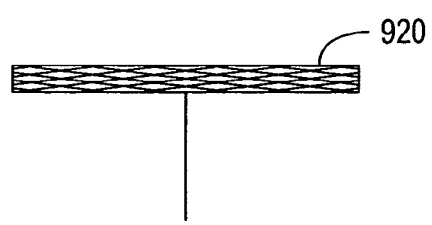

To deliver an improved buttressing capability in a T-tag fastener or T-pledget with a minimum delivery hole it is beneficial to use a "T" or pledget designed to expand after delivery. This can be beneficial in many clinical situations. In addition to rolling or compressing, alternate structures can include materials that expand when exposed to water such as hydrogels. FIGS. 93C and 93D show how a T-pledget 920 or T-tag 918 of woven cylindrical meshes that may be compressed or elongated to achieve a reduced diameter and expanded or shortened to become wider. Compared to a rectangular sheet, alternate configurations of a rolled and unrolled sheet can achieve a T-pledget 920 or T-tag 918 with increased projected width relative to its rolled diameter through the use of matching cutouts, as shown in FIGS. 93A and 93B. Though not as efficient in diameter-to-projected width ratio, is some cases it may be clinically desirable to have a "T" that is in a circular shape.

To resist bending perpendicular to the axis of the suture, it may be beneficial to use metals, for example Ti, SS or NiTi. In some clinical situations, encapsulating or coating the metal with a fluoropolymer or other coatings as described herein may also be beneficial.

T-tag with inflammatory reaction or other additives—The pledget material could be optionally coated or impregnated with materials and/or medicaments as described herein. For example the pledget can be coated with a material that would enhance inflammation and scar formation. Alternatively, a coating or medicament that would either encourage or discourage in-growth can be applied.

In some clinical situations it may be beneficial to use both these types of coatings. For example, though inflammation can lead to scarring fibrosis and ultimately strengthen tissue, the inflammatory process initially results in tissue weakening that can include tissue liquefaction. Therefore, it can be desirable that a fastener that induces an inflammatory response for long term strength also include means to support the tissue during the weakened stage.

Inflammatory reaction materials would be limited to a portion of the T-tag or T-pledget as the inflammatory response weakens tissue before the scarring fibrosis occurs. Therefore, for example, having the area at the center of the T or pledget with this inflammatory material and the ends of the "T" without this material could have an optimized balance of short term and long term strength.

Drug-eluting coatings may be used to encourage or discourage tissue ingrowth into the fasteners or other device attachment mechanisms described herein. A low inflammatory response is generally desirable for encouraging tissue ingrowth. Anti-inflammatory drugs that may be used include steroidal anti-inflammatory drugs, e.g. prednisone, and non-steroidal anti-inflammatory drugs (NSAID), e.g. chromalin. Conversely, drugs that may be used to control or reduce tissue ingrowth include Taxol (paclitaxel) (Bristol-Myers Squibb) and Sirolimus (rapamycin) (Wyeth-Ayerst Laboratories).

Embodiments designed for improved erosion resistance—The purpose of the "T" in a T-fastener is to distribute and resist the forces that could act to pull it through tissue, in this case the gastric wall. To better achieve this result the "T" should resist bending. Though a T-fastener is generally held parallel to the surface of the extragastric wall, at the ends of the "T" the gastric wall extends outward from the plane of the surface and the axis of the "T". In this case, the gastric wall could be at a 90-degree angle, or greater, to the ends of the "T". To reduce the potential for erosion at the end of the "T" in some clinical situations it could be beneficial for the ends of the "T" to have increased flexibility which will result in a reduction of the angle between the gastric wall and the ends of the "T". This would reduce the forces between the "T" and the gastric wall and therefore reduce the potential for erosion at the ends. Structures that could accomplish this could include tapered thickness or cross section to reduce the bending moment. Alternatively or in addition, changes in material properties such as hardness, bending modulus and/or elongation can accomplish the same result. For example the "T" near the stem could be of a material of a durometer such as Shore 65D or higher the material may change as one moves out along the arms of the "T" transitioning through 55D/100A to 90A durometer or lower. Rounding, smoothing and structures that otherwise distribute forces over a larger area will also serve to reduce erosion at the ends of the "T". A circular shaped "T" may be particularly desirable to reduce erosion.

Another method of intragastric stapling utilizes a pair of vacuum or mechanical graspers to capture the tissue to be joined, for example the stomach wall. The graspers approximate the tissue and present it to a stapling mechanism. Once the tissue has been presented to the stapling mechanism, a number of methods may be used:

1) a staple or clip may be applied to join the tissue together;
2) a precurved wire fastener, which may be constructed of a NiTi alloy or other material, may pierce the tissue on one side and then pierce the tissue on the other side as it curls to capture both;
3) a curved needle with attached suture can be passed through the tissue using known endoscopic suturing techniques.

These two methods (vacuum approximation and NiTi buttons) can also be combined.

Intra gastric stapling can be facilitated by external manipulation in a combined endoscopic/laparoscopic approach. Internal endoscopic manipulation can be combined with external laparoscopic stapling or external manipulation can be combined with internal endoscopic manipulation. Laparoscopic techniques can also be used inside the stomach.

In an alternative embodiment, the stoma may be a self-adjusting "smart stoma" that opens and/or closes in response to stomach conditions. FIGS. 7A-7B show an enlarged view of a smart stoma device 150 with a stoma aperture 152 that varies its diameter in response to conditions in the patient's stomach. In one embodiment shown in FIGS. 7A-7B, the smart stoma device 150 includes a fluid-filled bladder 154 surrounded by an osmotic membrane 156. One example of a suitable material for the osmotic membrane 156 is silicone (e.g. Dupont Silastic). The osmotic membrane 156 may be made of microporous silicone or other material similar to those used for hemodialysis membranes. In response to changing conditions, for example if the patient drinks a glass of water, water will move across the osmotic membrane 156 to swell the bladder 154 and shrink the stoma aperture 152 to restrict food intake.

In another embodiment shown in FIG. 8A-8B, the smart stoma device 150 may include a toroidal member 158 made of a swellable material, such as a hydrogel (e.g. Akina HydroTab). In response to changing conditions, for example if the patient drinks a glass of water, the toroidal member 158 will swell and shrink the stoma aperture 152 to restrict food intake. Alternately the hydrogel can expand in the presence of a specific chemical such as the glucose sensitive hydrogel material used in the Glucose Biosensor (M-Biotech)

FIGS. 9A-9B show an enlarged view of a smart stoma device 150 with a closed loop controlled variable diameter stoma aperture. Similar to the embodiment shown in FIGS. 7A-7B, this smart stoma device 150 includes a fluid-filled bladder 154 surrounded by an osmotic membrane 156. A first electrode 160 is connected to the osmotic membrane 156. The first electrode 160 and a ground electrode 166 placed elsewhere on the body are connected to a voltage source 162 such as a battery via a control circuit 164. When a voltage is applied between the first electrode 160 and the ground electrode 166, it increases the flow rate across the osmotic membrane 156 to quickly swell the bladder 154 and shrink the stoma aperture 152 to restrict food intake. Note that the polarity of the circuit in FIGS. 9A-9B is for reference only and can be altered based on material selection and fluid polarity. Similarly this type of stoma can use a polyacrylic acid hyrdogel which responds to applied positive polarity field by contracting and expelling water. The stoma device 150 may be configured to operate automatically in response to changing conditions, for example the control circuit 164 may include a sensor 168 for sensing water or certain nutrients, such as sugar, or an activity related to ingestion, such as swallowing or gastric response. Alternatively, the stoma device 150 may be configured to be remotely operated in response to a control signal from outside of the patient's body.

Figure 10A:
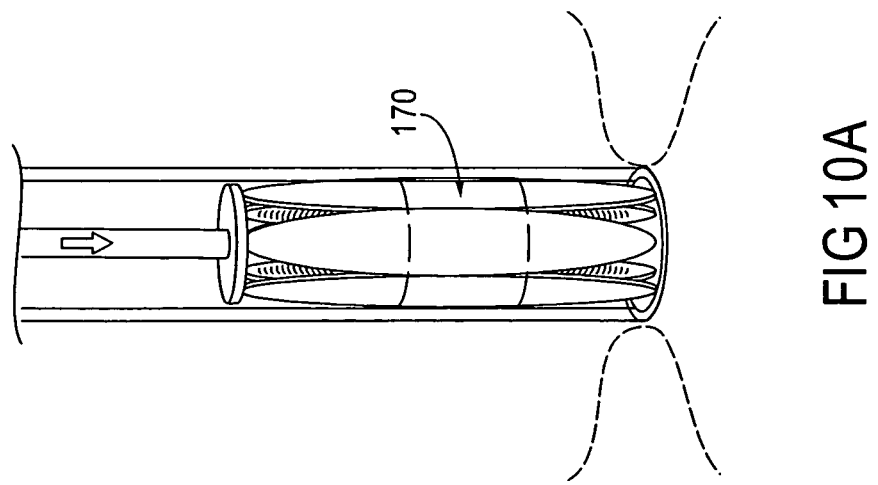
FIGS. 10A-10C show an artificial stoma device with a sutureless anchoring mechanism.
Figure 10B:
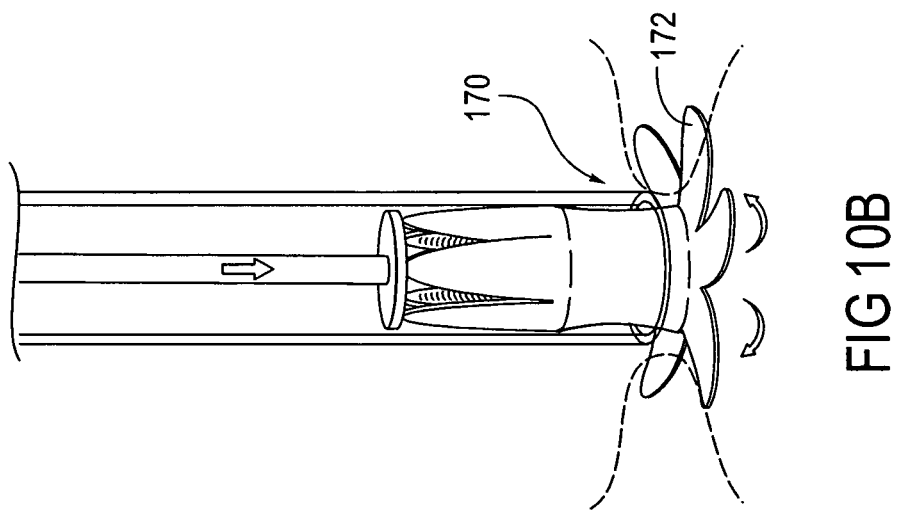
Figure 10C:
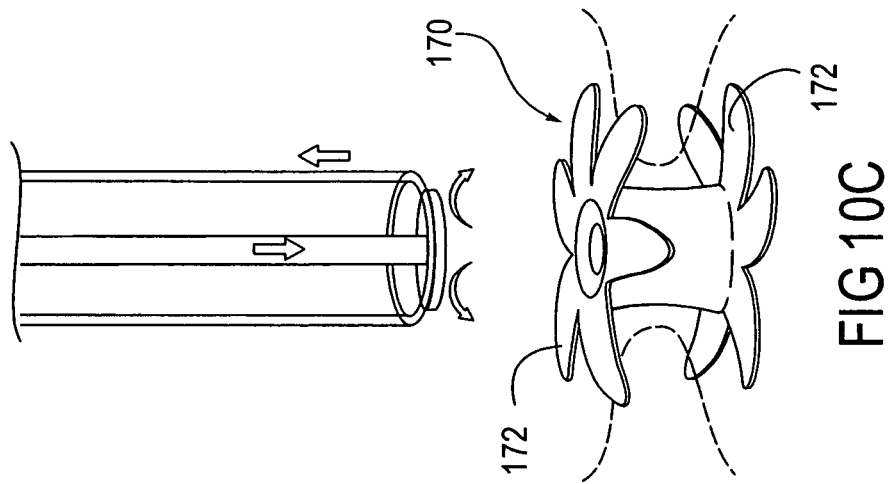

Alternatively, the artificial stoma may be anchored with a sutureless attachment that does not penetrate the esophageal or stomach wall. Sutureless attachment mechanisms may be used in conjunction with any of the stoma configurations discussed herein. FIGS. 10A-10C show an artificial stoma device 170 with a sutureless anchoring mechanism 172. The stoma device 170 has a retracted/compressed position wherein the stoma device 170 and the anchoring mechanism 172 have a small diameter that can easily pass through the patient's esophagus into the stomach, as shown in FIG. 10A. The stoma device 170 may be introduced mounted on a flexible endoscope or on a separate insertion device. Once the stoma device 170 is in the selected position in the stomach or lower esophagus, the sutureless attachment mechanism 172 is actuated to expand and hold the stoma device 170 in place, as shown in FIGS. 10B and 10C.

In one embodiment, the sutureless attachment mechanism 172 may be configured as an expandable wire stent that expands against the stomach or esophageal wall to hold the stoma device 170 in place. Preferably, the expandable wire stent is surrounded by an elastomeric membrane or the like to prevent leakage of liquids or food past the stoma device 170. The surface of the membrane may be treated to encourage tissue ingrowth to permanently anchor the stoma device 170 in place. Alternatively, or in addition, the sutureless attachment mechanism 172 may include hooks or barbs that pierce the tissue for additional anchoring. Such hooks or barbs may have an undeployed position in which they lie against the device and a deployed position in which they rotate or extend outward to grip the tissue. The stomach wall should be positioned such that the attachment mechanism 172 will grip the stomach wall when it is actuated.

In an alternative embodiment, the stoma device 170 may be configured to have a reversible sutureless attachment mechanism 172 for temporary implantation of the device. A reversible sutureless attachment mechanism 172 may have two modes of attachment, a temporary mode and a permanent mode. Thus, a stoma device 170 can be implanted in a patient's stomach for a trial period using the temporary attachment mode. After the trial period, if the therapy has been ineffective or if the implant was not well tolerated by the patient, the stoma device 170 can be removed. On the other hand, if the therapy has been effective and the implant is well tolerated by the patient, the stoma device 170 can be permanently attached by actuating the permanent attachment mode or simply leaving the implant in place to allow permanent attachment and tissue ingrowth to take place.

Preferably, the stoma device is constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted stoma device can be verified noninvasively in addition to endoscopic direct visualization.

Figure 11:
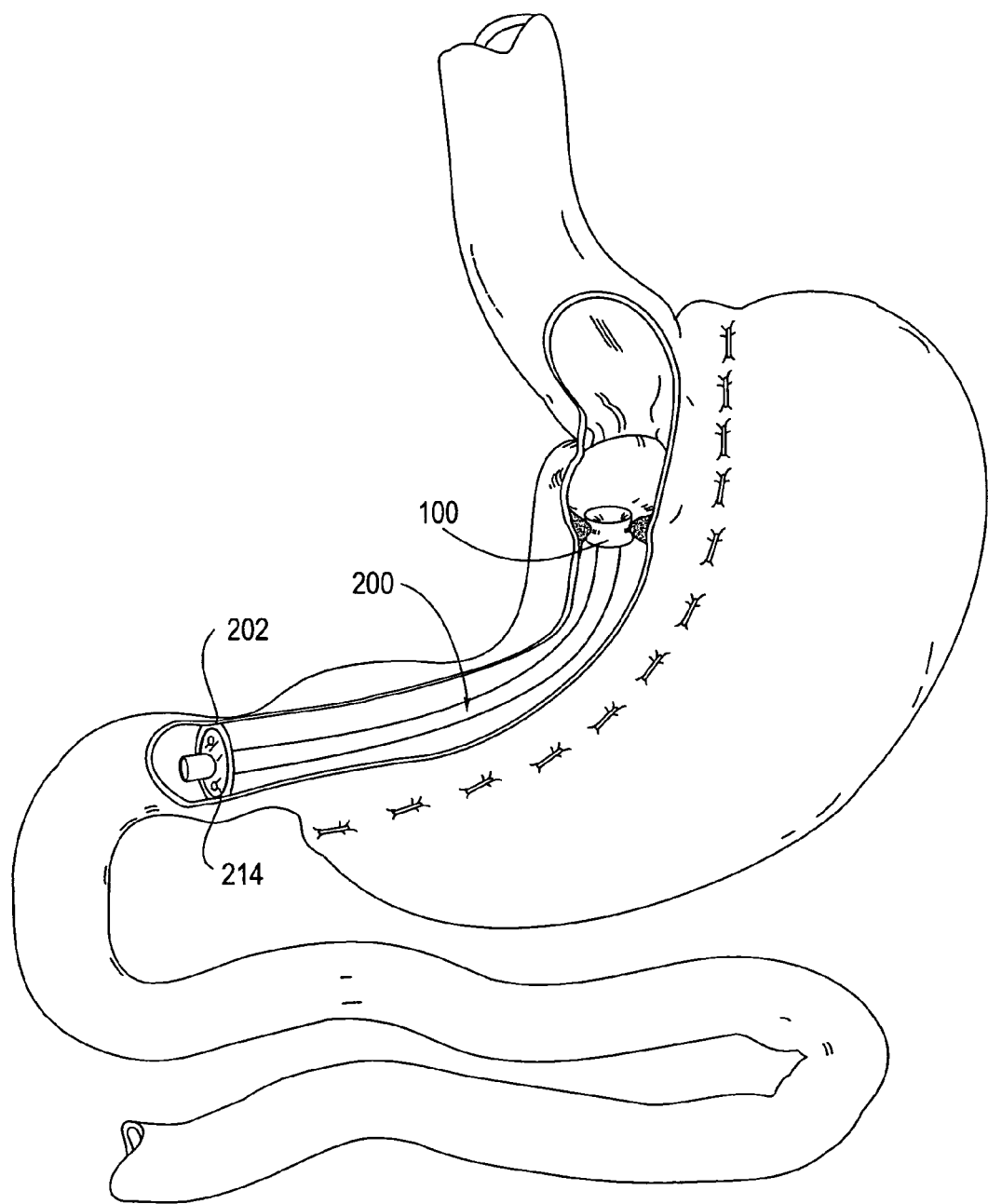
FIG. 11 shows a gastric sleeve device with an artificial stoma device and a pyloric sleeve anchor implanted within a patient's stomach with a line of gastroplasty sutures or staples parallel to the sleeve.

In another aspect, the system may include an internal gastric sleeve 200 that may be used separately or used with, attached to or integrated with the artificial stoma component 100. FIG. 11 shows a gastric sleeve device 200 with an artificial stoma device 100 implanted within a patient's stomach. Optionally the sleeve can be attached to the outlet of a surgically created stoma or pouch that does not include an artificial implanted stoma. The gastric sleeve device 200 may include a pyloric sleeve anchor 202 for anchoring the distal end of the sleeve 200 in the region of the pylorus. The pyloric sleeve anchor 202 can be configured with openings 214 to allow digestive secretions to pass through the pylorus into the small intestine. The internal gastric sleeve 200 effectively reduces the volume of the stomach because the flow of solid food is limited to the lumen of the sleeve 200. The entire gastric sleeve 200 or a portion of it can be porous or semipermeable to allow the flow of digestive secretions into the sleeve and to allow the flow of nutrients and/or fluids out through the wall of the gastric sleeve 200. Porosity can be achieved for example by forming holes in the sleeve using a laser or mechanical means. Semipermeable areas of the sleeve can be formed, for example, from silicone or materials used for hemodialysis membranes.

Pyloric anchors can be fixed to a predetermined location on the sleeve or be mobile. For example, a pyloric anchor could be slidable and slid into place before it is fixed to a structure on the sleeve. Structures for anchor fixation could include reinforcement and/or structures such as snaps, loops and/or holes to facilitate attachment of the anchor to the sleeve. Slidable or other structures that allow positing of an anchor can be used to set the distance between the attachment of the sleeve near the GEJ and the support or strain relief provided by the anchor at the pylorus. This distance can be set prior to placement of the device, based upon fluoroscopic or other measurements or in vivo. If the distance is set in vivo, structure could be provided to allow fixation using commercially available tools such as ENDOCINCH (Bard), ENDOSCOPIC SUTURING DEVICE (Wilson-Cook Medical) or PLICATOR (NDO Surgical Inc.) or an endoscopic grasper. Alternately, a structure that requires a special attachment device, such as the riveters described herein could be used.

In some clinical situations it could be beneficial to have an anchor designed to allow motion. This could include some means to bias the anchor to return to a predetermined location relative to a set position on the sleeve. This could be accomplished by incorporation of a spring, elastomeric structure or other such biasing structure.

Figure 12A:
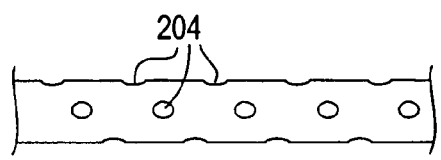
FIGS. 12A-12E are detail drawings showing additional features of a gastric or intestinal sleeve device.
Figure 12B:
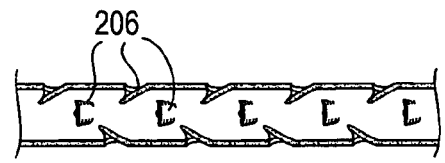
Figure 12C:
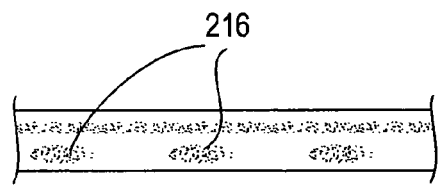
Figure 12D:
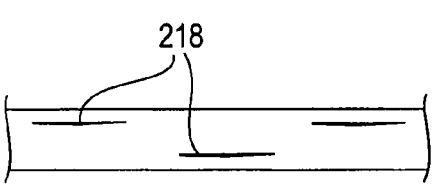
Figure 12E:
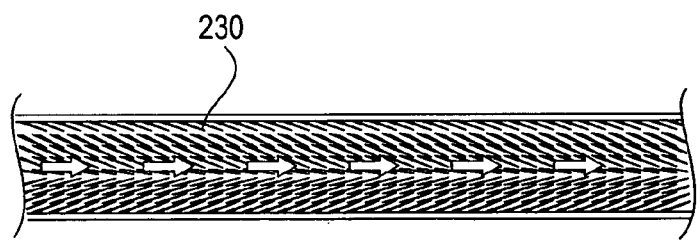

FIGS. 12A-12E are detail drawings showing additional features of a gastric or intestinal sleeve device. FIG. 12A shows a detail drawing of a gastric and/or intestinal sleeve device with openings 204 through the sleeve wall. Valves 206 may be provided in the wall of the gastric sleeve to allow digestive secretions to enter the sleeve, but to prevent solid food and/or nutrients from flowing out through the wall of the sleeve. FIG. 12B shows a detail drawing of a gastric and/or intestinal sleeve device with valved openings 206 through the sleeve wall. Examples of valves for this application include slit and flap type valves. Alternatively, the entire gastric sleeve 200 or a portion of it can be nonporous or impermeable to act as an internal gastric bypass. FIG. 12C shows a detail drawing of a gastric and/or intestinal sleeve device with porous sections 216 in the wall of the sleeve. FIG. 12D shows a detail drawing of a gastric and/or intestinal sleeve device with slits 218 in the wall of the sleeve. FIG. 12E shows a detail drawing of a gastric or intestinal sleeve device with artificial cilia 230 on the interior of the sleeve wall. The artificial cilia 230 facilitate the flow of food through the sleeve. Artificial cilia could be created by brushing or abrading the interior surface of the sleeve in the direction of food flow. This can raise a nap in the surface of the material biased to the direction of the abrasion. Alternatively, for example, the cilia could be molded into the surface of the sleeve. Alternatively or in addition, a hydrogel coating (for example polyvinyl pyrrolidone, hydromer) or other lubricious coating (for example PHOTOLINK LUBRICIO COATING, Surmodics Inc.) may be used to facilitate the flow of food through the sleeve.

The proximal (food entry) opening of the gastric sleeve is dimensioned to correspond to the opening of the esophagus, pouch outlet or artificial stoma. The outlet of the esophagus is generally free of restrictions to food passage while pouch outlets and stomas which are in some cases configured to restrict the passage of food. These outlets or stoma are generally less than 10-40 mm in diameter and, if restricted, are typically 15 mm or less. This distal end of the sleeve is reinforced and/or configured for attachment to the gastric wall, surgical or artificial stoma opening. This opening for attachment is preferably slightly larger than the diameter of the restricted opening. Past the attachment to the opening the sleeve itself is typically 20-40 mm in diameter with a smooth transition from the opening diameter to the main diameter. If the sleeve continues past the pylorus, at the pylorus this diameter may remain the same, or may reduce to a smaller diameter on the order of 10-20 mm. The sleeve should not be in sealing contact with the stomach wall or the pylorus to allow free passage of gastric secretions along the outside of the sleeve as described herein.

Figure 13:
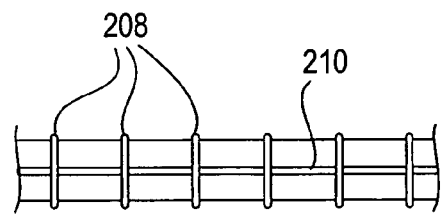
FIG. 13 shows a detail drawing of a gastric or intestinal sleeve device with reinforcement rings.
Figure 14:
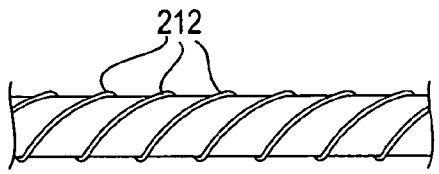
FIG. 14 shows a detail drawing of a gastric or intestinal sleeve device with a spiral reinforcement.

In certain embodiments, the wall of the gastric sleeve 200 is flexible to allow the peristaltic motions of the stomach to effect movement of food through the gastric sleeve 200. For example, blow molded 90A durometer polyurethane of a wall thickness on the order of 0.005" will work in this manner. Other suitable materials for construction of the gastric sleeve device 200 can include fluoropolymers, silicone and polyurethane. Some fluoropolymers can be thermoformed (e.g. PFA and FEP) while others such as PTFE can be expanded in a similar manner to the formation of a vascular graft as well known in that art. Silicone (e.g. Dow Silastic or similar material from Nusil Technologies) or polyurethane (e.g. Dow Pellethane) can be dip molded or cast. Polyurethane can also be blow molded. In some embodiments the wall of the sleeve may be reinforced with rings or a spiral made of wire and/or plastic to hold the sleeve open. FIG. 13 shows a detail drawing of a gastric and/or intestinal sleeve device with reinforcement rings 208. The reinforcement rings 208 are spaced apart at intervals along the length of the sleeve and the sleeve may include one or more longitudinal ribs 210 linking the reinforcement rings together along the length of the sleeve. FIG. 14 shows a detail drawing of a gastric and/or intestinal sleeve device with a spiral reinforcement 212. The reinforcement rings 208 or spiral reinforcement 212 should be resilient enough that peristaltic motions of the stomach and/or intestines can be transmitted through the wall of the sleeve with the sleeve springing back to its full diameter after the peristaltic contractions. The resiliency of the reinforcement rings 208 or spiral reinforcement 212 also allows the sleeve to be collapsed to facilitate endoscopic placement of the device. The reinforcement rings 208 or spiral reinforcement 212 may be made of or supported with stainless steel or a superelastic, or shape-memory NiTi alloy. The reinforcement rings 208 or spiral reinforcement 212 can also be plastic. The reinforcement rings 208 or spiral reinforcement 212 may be sized to fit loosely within the stomach or intestines or to provide a little bit of contact force to create a seal with the intestinal walls. As described herein in relation to the intestinal sleeve, it is important to control the coupling of forces that are transmitted by the action of the stomach (in this case) to the sleeve. Transmission of excessive force to the stomach attachment can be contraindicated in many clinical situations and in this case the coupling should be minimized. This can be accomplished, for example, through the use of low friction coatings on the sleeve exterior, using soft compliant (e.g <70A durometer non-metal reinforced) reinforcing rings and/or by not using reinforcing rings.

The interior and exterior of the sleeve can optionally be coated with a low friction material as described herein (e.g. a hydrogel) to reduce friction of food passage (interior) and reduce gastric irritation (exterior). The interior of the sleeve can optionally include flexible prongs angled toward the direction of food flow to act as artificial cilia and resist food moving retrograde along the sleeve, as shown in FIG. 12E. Optionally the distal end of the gastric sleeve can incorporate an enlarged reservoir portion proximal to the pylorus. Optionally the sleeve can include coatings on its interior and/or exterior to enhance the surface properties of the sleeve in clinically relevant manners. Coating examples include: 1) parylene coatings to increase the chemical resistance of a sleeve material, 2) coating with an antimicrobial agent to resist infection and/or 3) coating with an anti-inflammatory agent to reduce tissue inflammatory response, as described herein.

In conjunction with the gastric sleeve 200, the volume of the stomach can be reduced by suturing, stapling or banding using open, transesophageal or laparoscopic techniques. In the example shown in FIG. 10, a vertical line of gastroplasty sutures or staples 104 parallel to the sleeve 200 has been used to reduce gastric volume. Alternatively or in addition, a horizontal line of gastroplasty sutures or staples may be used to form a reduced volume gastric pouch. The sutures or staples may or may not be in a continuous line and may or may not be reversible. The stomach can also optionally be divided at the gastroplasty. These adjunctive techniques may assist in enhancing the effect of peristaltic motions of the stomach for moving food through the gastric sleeve.

Alternatively or in addition, a gastric balloon or other volume displacement device may be used in conjunction with the gastric sleeve to provide a feeling of satiety.

Preferably, portions of the gastric sleeve are constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted gastric sleeve can be verified noninvasively. However, the sleeve should not be completely radiopaque to allow visualization of the passage of ingested radioopaque contrast as in a "swallow" study.

Figure 15:
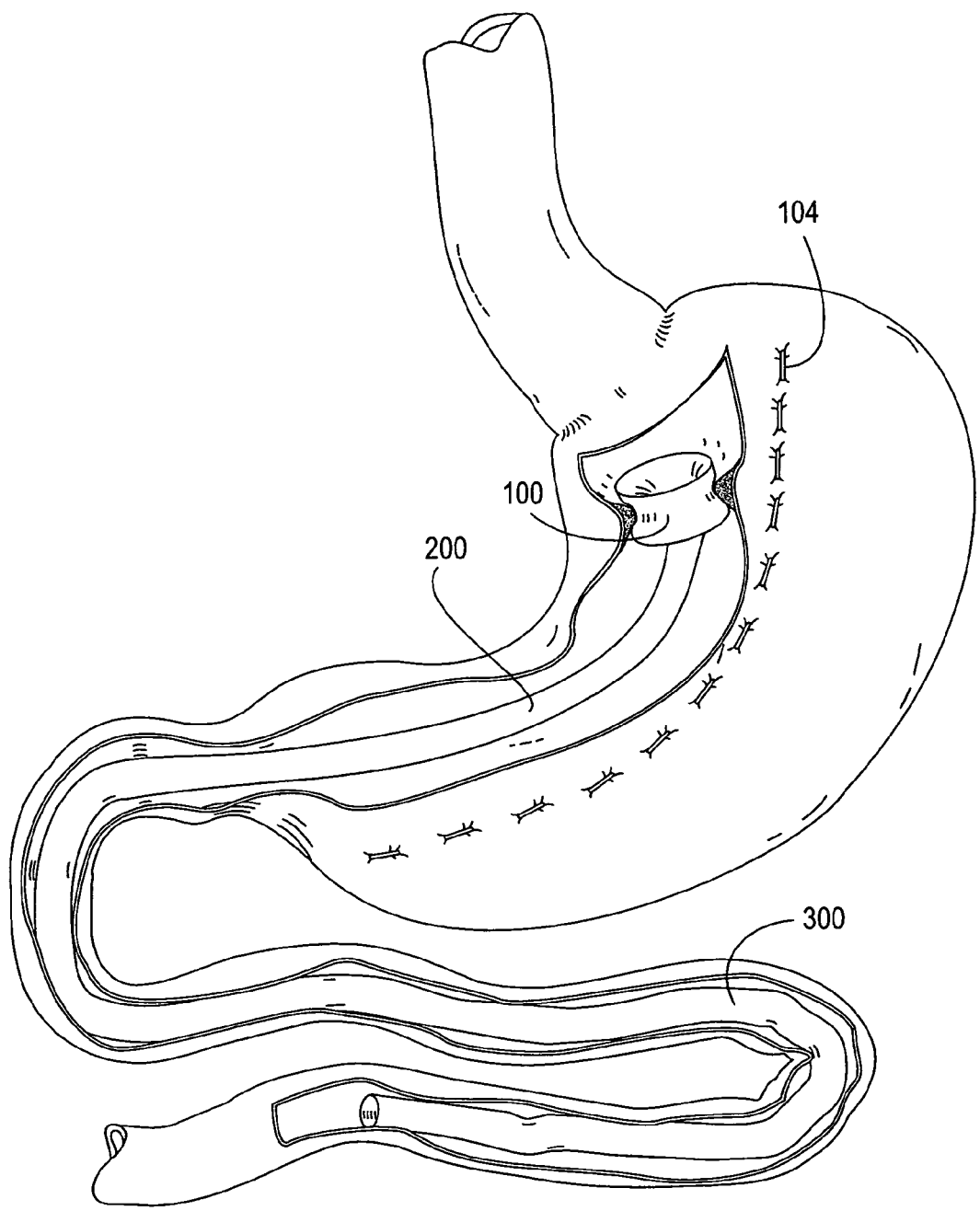
FIG. 15 shows a combined gastric and intestinal sleeve device with an artificial stoma device implanted within a patient's stomach with a line of gastroplasty sutures or staples parallel to the sleeve.

In another aspect, the system may include an internal intestinal sleeve 300 that may be used separately or used with, attached to or integrated with the internal gastric sleeve 200 and artificial stoma component 100. FIG. 15 shows a combined gastric 200 and intestinal 300 sleeve device with an artificial stoma device 100 implanted within a patient's stomach with a line of gastroplasty sutures or staples parallel to the sleeve 104. The entire intestinal sleeve 300 or a portion of it can be porous or semipermeable to allow the flow of digestive secretions into the sleeve and to allow the flow of nutrients and/or fluids out through the wall of the sleeve. Suitable materials for construction of the intestinal sleeve device 300 include fluoropolymers, silicone (e.g. Dow Silastic or similar material from Nusil Technologies) and polyurethane (e.g. Pellethane). For example, in one embodiment the intestinal sleeve device 300 may be constructed of blow molded 90A durometer polyurethane with a wall thickness on the order of 0.005". Some fluoropolymers can be thermoformed (e.g. PFA and FEP) while others such as PTFE can be expanded in a similar manner to the formation of a vascular graft as well known in that art. Openings 204 may be provided through the wall of the sleeve, as shown in FIG. 12A. Valves 206 may be provided in the wall of the intestinal sleeve to allow digestive secretions to enter the sleeve, but to prevent solid food and/or nutrients from flowing out through the wall of the sleeve, as shown in FIG. 12B. Alternatively, the entire intestinal sleeve or a portion of it can be nonporous or impermeable to act as an internal intestinal bypass. Valve and porosity structures to allow flow such as those described herein in relationship to the gastric sleeve can also be applied to the intestinal sleeve. In certain embodiments, the wall of the intestinal sleeve 300 is flexible to allow the peristaltic motions of the intestinal wall to effect movement of food through the intestinal sleeve. The interior and exterior of the sleeve can optionally be coated with a low friction material (e.g. a hydrogel) to reduce friction of food passage (interior) and reduce intestinal irritation (exterior). Other coatings such as those described herein in relationship to the gastric sleeve can also be applied to the intestinal sleeve. The interior of the sleeve can optionally include flexible prongs angled toward the direction of food flow to act as artificial cilia and resist food moving retrograde along the sleeve, as shown in FIG. 12E. The wall of the sleeve may be reinforced with rings 208 or a spiral 212 made of wire and/or plastic, as shown in FIGS. 13 and 14. Optionally the intestinal sleeve can include means for stabilization at the distal end such as a brush (as described by Berry), weight or inflatable balloon.

The intestinal sleeve diameter can be 10-40 mm, but it is typically 15-30 mm with an optional smaller diameter at the point the sleeve passes through the pylorus (if the sleeve passes through the pylorus). The diameter of the sleeve is optionally selected to be smaller that the diameter of the intestine. The sleeve should not be in permanent sealing contact with the intestinal wall or the pylorus if it is intended to control or allow passage of gastric, biliary, pancreatic and intestinal secretions along the outside of the sleeve.

Figure 16:
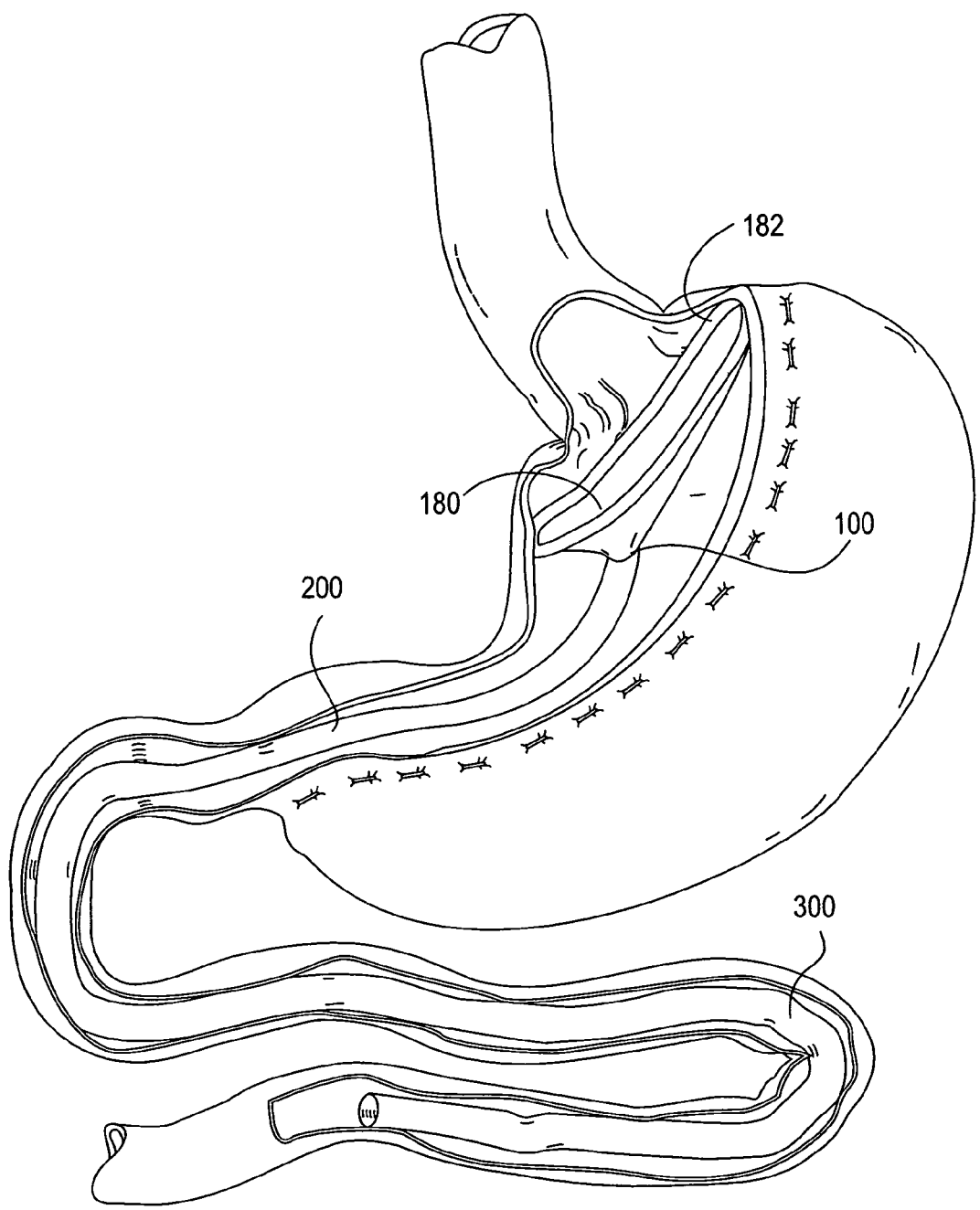
FIG. 16 shows a combined gastric and intestinal sleeve device with an artificial stoma device located within a funnel-shaped entry with a reinforced suture area.

Optionally, the intestinal sleeve 300 may have a proximal end with a reinforced anchoring segment or other anchoring mechanism for attachment in the region of the pylorus or the proximal end of the intestinal sleeve 300 may be attached to a stoma device or surgically created stoma at the outlet of a reduced stomach. Alternatively, the intestinal sleeve 300 may be attached to or continuous with the internal gastric sleeve 200. Optionally, the distal end of the intestinal sleeve 300 may include an anchoring mechanism. FIG. 16 shows a combined gastric 200 and intestinal 300 sleeve device with an artificial stoma device 100 located within a sleeve entry 180 with a reinforced suture area 182. The sleeve entry 180 creates a reduced-volume pouch within the patient's stomach that functions similarly to a surgically created gastroplasty pouch.

The intestinal sleeve 300 is typically approximately 60-180 cm in length, whereby partially digested or undigested nutrients exit from the sleeve into the jejunum where they can elicit a hormonal, neural and/or osmotic reaction in the jejunum and/or ileum. However, sleeve length can be either shorter or longer depending on clinical needs. Increasing the length of the sleeve can increase the degree of response in the ileum while reducing the length of the sleeve can have the opposite effect.

In relation to the example of the placement of a stoma 100 implanted into a surgically formed pouch described above, the gastric sleeve 200 and/or intestinal sleeve 300 may be implanted according to the following method:

Sleeve Placement

At any point in the procedure for stoma implantation described above, preferably prior to suturing of the gastric pouch (step 8), a gastric and/or intestinal sleeve device may be placed in the stomach and/or intestines. The distal end of the intestinal sleeve is placed endoscopically approximately 100 cm distal to the pylorus (for an intestinal sleeve with a nominal length to be 100 cm past the pylorus as defined by the relative position of the end of the gastric sleeve 200). The proximal end of the sleeve is attached, then the gastric pouch is sutured or stapled and the stoma placement procedure is resumed at step 9. Alternatively, the gastric and/or intestinal sleeve device may be placed after a pouch is formed and the stoma is placed, provided the stoma opening is sufficiently large to allow passage and manipulation of the sleeve and visualization apparatus. In the case of an intestinal sleeve, the proximal end would optionally be attached at the outlet of the stomach or at the pylorus. In the case of a gastric sleeve or combined gastric and intestinal sleeve, the proximal end would preferably be attached to a stoma device or surgically created stoma. Alternatively, the sleeve can be attached to the stomach or esophageal wall. In situations where it is desirable for the distal end of the sleeve to be placed further than 100 cm distal to the pylorus, or as an alternative means of placement, the sleeve will be inserted in a collapsed configuration through the pylorus and restrained in the collapsed configuration by a bioabsorbable/dissolvable means and passed through the intestines by the normal peristaltic action of the intestine. Optionally a balloon, ring or other means of increasing the coupling of the peristaltic action to the sleeve may be attached at the distal end of the sleeve. This is similar to the use of peristaltic action for passage of a Baker, or other long intestinal, tube as know in the art. Rings and/or other means of increasing the coupling of the peristaltic action may be placed at other locations along the length of the intestinal sleeve if clinically appropriate. In some clinical situations a method of use whereby the resiliency of the peristalsis rings can be selected to allow the intestines to use the rings in the manner of a ladder. In this case the intestine essentially crawls up the sleeve and takes on a pleated bellows like configuration. This can have the result of effectively lengthening the sleeve as food would now exit the sleeve at a more distal location within the intestine.

In an alternative method, the gastric and/or intestinal sleeve device may be used with a stoma device placed using standard surgical techniques, with a surgically created stoma, with surgical gastric banding or it may be used alone with no stoma device at all.

Preferably, portions of the intestinal sleeve are constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted intestinal sleeve can be verified noninvasively. However, the sleeve should not be completely radiopaque to allow visualization of the passage of ingested radioopaque contrast as in a "swallow" study.

FIG. 17 shows an artificial stoma device 100 implanted within a patient's stomach with a line of gastroplasty sutures or staples 104 to reduce the gastric volume. Also shown is a line of sutures or staples 304 longitudinally dividing the small intestine to create a bile/pancreatic channel 308 separate from the intestinal lumen 310. The biliopancreatic channel 308 serves to prevent the patient's bile from mixing with the food in the intestinal lumen 310, thus reducing the digestion and absorption of fat.

FIG. 18 shows a cross section of the patient's small intestine showing the bile/pancreatic channel 308.

Figures 19, 20:
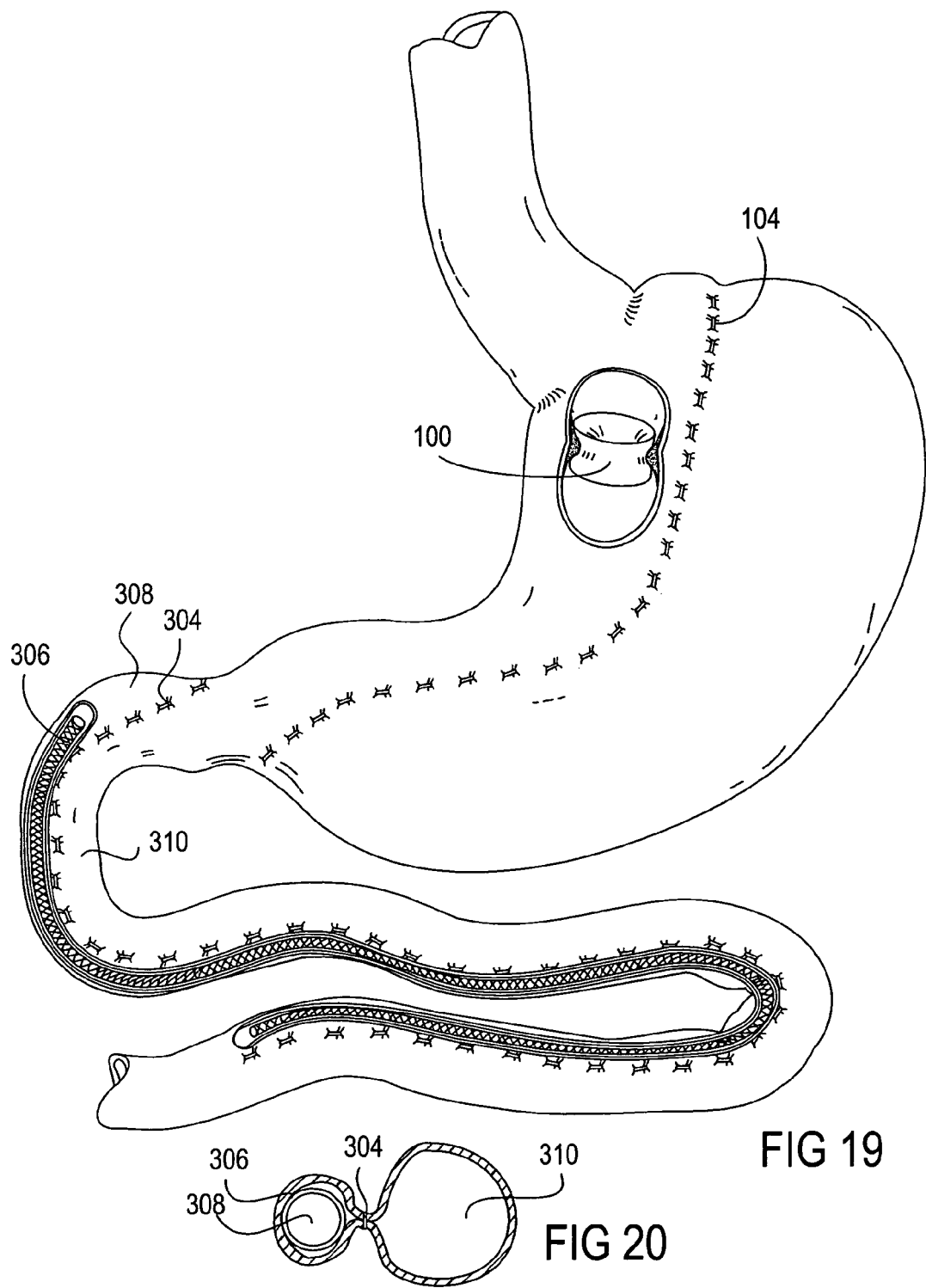
FIG. 19 shows an artificial stonia device implanted within a patient's stomach with a line of gastroplasty sutures or staples to reduce the gastric volume and a line of sutures or staples longitudinally dividing the small intestine to create a biliopancreatic channel with an optional stent.
FIG. 20 shows a cross section of the patient's small intestine showing the biliopancreatic channel with an optional stent.

FIG. 19 shows an artificial stoma device 100 implanted within a patient's stomach with a line of gastroplasty sutures or staples 104 to reduce the gastric volume and a line of sutures or staples 304 longitudinally dividing the small intestine to create a biliopancreatic channel 308 separate from the intestinal lumen 310 with an optional stent 306 to keep the bile/pancreatic channel 308 open and prevents collapse of the channel.

FIG. 20 shows a cross section of the patient's small intestine showing the biliopancreatic channel 308 with an optional stent 306.

Figure 21:
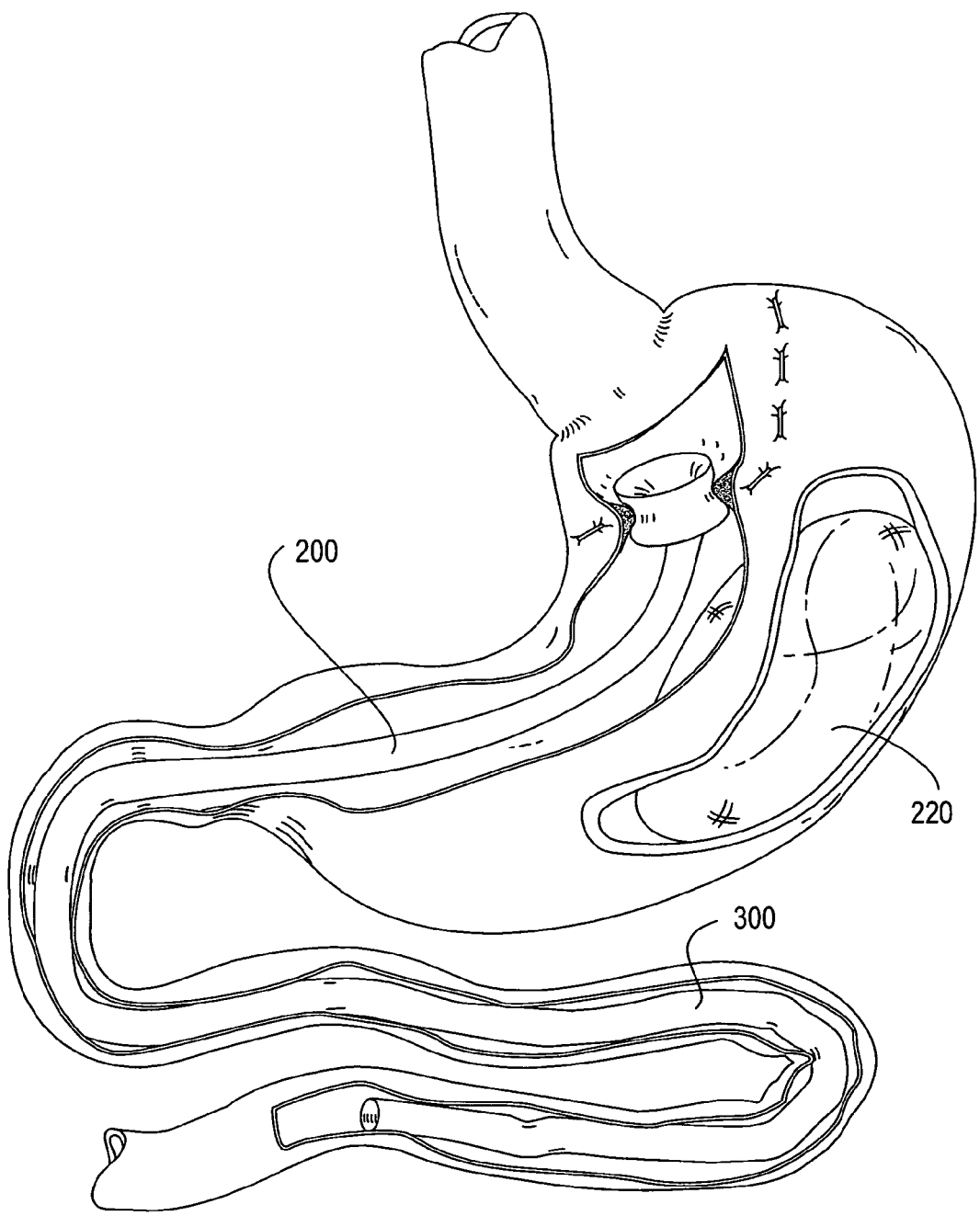
FIG. 21 shows a combined gastric and intestinal sleeve device implanted within a patient's stomach with a gastric balloon to reduce the gastric volume.

FIG. 21 shows a combined gastric 200 and intestinal 300 sleeve device implanted within a patient's stomach with a gastric balloon 220 to reduce the gastric volume.

In summary, one aspect of the invention provides a method and system for treatment of morbid obesity that has three components, an artificial stoma device, an internal gastric sleeve and an internal intestinal sleeve, which can be used separately or in combination. The artificial stoma device is implanted into a patient's stomach or lower esophagus and then can optionally be used to restrict food intake. The artificial stoma device may have a fixed aperture, an adjustable aperture or an aperture that varies in response to changing stomach conditions. The artificial stoma device may be implanted using sutures, staples, a reinforced anchoring segment, a sutureless or other attachment mechanism as described herein. A restriction can optionally be placed within the lumen of the gastric sleeve. The internal gastric sleeve may be separate from or integrated with the artificial stoma device. The internal gastric sleeve effectively reduces the patient's gastric volume and restricts the absorption of nutrients and calories from the food that passes through the stomach. The internal intestinal sleeve may be separate from or integrated with the internal gastric sleeve and/or the artificial stoma device. The wall of the internal gastric sleeve and/or internal intestinal sleeve may be constructed with reinforcing rings or a spiral reinforcement. The wall of the internal gastric sleeve and/or internal intestinal sleeve may have openings or valves to allow or restrict the digestive secretions and nutrients through the wall of the sleeve. Along with these components, the treatment system may also include an attachment system that uses wire fasteners for performing a gastrostomy and a stent for supporting a bile/pancreatic channel in the patient's small intestine.

The method provided by this invention has the capacity to combine these various components, as well as other components described herein, into a system that treats obesity by creating a pouch with an outlet restriction which can be optionally controlled or operable, placing means by which the food exiting the pouch is transferred via gastric and intestinal sleeves to a point in the intestine while being substantially isolated from (or allowed to contact a controlled amount) gastric, biliary, pancreatic and intestinal secretions, whereby this location in the intestine can be optionally selected to induce various reactions of the intestinal tissue which may include dumping syndrome, hormonal secretion and/or nervous stimulation.

In contrast to previous devices, the present inventors have found that in many cases an effective gastrointestinal sleeve device will preferably have the characteristics of each section of the device tailored to the function of the section of the gastrointestinal tract in which it resides. For example, in some clinical situations a potential issue with gastric pouch or sleeve systems could be a lack of physiological signals causing opening of the pylorus. If the pylorus were to remain tightly closed over a sleeve passing through, it could be problematic for the patient. In these clinical situations, one desirable characteristic of an effective gastrointestinal sleeve device could be for it to have sufficient volume and/or compliance in the area of the stomach immediately upstream of the pylorus to create enough pressure or wall tension in that area to trigger the opening of the pylorus to empty the stomach contents.

In addition, when normal functioning of the pylorus is clinically desired, the section of the sleeve device that passes through the pylorus must have enough wall flexibility or compliance to allow normal opening and closing of the pylorus and to allow drainage of stomach secretions around the outside of the sleeve. For example blow molded 90A durometer polyurethane of a wall thickness on the order of 0.005" or less will work in this manner. Other sections of the gastrointestinal sleeve device will also be tailored to the section of the gastrointestinal tract in which it resides.

The configuration of the gastrointestinal sleeve device enables a method of treatment for morbid obesity that includes isolating ingested food from the digestive secretions of the stomach and intestines as the food passes through the stomach, the duodenum and the upper part of the jejunum.

Figure 22:
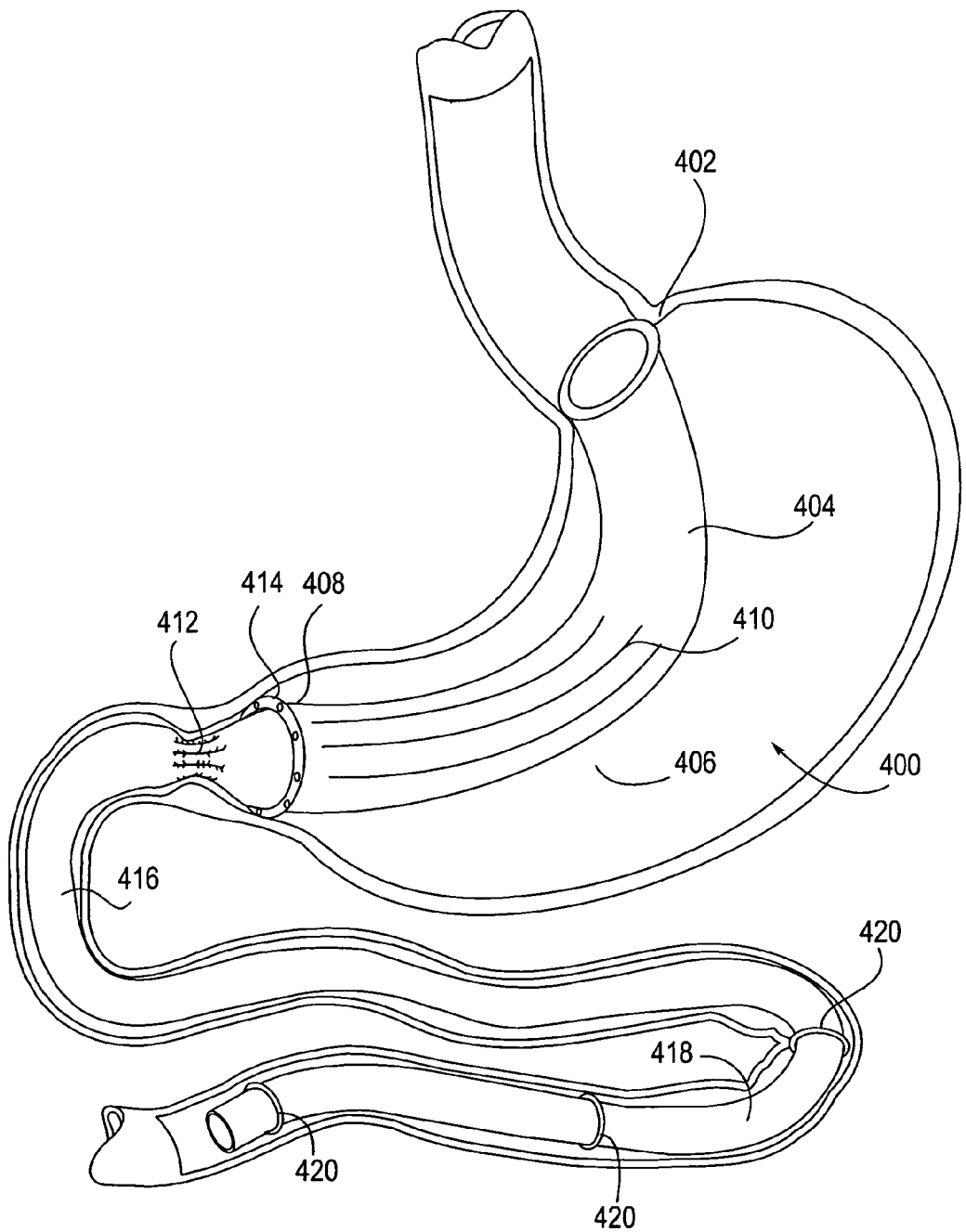
FIG. 22 illustrates an example of a gastrointestinal sleeve device deployed within a patient's gastrointestinal tract for treating morbid obesity.

FIG. 22 illustrates an example of a gastrointestinal sleeve device 400 constructed in accordance with the present invention. The gastrointestinal sleeve device 400 is shown deployed within a patient's gastrointestinal tract for treating morbid obesity. The characteristics of each portion or section of the gastrointestinal sleeve device 400 may be tailored to the function of the section of the gastrointestinal tract in which it resides.

The proximal opening 402 of the gastrointestinal sleeve device 400 is primarily designed to facilitate attachment of the sleeve within the patient's stomach. Depending on the clinical needs of the individual patient and the judgement of the physician, locations for attachment of the proximal opening 402 of the sleeve may include the gastroesophageal junction and the cardia or cardiofundal border. The gastroesophageal junction is advantageous as a possible attachment site because the tissue wall is relatively thick at this location and it is relatively easy to access via a per oral route. Attachment at the gastroesophageal junction excludes all gastric secretions from the interior of the gastrointestinal sleeve device 400. The cardiofundal border is also advantageous as a possible attachment site because it provides the ability to create a gastric pouch from the cardia of the stomach and the tissue wall is relatively thick at this location compared to the fundus. Attachment at the cardia or cardiofundal border allows the secretions of the cardia, which are primarily lubricious mucous, to enter the interior of the gastrointestinal sleeve device 400 and excludes the fundal secretions, which are high in acid content, from the interior of the sleeve. The lubricious mucous secretions from the cardia will help to lubricate the interior surface of the gastrointestinal sleeve device 400 and will facilitate passage of ingested food through the sleeve.

By way of example, the embodiment of FIG. 22 shows the proximal opening 402 of the gastrointestinal sleeve device 400 attached at the gastroesophageal junction. In this configuration, it can be preferred that the proximal opening 402 be sized to have a diameter approximately equal to, or slightly larger than the diameter of the esophagus at the gastroesophageal junction. In adult humans, the esophagus at this point typically has a diameter of approximately 1.5-2.0 cm.

Attachment of the proximal opening 402 of the gastrointestinal sleeve device 400 within the stomach can be accomplished using open, laparoscopic or endoscopic surgical techniques e.g. sutures, wires or staples or using any of the attachment methods described herein. Attachment is preferably optimized to distribute stress over an enlarged area and minimize stress or strain transmitted to the tissue where it is attached in order to minimize tissue erosion. During ingestion of food, the sleeve and the attachment must withstand the pressure created by swallowing as the food is forced into the sleeve. This is particularly true if there is a restriction downstream of the proximal sleeve opening. The sleeve and the attachment must also withstand any tensile forces created as a result of swallowing food and the presence of any food or liquid within the sleeve or pouch, as well as forces due to peristaltic action of the intestines or stomach.

Figure 23A:
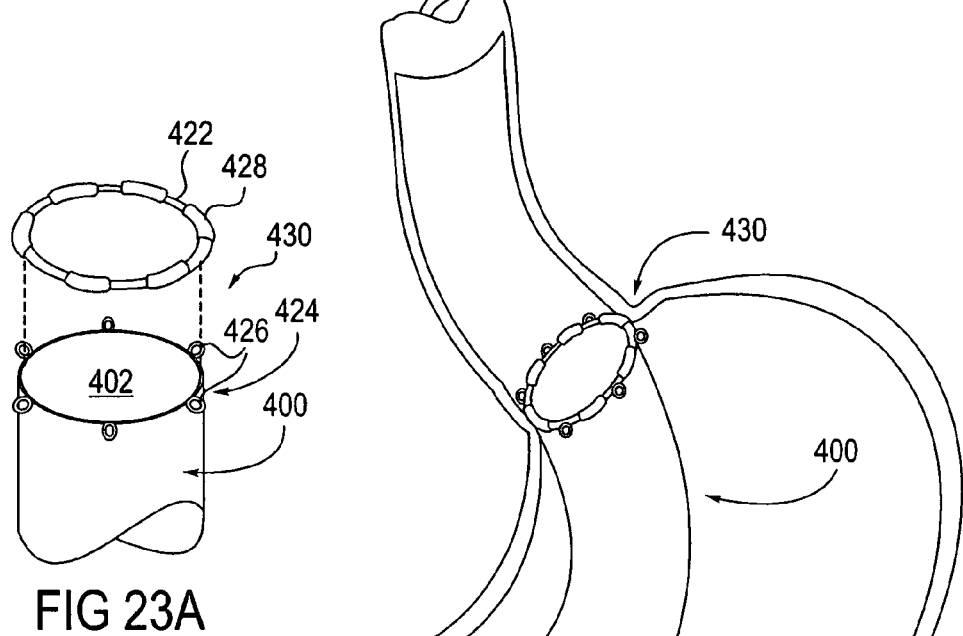
FIGS. 23A and 23B illustrate a gastrointestinal sleeve device with a healable, removable fixation system.
Figure 23B:
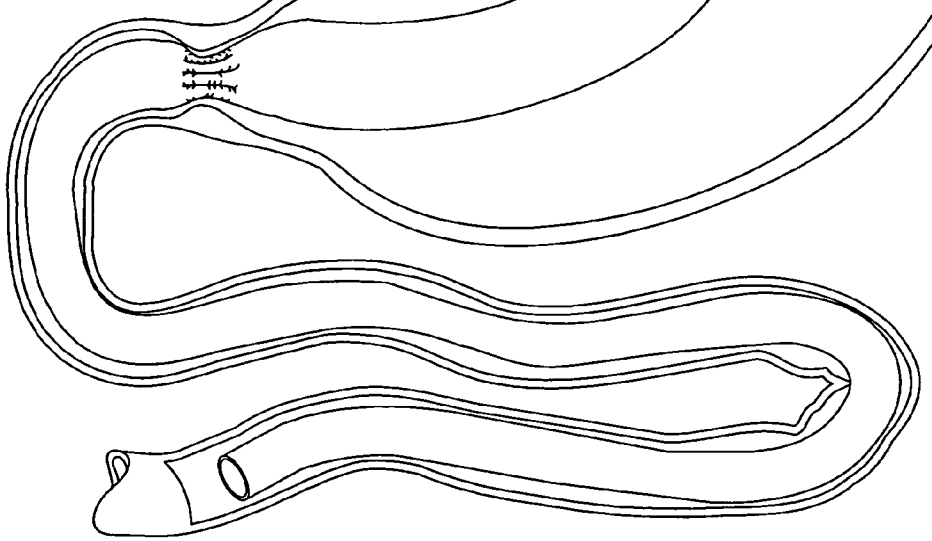

In one embodiment shown in FIGS. 23A and 23B, the proximal opening 402 of the gastrointestinal sleeve device 400 is attached to the stomach wall with an optionally removable, healable fixation system 430. The fixation system 430 is configured with two components: an anchor ring 422 and an attachment means 424 for connecting the gastrointestinal sleeve device 400 to the anchor ring 422. The attachment means 424 could be configured as part of the anchor ring 422 or the gastrointestinal sleeve device 400 or as one more separate components. The fixation system 430 is configured to operate in three different modes. It can provide a permanent or long-term attachment of the gastrointestinal sleeve device 400 to the stomach wall; it can allow replacement or revision of the gastrointestinal sleeve device 400 without removal of the anchor ring 422; and it can be removed completely to allow the stomach wall to heal where the anchor ring 422 had been attached.

The anchor ring 422, shown in FIG. 23A, may be configured as a continuous wire, polymer or wire-reinforced polymer ring with an exterior or coating that resists ingrowth and adhesion. The wire could be NiTi or SS. Suitable polymers would include silicone, Teflon (PTFE) and other fluoropolymers. Possible coatings include hydrophilic coatings, hydromers, hydrogels and fluoropolymers. Portions of the anchor ring 422 can be enclosed with a material 428 that encourages ingrowth of tissue. Between the portions of ingrowth material 428, the anchor ring 422 can be bare to discourage ingrowth and to provide attachment points for the gastrointestinal sleeve device 400. The ingrowth material 428 in this embodiment is preferably a biodegradable or resorbable material such as polyglecaprone (Monocryl, Ethicon), polyglactin (Vycril, Ethicon), or other known biodegradable or resorbable material. The ingrowth material 428 is configured so ingrowth results in a partial and intermittent encapsulation of the anchor ring 422. Areas of encapsulation would be interspaced with areas where ring was exposed.

In one example of the fixation system 430 shown in FIG. 23A, the attachment means 424 is configured with a plurality of clip rings 426 mounted around the exterior of the gastrointestinal sleeve device 400 near the proximal opening 402. The clip rings 426 are configured with gaps in the rings that allow the rings to clip onto the exposed bare portions of the anchor ring 422 to hold the gastrointestinal sleeve device 400 in position. In other embodiments, the attachment means 424 may comprise magnets, clips, hooks, staples, sutures or other known fasteners.

In one method, the anchor ring 422 would be implanted and allowed to heal before another device, such as the gastrointestinal sleeve device 400, would be attached to it. After sufficient healing has taken place, the device could be attached to the anchor ring at areas where ingrowth did not occur, as shown in FIG. 23B. In this method/structure a biodegradable ingrowth material is used and since the ingrowth material is biodegradable, it will eventually disappear after providing a scaffold for ingrowth resulting in intermittent encapsulation of the anchor ring.

FIG. 23B also shows no restriction at the attachment stoma and no restriction in the sleeve thereby showing the pylorus acting as a naturally controlled restriction as described herein.

In another example of an alternate embodiment the sleeve of FIG. 23B could use an attachment ring and ring interface as shown in FIGS. 77-84 which are attached to the stomach using T-tag fasteners or T-pledgets as described herein.

The anchor ring and the gastrointestinal sleeve device 400 can be left in place permanently. Alternatively, the gastrointestinal sleeve device 400 can be removed at a later date and replaced or revised. If and when it is desirable to remove the anchor ring, one or more or areas with no ingrowth can be used as access to sever or cut the ring. Since the ring exterior resists ingrowth and is nonadherent, it can be pulled out of the tissue without damaging the tissue. After removal of the anchor ring, the tunnel through the tissue formed by the encapsulation can heal.

As an alternative to a biodegradable material, a nondegradable scaffold material can be used. These materials become incorporated into tissue and are often made of naturally occurring or biological components, such as processed bovine tissue.

Figure 24A:
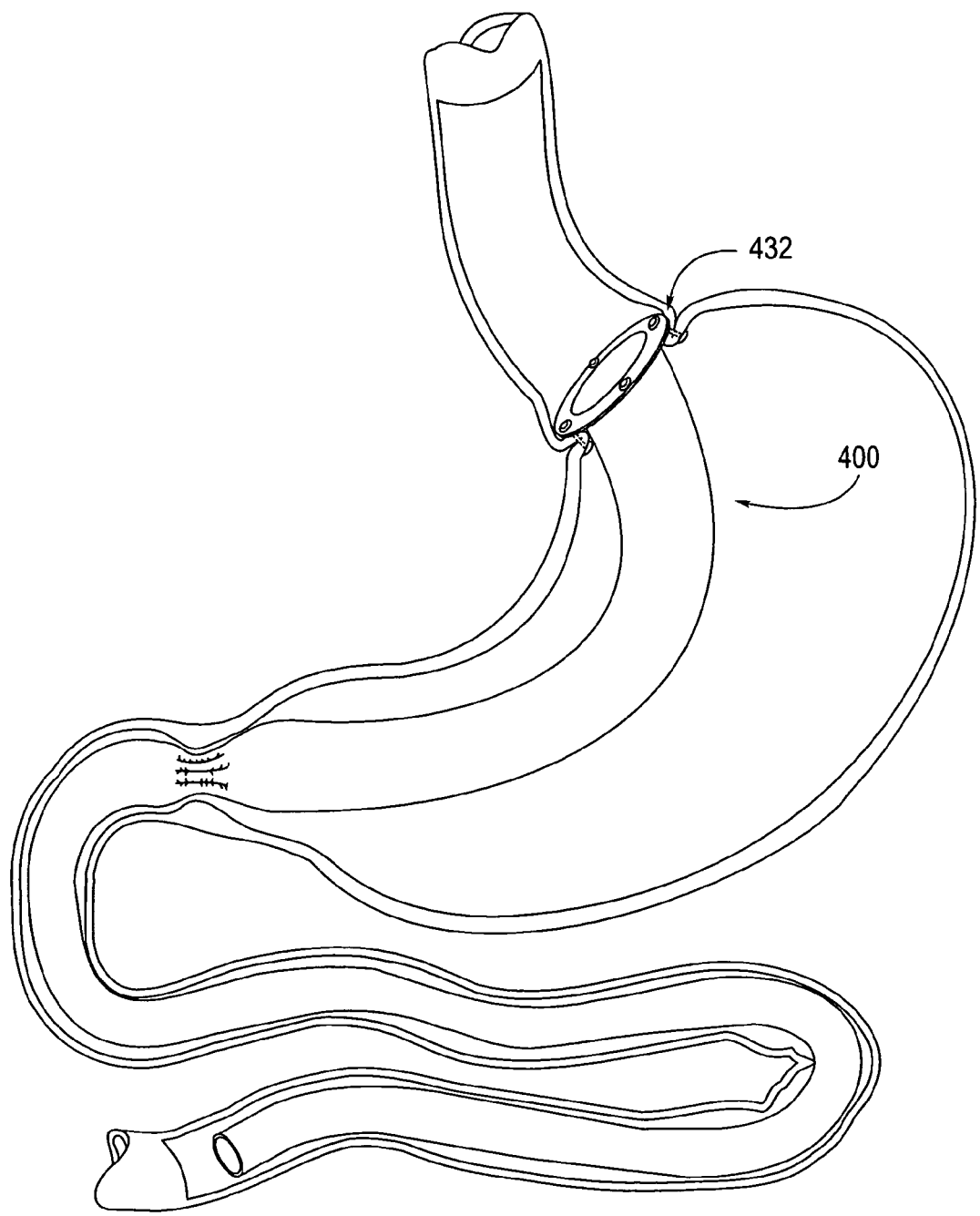
FIGS. 24A-24D illustrate various gastrointestinal sleeve devices attached within a patient's stomach.

FIG. 24A shows another way of attaching the proximal opening 402 of the gastrointestinal sleeve device 400 within the patient's stomach. A combined attachment/stoma device 432 is implanted into the patient's stomach to create a restriction and the gastrointestinal sleeve device 400 is attached to the stoma device. The stoma device 432 and the gastrointestinal sleeve device 400 may be implanted in a single procedure or they may be implanted in two sequential procedures as described above, leaving enough time for healing of the gastric wall in between the two procedures. The stoma device 432 may be attached at the gastroesophageal junction or it may be attached at the cardiofundal border to create a reduced volume reservoir upstream of the restriction (gastric pouch) using the tissue of the cardia, as shown in FIG. 24A. The gastrointestinal sleeve device 400 may be attached using any one of the stoma devices described herein. By way of example, the gastrointestinal sleeve device 400 of FIG. 24A is shown attached using a stoma device 432 in the form of a stomal ring clip.

In general, the proximal end of the gastrointestinal sleeve device 400 may be secured in the vicinity of the lower esophageal sphincter or z-line, using a stoma device 432 having any of a variety of configurations including those illustrated in FIGS. 24A-D. As used herein, the term "stoma device" includes devices which define an opening, without limitation to the relative size of the opening compared to the surrounding anatomy unless otherwise described.

Figure 24B:
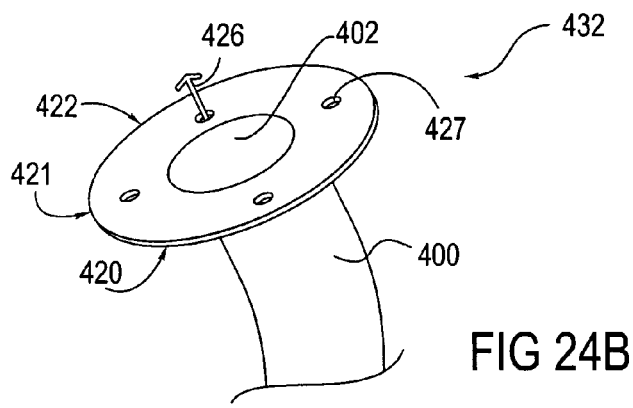
Figure 24C:
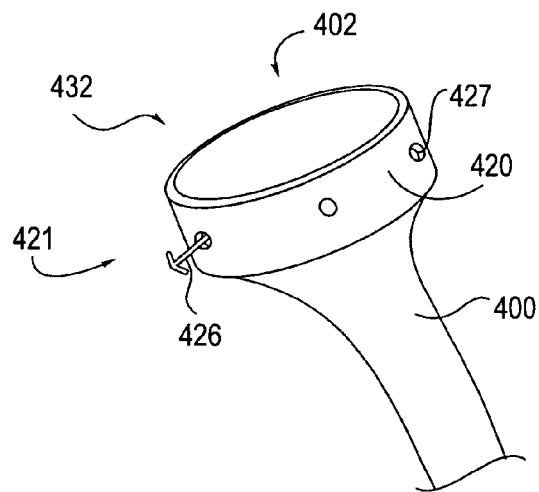

Referring to FIGS. 24A and 24B, the stoma device 432 includes at least one tissue contacting surface 420 for contacting tissue such as illustrated in FIG. 24A. The tissue contacting surface 420 may be carried by an anchor support 421 such as a transverse flange 422. In the illustrated embodiment, the transverse flange 422 comprises a continuous radially outwardly extending annular support. However, the anchor support 421 may comprise a plurality of radially outwardly extending connection tabs such as two or four or six or eight or more, which may be circumferentially symmetrically positioned about the longitudinal axis of the gastrointestinal sleeve 400. As is described elsewhere herein, the gastrointestinal sleeve 400 may be either permanently or detachably connected to the anchor support 421. The anchor support 421 may be provided with a plurality of apertures 427 such as to receive a "T" fastener or other tissue connector as is discussed elsewhere herein. Alternatively, the anchor support 421 may be pierceable by the deployment of the "T" fastener or other tissue connector.

In a modification of the anchor support 421 (see FIG. 24C), the at least one tissue contacting surface 420 faces radially outwardly from the longitudinal axis of the gastrointestinal sleeve 400. In this configuration, the "T" fastener or other tissue anchor may extend radially outwardly into adjacent tissue, as may be desirable depending upon the tissue anchor configuration. The tissue contacting surface 420 may also be inclined with respect to the longitudinal axis of the gastrointestinal sleeve 400.

Figure 24D:
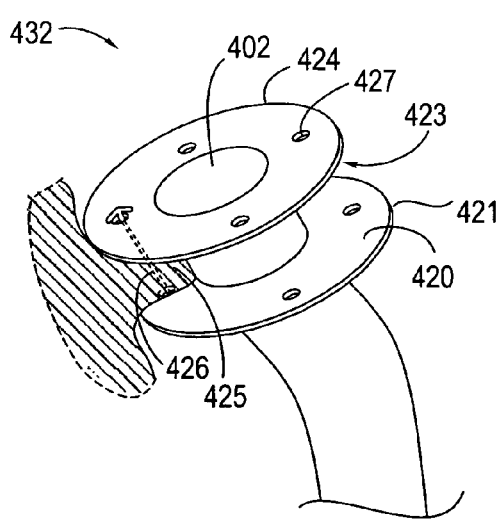

Referring to FIG. 24D, at least a first tissue contacting surface 420 is carried by a first anchor support 421 and at least a second tissue contacting surface 423 is carried by at least a second anchor support 424. In the illustrated embodiment, each of the first anchor support 421 and second anchor support 424 is illustrated as an annular flange. However, the anchor supports may take any of a variety of configurations as has been discussed. In addition, the first anchor support 421 and second anchor support 424 are spaced axially apart, to allow tissue 425 to be drawn therebetween. Tissue 425 may be drawn between the first and second anchor supports using vacuum, supplied by the deployment catheter. This configuration enables the advance of a fixation device 426 between the first anchor support 421, through the tissue 425 and into or through the second anchor support 424 as illustrated in FIG. 24D. The device shown in FIG. 24D can optionally be configured to enable full thickness plication and serosa-to-serosa contact at the fixation device 426 as described herein. The fixation device 426 may comprise a "T" fastener, a pin, or other structures disclosed herein. In the annular construction illustrated in FIG. 24D, two or four or more tissue extensions 425 may be drawn radially inwardly, for attachment to the stoma device 432.

The attachment described in FIG. 24A can also be used where the attachment is dimensioned so as not to create a restriction. In this case, a restriction can optionally be placed downstream within the gastric sleeve. It is generally clinically preferable for devices placed at the gastroesophageal junction to have the stoma downstream, while devices placed at the cardiofundal border may combine the restriction with the attachment to allow a smaller food reservoir upstream of the restriction.

Downstream of the proximal opening 402, the gastrointestinal sleeve device 400 has sleeve portions 404, 406 that reside in the fundus and the antrum of the stomach, respectively. In the example of FIG. 22, the gastrointestinal sleeve device 400 has an approximately constant diameter from the proximal opening 402 to the upstream end 408 of the pylorus, including the fundus portion 404 and the antrum portion 406 of the sleeve. In this embodiment, the sleeve through the fundus and antrum portions 404, 406 preferably has a diameter approximately equal to or slightly larger than the diameter of the esophagus at the gastroesophageal junction, which in adult humans is approximately 1.5-2.0 cm. Alternatively, the gastrointestinal sleeve device 400 may gradually taper outward or open immediately downstream of the proximal opening 402, as shown in FIG. 24A. In this embodiment, the gastrointestinal sleeve device 400 preferably has a proximal opening 402 with a diameter of approximately 1.0-1.5 cm where it is attached to the stoma device 432. Downstream of the proximal opening 402, the fundus and antrum portions 404, 406 of the sleeve have a diameter of approximately 1.5-2.0 cm.

The example illustrated in FIG. 24A may utilize any of a variety of dimensions, materials, attachment structures and other features disclosed elsewhere herein. In general, the example of FIG. 24A is provided with a substantially uniform inside diameter throughout its axial length. Axial lengths between the proximal opening 402 and a distal end of the device are generally in excess of 50 cm, often at least about 75 cm to 125 cm or more, depending upon the desired clinical performance as has been described elsewhere herein. In one implementation of the invention, the tubular wall of the gastrointestinal sleeve 400 is sufficiently flexible that the natural operation of the pylorus operates as an adjustable stoma on material traveling through the sleeve 400.

The sleeve 400 may be attached in the vicinity of the gastroesophageal junction, such as by attachment to a ring or cuff or directly attached to the cardia of the stomach adjacent the gastroesophageal junction. Attachment may be accomplished in any of a variety of ways including those disclosed elsewhere herein, such as "T" fasteners including T tags such as illustrated in FIG. 91A or T pledgets such as illustrated in FIG. 91B. Such anchors may be positioned utilizing the placement techniques illustrated, for example, in FIGS. 94A through 94C.

The sleeve 400 may comprise a homogenous material throughout. At least the gastric section may comprise a sufficient length to extend through the gastroesophageal junction, past the pylorus and into the duodenum. Materials such as a blow molded polyurethane, having a wall thickness of approximately 0.005" and a durometer of about 90A may be used. The sleeve 400 may additionally be provided with a lubricious coating on one or more of the interior and exterior surfaces. Diameters on the order of about 2.0 cm, ±50% or more may be utilized. Other dimensions and materials may be optimized by those of skill in the art in view of the disclosure herein.

The intestinal section of the sleeve 400 is dimensioned to start in the duodenum and extend at least about 50, often about 75 or 100 cm or more, to imitate a gastric bypass. The intestinal section of the sleeve 400 may be the same diameter as the gastric portion of the sleeve, or may be no more than about 90% or 80% or less of the diameter of the gastric sleeve portion. Delivery and retrieval techniques for the implementation of the invention illustrated in FIG. 24A have been disclosed elsewhere herein.

The function of the sleeve portion 404 located in the zone of the fundus is to transmit food through the gastrointestinal sleeve device 400. Accordingly, this portion of the gastrointestinal sleeve device 400 may be configured to resist kinking and provide a lubricious inner surface. Saliva and mucous secreted in the esophagus and/or cardia could facilitate passage of food. The zone of the fundus and/or the area of the cardiofundal border could be a possible location for a restriction if one is used. Location of the restriction is clinically relevant in that the volume between the restriction and the gastroesophageal junction effectively defines a restricted stomach volume.

The antrum of the stomach has muscular action to grind food and this muscular action can manifest as peristalsis. Based upon clinical requirements, the sleeve portion 406 in the antral zone could include stiffening members 410 or other means to prevent motion and/or kinking of the sleeve. The stiffening members 410, which may be made of a metal and/or polymer, may be oriented axially, as shown in FIG. 22, or they may be in a helical configuration or other geometry. This reinforcing should be configured so as to provide little or no interface for peristaltic motion to capture the sleeve and move it toward the pylorus. The sleeve should also be configured to resist or avoid forces that could be applied in a retrograde direction. Note that the retrograde force is caused by fluid flow. As the antrum undergoes peristalsis, food and secretions can flow retrograde. A slippery hydrophilic or other coating, as described herein, on the exterior of the sleeve in the antrum portion 406 may be preferred.

Figure 25:
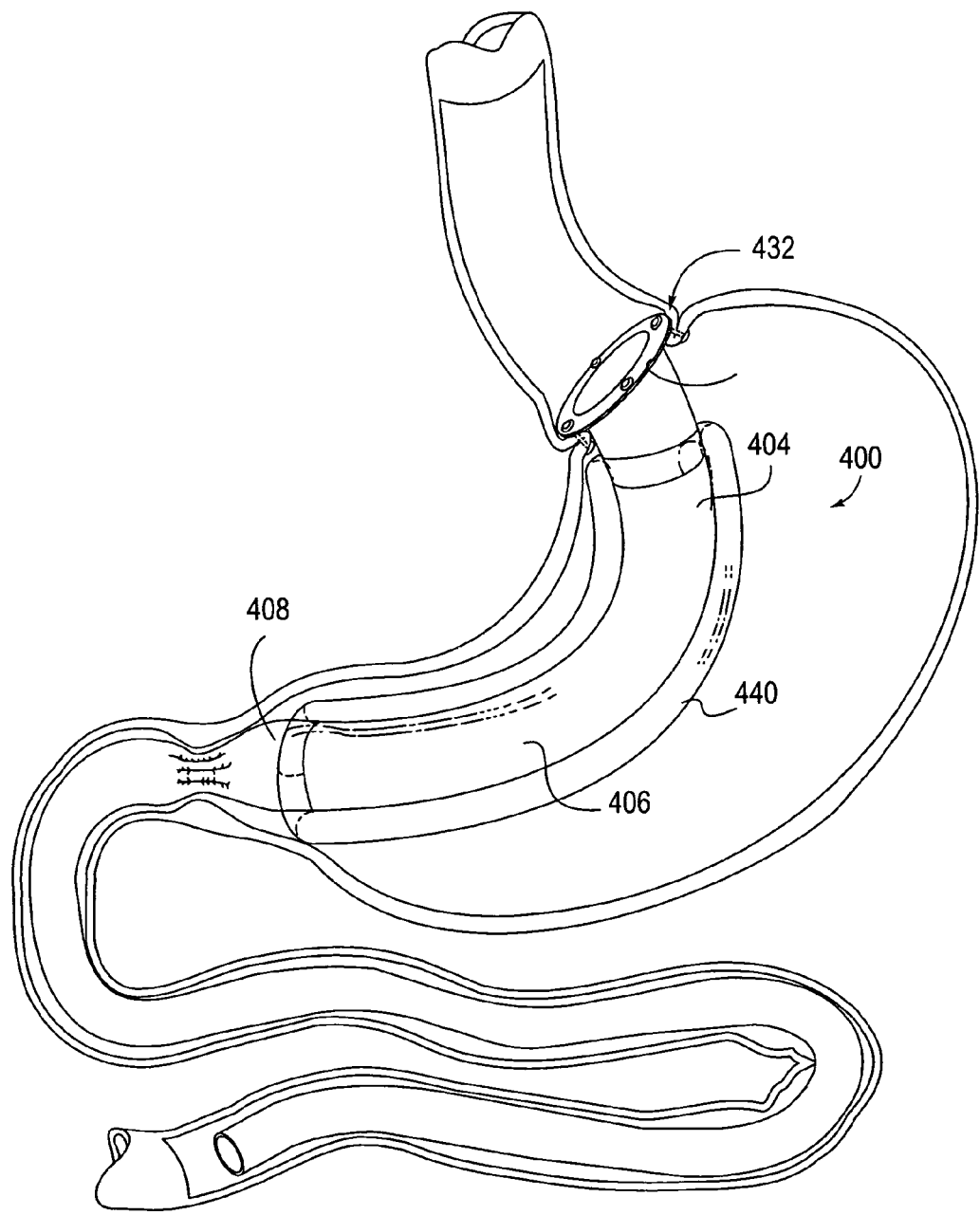
FIG. 25 illustrates a gastrointestinal sleeve device with a coaxial inflatable balloon surrounding the sleeve within the patient's stomach.

In an alternate construction illustrated in FIG. 25, the fundus portion 404 and/or the antrum portion 406 of the gastrointestinal sleeve device 400 may be stiffened using a coaxial inflatable balloon 440 that surrounds the sleeve. The coaxial balloon 440 may be inflated within the patient's stomach using a detachable tether and a self-sealing valve as described in the prior art (e.g. Pevsner). With proper selection of inflation media (compressible air or incompressible liquid) inflation pressure and inner and outer wall compliance, the coaxial balloon 440 can optionally provide axial stiffening, and can optionally serve to transmit peristaltic motion to the interior of the gastrointestinal sleeve device 400 to help ingested food transit through the sleeve.

Downstream of the antrum portion 406, the gastrointestinal sleeve device 400 may optionally include a pyloric anchor 414 at the upstream end 408 of the pylorus, as shown in FIG. 22. In one embodiment, the pyloric anchor 414 is configured as a perforated collar slidable along the exterior of the sleeve for custom fit to the patient. The outer circumference of the pyloric anchor 414 is optionally attached to the stomach lining at the upstream end 408 of the pylorus, then the slidable collar is cinched around or otherwise attached to the sleeve to anchor it in position. Perforations or channels in the collar allow gastric secretions to pass from the stomach into the pylorus without obstruction. The pyloric anchor 414 can be constructed from a variety of biocompatible materials with different properties. For example, fluoropolymers such as Teflon (Dupont) can be used to avoid ingrowth or, alternatively, polyester cuff materials (e.g. Dupont Dacron) can be used to encourage ingrowth if desired. As an alternative to attaching the pyloric anchor top the stomach wall, it can be constructed with sufficient stiffness and sized to be retained in the antrum of the stomach by being too large to pass through the pylorus.

An anchor placed in the antrum can also be used as a platform to support devices placed in the stomach. For example, combining such an anchor located in the antrum with the reinforced sleeve or coaxial balloon as described herein can be used to support an attachment ring and reduce the forces transmitted to the attachment at the stomach wall. Structures that are not a part of the gastric sleeve such as self-expanding wire meshes of NiTi or stainless steel could also be used where clinically indicated. Antral support structures could also be independent, as a sleeve anchor and could optionally be used to support other devices as described herein.

In certain embodiments, the sleeve is configured to open and to collapse as it passes through the pylorus to facilitate internal passage of food and external passage of gastric secretions and to minimize irritation and/or damage to the pylorus. Additionally, the gastrointestinal sleeve device 400 may optionally narrow slightly in diameter as it passes through the pylorus so that it facilitates passage of gastric secretions along the exterior of the sleeve through the pylorus when it is opened. This diameter may be on the order of 0.75-2.5 cm. The pylorus section 412 of the gastrointestinal sleeve device 400 must have enough wall flexibility or compliance to allow normal opening and closing of the pylorus and to avoid irritation of the pylorus. For example blow molded 90A durometer polyurethane of a wall thickness on the order of 0.005" or less will work in this manner. With this configuration one can optionally use the pylorus as a natural stoma by allowing the sleeve to be closed by the pylorus and then opened to allow passage of food when the muscles of the pylorus relax.

Conversely, in some patients it may be desirable to hold open the pylorus. In such cases where the device is configured for holding open the pylorus, it should also include means of draining gastric secretions, e.g. tubes or channels, along the exterior of the sleeve.

A collapsible or collapsed tubular gastrointestinal sleeve device can allow gastric and intestinal secretions to pass along its outer surface. Spiral reinforcing can facilitate passage of the secretions if the sleeve between the reinforcing is configured to form channels where secretions can flow between the reinforced sleeve and the wall of the intestine or pylorus with which it may be in contact. This could be of particular use in the pylorus where food in the sleeve could be competing with gastric secretions to pass through the pylorus outside the sleeve. In the case of a flaccid sleeve, whichever of the food or secretions has the higher pressure would pass through the pylorus. In the case of a spiral reinforced sleeve with channels or other means (e.g. tubular lumens passing through the pylorus and with openings both proximal and distal to the pylorus) of enabling passage of secretions along the pylorus, the food and secretions could pass at the same time.

The gastrointestinal sleeve device 400 continues below the pylorus and passes through the duodenum and into the jejunum. The duodenum portion 416 and the jejunum portion 418 may have a total length of approximately 50-200 cm, depending on the clinical needs of the individual patient and the judgement of the physician. Shorter lengths may be used if it is desirable for the sleeve to empty into the duodenum or proximal jejunum. Longer lengths can be used if it is desirable to have the sleeve empty in the distal jejunum or ileum. In certain embodiments, the sleeve 400 may be configured with a length of 100 cm as this is a standard length of the roux limb in a Roux-en-Y gastric bypass. A sleeve 400 with a length of approximately 500 cm or more can be used to perform a nonsurgical biliopancreatic diversion for achieving results similar to a Scopinaro procedure. In one configuration, the gastrointestinal sleeve device 400 has an approximately constant diameter of approximately 0.75-2.5 cm through the duodenum portion 416 and the jejunum portion 418. This diameter is less than the internal diameter of the small intestine through these sections to allow free flow of gastric, biliary, pancreatic and intestinal secretions along the outside of the sleeve. This diameter can be optimized for individual patients where a smaller diameter may be tolerated better and a larger diameter may be superior regarding the passage of food. Collapsibility may allow use of larger diameter sleeves, while sleeves of smaller diameter and greater resilience may be clinically indicated to minimize irritation.

Past the pylorus and past the duodenum, the gastrointestinal sleeve device 400 may include means to couple peristaltic muscular action of the intestine and use it to apply antegrade tension to the sleeve. One or more rings 420 in the sleeve may provide this coupling. The rings 420 may include a metallic spring to return the ring to its circular shape if collapsed by either the installation procedure or by peristaltic action of the intestine. The rings 420 may be positioned in the jejunum, as the duodenum exhibits little or no peristalsis. Alternatively, the exterior of the sleeve may be configured with small bumps or other features to provide a small amount of friction for coupling with the peristaltic muscular action of the intestine.

A balance can be struck between friction and lubricity on the exterior of the sleeve. There should be enough friction so that peristalsis will act to straighten the sleeve and apply a small amount of tension to keep it in place. Too much friction, however, will allow the intestinal wall to "climb" up the exterior of the sleeve due to peristalsis, which would generally not be desirable. For example, this balance can be achieved using a smooth polyurethane sleeve with PHOTO-LINK LUBRICIO COATING (Surmodics Inc.) or other**. However, in some clinical situations it may be desirable to achieve this end result. This can be achieved by using rings or other means of mechanically coupling the sleeve with the intestinal peristaltic action. In this case the intestine essentially crawls up the sleeve and takes on a pleated bellows like configuration. This can have the result of effectively lengthening the sleeve, as food would now exit the sleeve at a more distal location within the intestine.

It may be desirable in some clinical circumstances to provide a temporary peristalsis coupling that can straighten the sleeve for a period of time after insertion and not couple with the peristaltic action after this period. This will tend to reduce the climbing of the intestine and can allow any previous change in the position of the intestine to return to normal. This can be accomplished by using a biodegradable coupling means such as a dissolvable peristalsis ring or a high friction coating that comes off, leaving a lubricious surface. A balloon that detaches or deflates could be another means of accomplishing this end. For example, the balloons and other features in FIGS. 32A, 32B and 32C can be configured for this application. Such balloons can be made self-deflating by the inclusion of a dissolvable portion or by inflation with a hypo-osmolar fluid combined with use of osmotically active balloon membrane. In this event the inflation fluid will escape the balloon through the membrane due to the osmotic imbalance between the inflation fluid and the contents of the intestine.

Optionally, the gastrointestinal sleeve device 400, along some or all of its length, may be configured by means of controlled wall thickness or reinforcing so that, if the sleeve is folded or kinked, open channels 442 will be maintained, as shown in FIGS. 26A, 26B and 26C. In this case locally increased wall rigidity may also be used to control the fold preferences of the sleeve.

Alternatively, the gastrointestinal sleeve device 400, along some or all of its length, may include axial channels 444, as shown in FIGS. 27A and 27B. The axial channels would be configured so that, in the event of a fold or kink in the sleeve, the lumen of the sleeve remains patent and open. These channels can also be formed by peaks and valleys in a constant thickness sleeve wall in addition to the manner diagrammed.

In one embodiment of the gastrointestinal sleeve device 400, the gastric and intestinal portions of the sleeve are constructed to be normally collapsed to a somewhat flattened configuration when in a rest position, such as is shown in FIG. 26B, 26C or 27B. This can minimize the potential for irritation of the mucosa in the stomach, the pylorus and the intestine and other structures such as the ampula of Veder. The sleeve may open or expand to a circular cross section, as shown in FIG. 26A or 27A, for the passage of ingested food. Thus the stomach and intestinal walls would not be constantly subjected to stimulation, which could result in increased secretion and/or peristaltic action. Alternatively, some or all of the gastric and intestinal portions of the sleeve may be constructed to remain in an open or expanded configuration when in a rest position and to easily collapse when subjected to external pressure, for example to allow passage of digestive secretions along the exterior or the sleeve. This second option may also include diametric sizing based upon the clinical desirability of stimulating the passage wall (similar diameter to passage) or not (smaller diameter than passage).

The gastrointestinal sleeve device 400 is generally impermeable along its entire length to isolate ingested food from digestive secretions. However, it may be desirable to have the gastrointestinal sleeve device 400 having semipermeable or controlled permeability properties along some or all of its length to allow absorption of certain nutrients at the appropriate location in the stomach or intestine in order to avoid malabsorption complications while still limiting caloric absorption. For example, in the duodenal portion it would be beneficial to allow Iron and B-12 to exit the sleeve so that it can be absorbed through the intestinal wall.

FIG. 28 illustrates an optional one-way valve 450 feature of the gastrointestinal sleeve device. Positioning of valves may be patient dependent. One clinically significant location could be at or near the transition from the duodenum, where there is little or no peristaltic action and the jejunum where peristalsis occurs. Other significant locations include the distal opening of the device (to prevent flow into the sleeve), the proximal opening of the device (to prevent reflux into the esophagus) and at or near the pylorus (to help ingested food pass through the pylorus and duodenum). A valve upstream of a restriction may also help, in combination with contractions or peristalsis of the stomach, to force ingested food through the restriction.

Figure 29:
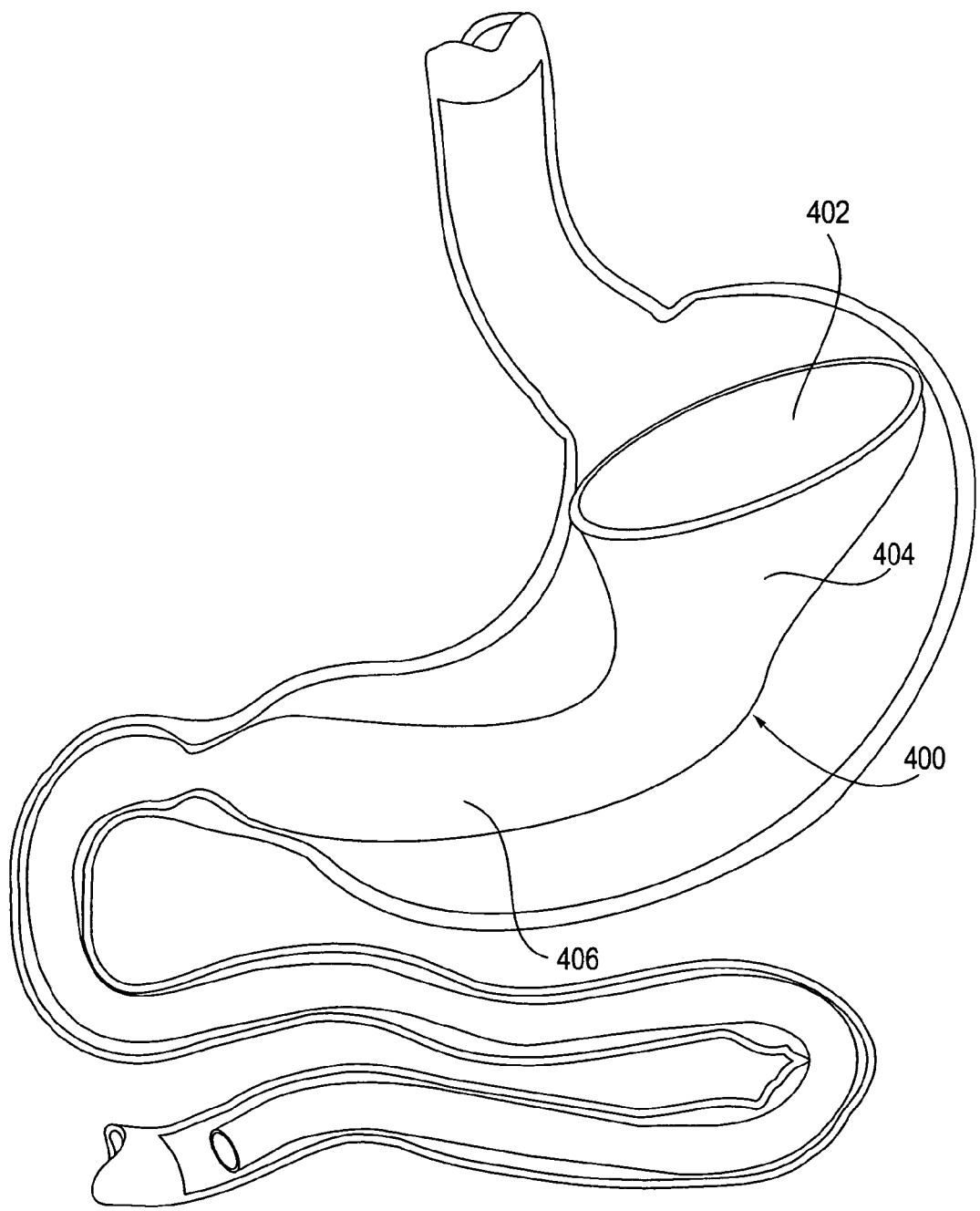
FIG. 29 illustrates another example of a gastrointestinal sleeve device deployed within a patient's gastrointestinal tract for treating morbid obesity.

FIG. 29 illustrates another example of a gastrointestinal sleeve device 400 deployed within a patient's gastrointestinal tract for treating morbid obesity. In this embodiment, the proximal opening 402 of the gastrointestinal sleeve device 400 has a flared opening that is configured for attachment at the cardiofundal border. Attachment at the cardiofundal border confers different advantages to the gastrointestinal sleeve device 400, as described above. Attachment can be made using any of the methods described herein. The proximal opening 402 has a diameter of approximately 2-10 cm, which smoothly tapers down to a diameter of approximately 1.5-4.0 cm through the fundus portion 404 and the antrum portion 406 of the sleeve. The remainder of the gastrointestinal sleeve device 400 may be configured similarly to the embodiment described in connection with FIG. 22.

Figure 30:
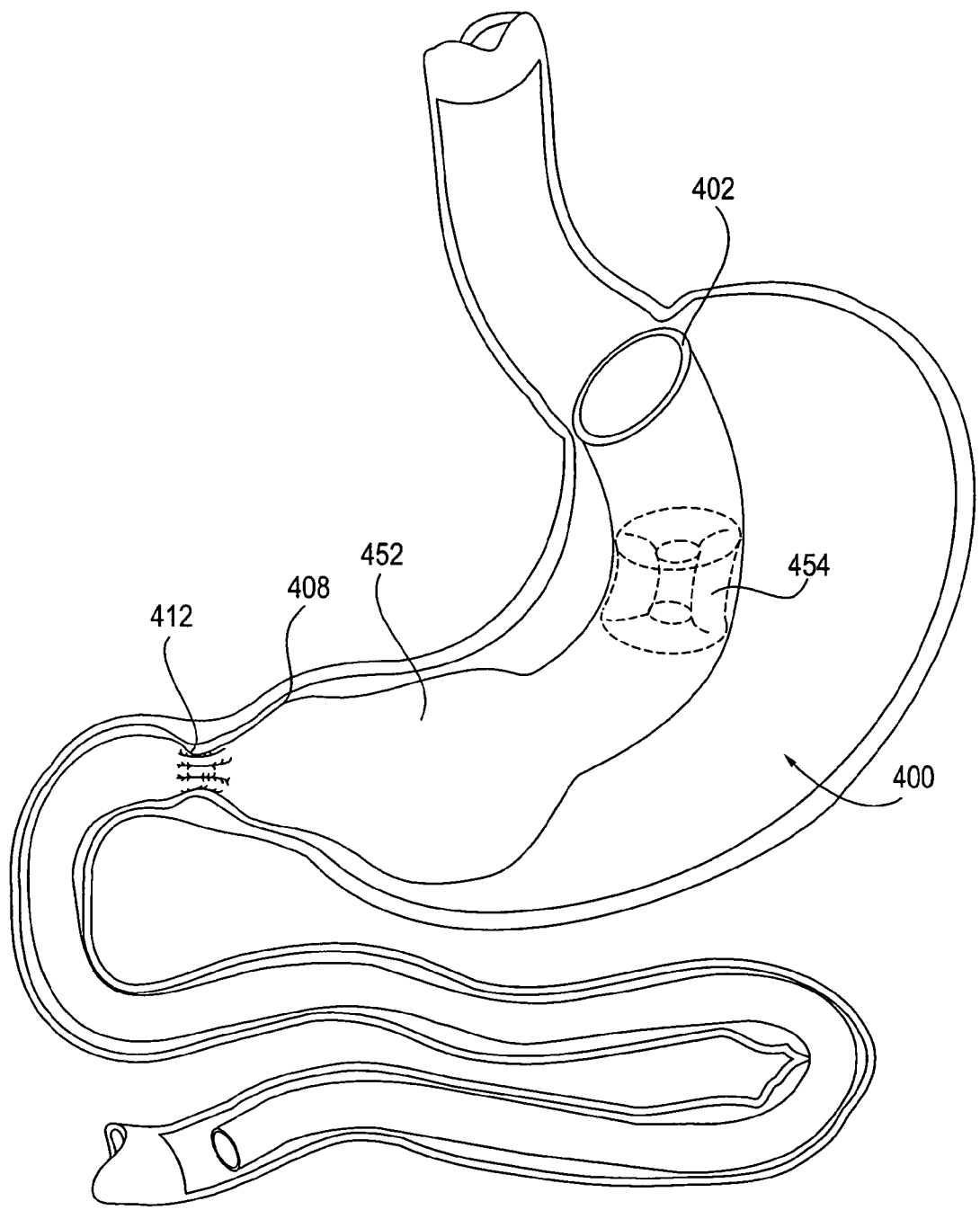
FIG. 30 illustrates another example of a gastrointestinal sleeve device having a reservoir located above the patient's pyloric sphincter.

FIG. 30 illustrates another example of a gastrointestinal sleeve device 400 having a reservoir 452 located above the patient's pyloric sphincter. The reservoir 452 allows ingested food to accumulate in the antrum of the stomach and to apply pressure against the pylorus, which may contribute to periodic opening of the pyloric sphincter for proper emptying of the stomach contents. Alternatively or in addition, a reservoir 452 may be positioned elsewhere in the gastrointestinal system, for example just below the GEJ, to provide a sensation of fullness and satiety. FIG. 30 also illustrates the optional feature of a restriction 454 in the gastrointestinal sleeve device 400 between the proximal opening 402 and the upstream end 408 of the pylorus. The restriction 454 can be provided by a simple narrowing of the sleeve 400 or, as illustrated in this embodiment, can be provided by a stoma device 454 positioned within the lumen of the sleeve 400. The stoma device 454 can be an adjustable stoma device, a smart stoma or any of the stoma devices described herein. Positioning of the stoma device relative to the proximal sleeve opening can be selected as clinically indicated to provide a reservoir for food proximal to a restriction that is appropriate for the desired weight loss. In other embodiments of the gastrointestinal sleeve device 400, sufficient reduced volume or resistance to ingestion of food for encouraging weight loss may be provided by the length and diameter of the gastric portion of the sleeve 400** without the need for a stoma device or other restriction other than the use of the pylorus as a natural restriction as described above.

When the pylorus is used as a natural stoma to control food flow, an electrical stimulation system can optionally be used to control the opening and closing of the pylorus. This system could include one or more electrodes for stimulating the pylorus, a stimulator (including power source and controlling electronics) and one or more optional sensing electrodes.

Figure 31:
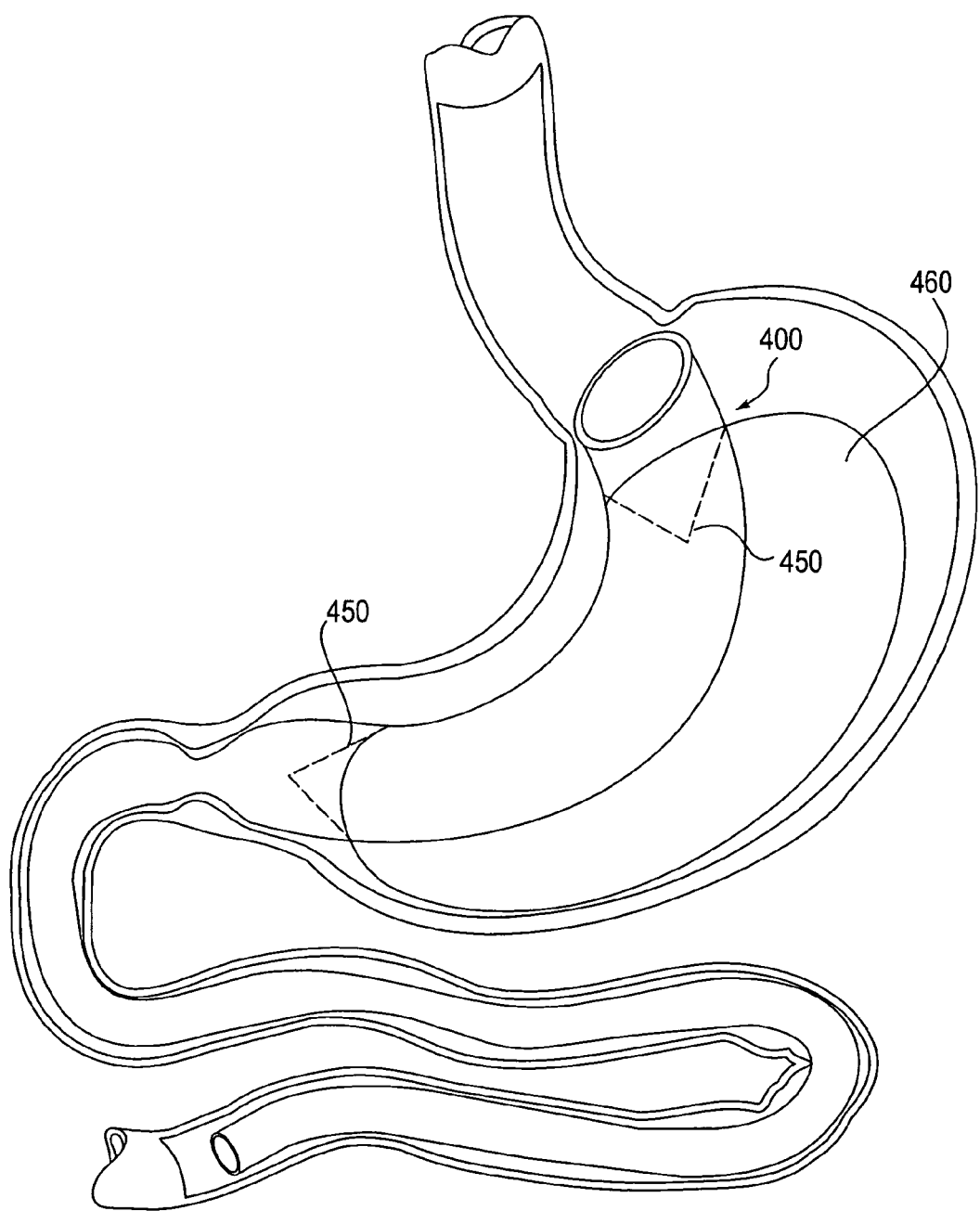
FIG. 31 illustrates another example of a gastrointestinal sleeve device having an inflatable gastric balloon.

FIG. 31 illustrates another example of a gastrointestinal sleeve device 400 having an inflatable gastric balloon 460 to enhance satiation by taking up volume in the stomach. The gastric balloon 460 may be arranged coaxially around the sleeve or it may be configured to inflate preferentially toward the greater curvature of the stomach, as shown in FIG. 31. The gastric balloon 460 may be inflated within the patient's stomach using a detachable tether and a self-sealing valve. Alternatively, the gastric balloon 460 may be made self-inflating by having a hyperosmolar material within the gastric balloon 460 and an osmotically active balloon membrane (complete or partial). The gastric balloon 460 can be configured to transmit peristaltic motion to the interior of the gastrointestinal sleeve device 400 to help ingested food transit through the sleeve as described above. Optionally, the sleeve under and around the gastric balloon 460 may be combined with one or more one-way valves 450 positioned upstream and/or downstream of the gastric balloon to assist peristaltic action to urge ingested food through the sleeve.

FIGS. 32A, 32B, 32C and 32D illustrate optional features to assist in the deployment of the gastrointestinal sleeve device within a patient's gastrointestinal tract. FIG. 32A illustrates a gastrointestinal sleeve device 400 having an inflatable balloon 462 on its distal end. The balloon 462 is inflated via an inflation lumen 464 that extends through the gastrointestinal sleeve device 400. The inflation lumen 464 can be incorporated into the wall of sleeve 400 or it can be in a coaxial tubular tether that can be separated from the sleeve 400 to deflate the balloon 462 once the sleeve is fully deployed within the patient's intestine. The balloon 462 is inflated after the distal end of the sleeve 400 is past the pylorus and the inflated balloon is carried distally by peristaltic action of the intestines. Once the sleeve is fully deployed within the patient's intestine, the balloon 462 can be deflated. The balloon can alternately be inflated prior to insertion into the body, thereby not requiring an inflation lumen the length of the device, and can either deflate naturally or have an active means of deflation as described herein. In an alternate embodiment the means to attach the balloon to the distal sleeve would be biodegradable and after the degradation of the attachment means the balloon would pass through the digestive tract naturally.

FIG. 32B illustrates a gastrointestinal sleeve device 400 having a sponge or foam member 466 on its distal end. The use of a foam member 466 simplifies the gastrointestinal sleeve device 400 in that an inflation lumen is unnecessary to expand the foam member 466. The foam member 466 is allowed to expand after the distal end of the sleeve 400 is past the pylorus and the expanded foam member 466 is carried distally by peristaltic action of the intestines. The foam member 466 can be biodegradably attached, as described above, or made of a dissolvable or digestible material so that it disappears after it has served its purpose.

FIG. 32C illustrates a variation of the gastrointestinal sleeve device 400 of FIG. 32A, wherein the inflatable balloon 462 is mounted on a flexible tail 468 formed on or attached to the distal end of the sleeve.

FIG. 32D illustrates a variation of the gastrointestinal sleeve device 400 of FIG. 32C, wherein the inflatable balloon is replaced with a magnet 470. This magnet 470 can be used in conjunction with other magnets, to guide the deployment of the intestinal sleeve. Matching guide magnets of opposing polarity can be used internal to the intestine in conjunction with an endoscope, within the abdomen external to the intestine in conjunction with a laparoscope or external to the body in a manner similar to that described by Gabriel in U.S. Pat. No. 5,431,640. In an alternate embodiment the means to attach the magnet to the distal sleeve would be biodegradable and after the degradation of the attachment the magnet would pass through the digestive tract naturally.

In summary, the present invention provides a gastrointestinal sleeve device which allows separation of ingested foods and liquids from digestive secretions through the stomach and past the duodenum and optionally into the jejunum or ileum. This is of particular significance because gastric acids are neutralized by bile and duodenal secretions. This prevents digestion from gastric acid taking place even if the food and gastric secretions are allowed to mix at a later point in the intestines.

Figure 33:
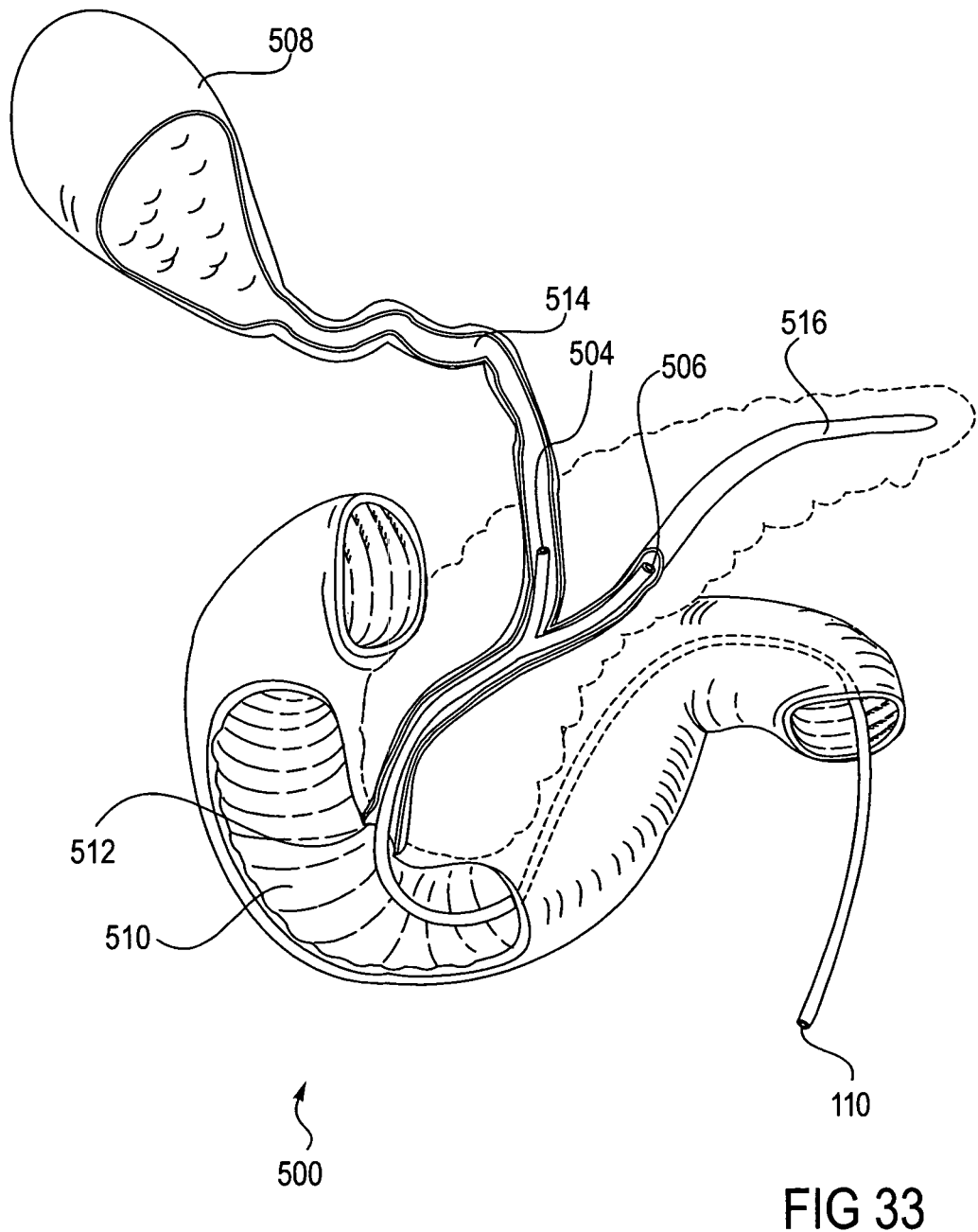
FIG. 33 shows a cutaway view of a portion of a human digestive system, with an embodiment of a biliopancreatic diverter tube in situ.

FIG. 33 shows a cutaway view of a portion of a human digestive system, with an embodiment of the biliopancreatic diverter tube 500 in situ. The biliopancreatic diverter tube is comprised of a tube that diverts bile salts released from the gallbladder 508 and pancreatic juices from the pancreas (shown with dotted lines) from being discharged into the duodenum at the duodenal papilla 512, and instead allows for discharge of these fluids farther downstream within the small intestine 510 from the distal tip 502 of the device.

The proximal end of the embodiment of FIG. 33 is bifurcated, so that the proximal end of the device has two branches, a bile duct branch 504 that extends into the common bile duct 514, and a pancreatic duct branch 506 that extends into the pancreatic duct 516.

Figure 34:
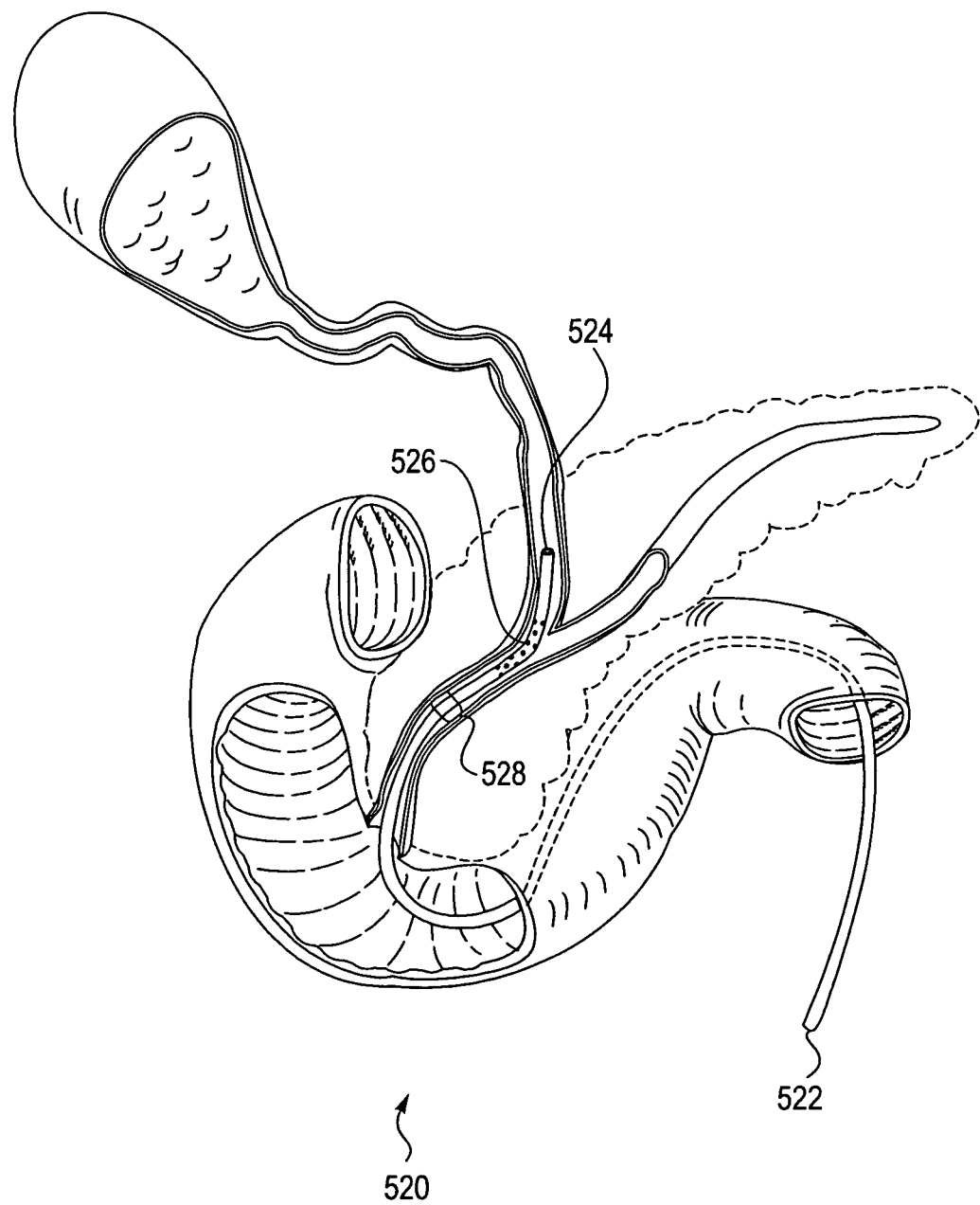
FIG. 34 shows an alternative embodiment of the biliopancreatic diverter tube in situ.

FIG. 34 shows an alternative embodiment of the biliopancreatic diverter tube 520 where the proximal end is not bifurcated. Instead, the proximal tip 524 extends into the common bile duct as shown, and the proximal end has an array of inlet ports 526, or a single larger inlet port, for collecting pancreatic juices from the pancreatic duct. The pancreatic juices and bile salts collected at the proximal tip 524 and the array of inlet ports 526 flow through a common lumen connecting to the distal tip 522 of the diverter tube 520. The pancreatic juices and bile salts are prevented from avoiding the diverter tube by an annular stop member 528 that forms a seal between the device 520 and the surrounding duct. Alternatively, the tube may be sized for a tight fit in the duct, obviating the need for the annular stop member.

In addition to the two embodiments shown, other configurations may be necessitated by anatomical variations.

In an alternative embodiment, the device 520 could have a dual lumen aligned coaxially, so that an inner lumen would collect bile salts from the proximal tip 524, perhaps tapered so that only the inner lumen's proximal orifice is exposed at the proximal tip, and the outer lumen would collect pancreatic juices from the array of inlet ports 526 or single inlet port. Alternatively, the device 520 could have a dual lumen aligned side-by-side, or in some other arrangement.

Alternatively, the proximal tip 524 of the device could be placed within the pancreatic duct, and the array of inlet ports 526 or single inlet port would collect bile salts.

The portion of the device in the intestine may be semipermeable, allowing certain materials from the intestine to pass into the tube, such as acids. Alternatively, the portion of the device in the intestine may only allow certain materials from inside the device to permeate out, such as bases to neutralize stomach acids. It should be noted that the duodenum also excretes bases to neutralize stomach acids.

The lumen of the diverter tube is preferably of a diameter to allow flow of bile and pancreatic secretions the tube. Optionally, the diverter tube may be constructed with flexible walls to allow peristaltic motions of the intestinal wall to effect movement of bile and pancreatic juices through the diverter tube.

The interior and/or exterior of the diverter tube can optionally be formed from a relatively inert material such as a polyolefin (e.g. polyethelene) or a fluoropolymer (e.g FEP or PFA) or coated with a low friction material (e.g. a hydrogel) to reduce friction of bile and pancreatic juices (interior) and reduce native luminal irritation (exterior).

The interior of the diverter tube can optionally include a coating to resist crystallizing and/or deposition of bile and pancreatic secretions which could obstruct flow through the tube.

The wall of the diverter tube may be reinforced with rings or a spiral made of wire and/or plastic. Optionally the diverter tube can include means for stabilization at the distal end such as a brush (as described by Berry, U.S. Pat. No. 5,306,300), weight, or inflatable balloon.

Figure 35:
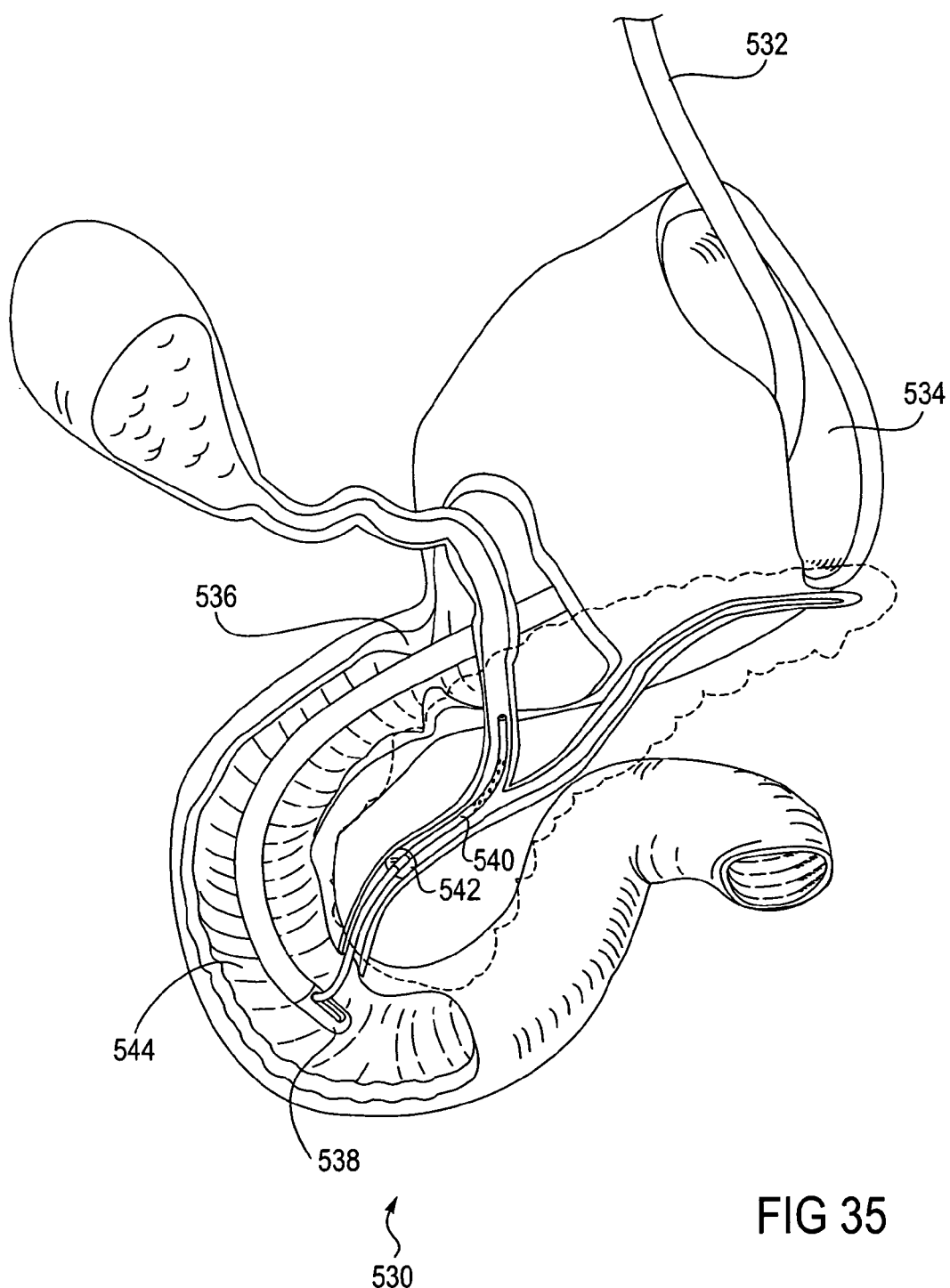
FIG. 35 shows a method of delivering an embodiment of the biliopancreatic diverter tube.

FIG. 35 shows an embodiment of the biliopancreatic diverter tube 530 being delivered using a transesophageal approach under visualization with a flexible endoscope 532. The endoscope 532 is passed through a patient's mouth, down the esophagus, into the stomach 534, past the pyloric sphincter 536, and into the duodenum 544. The distal end 538 of the endoscope is positioned adjacent to the duodenal papilla. A guidewire is then passed through the endoscope and out of its distal end 538, into the opening of the biliopancreatic duct at the duodenal papilla, and advanced within the duct or ducts where an embodiment of the biliopancreatic diverter tube will eventually be positioned. An embodiment of the biliopancreatic diverter tube 540 is then passed over the guidewire. The guidewire is then removed.

Optionally, laparoscopic or open surgical techniques may be used to assist in or complete the implantation of the device.

The proximal end of the device may be anchored in place with a variety of means. One means of anchoring the device is with an annular stop member 542, as shown, that may be inflated to make contact with the surrounding walls of the duct. Other means for anchoring an embodiment of the biliopancreatic diverter tube include integrating a self-expanding stent-type anchor on the proximal end of the device. Such a stent may be coated with a dissolving material to delay expansion of the stent portion of the device until it is properly seated. Alternatively, a balloon expandable stent-type anchor may be used, or the proximal end of the device may be barbed or toggled, or the tube itself could be self-expanding, or the proximal end may be formed with a pigtail curve, or the proximal end could be manufactured of a material that swells up with moisture, for example a hydrogel, hydromer or other materials as described herein. In addition, the outer surface of the proximal end of the device may be covered with a fabric to facilitate ingrowth of tissue to secure the device in place. Some of these attachment means will require the proximal tip of the device to be placed in the gallbladder while others will attach within the bile duct. Stent-type anchors can also be configured for use as inlet ports to allow entry of pancreatic secretions into the tube.

Once anchored in place, the distal end of the device may be deployed from the endoscope. The endoscope could be pushed downstream within the small intestine as an embodiment of the biliopancreatic diverter tube is pushed out of the distal end of the endoscope. Alternatively, the endoscope could remain stationary, or even be retracted as an embodiment of the biliopancreatic diverter tube is pushed out the distal end of the endoscope, allowing peristalsis to then carry the distal end of the device downstream.

Typically, the device will be 50-510 cm in length and have an inner diameter of 1.0-7.5 mm. The device could be made from a silicone, polyurethane, polyethylene or a fluoropolymer such as PFA. Device coatings could include hydrogels such as PVP (polyvinylpyrolidone or other coating such as parylene as described herein. Stent-type retention components could be stainless steel or NiTi.

Preferably, the diverter tube is constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted intestinal sleeve can be verified noninvasively.

The biliopancreatic diverter tube 500 is an alternative to dividing intestine as described in FIGS. 17-20. It should be noted that the biliopancreatic diverter tube does not isolate ingested food from the gastric juices, but neutralization of acid and action of biliopancreatic secretions is delayed.

The biliopancreatic diverter tube is intended for use in conjunction with other surgical and/or interventional procedures for a combined treatment, for example using any of the devices and methods for treatment of morbid obesity described herein.

In one aspect, the invention describes a number of fastener systems that can be used in situations where it is desirable to replace a portion of the fastening system, and any device or devices held in place by the fastener, while other portions of the system remain in place.

In particular, these systems are useful in attaching devices to the inside of hollow organs such as the stomach. Though these fastening systems generally consist of two or three components at each attachment point, various components can be combined or connected. Some of the fastener systems can be applied to attachment ring systems and stomal ring clip systems as described herein.

Figure 36:
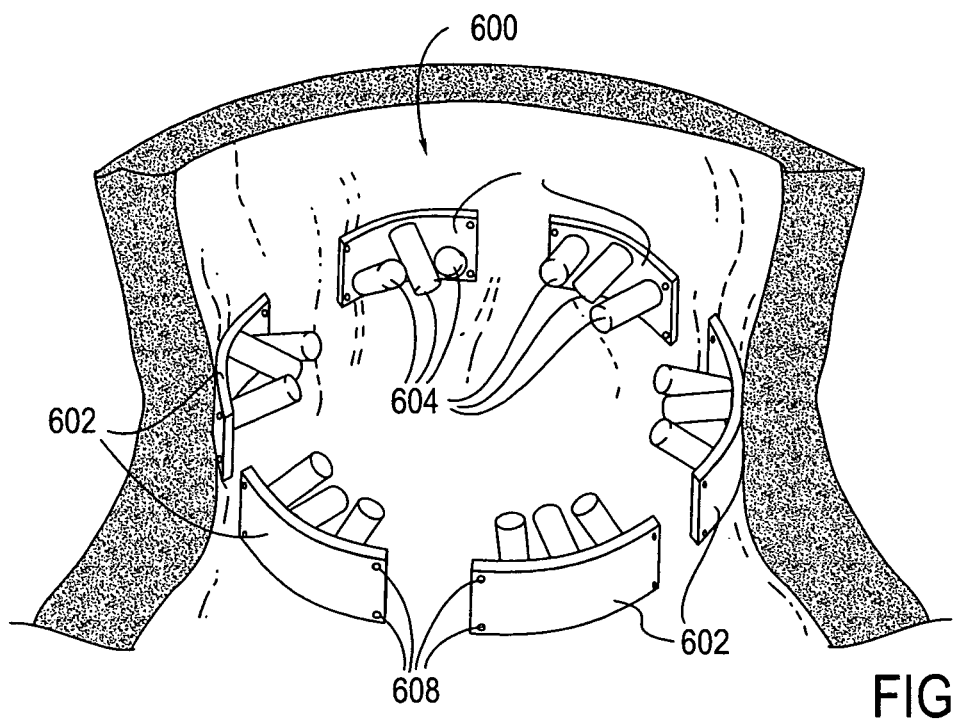
FIG. 36 illustrates, several fastener segments, each segment having gripping fingers for attachment of a surgical appliance within a hollow organ in a patient's body.
Figure 38:
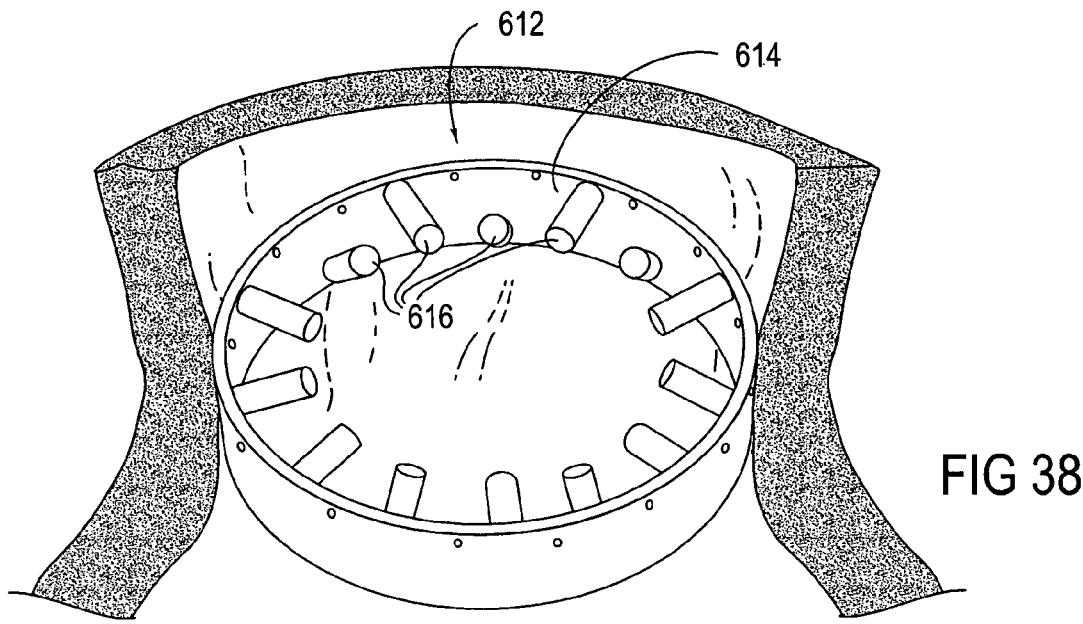
FIG. 38 shows an alternative fastener system comprising an annular shaped member having gripping fingers for attachment of a surgical appliance within a hollow organ in a patient's body.

FIG. 36 illustrates a fastener system 600 with several fastener segments 602, each segment having gripping fingers for attachment of a surgical appliance. As shown in FIG. 36, six individual segments 602 are positioned within a passageway of the body along a plane that lies approximately perpendicular to the passageway, such that collectively they form an annular mounting surface along the perimeter of the passageway with grasping fingers 604 extending away from the perimeter of the passageway, for attachment with another device. The fasteners segments 602 and the grasping fingers 604 are preferably constructed of a biocompatible metal or polymer or a composite or combination thereof. Suitable materials include, but are not limited to, stainless steel, titanium, NiTi alloys, cobalt alloys such as Elgiloy or MP35, elastomers such as silicone or polyurethane and other rigid or flexible plastics. In some embodiments, it may be desirable to construct a part or all of the fastener of a biodegradable or bioresorbable material. In certain applications, it may be advantageous to have individual fastener segments rather that one integrated device as shown in FIG. 38. That decision may be informed by the following characteristic, the fastener segments of FIG. 36 may be more flexible than the device of FIG. 38 because they can move more independently of one another, and thus do not transmit forces to one another.

Figure 37:
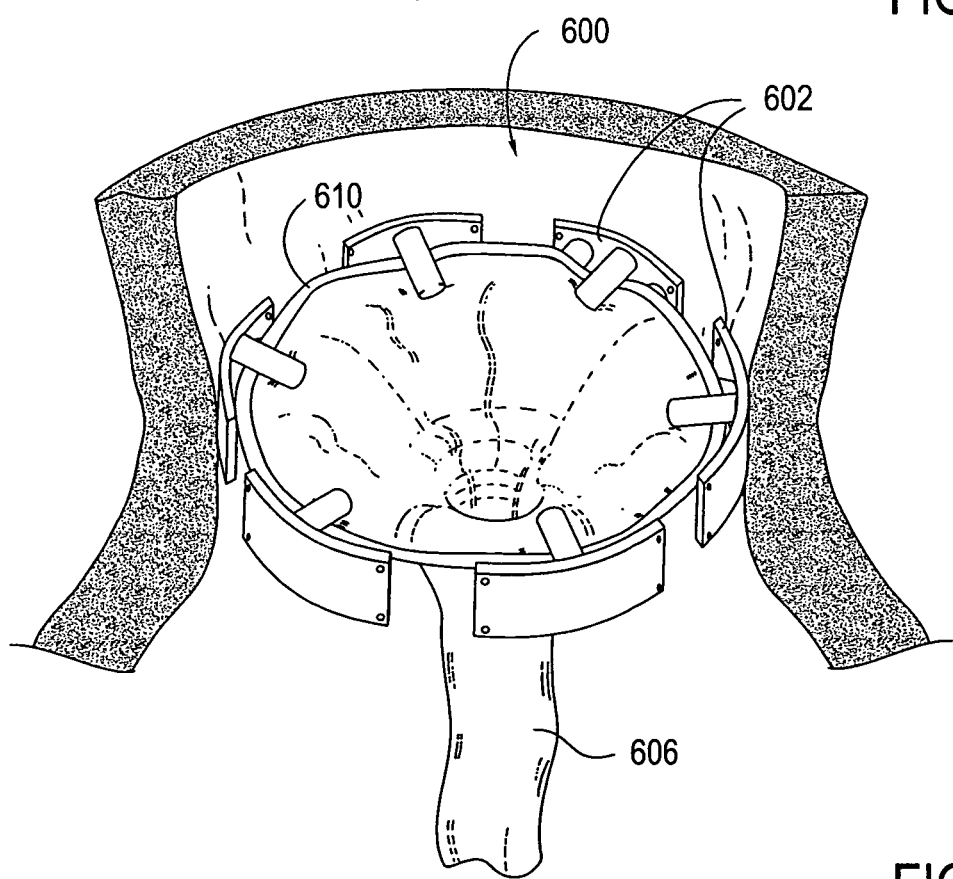
FIG. 37 illustrates a gastrointestinal sleeve device installed within a patient's stomach using the fasteners of FIG. 36.

FIG. 37 illustrates a sleeve member 606 that has been attached to the annular mounting surface created by the fastener system 600. When used within the stomach, the sleeve member 606 and related components and features function as a conduit for food within the gastrointestinal tract that essentially restricts the flow of food downstream with a narrow opening. These devices encourage weight loss by limiting the rate at which food can be consumed, and by contributing to the feeling of being full, or satiated and other mechanisms. It should be noted that although the sleeve member restricts the flow of food, the flow of food is not substantially inhibited by the fastener segments. The fastener segments 602 do remain attached to the perimeter of the passageway, and only slightly protrude into the passageway. In addition, the fastener segments 602 do not rely on folded tissue for anchoring purposes, and this allows the inner diameter of the passageway to retain its original diameter. In some situations it is clinically preferable that this diameter is the same as the resting diameter of the hollow organ so as to transmit minimal force and result in little or no deformation of the wall from its resting position.

An example of a method of use that may be used with any embodiment of the fastener system of the present invention as described herein, the fastener or fasteners may be implanted into the stomach or another hollow organ and allowed to heal for a period of days or weeks. After sufficient healing time, a surgical appliance, such as a gastrointestinal sleeve device, may be installed by attaching it to the fastener system. Alternatively, the surgical appliance may be installed at the same time as the implantation of the fasteners. In another exemplary method, a first surgical appliance, such as a gastrointestinal sleeve device, may be initially installed (either immediately or after a period of healing as described above.) Subsequently, the first surgical appliance may be removed and, if desired, replaced with a second surgical appliance. For example, a first gastrointestinal sleeve device with an initial stoma size may be replaced with a second gastrointestinal sleeve device with a larger or smaller stoma size. This could be used to modify the treatment regimen as the patient gradually becomes accustomed to consuming less food or it may be used to modify a treatment regiment to obtain better effective weight loss. Alternatively, gastrointestinal sleeve devices with incrementally larger restrictive stoma sizes may be installed at the end of a successful treatment regimen to wean the patient back to normal dietary guidelines for maintaining the weight loss.

The fastener system of the present invention may also be used for attachment and subsequent removal or replacement of a valve or restriction at the gastroesophageal junction for treatment of gastroesophageal reflux disease. In the alternative, the fastener system may be used in other hollow organs for attachment and subsequent removal or replacement of other surgical appliances, as described above.

Although FIG. 36 shows six individual fastener segments 602, it should be noted that as few as two segments could be used, more than six could be used, and that between four and six segments can be preferred. Each segment 602 is shown having three gripping fingers 604, each oriented approximately perpendicular to the surface of the passageway, with two opposed relative to the third so that another device can be snapped between opposing fingers. The fingers 604 are flexible, yet rigid enough to hold a device 606 in place, such as shown in FIG. 37, while also allowing that device to be removed at some later time, perhaps to be replaced by another device.

The individual fastener segments 602 of FIG. 36 can be attached to the body passageway in several ways. As shown, each segment 602 can be attached with sutures that pass through holes 608 positioned in each corner of each fastener segment. Alternative to sutures, wire, a staple, rivet or other type of fastener may be passed through each hole. In addition, the surface of each segment adjacent to the body's tissues may be coated with tissue growth promoting materials, such as Dacron felt or mesh, to improve the attachment of the device to the body. Tissue growth promoting materials may be used in conjunction with all embodiments herein to improve attachment. The embodiment shown in FIG. 36 is preferably configured so that its installation does not narrow the passageway of the organ.

One skilled in the art can envision a corresponding insertion tool, which will temporarily deform the annular ring 610 or other attachment surface of the device 606 to allow facilitated passage of the device 606 over the grasping fingers 604 of FIG. 36. One can also imagine that by cutting the annular ring 610 of the depending device 606 it could easily be removed.

FIG. 38 shows an alternative embodiment of a fastener system 612 comprising an annular shaped member 614 having gripping fingers 616 for attachment of a surgical appliance 606 within a hollow organ in a patient's body. The annular member 614 and the grasping fingers 616 are preferably constructed of a biocompatible metal or polymer or a composite or combination thereof. Suitable materials include, but are not limited to, stainless steel, titanium, NiTi alloys, cobalt alloys such as Elgiloy or MP35, elastomers such as silicone or polyurethane and other rigid or flexible plastics (e.g. polyolefins or fluoropolymers). In some embodiments, it may be desirable to construct a part or all of the fastener of a biodegradable or bioresorbable material. The fastener shown here may be configured as a single component, and this feature means that it is more rigid within the body compared to an embodiment comprising two or more fastener segments. This feature may be desirable in certain applications, such as for use within the circulatory system. However, when the device has portions made of a highly flexible material, such as a low durometer silicone material, it can be made stretchable or deformable so that it can move with motion of the wall of the passageway, yet still maintain a grasp on any attached device with its fingers which are preferably made from a less elastic or rigid material such as a higher durometer silicone, a rigid plastic or metal such as stainless steel or titanium.

In an alternative embodiment, the fastener system shown in FIG. 38 may be designed so that it is essentially the fastener system of FIG. 36 held together by bioresorbable material as polyglecaprone (Monocryl, Ethicon), polygalactyn (Vycril, Ethicon) or other known in the art, thus facilitating installation. In this configuration, the one piece device of FIG. 38 could be installed relatively easily compared to the multi-piece device shown in FIG. 36, and also enjoy the flexibility of the device of FIG. 36 once the bioresorbable material has dissipated.

The embodiment shown in FIG. 38 is preferably configured so that its installation does not narrow the passageway of the organ. The annular dimension is sized so that when the device is attached to the hollow organ it essentially fits into the organ with little or no stress on the organ walls. The passageway of the organ substantially retains its original diameter.

Figure 39:
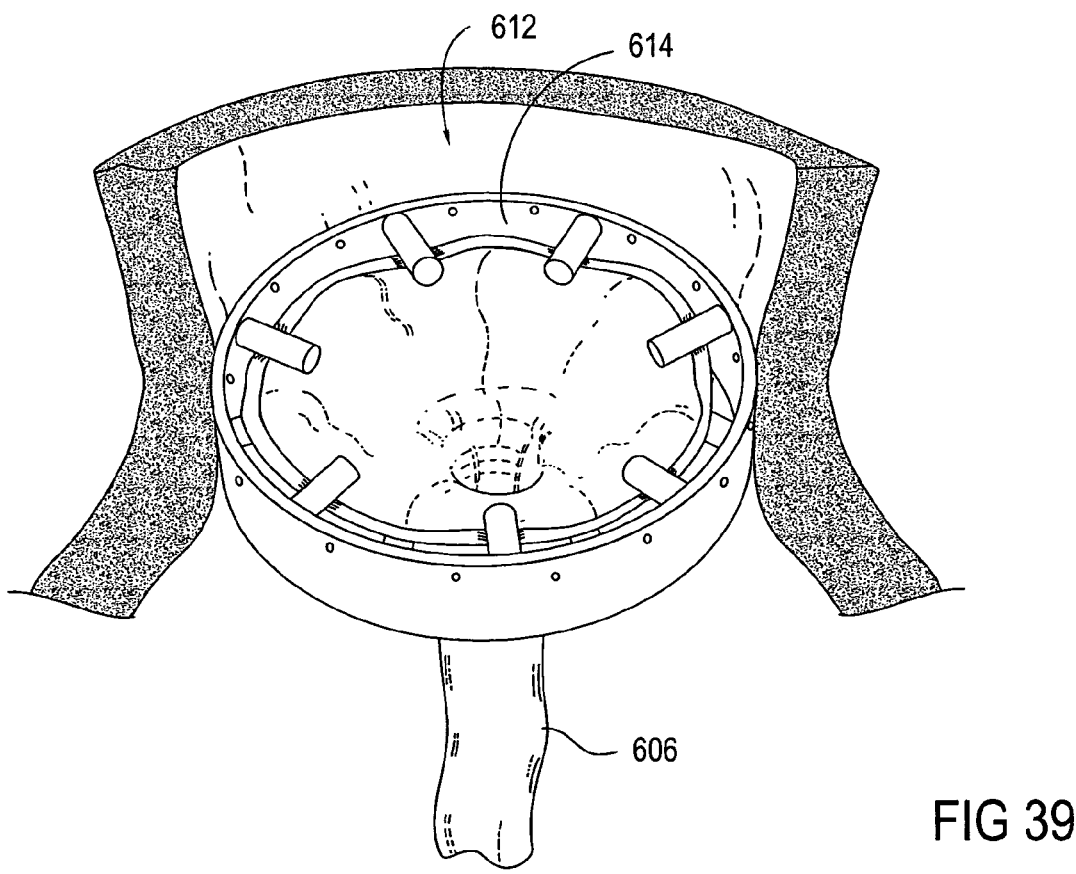
FIG. 39 shows the device of FIG. 38 with a surgical appliance attached.

FIG. 39 shows the fastener system 612 of FIG. 38 with a surgical appliance 606 attached. The means of attachment shown in FIG. 39 with the use of fingers 616 is just one of many possible means of attachment. For example, the device of FIG. 38 could be reconfigured so that it can accommodate a bayonet mount (a fitting engaged by being pushed into a socket and twisted), wherein the sleeve member could be pushed into a socket formed by the annular shaped member and then twisted. Also, an interference type of fit could be used wherein the sleeve member, for example, could be attached to the annular member by simply resting over the annular member because the sleeve member has a larger inner diameter at its proximal opening than the inner diameter of the annular member. The fitting may not alter the original diameter of the passageway. The engagement means would be configured to secure the depending device to an attachment device that could be flexible, deformable and with a variable opening diameter. In addition to these types of attachment means, magnets and barbs may also be employed.

Figure 40A:
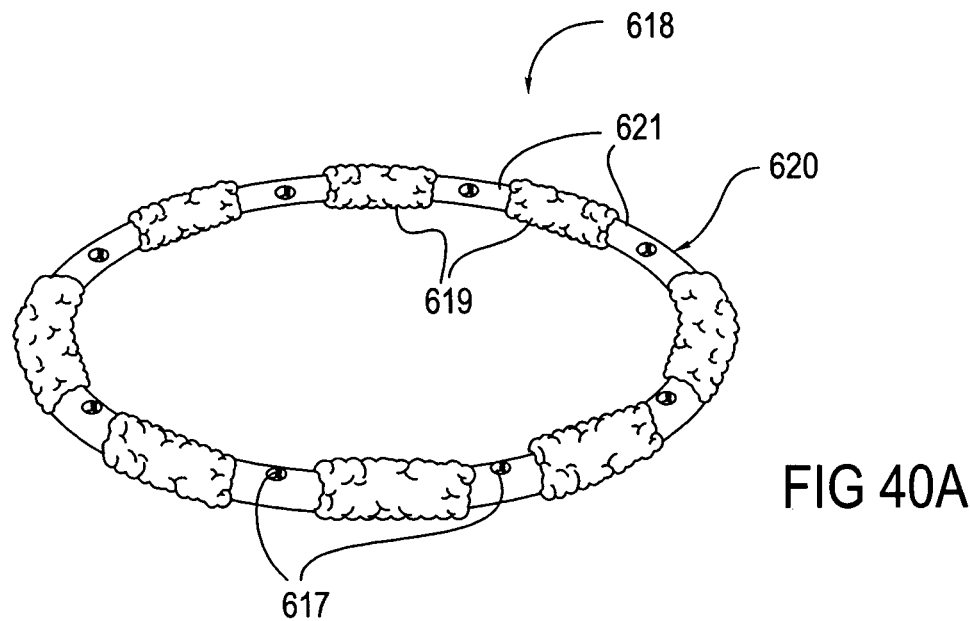
FIG. 40A shows an alternative fastener system comprising an annular shaped member wherein the surface of the annular shaped member alternates between having tissue growth promoting materials, and non-tissue growth promoting materials.

FIG. 40A shows an alternative fastener system 618 comprising an annular shaped member 620 wherein the surface of the annular shaped member alternates between having tissue growth promoting materials 619 such as Dacron felt or mesh, and non-tissue growth promoting materials 621 such as a fluoropolymer. The tissue growth promoting materials 619 are illustrated as having a rough surface, and are intended to become assimilated with the adjacent body tissue to supplement other attachment means such as sutures, staples, clips or other means known in the art. The surface 621 of the annular shaped member that lacks tissue growth promoting materials may be used for attaching another appliance or device. FIG. 40A illustrates this surface as having a hole or void 617 that can be used for attaching a hooking device, or the functional device itself.

Figure 40B:
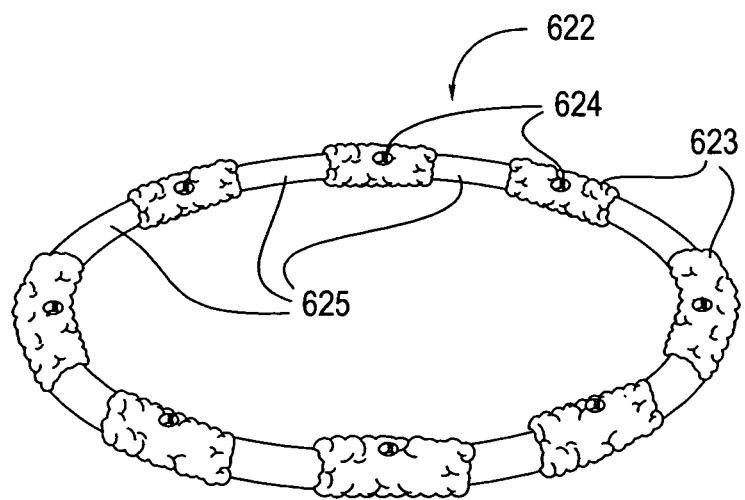
FIG. 40B shows a fastener system comprising fastener segments connected with a bioresorbable material to ease installation.

FIG. 40B shows a fastener system 622 comprising fastener segments 623 connected with segments of a bioresorbable material 625, as discussed herein, to ease installation. The fastener segments 623, illustrated with a rough surface to indicate that they are also coated with a tissue growth promoting material, are surgically attached to the adjacent tissue wall. Each segment is also shown as having a hole or void 624 that can be used for attaching a hooking device, or another device. The bioresorbable segments 625, shown having a smooth surface, would dissipate over time, leaving the fastener segments 623 in place to support a load. This device would be simple to install, and once the bioresorbable material has dissipated, it would have individual segments 623 that could move independently of one another, and not transmit these forces to other segments. The embodiments shown in FIGS. 40A and 40B are preferably configured so that installation does not narrow the passageway of the organ.

Figure 41A:
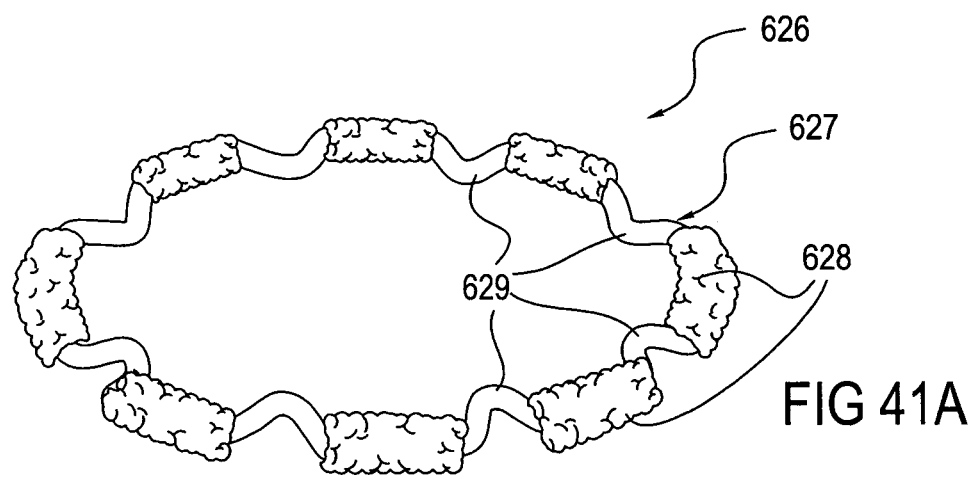
FIG. 41A shows an alternative fastener system comprising an annular shaped member wherein the surface of the annular shaped member alternates between having tissue growth promoting materials, and non-tissue growth promoting materials.

FIG. 41A shows an alternative fastener system 626 comprising an annular shaped member 627 wherein the surface of the annular shaped member alternates between having tissue growth promoting materials 628 and non-tissue growth promoting materials 629. This embodiment shows the surface 629 of the annular shaped member that lacks tissue growth promoting materials shaped to form a hanging or attachment platform for another device by extending away from and then back into the tissue growth promoting surfaces 628. This attachment platform can be used for various items such as sutures, clips, rings, hooks, hangers, etc., that can depend form the attachment platform.

Figure 41B:
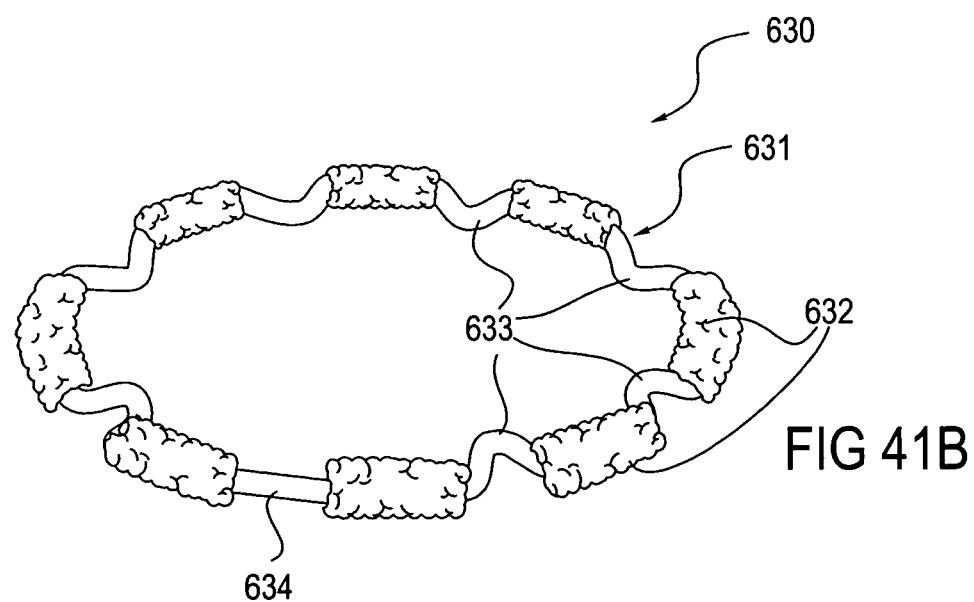
FIG. 41B shows an alternative fastener system comprising an comprising an annular shaped member wherein the surface of the annular shaped member alternates between having tissue growth promoting materials, and non-tissue growth promoting materials.

FIG. 41B shows an alternative fastener system 630 comprising an annular shaped member 631 wherein the surface of the annular shaped member alternates between having tissue growth promoting materials 632 and non-tissue growth promoting materials 633. In this embodiment, the segments 632 of the device having the rough surface would be the segments attached to the adjacent tissue wall. The coupled smooth segments 633 are made from an elastic material that can be stretched, as illustrated with one segment 634 drawn tight. This configuration allows the attached rough segments 632 to move almost independently of one another, and also provides a platform from which a load can be supported, that platform being the entire annular shaped member 631. Whatever device is eventually coupled to the annular shaped member 631 could be coupled using any or all portions of the annular shaped member for support. The embodiments shown in FIGS. 41A and 41B are preferably configured so that installation does not narrow the passageway of the organ.

Figure 42A:
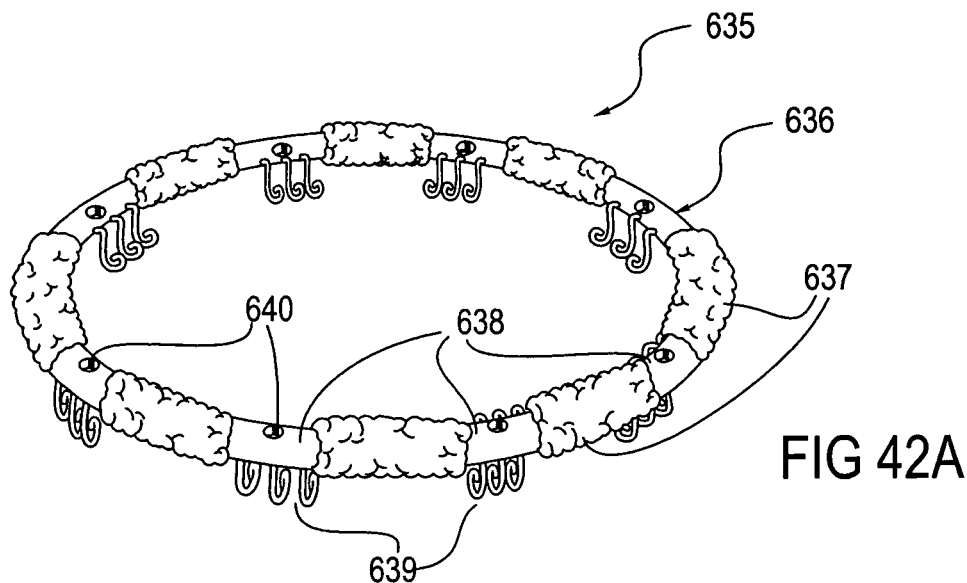
FIG. 42A shows an alternative fastener system comprising an annular shaped member wherein the surface of the annular shaped member alternates between having tissue growth promoting materials, and non-tissue growth promoting materials.

FIG. 42A shows an alternative fastener system 635 comprising an annular shaped member 636 wherein the surface of the annular shaped member alternates between having tissue growth promoting materials 637 and non-tissue growth promoting materials 638. This embodiment shows the surface 638 of the annular shaped member that lacks tissue growth promoting materials to have hooks 639 extending from the plane of the annular shaped member 636. These hooks 639 can be used for attaching another device or appliance. Also shown are holes 640 in this embodiment which may be used to pass a suture or other attachment structure, as described herein, through to help secure the device in place. The hooks 639 can be curled to retain other devices, or could have specific mating couplings for example wherein a quarter turn will lock the coupling to the hooks 639.

Figure 42B:
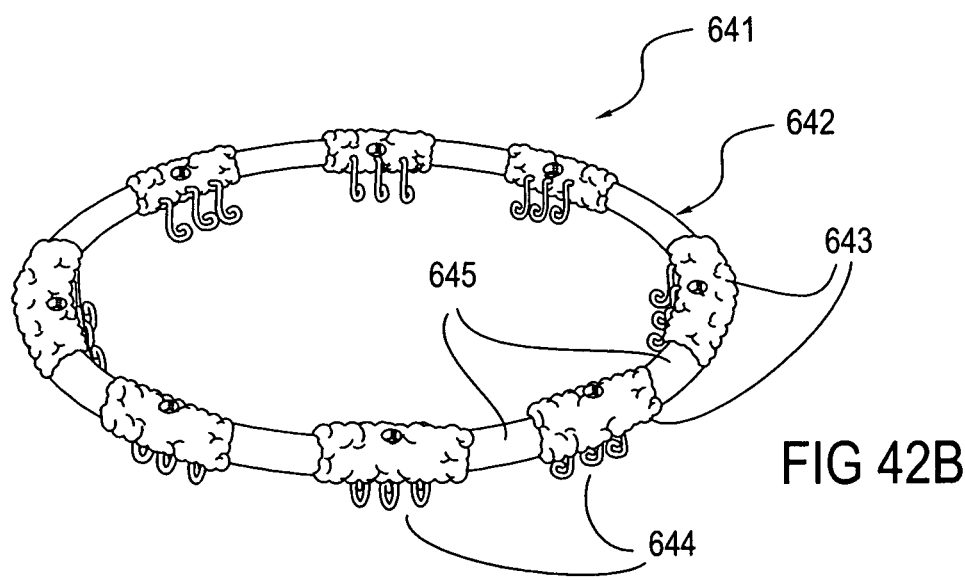
FIG. 42B shows an alternative fastener system comprising an annular member of rough segments having hooks coupled to smooth segments that are made of a bioresorbable material.

FIG. 42B shows an alternative fastener system 641 comprising an annular member 642 of rough segments 643 having hooks 644 coupled to smooth segments 645 that are made of a bioresorbable material. The rough segments 643 are coupled to the adjacent tissue wall and remain in place to support a load after the bioresorbable segments 645 have dissipated. This embodiment is thus simple to install, and enables each segment 643 to move independently of one another once the bioresorbable smooth segments 645 have dissipated.

The embodiment shown in FIGS. 42A and 42B are optionally configured so that installation does not narrow the passageway of the organ.

Figure 43:
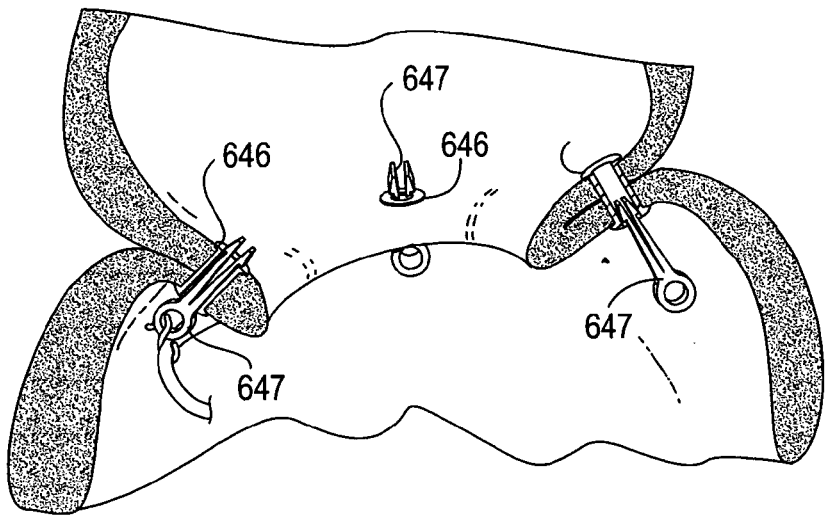
FIGS. 43-45 show various embodiments of a fastener system that also functions to create a stoma within a passageway that is more narrow than the original passageway.
Figure 44:
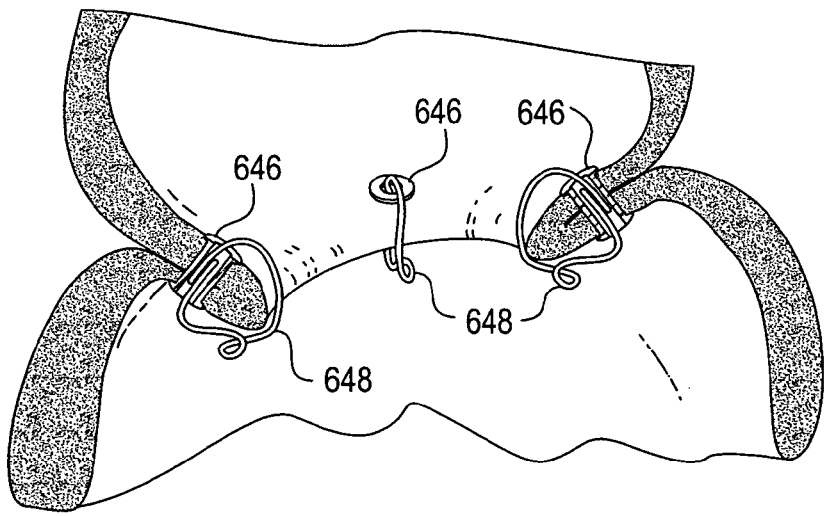
Figure 45:
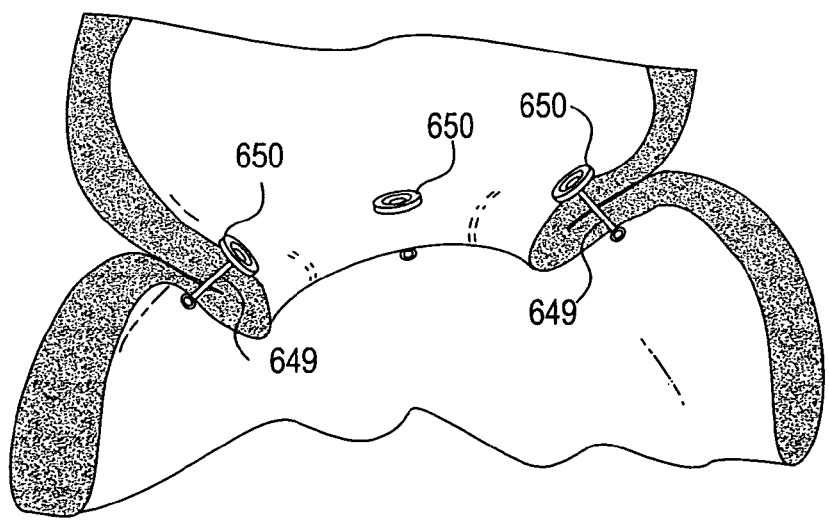

FIGS. 43-45 show various embodiments of a fastener system that can optionally function to create a stoma within a passageway that is more narrow than the original passageway. The stoma can be created by plicating or pinching the tissue of the passageway such that it is folded in the manner shown in FIGS. 43-46A. The folds are held in place with the fasteners which pass through both tissue layers and hold them together. In addition, these fasteners also function as attachment surfaces for another device or devices, such as a clip supported by a fastener, and a device supported from the clip.

The use of plications (folds) is often useful in overcoming the difficulties of coupling a fastener device to a hollow walled organ because the folds give the added strength of a double layer attachment point, and also protect against leaks because the hole passes from the inside of the organ and back to the inside of the organ. Another advantage is that the outermost wall of the gastrointestinal tract, the serosa, appears to heal well because when it is in contact with itself, such as within a fold, it tends to heal together. This will further serve to prevent leaks by sealing the channel formed by the placement of the fastener through the fold. Plications can be formed by a fastener system or can be formed by standard techniques such as sutures with a fastener attached either to the suture or directly to the plication after it is formed. Alternately, plications can be formed and fasteners inserted that the fasteners pass through the muscularis layer of the gastrointestinal wall but do not pass through the serosa. This may be clinically preferred as a means to prevent leaks as the serosa provides a sealing layer. This also applies to the fasteners shown in FIGS. 47A-F and 48.

FIG. 43 shows a fastener system comprising a hollow plication element 646 that may be used to hold tissue together, as well as an attachment element 647 that is shown capable of passing through the hollow plication element 646 and snapping into place. The attachment element 647 thus provides a platform for attaching other devices or hooks. Alternatively, a device may clip in directly to the hollow plication element 646, thus obviating the need for an attachment element 647. The hollow plication element 646 could have a cone shaped end that is able to pierce through the tissue layers, and this cone shaped end would then expand to remain in place.

FIG. 44 shows an alternative embodiment of a device similar to the device of FIG. 43, wherein the attachment element 648 differs. The attachment element 648 is in the form of a wire clip that attaches to the hollow plication element 646.

FIG. 45 shows an alternative embodiment of a device for both holding two layers of tissue together and providing a platform from which another device or hanger can be attached. In this embodiment, the device comprises two components, a post 649 having an attachment platform, as well as a snap cap 650 to hold the tissue layers together. This embodiment has a solid, rather than hollow element for connecting the tissue layers which may be advantageous in certain applications, especially where less tissue is available for folding, or where it may be desirable to have the original diameter of the passageway kept as wide as possible. Note that though all fasteners in FIGS. 43-45 are shown passing through the serosa of both layers of the plications, this is not a requirement of the devices or methods.

Figure 46A:
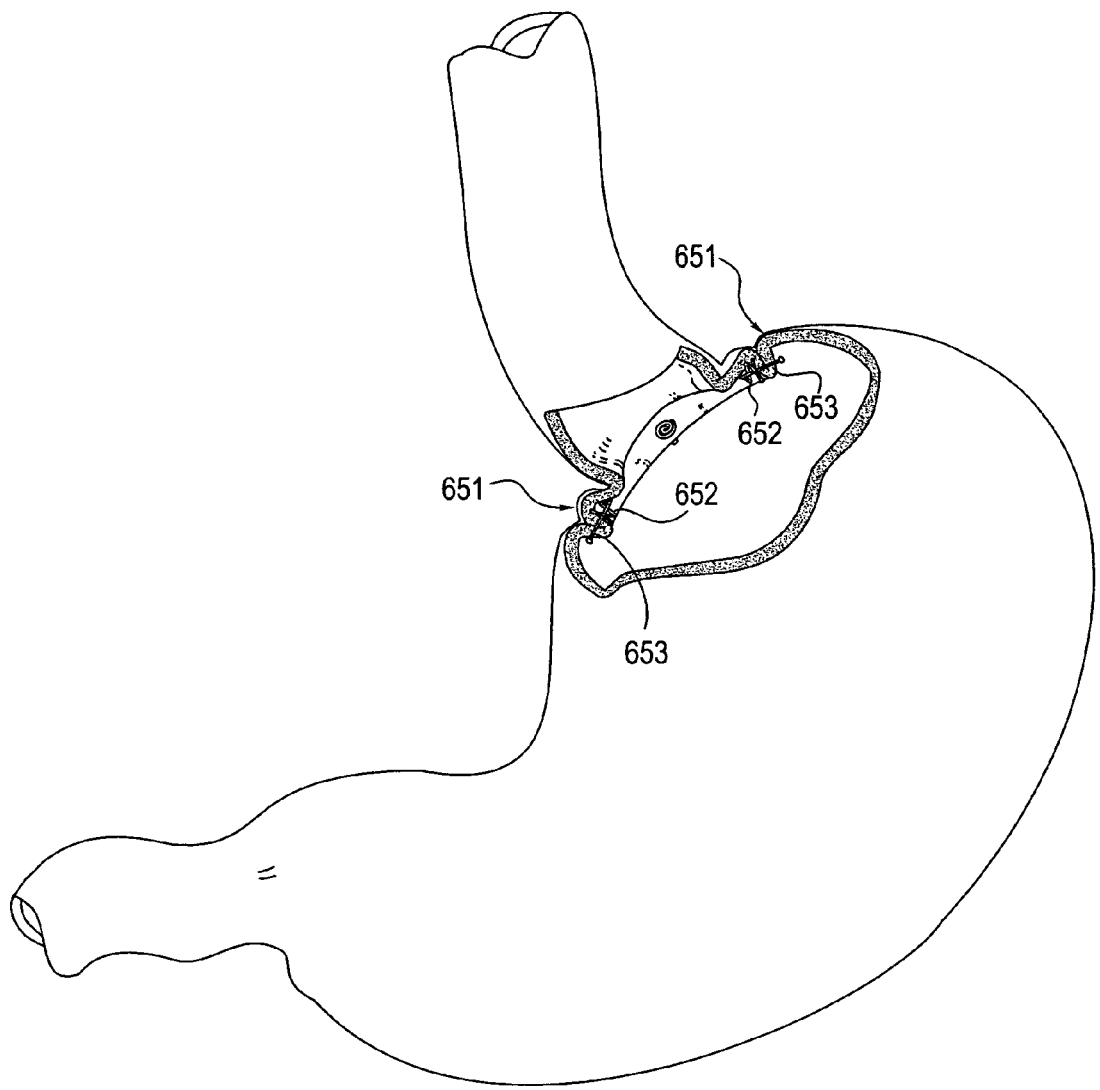
FIG. 46A shows an alternative embodiment of a fastener system.

FIG. 46A shows an alternative embodiment of a fastener system. This embodiment includes a fastener 651 that can be made from a metal having superelastic or shape memory characteristics such as Nitinol, so that the device can be loaded within a delivery device, such as a hypodermic tube. Once the tissue has been folded, the fastener 651 can optionally be sent through both tissue layers to hold them together to create a stoma, and also optionally function to provide a platform for attaching another device or hanging element. The curled portion 652 of the device can be straightened out and stored so that it lies essentially parallel to the post 653 that is positioned between the tissue layers. When the curled portion 652 of the device is released from the delivery device and allowed to expand, it then forms a cone shaped spring to hold the tissue layers together. The relative dimensions of the cone shaped spring are exaggerated for illustration purposes. The cone shaped spring distributes force onto adjacent tissue over a relatively large area, and centers that force onto the post. The cone also prevents the fastener from being pulled through the hole. This particular geometry is intended to be exemplary and other geometries which increase the area of the portion of the fastener which bears the weight (force) of the dependent device and thereby helps resist pull-through.

Figure 46B:
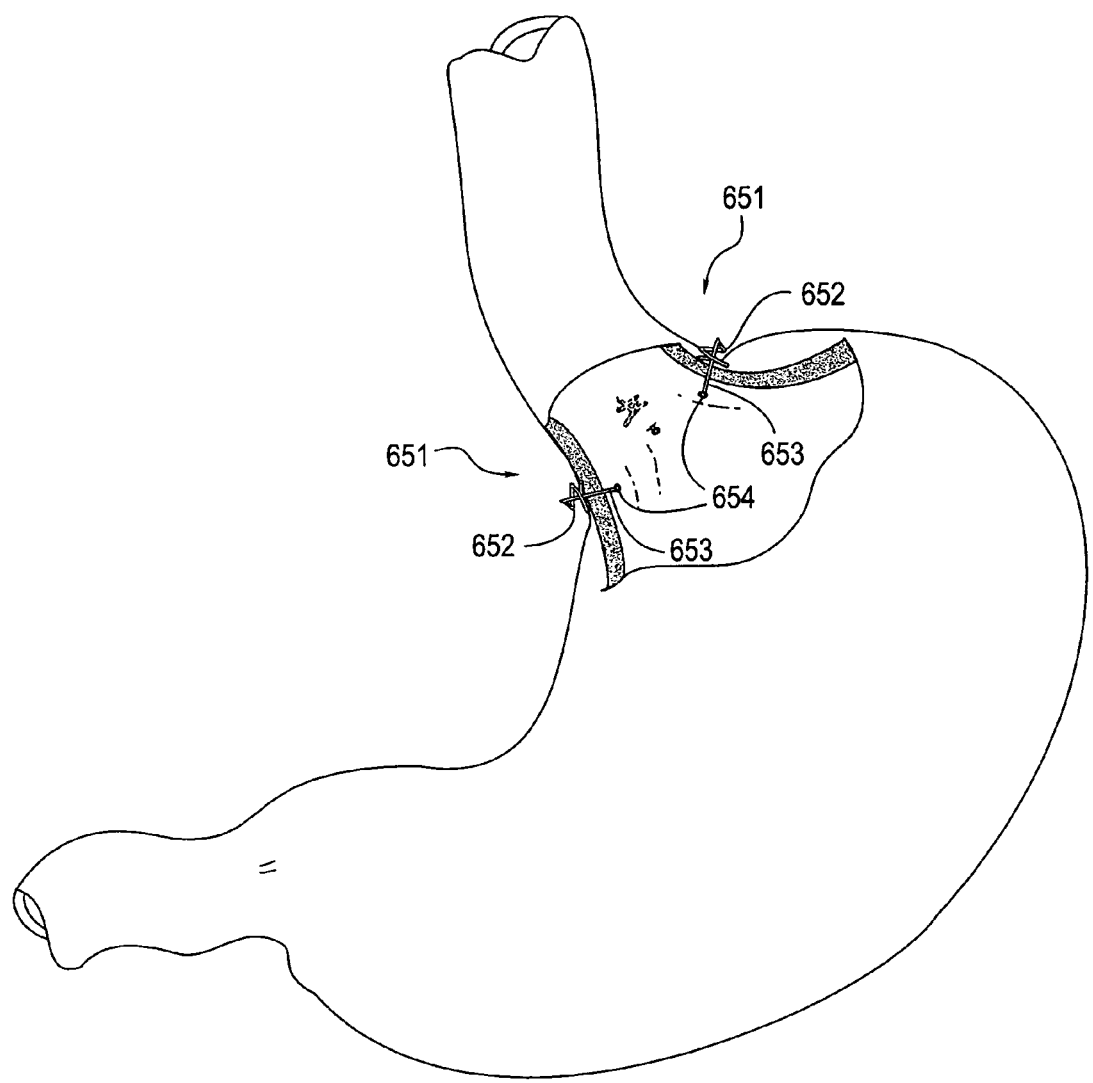
FIG. 46B shows the device of FIG. 46A being driven through a single tissue layer, with the attachment means positioned within the passageway and the cone shaped spring positioned on the opposite side.

FIG. 46B shows the fastener device 651 of FIG. 46A being driven through a single tissue layer, with the attachment means 654 on the end of the post 653 positioned within the passageway, and the cone shaped spring positioned 652 on the opposite side. The embodiment shown in FIG. 46B is preferably configured so that its installation does not narrow the passageway of the organ. Delivery of fastener embodiments communicating with the exterior of a hollow organ as shown in FIG. 46B (also FIGS. 6B-D) may incorporate means to control capture of other structures. Though it may be clinically desirable to capture other structures as in the case of capturing the diaphragm by fasteners placed in the cardia of the stomach it is more likely that this would be undesirable. Fastening means could incorporate shielding means and/or means to invaginate the organ wall as the fastener is advanced through the organ wall.

FIG. 47A shows a clip 655 that can be used to plicate tissue, and also provide a platform for attaching another device or hanger. The clip 655 is shown being used with one embodiment for a plication tool 656. The plication tool 656 is capable of folding tissue in a desired way and then delivering a clip 655 to hold the tissue in a folded configuration. This is accomplished by grabbing the wall of a tissue at two points, and then pinching the wall (either with the tool itself or the fastener) and delivering a clip 655 to hold the fold together. Various means may be employed to ensure that the fold occurs properly, such as suction, or pushing the tool 656 into the tissue wall as it pinches.

FIGS. 47B-47D show the sequence of steps used to deliver the clip 655 of FIG. 47A. This process may be repeated to collectively form a support structure for another device. The plication tool 656 may include suction or other mechanical means such as hooks or barbs to encourage the tissue to fold as shown in the figures.

FIG. 47B shows a side view of the plication tool 656 loaded with a clip 655. The clip 655 is positioned adjacent to a tissue wall, as shown.

FIG. 47C shows the clip 655 being compressed. The clips distal ends pierce the adjacent tissue, and then fold it as the clip 655 is compressed with the plication tool 656.

FIG. 47D shows the clip 655 being compressed further. The direction arrows above the plication tool 656 indicate that the plication tool 656 could be biased towards the closed position with a spring mechanism, or that some type of direct mechanical force could operate the tool.

The clip 655 may be designed so that it is normally closed or normally open. If the clip 655 is designed normally open, it will need to be compressed and remain compressed. Therefore, the clip 655 is preferably made of a deformable or malleable material, such as an annealed metal, that can be deformed by the application tool 656 such that the clip will retain the deformed position. The tool 656 used to compress the clip transmits force to close the clip 655, using for example, a wire or rod that is optimized to transmit a push force to compress the clip. However, if the clip 655 is designed to be normally closed, it is preferable that the clip 655 be made of an elastic material that can be opened up, and then close on its own or with the assistance of a plication tool 656. The plication tool 656 would need to be able to hold a clip 655 that is normally closed in the open position, and should be designed to do such a task with an appropriately designed clip. The normally closed clip 655 may be preferred in some circumstances because it easier to hold tension in a tool and then release it than to transmit force through a tool. The normally closed clip 655 will be easier to pass into the body when closed and mechanisms to open the clip in vivo can be accomplished using pull wire actuators as well known in the art.

FIG. 47E shows another device 606 that is positioned to hang from several clips 655 positioned within a passageway. The embodiment shown in FIG. 47E is preferably configured so that its installation does not narrow the passageway of the organ. The vertical lines indicate that this device has been positioned within an organ, such as the stomach, such that the inner diameter of the device is not more narrow than the inner diameter of the tissue upstream of it, in this case the esophagus.

FIG. 47F shows an alternative clip embodiment 659 having two separate attachment platforms 657, 658. One platform 657 is positioned at the hinge portion of the clip 659, and a second platform 658 is positioned along the bottom half of the clip 659, as shown in FIG. 47F. One or both platforms 657, 658 may be used, and the second platform 658 can be easily repositioned on the clip, if desired. Note that if the sleeve device 606 of FIG. 47E were supported by the second platform 658 of the clip 659 of FIG. 47F, a larger diameter sleeve device can be employed.

Figure 48:
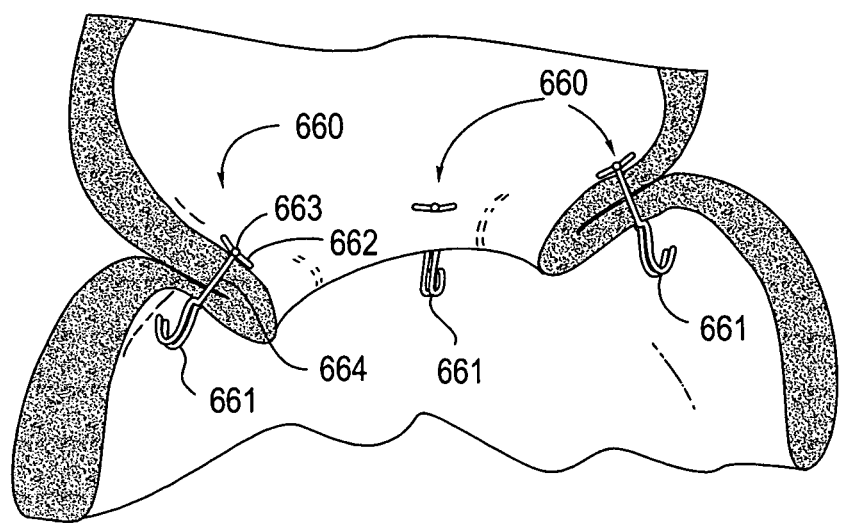
FIG. 48 shows another embodiment of a fastener system, comprising a hanger that also functions to hold two layers of folded tissue together. This fastener has a toggle that pivots on a hinge so that is can be aligned with the post as it is passed through tissue layers, and can then be pivoted to hold the tissue layers together.

FIG. 48 shows another embodiment of a fastener 660 comprising a hanger 661 that also functions to hold two layers of folded tissue together. This fastener has a toggle 662 that pivots on a hinge 663 so that is can be aligned with the post 664 as it is passed through tissue layers, and can then be pivoted to hold the tissue layers together.

The toggle 662 helps to distribute forces that hold the fastener 660 in place over the length of the toggle 662, and also prevents the fastener 660 from being pulled through the hole. Alternative to the toggle 662, a similar functioning apparatus such as a multi-arm umbrella could also be used to distribute forces on the adjacent tissues while preventing the fastener 660 from passing through the hole. This fastener functions similarly to the T-tag fasteners described herein.

In summary the fastener system can include:
an implantable surface for mounting a functional element that may attach to the tissue itself with a suture, staple, clip, T-tag or pass through one or more layers of tissue including a fold of tissue.

The fastener system, optionally including:
an interface element, and
a functional element, wherein the interface element couples the implantable surface for mounting a functional element to the functional element.

The fastener system, optionally including:
a functional element, wherein the functional element couples to the implantable surface for mounting a functional element.

The fastener system, optionally including:
a plication tool for folding a tissue wall such that the tissue wall is pinched and pulled toward the tool and the interior of a body organ, and
an implantable surface for mounting a functional element delivered by the plication tool for maintaining the fold, and that also provides a platform for attachment of another element.

The fastener system, optionally including:
a removal tool that can be used to remove a functional element by, for example, unhooking it, cutting it, turning it, unlocking it.

A method for positioning the fastener system and using it can include:
attaching an implantable surface for mounting a functional element that may attach to the tissue itself with a suture, staple, clip, T-tag or pass through a fold of tissue,
optionally attaching one or more interface elements to interface between the implantable surface for mounting a functional element and a removable functional element, and
attaching a removable functional element that attaches either to implantable surface for mounting a functional element itself, or to the interface element.

A method for removing the functional element can include:
using a removal tool to remove the functional element by, for example, unhooking it, cutting it, turning it, unlocking it.

In the case of an attachment ring the ring does not necessarily create a restriction. In many embodiments, a second element generally creates a restriction using a restricting device (for example stoma 100). The restriction may or may not be co-located with the attachment ring. In the case of the stomal ring clip (SCR) the ring clip creates the restriction by positioning natural tissue to create the restriction. Therefore they differ in that the SRC: 1) preferably uses tissue to create the restriction and 2) always has the restriction at its location. This is the case even where a sleeve is passed through the stoma created by an SRC. Please note that many apparatus (including fastening systems) can be applied to either use and some could be applied interchangeably. Please also note that the structures described as an SRC can generally be used as components of an attachment ring system in which case the restriction is not necessarily collocated.

One aspect of present invention provides apparatus and methods for performing gastric and esophageal surgery. The apparatus of the invention includes a surgical instrument for creating a stoma or restriction in a patient's stomach or esophagus using minimally invasive surgical techniques. This apparatus can also be used to create a plication or fold in the stomach or esophagus and furthermore can then be used to attach other devices including those described herein, to the fold thereby created. The apparatus can also include stomal ring clip devices implantable within the patient's stomach for forming and maintaining the stoma or restriction. The surgical instruments and the implantable stomal ring clip devices may be used separately or in combination depending on the needs of the individual patient. Methods are described using the surgical instruments and the implantable stomal ring clip devices separately and in combination for creating a stoma or restriction in a patient's stomach or esophagus. The apparatus and methods are useful for treatment of morbid obesity and can be combined with other surgical techniques or devices as part of a complete treatment regimen. The apparatus and methods are useful for treatment of gastroesophageal reflux disease (GERD) by creating a restriction or a valve-like structure at the gastroesophageal junction to prevent reflux of the stomach contents.

Figures 49, 50, 51:
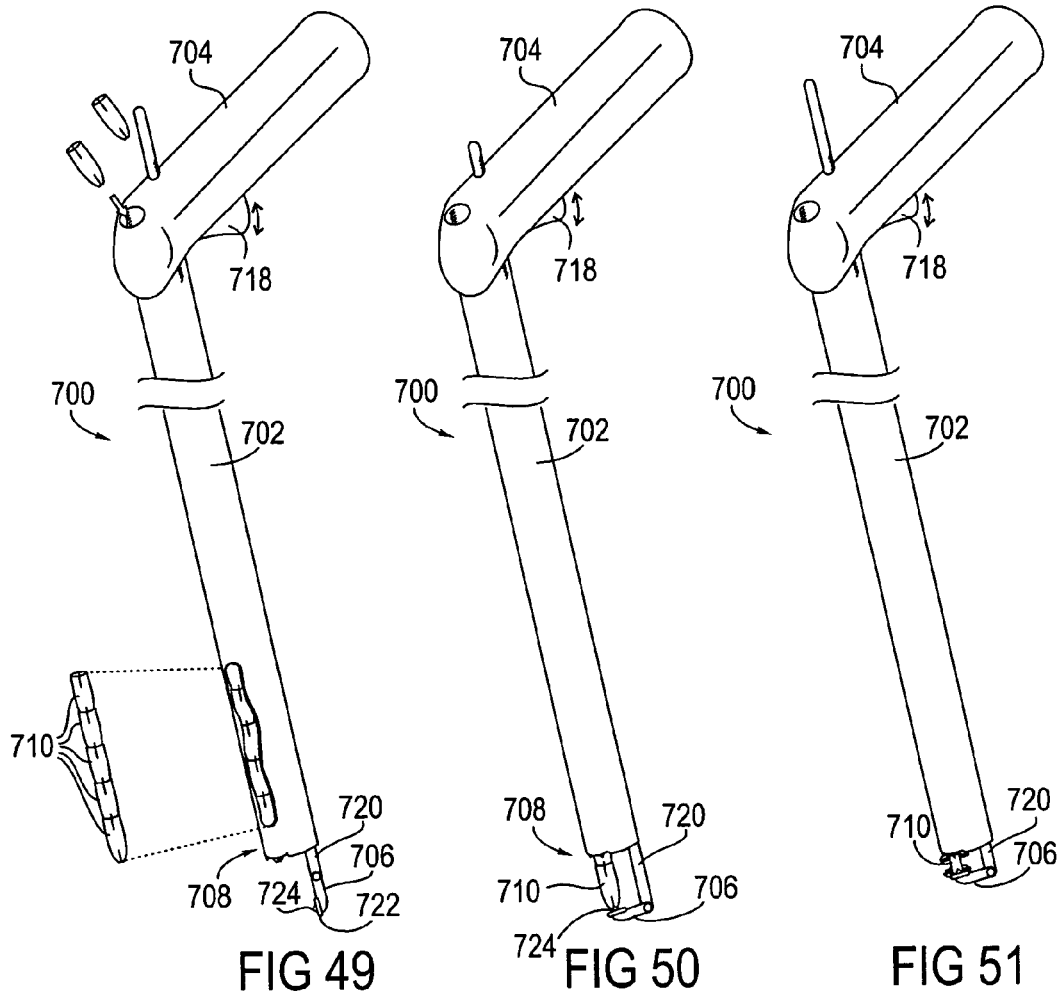
FIGS. 49-51 illustrate a surgical instrument for fastening tissue.
Figure 53:
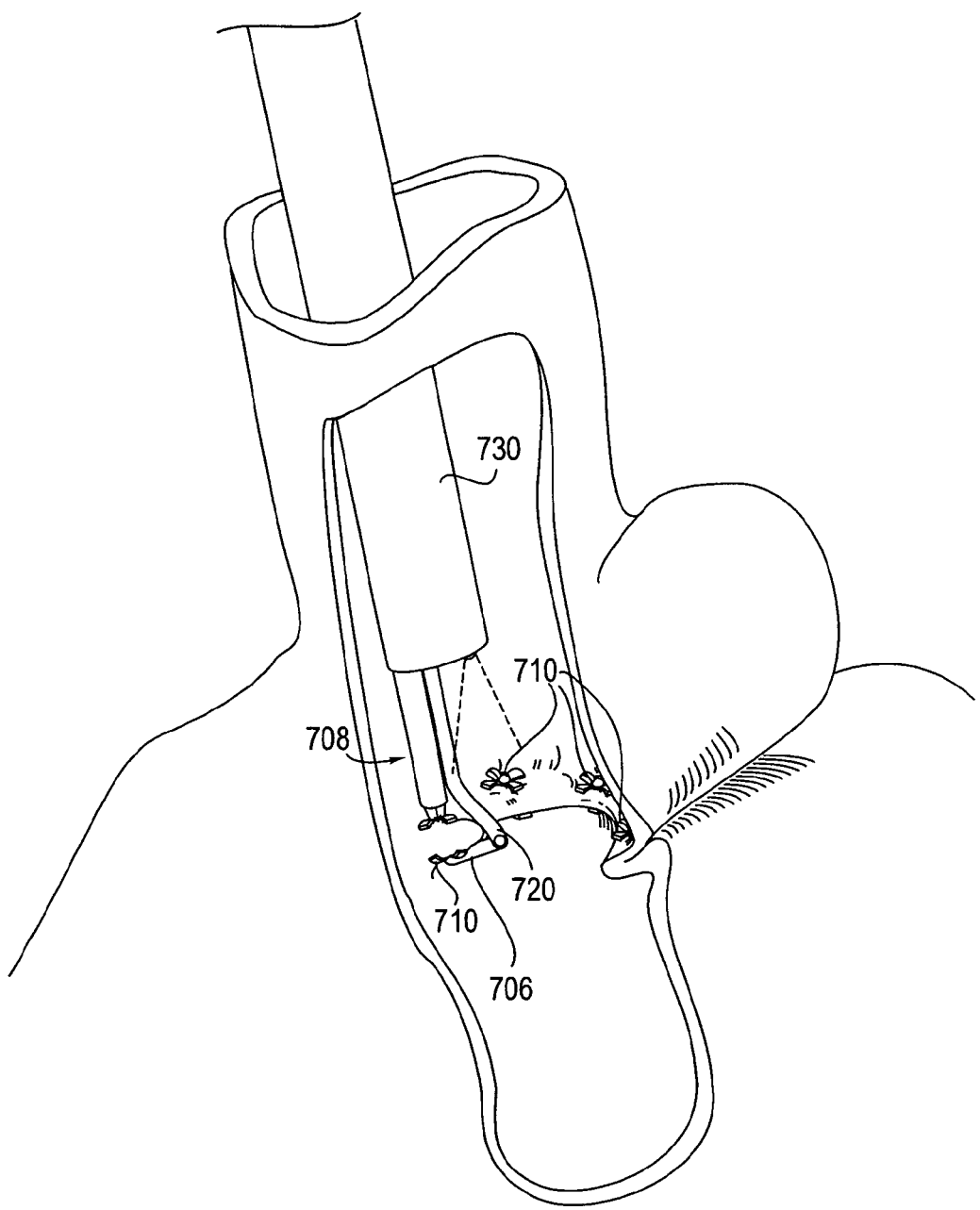
FIG. 53 shows a surgical instrument comprised of a fastener delivery mechanism, and an anvil hingedly attached to an extension arm, used for creation of a stoma or restriction in a patient's stomach that is sized for passage through an endoscope.

FIGS. 49-51 illustrate a surgical instrument 700 constructed in accordance with the present invention. The instrument 700 has an optionally flexible elongated body 702 with a handle 704 on its proximal end. At the distal end of the flexible elongated body 702, the surgical instrument 700 includes a fastener delivery mechanism 708 and an articulated arm 706 with means for grasping and plicating a portion of tissue, such as the stomach wall, and for fastening the tissue with rivets or similar fasteners 710. Optionally, as shown in FIG. 53, the device is sized to pass through the working channel of an endoscope. The articulated arm 706 is pivotally mounted on an extension arm 720 extending from the distal end of the flexible elongated body 702. Optionally, the extension arm 720 may be extendable and retractable from the flexible elongated body 702. This option allows the articulated arm 706 to capture varying sizes of tissue folds including those that can optionally result in the fastener passing through layers of serosa. The articulated arm 706 has an anvil 722 for heading the rivets 710 and may have one or more spikes or teeth 724 for securely grasping the tissue. FIG. 49 shows the surgical instrument 700 with the articulated arm 706 pivoted outward. FIG. 50 shows the surgical instrument 700 with the articulated arm 706 pivoted inward toward the fastener delivery mechanism 708. FIG. 51 shows the surgical instrument 700 with the articulated arm 706 heading or expanding a rivet 710. The articulated arm 706 may be actuated from a control button 718 on the handle 704 by cables, rods or other actuation mechanism within the flexible elongated body 702. Optionally, the articulated arm 706 may be normally in the position shown in FIGS. 2 and 3 and require actuation to open to the position shown in FIG. 49.

The fasteners 710 may take one of several possible forms. The fasteners 710 may be in the form of double-ended rivets with an expandable head on the leading and trailing ends, as shown in FIGS. 49-51 and 55-57. The fastener 710 is pushed through the tissue, then the expandable head on the leading and trailing ends is expanded by the force of the anvil 722. Alternatively, the fasteners 710 may have a fixed head on the trailing end of the fastener and an expandable head on the leading end. In another alternative configuration, the fasteners 710 may be in the form of blind fasteners, of the type commonly known as pop rivets. Additionally, the fasteners 710 could be self-expanding so that once passed through the tissue of the stomach, they expand to hold the plicated stomach tissue together. These fasteners 710 may be biased, or spring loaded, so that minimal contact with the anvil causes the fastener to expand below the plicated tissue. In this embodiment, fasteners 710 could include a trailing end that self expands as it exits lumen 114 of FIG. 52 thereby capturing the tissue in a plication. Also, the fasteners could have a self-expanding end, and a non self-expanding end. Perhaps the non self-expanding end is already expanded, or could be made to expand with additional force.

The fasteners 710 can be permanent or biodegradable. The fasteners 710 may be constructed of a biocompatible metal or polymer or a combination or composite thereof. Alternatively, the entire fastener 710 or a portion of it may be constructed of a bioresorable material. Additionally, the fasteners 710 can include enhanced scar forming means such as a coating of lower that normal pH or a material such as polyglactin (Vycril, Ethicon).

The articulated arm 706 section of the device can be configured to capture varying sizes of tissue folds, with some embodiments enabling capture of folds of greater dimension than the width of the device. This may involve use of curvilinear, bendable and/or multiple articulated arms 106. In another embodiment the rivet lumen exit can be angled to cooperate with a larger articulating arm 706 to capture a larger fold of tissue.

The surgical instrument 700 is preferably configured for performing surgery on the stomach or esophagus via a peroral endoscopic approach. As such, the flexible elongated body 702 may be sized and configured to fit through the instrument channel of a gastroscope or to fit through the patient's esophagus alongside a gastroscope. Otherwise, the flexible elongated body 702 may be configured with a lumen or channel to accept a gastroscope or other endoscope or imaging device through the surgical instrument 700. Alternatively, the surgical instrument 700 may be reversibly attached to or integrated with a gastroscope or imaging device.

Figure 52:
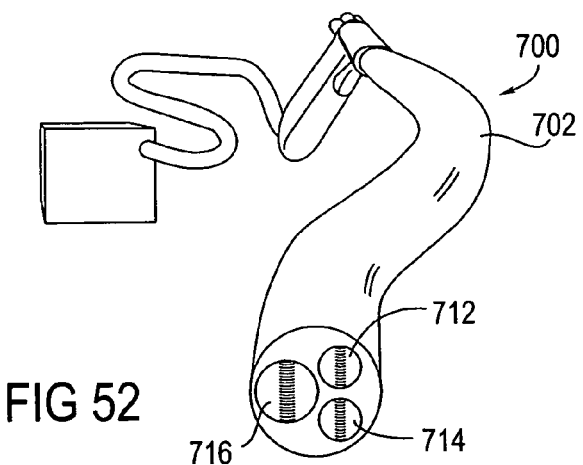
FIG. 52 shows a cross section of one possible configuration of the surgical instrument shown in FIGS. 49-51.

FIG. 52 shows a cross section of one possible configuration of the surgical instrument 700 shown in FIGS. 49-51. The flexible elongated body 702 has a first lumen or channel 712 for the articulated arm 706, a second lumen or channel 714 for the fastener delivery mechanism 708 and a third lumen or channel 716 for passage of an endoscope or other instrument. The channel 714 for the fastener delivery mechanism 708 may include a protrusion (not shown) that extends from the distal end of the channel 714 to capture the holes in the stomal ring clip (described below) to hold it in place, and assure that a fastener is delivered accurately through a stomal ring clip. In other embodiments, such as that of FIG. 53, the articulated arm 706, and fastener delivery mechanism 708, can be passed down the lumen of an endoscope 702.

Figure 54:
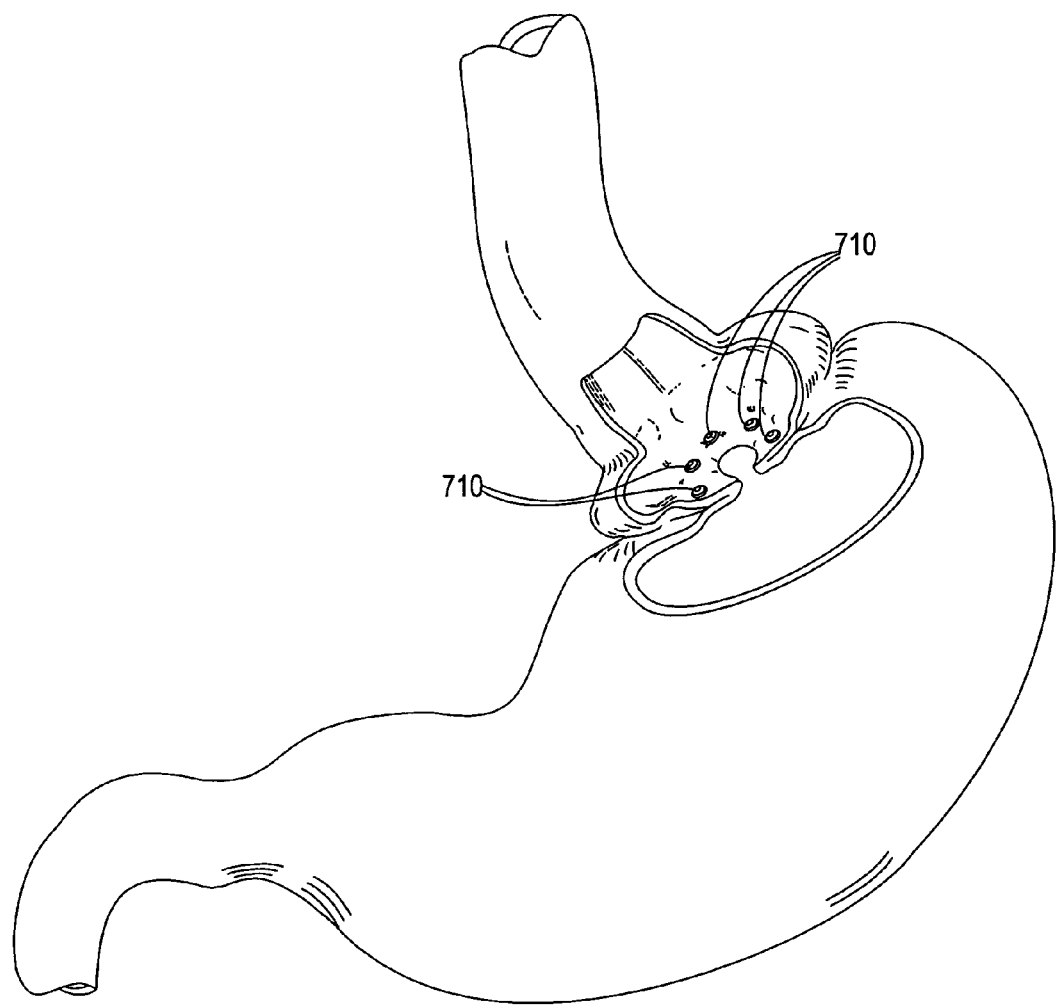
FIG. 54 shows a stoma created using fasteners.

FIG. 53 shows a surgical instrument comprised of a fastener delivery mechanism 708, and an anvil attached to an extension arm 720 with a hinge or hinge-like structure, used for creation of a stoma or restriction in a patient's stomach that is sized for passage through an endoscope. The extension arm 720 in this embodiment is shown to curve away from the fastener delivery mechanism 708 so that the surgical instrument can plicate a greater amount of stomach tissue. This allows the fastener to gain the advantage of passing through two complete layers of stomach tissue because the fastener is no longer near the edge of the fold. The surgical instrument is inserted within an endoscope 730. The endoscope has been introduced into the patient's mouth and down through the esophagus into the patient's stomach. The surgical instrument is then passed through the endoscope 730. The articulated arm 706 is pivoted outward, as shown in FIG. 49, to grasp a portion of the stomach wall using the spike 724. The articulated arm 706 is then pivoted toward the fastener delivery mechanism 708, as shown in FIG. 50, to plicate or fold the stomach wall. The rivet or fastener 710 is driven through the fold in the stomach wall, and the anvil 722 on the articulated arm 706 heads or expands the rivet or fastener 710 to secure the tissue fold as shown in FIG. 53. The surgical instrument 700 is rotated, independently or with the endoscope, and the process is repeated to place a series of fasteners 710 in a circular pattern to form a stoma or restriction in the patient's stomach as shown in FIG. 54, perhaps moving to the opposite side of the stomach from the previous fastener, rather than to an adjacent position, to create a uniform stoma. In the example shown, when the stoma forms a restriction, the stoma is typically sized between one half and two centimeters in diameter, to restrict food intake into the stomach for treatment of morbid obesity. Alternatively, the surgical instrument 700 may be used to create a valve-like flap at the gastroesophageal junction for treatment of gastroesophageal reflux disease.

Figure 57:
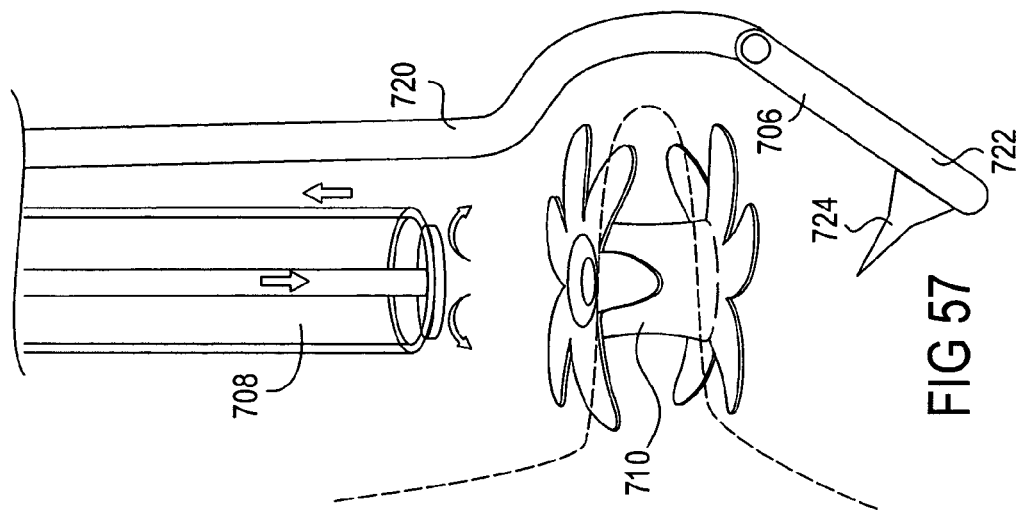
FIGS. 55-57 show the sequence of steps for inserting a fastener in greater detail.
Figure 56:
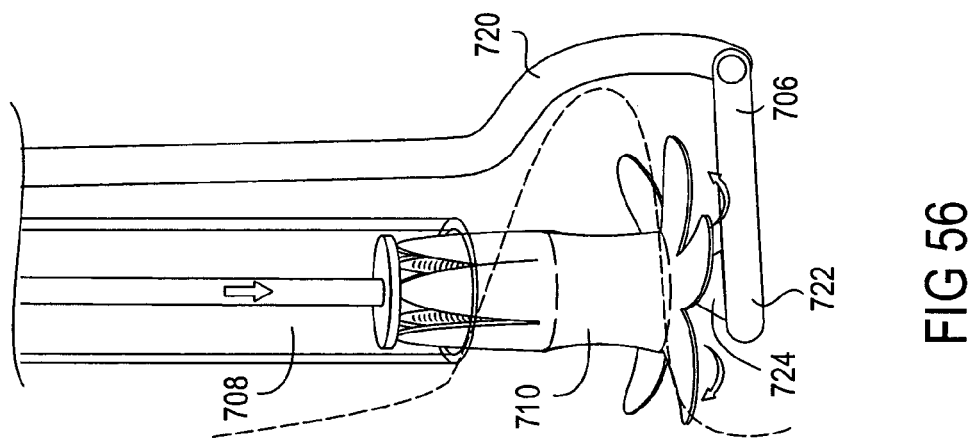
Figure 55:
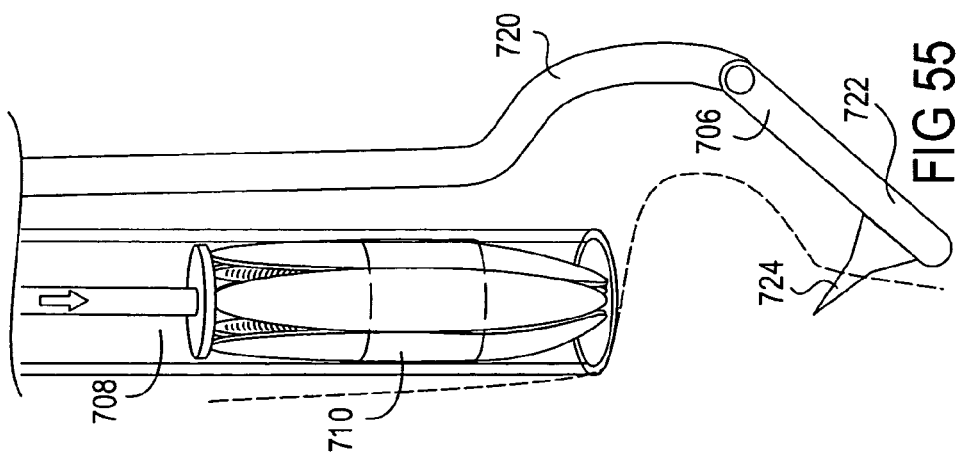

FIGS. 55-57 show the sequence of steps for inserting a fastener 710 in greater detail. These figures also illustrate one embodiment of a fastener 710 having a pointed cone-shaped distal end to allow it to be easily passed though stomach tissue, and perhaps a stomal ring clip (as discussed below).

FIG. 55 shows the spike 724 positioned on the terminal end of the anvil 722. The articulated arm 706 is initially extended parallel to the extension arm 720. The spike 724 is then moved toward the stomach tissue. Once the spike 724 has gotten hold of the stomach tissue, the anvil 722 is rotated toward the fastener delivery mechanism 708, as shown in FIG. 56.

FIG. 56 shows the distal end of the fastener 710 in the expanded position. As previously discussed, this fastener 710 could be self-expanding, whereupon contact with the anvil 722 forces the fastener 710 to expand. In this figure, the spike 724 is shown to engage the biased spring of the fastener, which then expands with the impetus provided by the force of pushing the fastener 710 over the spike 424. In this embodiment, the proximal end of the fastener 710 is self-expanding and expands as soon as it exits the delivery lumen 708. Alternatively, a trigger (not shown) may be provided within the fastener 710 that allows the distal end of the fastener to expand. This same trigger mechanism may then encourage the proximal end of the fastener 710 to expand once released from the fastener delivery lumen.

FIG. 56 also shows the curved extension arm 720 in proximity to the stomach tissue. If necessary, the curved extension arm 720 could prevent the stomach tissue from expanding back over the distal end of the fastener prior to the fastener's release from the fastener delivery lumen.

FIG. 57 shows the fastener 710 in situ. The fastener delivery lumen 708 is retracted, as is the anvil 724. The process is repeated in a circular pattern to create a stoma as in FIG. 54.

Figure 58:
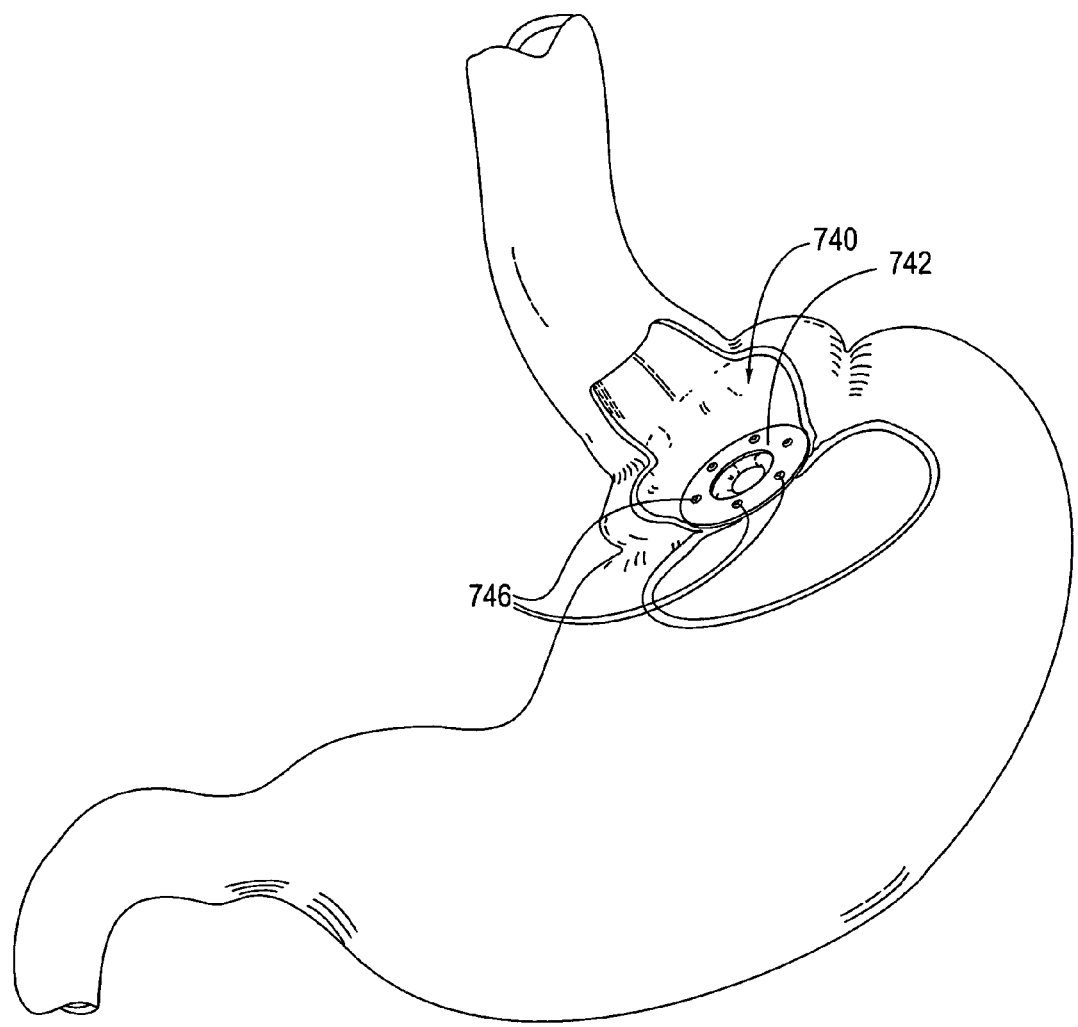
FIG. 58 shows an example of a stomal ring clip device with only an upper ring implanted in a patient's stomach, held in place with fasteners.

FIG. 58 shows an example of a stomal ring clip device 740 with only an upper ring 742 implanted in a patient's stomach, held in place with fasteners 746. It should be noted that a ring can be used either above or below the tissue plication. The stomal ring clip device 740 helps to maintain the dimensions of the stoma that is formed by resisting inadvertent or deliberate stretching of the stomal opening, adding to the overall success of the treatment. The stomal ring clip is constructed from a material that will resist the forces that could stretch the stomal opening beyond its intended dimension. Alternatively, the material can be elastic and be selected to resist most stresses and if stretched return the stomal opening to its original size.

FIG. 58 also illustrates the placement of a stomal ring clip device relative to the plicated stomach tissue, showing that the plicated stomach tissue diameter is actually narrower than the stomal ring clip's inner diameter, in some embodiments. This type of placement has the added advantage of allowing for a variable stomal diameter. For example, the plicated stomach tissue may have a diameter of 1 cm, and the inner diameter of the stomal ring clip may be 2 cm. The plicated stomach tissue's diameter can expand if necessary, up to the diameter of the stomal ring clip. This allows a patient who inadvertently swallows a large piece of food to have a larger stomal opening to accommodate that larger piece of food. The inner diameter of the stomal ring clip could be made large enough to accommodate anything that makes it down the esophagus, while the plicated stomach tissue's diameter could be made small enough to slow the rate of consumption and increase the feeling of satiation, leading to a decrease in the amount of overall food consumption for the patient, and thus resulting in weight loss. Alternatively, the diameter of this tissue can be sized to create little or no restriction to food flow as discussed herein.

FIGS. 59-64 show a sequence of steps for using a surgical instrument 700 to implant a stomal ring clip device 740 similar to the stomal ring clip device of FIG. 58.

Figures 59, 60:
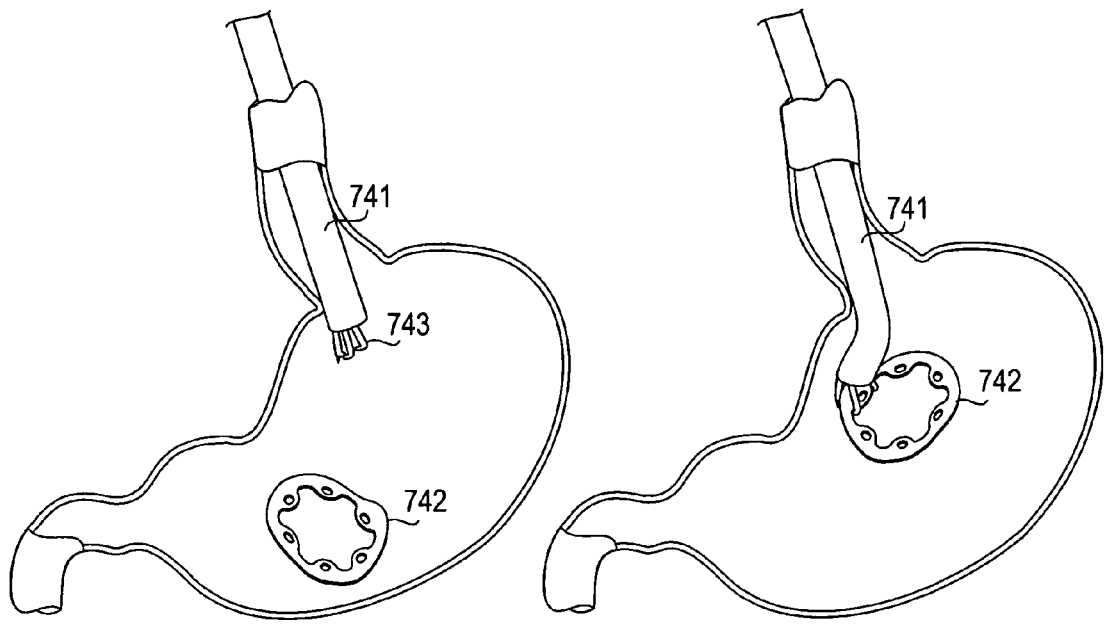
FIGS. 59-64 show a sequence of steps for using a surgical instrument to implant a device similar to the device of FIG. 58.

In one method of application, the ring 742 of the stomal ring clip device 740 is rolled or folded and passed into the patient's stomach through the patient's esophagus or through a sleeve temporarily placed in the esophagus to protect the esophagus or through the instrument channel of an endoscope or surgical instrument 700. The ring 742 is then allowed to return to its flat state within the patient's stomach, as shown in FIG. 59. FIG. 59 also shows an embodiment of a surgical instrument 700 for attaching the stomal ring clip positioned at the top of the stomach. In this embodiment, the surgical instrument 700 has an additional feature for retrieving the stomal ring clip. It is comprised of three prongs 743 that can be used to grasp a stomal ring clip. Two prongs 743 grasp the stomal ring clip's inner surface, preferably grasping the clip on either side of a lobe. The third prong 743 grasps the outside surface of the stomal ring clip and opposes the grasping force from the inner two prongs. Also, the third prong 743 is shown to have a spike 745 on it. The spike 745 may be used to oppose the force created by the upwardly moving articulated arm 706 (refer to FIG. 62). The prongs 743 may also curve at their terminal ends to improve their grip on the stomal ring clip. The prongs 743 can be retracted and extended within their respective lumens, and also can be moved inward and outward to grasp and release the stomal ring clip 742. In some embodiments, only the inner or outer prongs may be moved inwardly or outwardly.

FIG. 60 shows a surgical instrument 700 holding a stomal ring clip 742. In this embodiment, the surgical instrument 700 is shown to grasp a stomal ring clip 742 having lobes. The lobes may be useful for increasing the surface area around the preformed holes in a stomal ring clip, or for increasing the surface area for a fastener to make contact with in embodiments of a stomal ring clip not having preformed holes (in these embodiments, the stomal ring clip is made from a material that may be pierced by the fastener as it is being deployed). Another use for the lobes is to aid in the orientation of the stomal ring clip relative to the fastener delivery mechanism. In this embodiment, the fastener delivery mechanism would be aligned over the lobe area for placement of a fastener.

Figure 61:
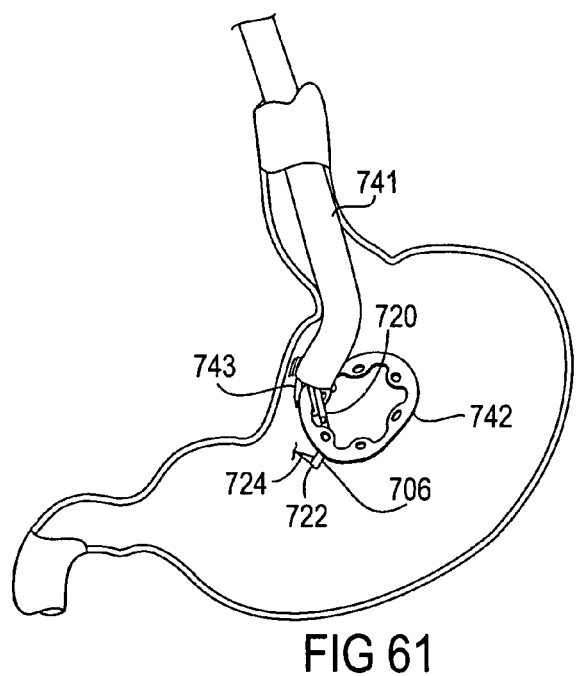

FIG. 61 shows the next step of the process in which the stomach tissue is folded. The extension arm 720 and anvil 722 are deployed, extending through the interior of the stomal ring clip 742. The anvil is able to pivot so that it moves away from the stomal ring clip to avoid catching the spike, and then pivot in the opposite direction to engage the stomach tissue. It should be noted that the spike is shown relatively large in this embodiment for illustration purposes. It should also be noted that a spike may be positioned elsewhere on the device relative to the anvil, such as is shown in FIG. 49.

FIGS. 59-64 show an embodiment of the surgical instrument 700 for attaching the stomal ring clip positioned at the top of the stomach above a plication. Alternatively, if it is desirable to attach a stomal ring clip below the plication, grasping prongs could be placed on the articulating arm. In this case, secondary grasping means can be used to assist in positioning stomach tissue to form the plication prior to fastening.

Figures 62, 63:
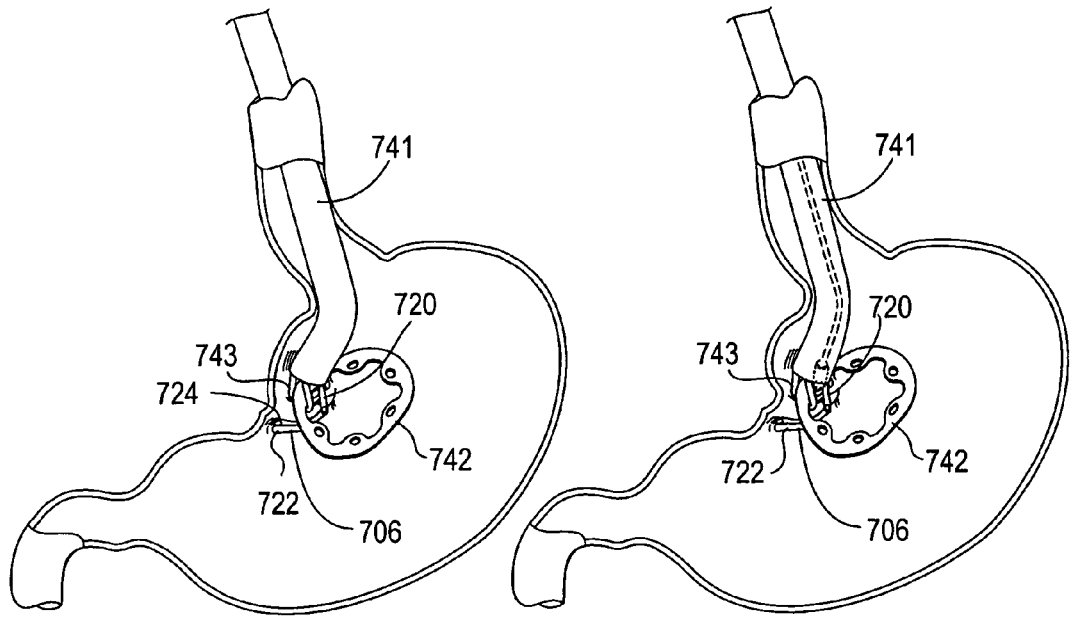

FIG. 62 shows the anvil 722, with the spike 724 engaging adjacent stomach tissue, and beginning to be rotated toward the stomal clip 742, thus folding the stomach tissue.

FIG. 63 shows the next step of the procedure, comprising the delivery of a fastener 710. Note that the spike 724, or additional spikes, may be positioned elsewhere along the anvil 722 or articulated arm 706 to facilitate the formation of the plication.

Figure 64:
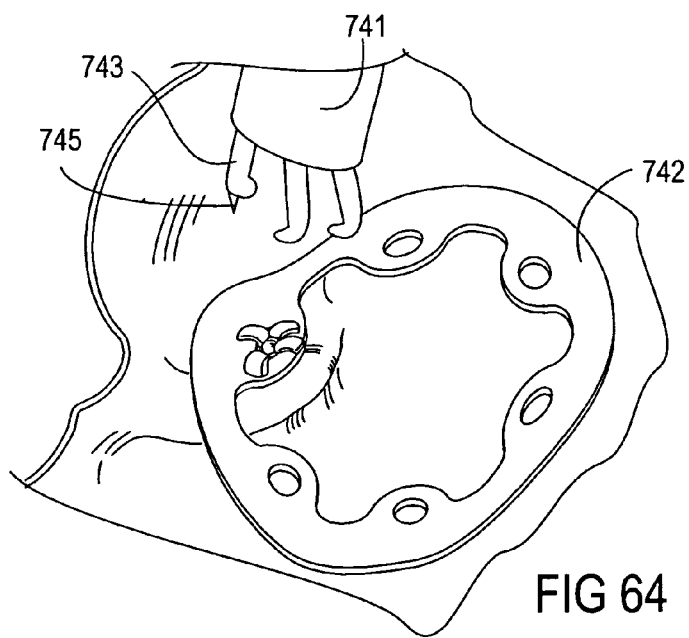

FIG. 64 shows a close-up view of a single fastener 710 in place.

The device is then used to plicate additional stomach tissues and insert fasteners 710 as described before, perhaps moving to the opposite lobe rather than to an adjacent lobe on the stomal ring clip 742, to create a uniform stoma.

Figure 65:
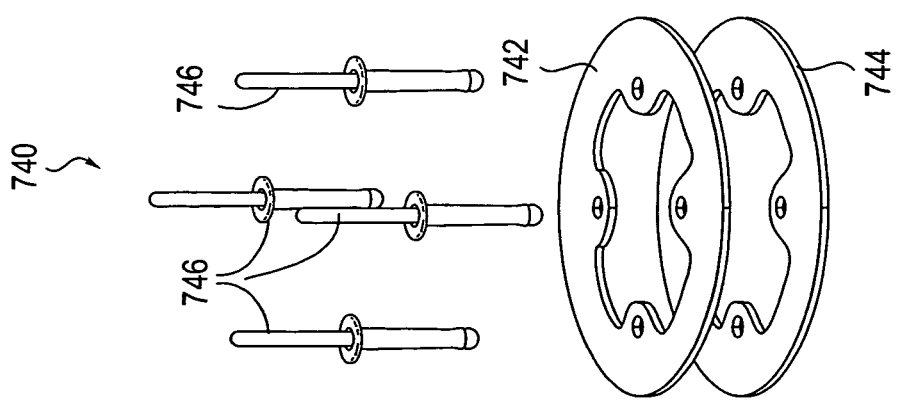
FIG. 65 is an exploded view of a stomal ring clip device having upper and lower rings for forming a stoma or restriction in a patient's stomach.

FIG. 65 is an exploded view of a stomal ring clip device 740 having upper 742 and lower 744 rings for forming a stoma or a restriction in a patient's stomach. FIG. 65 shows an alternate embodiment of the rivets 746 in which the rivets are blind fasteners of a "pop rivet" type configuration where instead of the distal head of the rivet being expanded by pressing against an anvil, the rivets include an internal expander which is drawn proximally into the rivet to expand its distal end. In this configuration, the rivet delivery lumen 714 can include grasping and articulating means to deploy the rivet expander, hold the rivet in place as the expander is drawn proximally, and then remove the undesired portion of the expander after deployment. The undesired portion of the expander could be caught with a magnet or some other means, and then retracted. As previously stated, other types of fasteners could also be used, for example double-ended rivets, single-ended rivets or rivets designed to expand with anvils without spikes.

Figure 66:
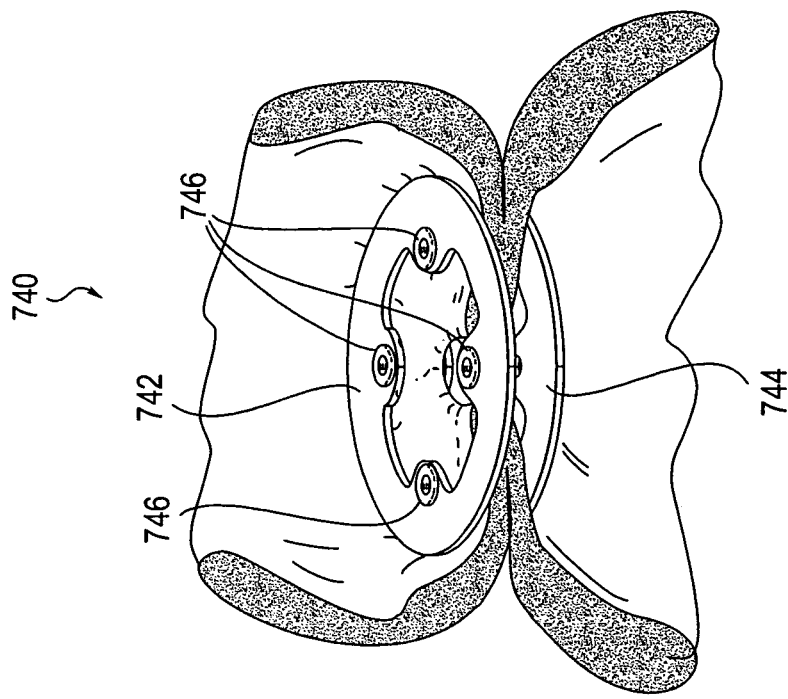
FIG. 66 shows an assembled view of the stomal ring clip device implanted in a patient's stomach.

FIG. 66 shows an assembled view of the stomal ring clip device 740 of FIG. 65 implanted in a patient's stomach. The stomal ring clip device 740 is configured to be implantable within the patient's stomach using a peroral endoscopic approach with the surgical instrument 700 of FIGS. 49-51, or one of the other embodiments discussed. Alternatively, the stomal ring clip device 740 may be implanted with standard endoscopic instruments or it may be implanted via alaparoscopic approach or a combined endoscopic and laparoscopic approach. The stomal ring clip can be fastened in place using open surgery, laparoscopic techniques, standard endoscopic suturing techniques or use specialized sewing devices such as the ENDOCINCH" (CR Bard Inc.) or others described herein. The stomal ring clip device 740 includes an upper ring 742, a plurality of fasteners 746 and, optionally, a lower ring 744. The upper ring 742 and the lower ring 744 are generally flat and have an inner diameter and an outer diameter. The inner diameter is preferably larger than the diameter of the desired stoma opening such that the folded tissue rather than the stomal ring clip material form the actual stoma opening. This would result in an inner diameter of approximately one to three centimeters. The width of the stomal ring clip is dimensioned to allow placement of attachment means and may include ribs or ridges to restrain the tissue captured in the folds between the rings. In one embodiment, both the upper ring 742 and the lower ring 744 are made of a flexible, resilient material that can be folded or rolled to a diameter small enough to be delivered easily through the patient's esophagus or through the instrument channel of an endoscope or surgical instrument and which will return to its flat state for deployment in the patient's stomach. Suitable materials for the upper ring 742 and the lower ring 744 include resilient metals, such as spring-tempered stainless steel and superelastic NiTi alloys, and resilient polymers (fluoropolymers, polypropylene, polyethylene, nylon or Pebax), elastomers (silicone, polyurethane) or composites or reinforced versions thereof. Commercially available materials such as Goretex (Gore) or Marlex (Davol) mesh could also be configured for use as a stomal ring clip. Materials can be permanent or biodissolvable. Though it is preferable for the rings to be resilient and have the ability to be folded or rolled, the rings could be made of rigid material (e.g. titanium or rigid plastic such as polyester) and be designed with hinges or articulations to allow passage through the esophagus after which, upon entering the stomach, they could be opened to their full size prior to attachment. Alternatively, the stomal ring clip may be constructed of sections made of rigid materials connected by sections of flexible material.

Figure 67:
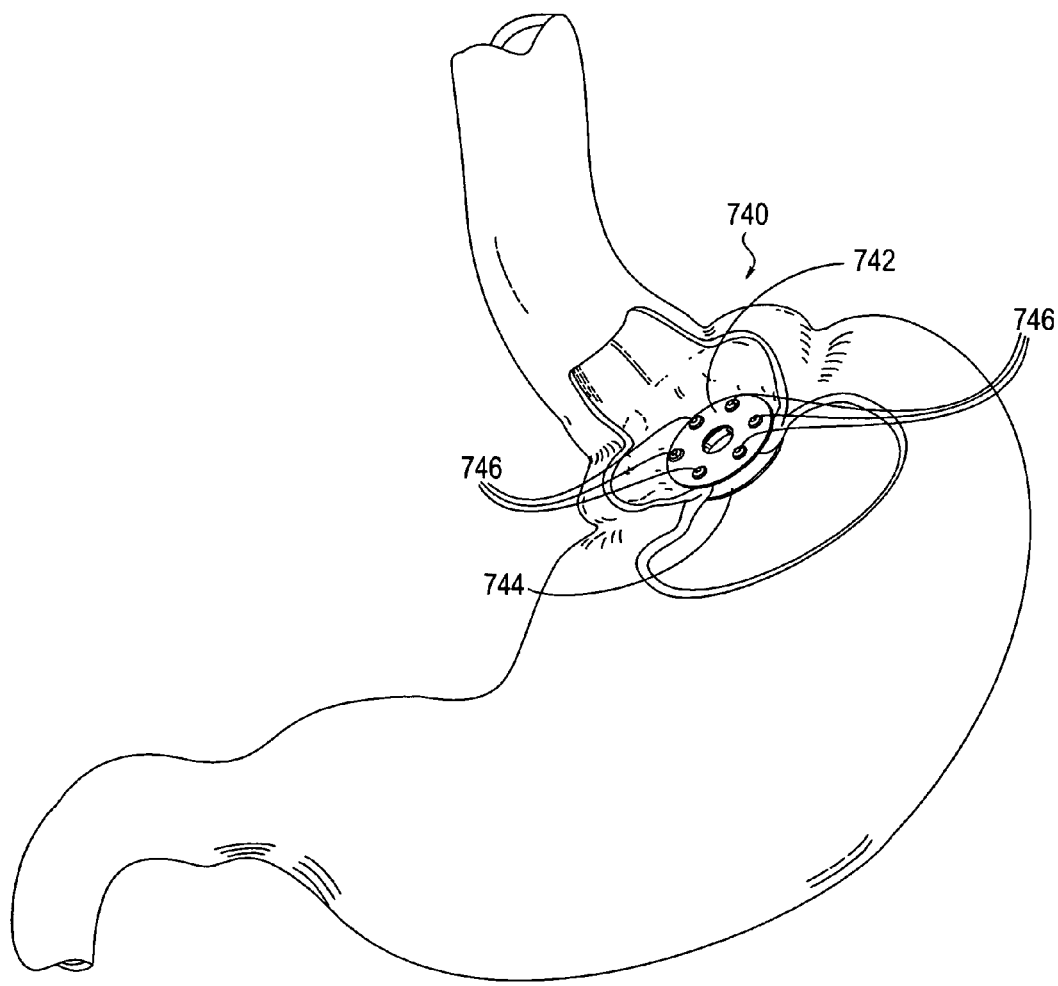
FIG. 67 shows an example of a stomal ring clip device with an upper ring and a lower ring implanted in a patient's stomach.

FIG. 67 shows an example of a stomal ring clip device 740 with an upper ring 742 and a lower ring 744 implanted in a patient's stomach. In this example, the stomal ring clip device 740 has a diameter smaller than the diameter of the opening formed by the plicated tissue.

The upper ring 742 and the lower ring 744 optionally have a plurality of preformed holes sized to accept the plurality of fasteners 746. In one embodiment, the plurality of fasteners 746 are in the form of rivets or similar fasteners that are deliverable using the surgical instrument 700 of FIGS. 49-51. Alternatively, the fasteners 746 can be integrated into one or both of the rings 742, 744 so that the two can be fastened together without separate fasteners. Alternately fasteners and holes can be designed so the fasteners secure themselves to the rings as they are placed through the ring material. This can obviate the need for an expandable distal head on the fastener. Similarly, the proximal head of a fastener can be dimensioned larger than the shaft of the fastener and the hole through which the shaft passes in the upper ring thereby obviating the need for an expandable proximal head. Alternately constructing the rings 742 and/or 744 of a pierceable material, such as Goretex or Marlex or materials commonly used for vascular grafts or other materials described herein, would allow a fastener of an appropriate piercing design would allow implantation without requiring the lining up of preformed holes.

In a variation of the method for placing a single ring, a lower ring 744 may be passed into the patient's stomach prior to the upper ring 742. A surgical instrument, which may be inserted laparoscopically, holds the lower ring 744 from below, while another instrument, inserted endoscopically, holds the upper ring 742. The stomach wall is plicated or invaginated between the upper ring 742 and the lower ring 744 and the fasteners 746 are driven through both rings, effectively sandwiching a fold of the stomach wall tissue between the two rings. FIG. 67 shows an example of a stomal ring clip device 740 with an upper ring 742 and a lower ring 744 implanted in a patient's stomach.

Figures 68, 69:
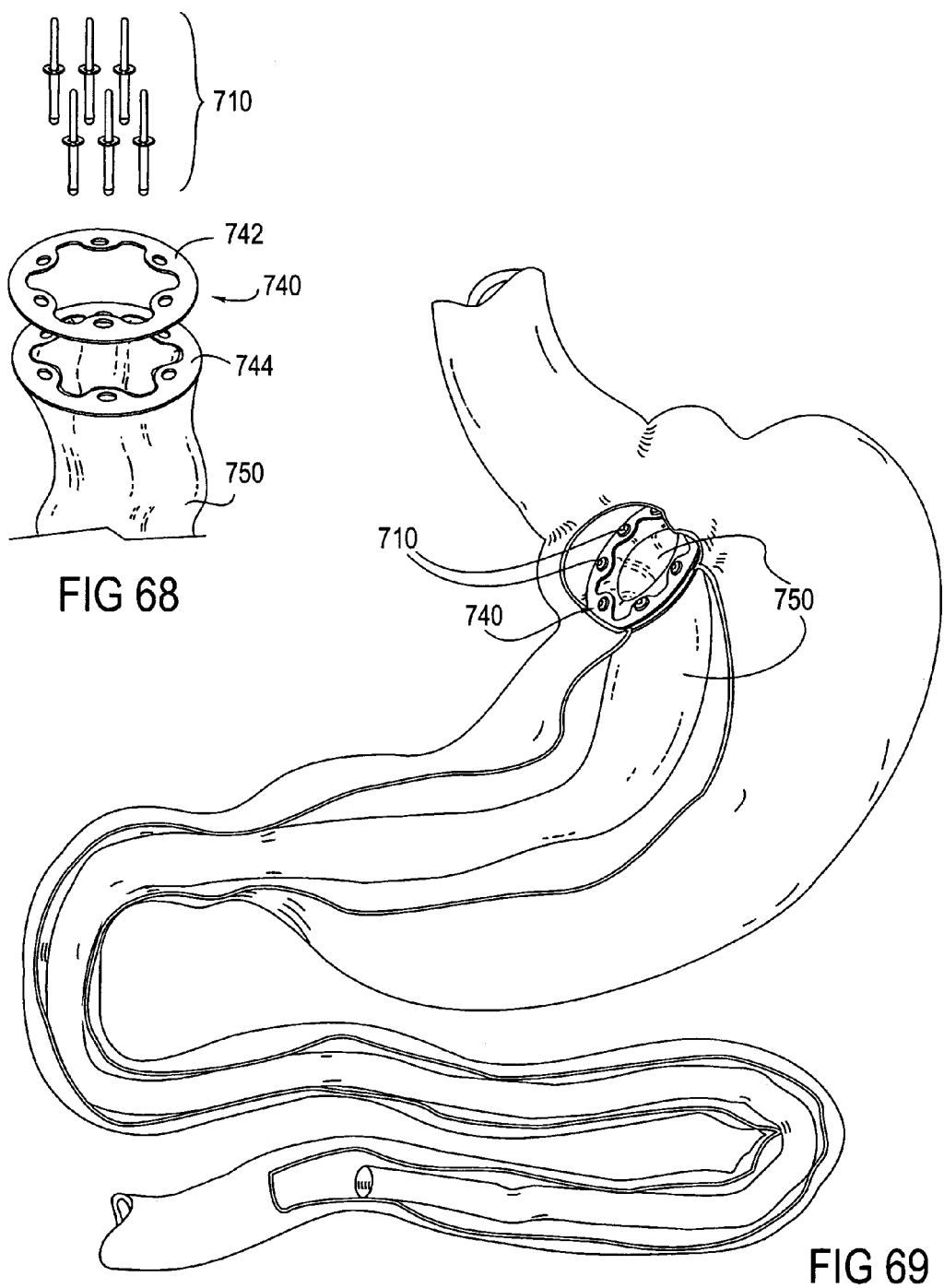
FIG. 68 is an exploded view of an embodiment of a stoma ring clip with a dependent gastrointestinal sleeve device.
FIG. 69 shows the device of FIG. 68 in situ.
Figure 70:
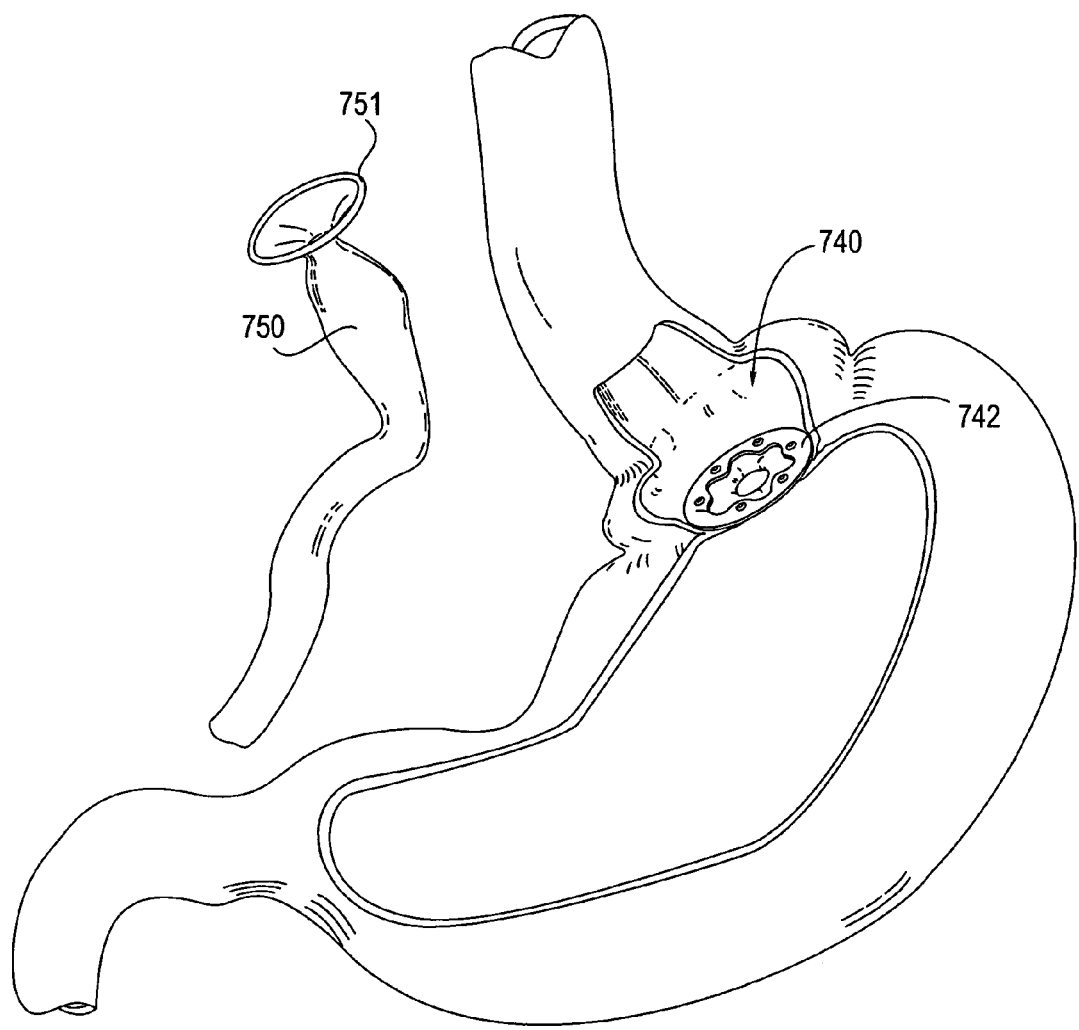
FIG. 70 shows an embodiment of gastrointestinal sleeve device.

These apparatus and methods can be combined with other surgical techniques or devices described above as part of a complete treatment regimen for treatment of morbid obesity. By way of example, FIGS. 68 and 70 show two embodiments of gastrointestinal sleeve devices 750 attached by stomal ring clip devices 740. These sleeve devices 750 interrupt the digestion process by delaying various digestive juices from interacting with ingested food until the food reaches a desired location in the intestine.

FIG. 69 shows the device of FIG. 68 in situ. The sleeve portion 750 of the device is attached to a lower stomal ring clip 744. The sleeve 750 is flexible as described herein, allowing it to conform to the various curves involved with the gastro-intestinal (GI) tract. The sleeve portion 750 of the device may also be compressible, collapsible or foldable, allowing the pyloric sphincter to open and close, as well as expandable for larger pieces of food. In this embodiment the sleeve 750 is attached to the outer diameter of the lower stomal ring clip 744 thereby allowing the suturing or fastening device access to the stomal ring clip 740 for fastening without damaging or piercing the sleeve 750. This type of sleeve 750 is generally placed at the same time as the stoma, however the sleeve 750 and stomal ring clip 740 can be constructed with removable and replaceable connections for the exchange of sleeves on a previously implanted stomal ring clip.

FIG. 70 shows an embodiment for a sleeve device 750 that may be used with an existing stoma or stomal ring clip 740. The sleeve device 750 is made of a flexible material like the device of FIGS. 68 and 69, and is attached to a ring or connector 751 constructed to have a rigidity greater than that of the sleeve 750 and having a diameter that is larger relative to the stoma and preferably larger than the inner diameter of the upper stomal ring clip 742, thus preventing the sleeve device 750 from slipping through the stoma and moving downstream within the GI tract. These sleeve devices 750 provide for a variable stomal diameter. For example, the devices shown are in a non-stressed state, and the sleeve can be made of a flexible or elastomeric material, and in this case the diameter of the stoma can actually increase if stretched by a large piece of food. This type of sleeve 750 is generally placed after the stoma or stomal ring clip 740 is positioned. This can facilitate exchange of sleeves, for example, if a longer sleeve is considered desirable. In some embodiments the ring connector 751 on the sleeve 750 will attach and secure to the upper stomal ring clip 740.

Figure 71:
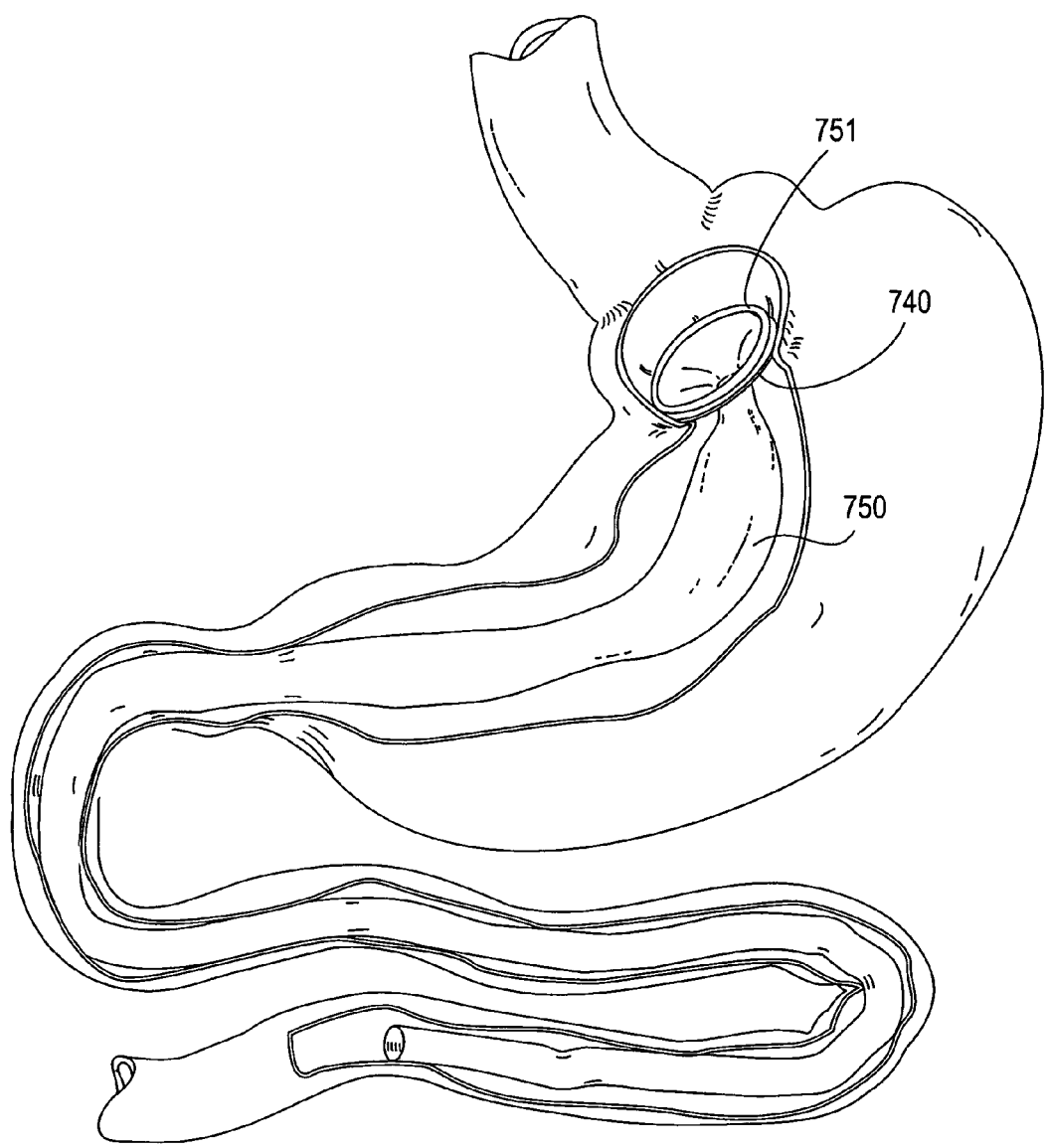
FIG. 71 shows the device of FIG. 70 in situ.

FIG. 71 shows the device of FIG. 70 in situ. The sleeve device 750 shown in FIG. 70 can be used with a stoma (either created with fasteners alone, or created with fasteners and a stomal ring clip device 740) to pass food from the mouth to someplace downstream within the GI tract, thus preventing the digestion.

An added benefit of the device of FIG. 70 is that when positioned in the stomach, as shown in FIG. 71, the sleeve device 750 can completely cover a stoma ring clip 740, and thus prevent food from getting stuck and caught up in the ring and fasteners, thus improving the flow of food through the stoma.

The devices may be positioned as follows, after the stoma is created (as previously discussed), a sleeve device is then passed through the mouth and into the stomach (as previously discussed for a stomal ring clip), and then the distal portion of the sleeve device is passed through the stoma and preferably past the pylorus and duodenum and the distal end is carried downstream within the GI tract (either pushed or via peristalsis), and the proximal end is eventually left to sit atop the stoma. The sleeve can be dimensioned, as described herein, to locate the restriction to food flow at the stomal ring clip or at some other more distal location. In other embodiments the sleeve diameter will not create the restriction and the restriction will use the pylorus as a natural restriction or the restriction will be created at the stoma ring clip. For additional security, the proximal end may be attached to the stoma by some means, perhaps clicking into place on a stomal ring clip designed to accept the proximal end of a sleeve device, sutured into place or attached using one of the other structures described herein.

Figure 72:
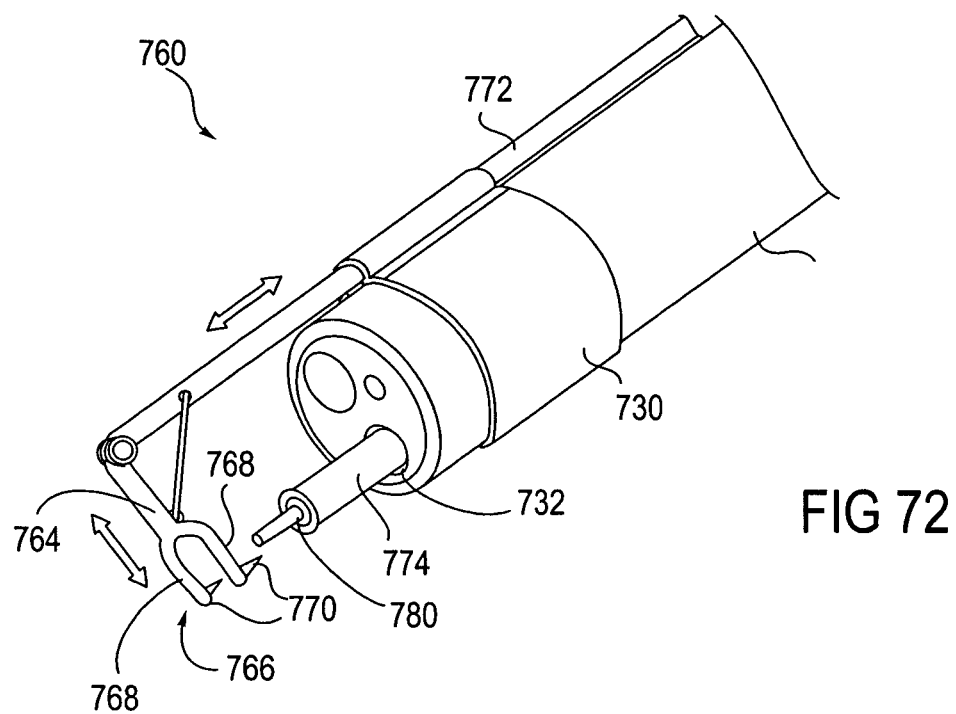
FIG. 72 illustrates another embodiment of a surgical instrument for fastening tissue.

FIG. 72 illustrates another embodiment of a surgical instrument 760 for fastening tissue. In one embodiment, the surgical instrument 760 is mounted on the exterior of a gastroscope or other flexible endoscope 730 with a mounting ring or clamp 762. The surgical instrument 760 has an articulated arm 764 with a plicator/riveter support 766 having a pair of spaced apart support fingers 768 mounted to it. A flexible control cable 772, which extends to the proximal end of the gastroscope 730, allows the operator to move the articulated arm 764 and plicator/riveter support 766 axially and radially with respect to the gastroscope 730. In certain embodiments, the support fingers 768 include one or more retractable tines 770 for grasping and manipulating the tissue. Rivet-like surgical fasteners 780 are delivered with an insertion pusher tube 774 through the working channel 732 of the gastroscope 730.

Figure 73:
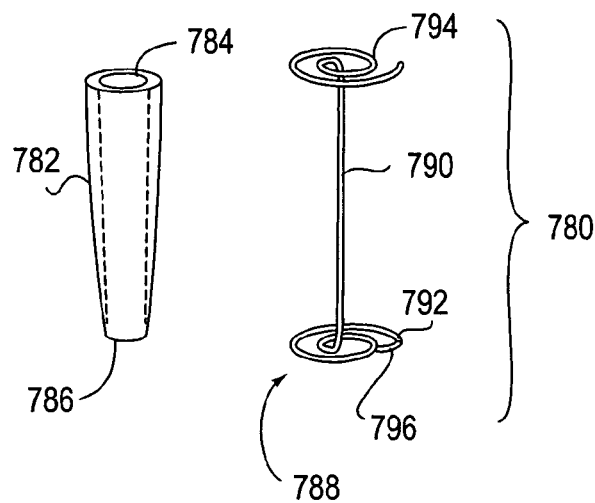
FIG. 73 is an exploded view of a surgical fastener for use with the surgical instrument of FIG. 72.

FIG. 73 is an exploded view of a rivet-like surgical fastener 780 for use with the surgical instrument of FIG. 72. The surgical fastener 780 has two components a rivet tube 782 and a rivet cap wire 788. The rivet tube 782 can be made of a biocompatible polymer or metal. The rivet tube 782 has a tapered distal end 786 an internal lumen 784 sized to allow passage of the rivet cap wire 788 in a straightened condition. In its deployed condition, the rivet cap wire 788 has a straight piercing section 796 on its distal end, followed by the distal button 792, which is a section of the wire formed into a circle or spiral. Next, is a straight central section 790 that connects the distal button 792 to the proximal button 794, which is another section of the wire formed into a circle or spiral. In certain embodiments, the rivet cap wire 788 is made of a highly resilient material, for example a superelastic NiTi alloy, which can be preformed into this geometry by cold working and/or heat treatment, and which will return to this geometry after being straightened out for insertion through the internal lumen 784 of the rivet tube 782. Rivet tube 782 can be constructed of a relatively bioinert material such as 304 or 316 SS or Ti unless the clinical situation suggests that a material that encourages a scar forming healing response as discussed earlier is desirable. Rivet tube 782 will typically have an outer diameter of approximately 0.25-1.5 mm with the inner diameter large enough to provide for passage of a pre-formed NiTi wire of approximately 2×-6× the diameter of the wire. The tapered tip will preferably have a minimum clearance to allow free passage between its inner diameter and the outer diameter of the NiTi wire. Wall thickness of tube 782 will typically be on the order of 0.002-0.005".

Figure 74:
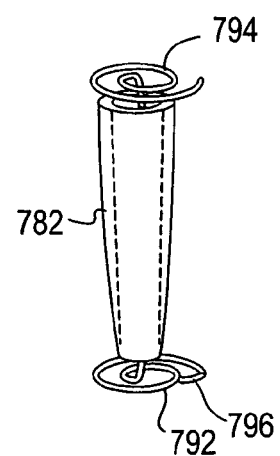
FIG. 74 shows the surgical fastener of FIG. 73 in a deployed condition.

FIG. 74 shows the surgical fastener 780 of FIG. 73 in a deployed condition. The straight central section 790 of the rivet cap wire 788 extends through the internal lumen 784 of the rivet tube 782, and the distal button 792 and proximal button 794 are formed into a substantially planar tissue-retaining geometry approximately perpendicular to the rivet tube 782 at the proximal and distal ends of the rivet tube 782.

The straight piercing section 796 may be bent inward slightly so that the distal button 792 protects it from inadvertently piercing any adjacent tissue structures when in the deployed condition.

FIGS. 75A-75F show a sequence of steps for deploying the surgical fastener 780 of FIGS. 73 and 74. The tines 770 of the plicator/riveter support 766 grasp the tissue to be fastened, for example the stomach wall, and the articulated arm 764 draws it toward the gastroscope 730 to plicate the tissue. The support fingers 768 of the plicator/riveter support 766 are positioned astride the working channel 732 of the gastroscope 730. A surgical fastener 780 is advanced through the working channel 732 of the gastroscope 730 by the insertion pusher tube 774. The surgical fastener 780 is positioned with the tapered distal end 786 of the rivet tube 782 facing distally and the rivet cap wire 788 straightened out and inserted through the insertion pusher tube 774 and through the internal lumen 784 of the rivet tube 782 with the straight piercing section 796 extending slightly beyond the distal end of the rivet tube 782.

Figure 75A:
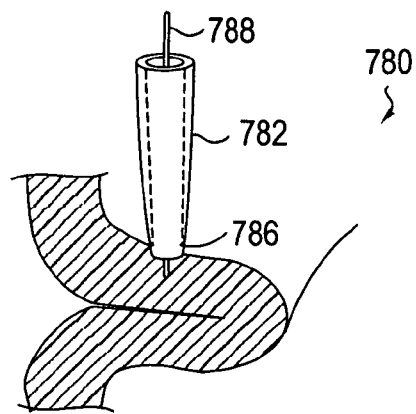
FIGS. 75A-75F show a sequence of steps for deploying the surgical fastener of FIG. 73.
Figure 75B:
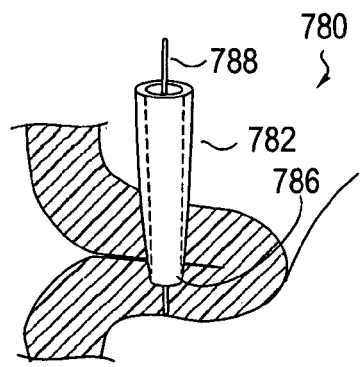
Figure 75C:
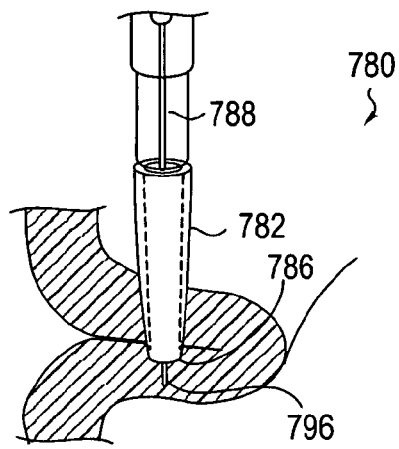
Figure 75D:
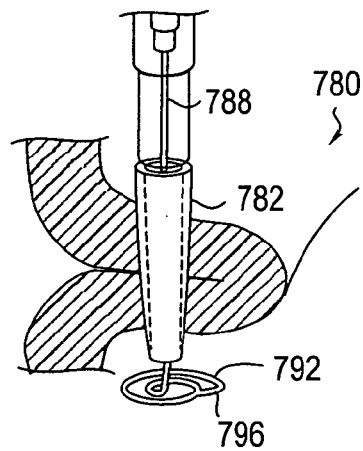
Figure 75E:
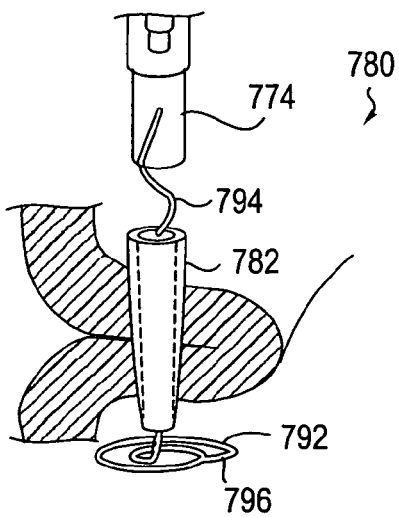
Figure 75F:
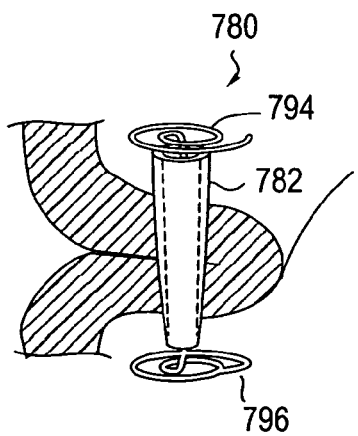

The straight piercing section 796 of the rivet cap wire 788 pierces the plicated tissue, as shown in FIG. 75A. Then the insertion pusher tube 774 pushes the tapered distal end 786 of the rivet tube 782 through the tissue, as shown in FIG. 75B, until the rivet tube 782 has passed all the way through the tissue, as shown in FIG. 75C. Next, the rivet cap wire 788 is advanced until the distal button 792 reforms to retain the plicated tissue the distal end of the rivet tube 782, as shown in FIG. 75D. The insertion pusher tube 774 is then withdrawn, as shown in FIG. 75E, allowing the proximal button 794 to reform to retain the plicated tissue the distal end of the rivet tube 782. The fully deployed surgical fastener 780 holding the plicated tissue is shown in FIG. 75F.

Figure 76:
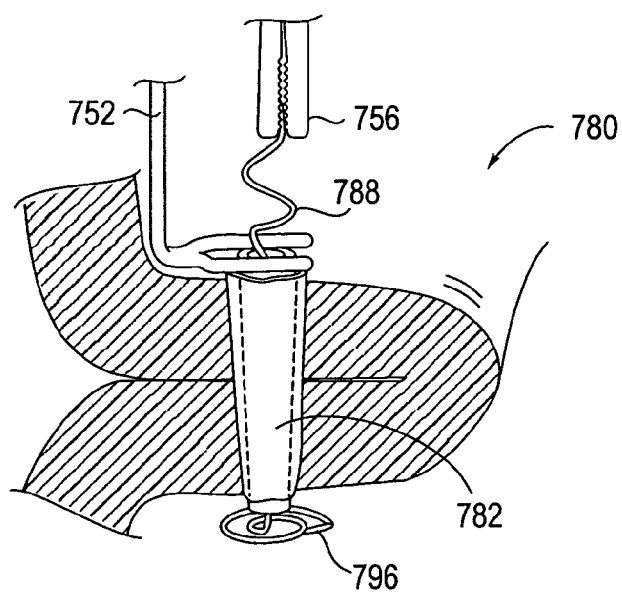
FIG. 76 shows the surgical fastener of FIG. 73 being removed.

The construction of the surgical fastener 780 allows it to be removed if it is desired to reverse or revise the surgical procedure. FIG. 76 shows the surgical fastener 780 of FIG. 73 being removed. A grasping tool or other rivet tube retaining tool 752 engages the proximal end of the rivet tube 782 and a grasper 756 grasps the rivet cap wire 788 near its proximal and withdraws it from the rivet tube 782 to release the fastened tissue.

The attachment device and fasteners described in FIGS. 72-76 share many attributes with the attachment device and fasteners described in FIGS. 49-65. With appropriate design adjustment features of the attachment devices and fasteners can be combined and/or interchanged.

Figure 89A:
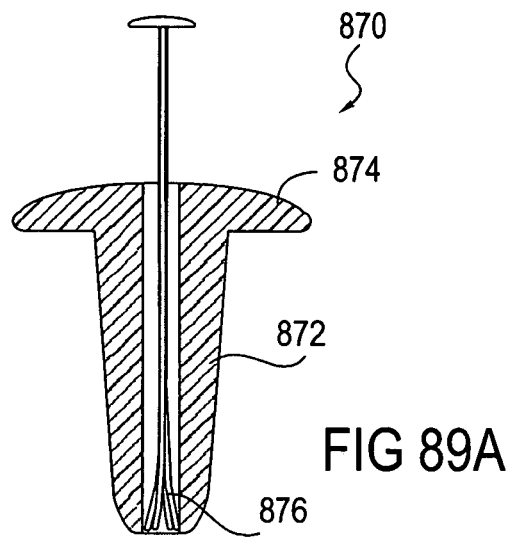
FIGS. 89A-89D illustrate an alternate rivet design.
Figure 89B:
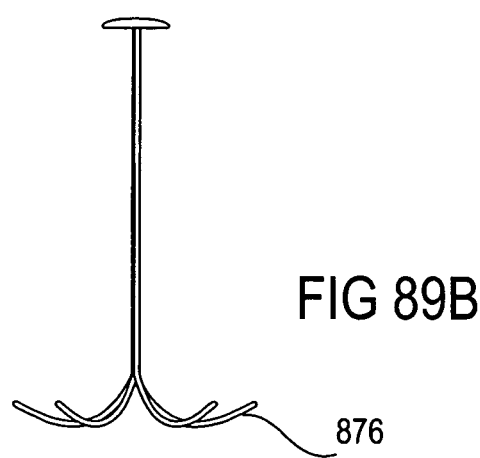
Figure 89C:
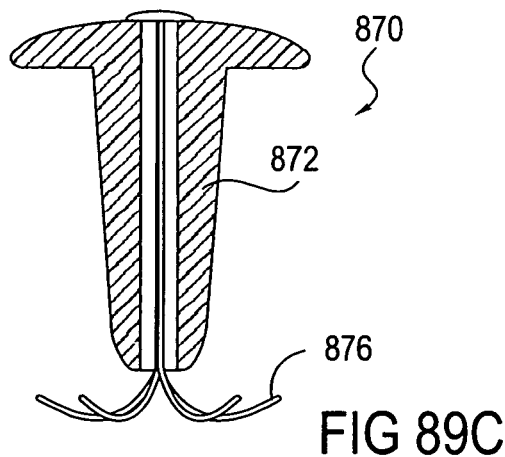
Figure 89D:
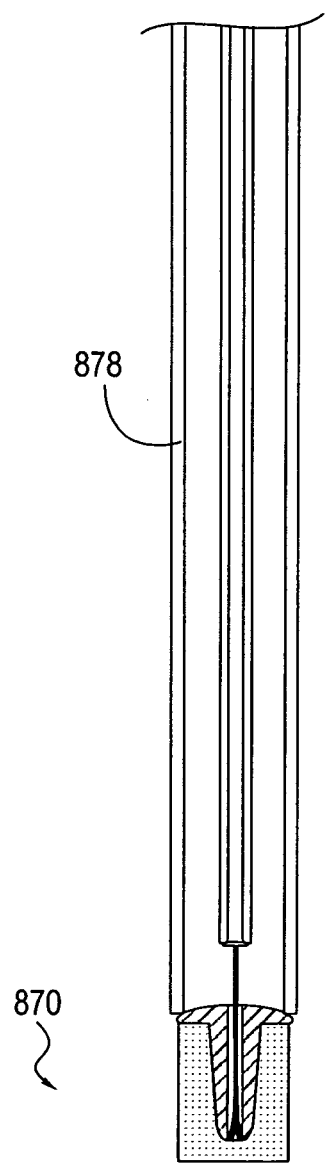

FIGS. 89A-89D shows an alternate rivet design 870 in which the rivet tube 872 is provided with an attached or formed in place proximal rivet cap 874. The proximal rivet cap 874 can be formed as described earlier or formed as shown in FIG. 89A. FIG. 89B shows a multi fingered distal cap 876 that can be deployed by an axial advancement of the fingers, as shown in FIG. 89C. With a design that includes a proximal eye or other means of coupling, the fingers could also be retracted back into the rivet body 872 if so desired. The fingers 876 of this rivet do not require the degree of superelasticity of the rivets described in FIGS. 72-79 and could optionally be made from 304, 316 or other stainless steels in addition to NiTi alloys, as well as other metals. FIG. 89D shows an exemplary apparatus 878 for deploying this type of rivet.

FIG. 77 shows a top view of an attachment ring device 800 for attaching a gastrointestinal sleeve device within a patient's stomach. FIG. 78 shows a cross section of the attachment ring 800 of FIG. 77 attached at a plication formed in a stomach wall of a patient. The attachment ring device 800 provides strain relief to distribute the stress of attachment to a substantial area of the stomach wall. The attachment ring device 800 has a first, outer ring 802 that engages and seals against the stomach wall. A second, slightly smaller diameter ring 804 is connected to the first ring 802 by a first annular sheet of material 806 that can support and seal to the sleeve interface. The first ring 802 and the second ring 804 are preferably wire-reinforced plastic rings. Suitable materials for the first annular sheet of material 806 include, but are not limited to, polyurethane, silicone and Teflon. Inside of the second ring 804 is a second annular sheet of material 808 that is easily pierced with a surgical fastener, such as the surgical fastener 780 previously described, or other surgical rivet, staple or suture. Suitable materials for the second annular sheet of material 808 include, but are not limited to, Teflon fabric, Goretex or Marlex or materials commonly used for vascular grafts. The second annular sheet of material 808 may be slit or perforated to enhance the flexibility of the fabric.

FIG. 79 shows a cross section of the attachment ring device 800 of FIG. 77 with a gastrointestinal sleeve device 400 installed. The gastrointestinal sleeve device 400 has a sleeve ring 810 that is sized to have a diameter slightly smaller than or the same size as the first ring 802 and slightly larger than the diameter of the second ring 804. The sleeve ring 810 is preferably a wire-reinforced plastic ring that may be somewhat more rigid than first ring 802 and the second ring 804. For installation, the sleeve ring 810 is compressed slightly so that it can slip past the first ring 802, then it is allowed to expand so that it engages and seals against the first annular sheet of material 806 between the first ring 802 and the second ring 804.

Some configurations of attachment rings, such as the one illustrated in FIG. 79, could be placed with a stapling device similar to circular anastomotic staplers. In this method, the stapling device would be placed via a peroral route with the attachment ring preferably pre-positioned on the stapling device. The device would then use suction, stay sutures or other mechanical means to draw gastric wall into the gap between the anvils of the stapling device in a manner that forms a plication adjacent to the attachment ring. Dimensioning of the device can be selected to obtain stapling within the muscularis or a full thickness plication that also goes through the serosa as indicated by the clinical situation. Firing of the stapling device would then result in an attachment similar to that shown in FIG. 78 with the substitution of the rivet as shown with one or more rows of staples. One embodiment of the stapling device would include a tilting or collapsible distal anvil that could be withdrawn through the stapled in-place attachment ring after the completion of the stapling procedure. Buttressing of the staples with bovine or porcine tissue, Teflon pledges or other buttressing material, may be indicated in some clinical situations.

A leak shield may be used with any of the gastrointestinal sleeve devices described herein to help assure an adequate seal between the sleeve and the stomach wall at the proximal end of the device. The leak shield may be a separate component or it may be integral to the gastrointestinal sleeve device or to the attachment device. FIG. 80 shows a cross section of the attachment device 800 and the gastrointestinal sleeve device 400 of FIG. 79 with an optional leak shield 812 installed. The leak shield 812 in this example is constructed integrally with the gastrointestinal sleeve device 400. The leak shield 812 is a tubular extension of the gastrointestinal sleeve device 400 that has a resilient leak shield ring 814 at its proximal end. The leak shield ring 814 is preferably a wire-reinforced plastic ring. The leak shield 812 may be made of the same material as the gastrointestinal sleeve device 400 or, more preferably, it may be made of a material chosen for its ability to provide a reliable seal against the stomach wall such as silicone, polyurethane or other flexible film. It would be expected that the material of the leak shield would generally be of equal or greater flexibility and equal or lower durometer than the sleeve due to the desire for it to conform and seal as well as the lower forces it would be expected to withstand without failure.

Figure 82:
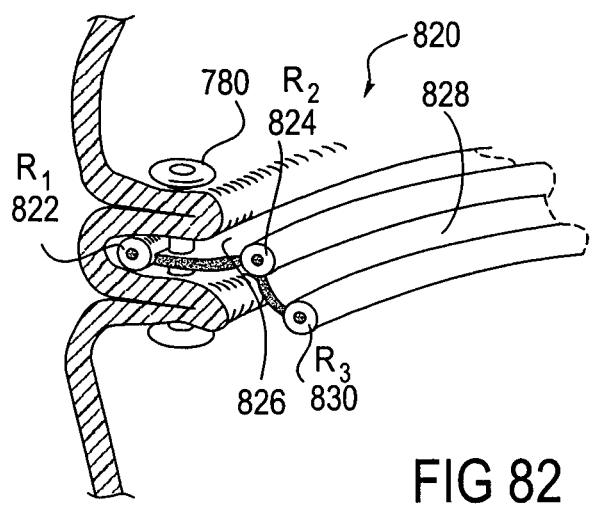
FIG. 82 shows a cross section of the attachment ring device of FIG. 81.
Figure 81:
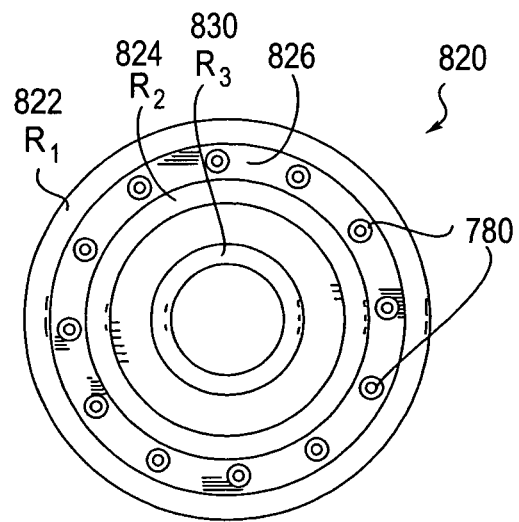
FIG. 81 shows a top view of another embodiment of an attachment ring device for attaching a gastrointestinal sleeve device within a patient's stomach.

FIG. 81 shows a top view of another embodiment of an attachment ring device 820 for attaching a gastrointestinal sleeve device within a patient's stomach. FIG. 82 shows a side view of the attachment ring device 820 of FIG. 81, which, by way of example, is shown attached between two plications formed in a stomach wall of a patient. The attachment ring device 820 could alternately be attached to a single plication. The attachment ring device 820 has a first, outer ring 822 that engages and seals against the stomach wall. A second, slightly smaller diameter ring 824 is connected to the first ring 802 by a first annular sheet of material 826 that is easily pierced with a surgical fastener, such as the surgical fastener 780 previously described, or other surgical rivet, staple or suture. A third ring 830 is connected to the first ring 802 by a second annular sheet of material 828 that can support and seal to the sleeve interface. The first ring 822, second ring 824 and third ring 830 are preferably wire-reinforced plastic rings.

The double plication illustrated in FIG. 82 as a structure and method of attaching a device can be a preferred embodiment in certain clinical situations. As mentioned previously in relation to FIGS. 43-45 the use of a plication can confer certain advantages to an attachment structure and method. All of these advantages also exist with a device attached between a double plication. The geometry created by the capture of a device in a double plication is analogous to the placement of an o-ring in a grove. Though not 100% encapsulation, tissue would be in contact with the implanted ring on three sides that would improve the leak resistance of the attachment. The use of the double plications would also serve to stabilize the attachment and result in a favorable distribution of forces that might be transmitted to the ring as a result of its connection to a sleeve and/or stoma. A further advantage of the double plication attachment would be the doubling of the tissue attachment area. This would serve to distribute the forces transmitted to the ring over double the area resulting in a lowering of the pressure applied to the tissue. Clinically, suture and other attachment failure can often be attributed to localized ischemia and ischemia can be related to the pressure applied to the tissue by the suture or fastener. Therefore, if a double plication may reduce the pressure transmitted to the tissue by the attachment means, attachment failure will be reduced.

In a related aspect of an embodiment that could be clinically preferred, one should consider that when suturing or otherwise securing an attachment ring or other device in place it is beneficial to reduce the pressure transmitted to the tissue. This has been discussed previously related to the use of force distributing pledgets, fastener structures and rivet end caps. These previously discussed structures and methods relate to reducing pressure along the axis of the fastener system. The double plication addresses pressures that are perpendicular or radial to the axis of the fastener. Increased fastener diameter would serve to reduce pressures in this direction however one can imagine that this would eventually have diminishing returns, as the area of tissue available to resist these forces would eventually be reduced below an optimum level. With single and double plications and a fastener system that uses thin wires or sutures approximately between 0.2 and 0.5 mm in diameter or less, a simple method and structure to reduce pressure would be use of an increased fastener density. In particular, use of paired parallel fasteners is well suited to this end. One method would apply a single continuous suture or wire that passed through all layers to be fastened and then secured at one point. Of course two separate sutures or wires could then be secured to each other on either side of the layers to be attached. Alternately, the two separate sutures or wires could be secured by, and/or to, a common end cap. A pair of thin rivets could also use a common end cap to achieve this end.

In another aspect the embodiment of FIGS. 81 and 82 can be modified to include two or more easily pierced material faces 826 and their associated rings 822. For example, using a 3 faced ring in the double plication attachment of FIG. 82 where the material faces are sandwiched around both plications such that rivets 780 would pierce 3 layers of the face material in addition to 4 layers of stomach wall. In FIG. 91B a 2 faced ring is shown attached with a T-pledget fastener as described herein. In an alternate variation the attachment ring shown in FIGS. 77 and 78, the easily pierced material 808 can be lengthened to a sufficient length to fold over the plication and be in a position to buttress the rivet 780 in FIG. 78 on both sides of the plication. Other structures can accomplish the same result.

In an additional aspect of the method of using the attachment ring shown 820 in FIGS. 81 and 82, FIG. 91A shows how this type of attachment ring could be attached using a transmural T-Tag 918. In some clinical situations it may be desirable to have additional attachment in which case one method to achieve this result would be to use two rows of T-tags 918 in a variation of what is shown in FIG. 91A. In this example the material face 826 (between rings 822 and 824) can have an increased width to provide additional room for the attachment of the additional row of T-Tags.

Figure 83:
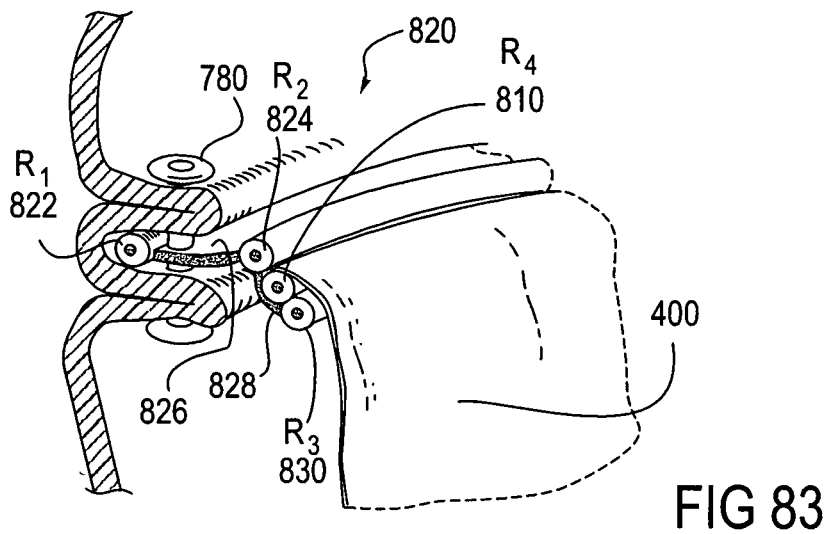
FIG. 83 shows a cross section of the attachment ring device of FIG. 81 with a gastrointestinal sleeve device installed.

FIG. 83 shows a cross section of the attachment ring device 820 of FIG. 81 with a gastrointestinal sleeve device 400 installed. The gastrointestinal sleeve device 400 has a sleeve ring 810 that is sized to have a diameter slightly smaller than or the same size as the second ring 824 and slightly larger than the diameter of the third ring 830. For installation, the sleeve ring 810 is compressed slightly so that it can slip past the second ring 824, then it is allowed to expand so that it engages and seals against the second annular sheet of material 828 between the second ring 824 and the third ring 830. Optionally, an integral or separate leak shield may be used with this embodiment of the attachment ring device 820.

Optionally, magnets can be used to facilitate alignment of the attachment ring device 820 and the gastrointestinal sleeve device 400. One or more magnets would be positioned in the attachment ring device 820 and an equal number of magnets, arranged with opposite poles facing, would be positioned in the gastrointestinal sleeve device 400, When the attachment ring device 820 and the gastrointestinal sleeve device 400 are moved into proximity with one another, the magnets cause the two components to align automatically. The magnets will also help to create and maintain a seal between the two components.

The structures and methods associated with FIGS. 77-83 can also be applied to other attachment methods and structures as described herein. Examples include 1) incorporating the structure of FIG. 77 or 81 could be incorporated into a stoma ring clip; 2) attaching these rings with T-tags in place of rivets and 3) use of multiple rows of attachment in place of a single row as shown.

Figure 84A:
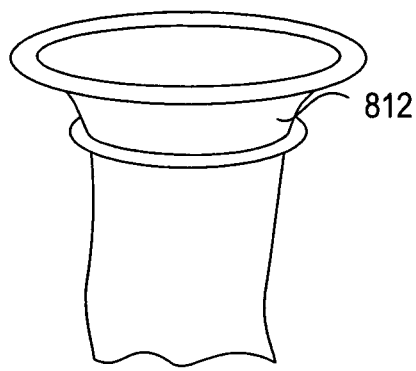
FIGS. 84A-84C show a gastrointestinal sleeve device with an integral leak shield.
Figure 84B:
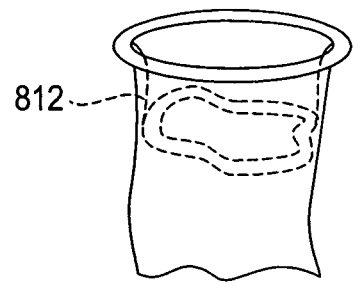
Figure 84C:
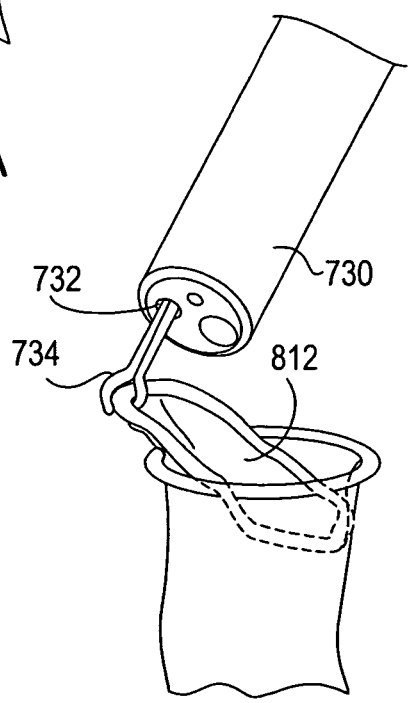

FIGS. 84A-84C show a gastrointestinal sleeve device 400 with an integral leak shield 812 similar to that shown in FIG. 80. FIG. 84A shows a cross section of the proximal end of the gastrointestinal sleeve device 400 with the leak shield 812 in a deployed position. In some clinical situations, the leak shield ring 814 has a diameter slightly larger than the diameter of the sleeve ring 810. For installation, the leak shield ring 814 is compressed slightly and stuffed past the sleeve ring 810 into the proximal end of the gastrointestinal sleeve device 400, as shown in FIG. 84B so that it will not interfere with the installation of the sleeve ring 810. Once the sleeve ring 810 has been installed in the chosen attachment ring device, a grasper 734 is inserted through the working channel 732 of the gastroscope 730 to grasp the leak shield ring 814 and pull it out of the gastrointestinal sleeve device 400 to the deployed position, as shown in FIG. 84C.

Figure 85:
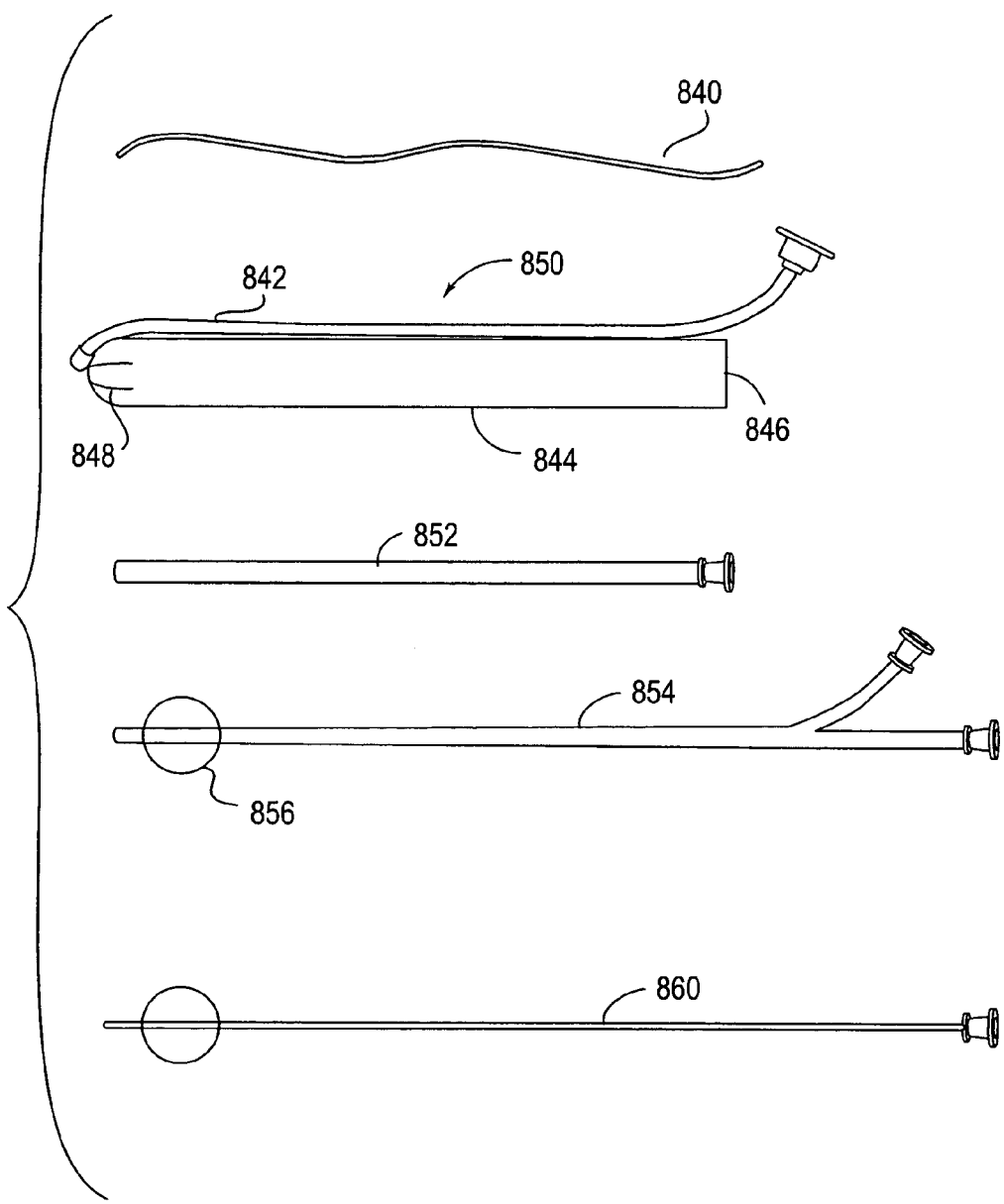
FIG. 85 illustrates the components of a kit for delivering and deploying a gastrointestinal sleeve device.

FIG. 85 illustrates the components of a kit for delivering and deploying a gastrointestinal sleeve device. In one embodiment, the kit includes an optional guidewire 840, a pyloric/duodenal introducer 850, and either a distal pusher catheter 852 or a distal balloon seal 856 and pusher catheter 854. A balloon catheter 860 for removal of the gastrointestinal sleeve device may be included as part of the kit or supplied as a separate item. For example this balloon catheter can be used for retrieval as described in step 12 of the method outlined below. As an alternative to the use of a balloon catheter for retrieval, an endoscopic grasper such as those in the MAXUM line (Wilson-Cook) can be passed coaxially down the sleeve or delivered externally to the sleeve through the working channel of an endoscope then clamped onto the sleeve at some distal location and then used to retract the distal sleeve.

The pyloric/duodenal introducer 850 has a tubular body 844 with an introducer lumen 846 sized to pass through the gastrointestinal sleeve device. The tubular body 844 has a length sufficient to reach past the patient's pylorus into the duodenum via a peroral route. In certain embodiments, the tubular body 844 has a slit flowering distal end 848 for atraumatic crossing of the pylorus. An optional distal infusion lumen 842 parallels the introducer lumen 846 and allows infusion of fluids near the distal end of the introducer 850. For example, the introducer can be used as described in step 10g of the method outlined below.

Figure 86A:
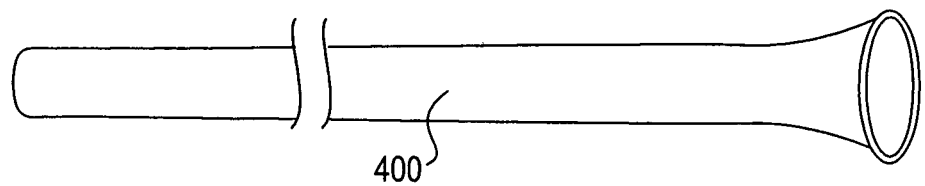
FIGS. 86A-86C illustrate three options for preloading a gastrointestinal sleeve device for delivery and deployment.
Figure 86B:
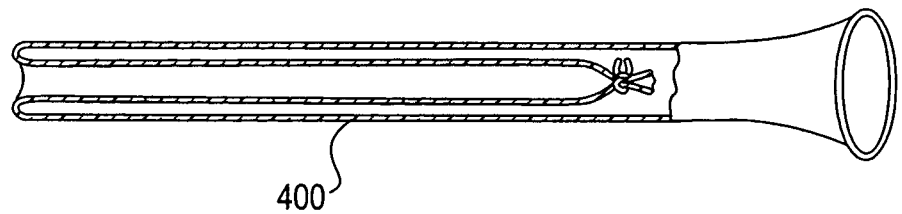
Figure 86C:
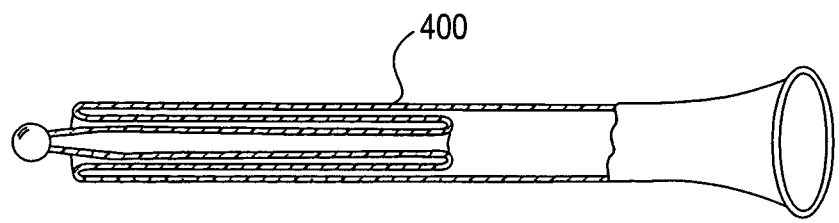

FIGS. 86A-86C illustrate three options for preloading a gastrointestinal sleeve device 400 for delivery and deployment. FIG. 86A shows a gastrointestinal sleeve device 400 in a straight configuration. This configuration is the simplest for construction and loading of the gastrointestinal sleeve device 400, however it poses some challenges for delivery and deployment within the patient's gastrointestinal system. The straight gastrointestinal sleeve device 400 would have to be inserted full-length into the patient's small intestines, which would be challenging because of the torturous path of the small intestines. Another strategy is to invert the gastrointestinal sleeve device 400 so that it would only have to be directly inserted past the patient's pylorus, with peristaltic action assisting the deployment of the device within the patient's small intestines by eversion of the inverted sections. FIG. 86B shows a gastrointestinal sleeve device 400 loaded in a fully inverted configuration. FIG. 86C shows a gastrointestinal sleeve device 400 loaded in a double-inverted configuration. This simplifies the delivery and deployment of the device, but it adds some additional constraints to the configuration of the device. The inverting segments can have very thin walls and inverting interfaces can be highly lubricious for easy and reliable deployment. For example blow molded 90A durometer polyurethane of a wall thickness on the order of 0.005" or less, most preferably about 0.002", with a lubricious coating will work in this manner. The double inverted configuration has the advantage of having the option to use a distal balloon, or other structure as described earlier, to assist the peristalsis working on its distal end to evert the sleeve. This may avoid the need to use internal pressure to accomplish the eversion.

Figure 87A:
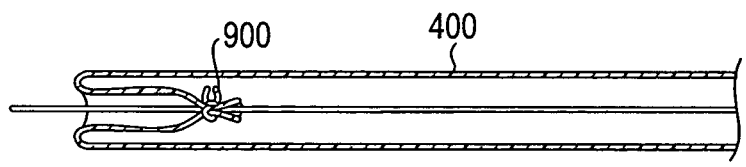
FIGS. 87A-87D illustrate four options for sealing the distal end of a gastrointestinal sleeve device during delivery and deployment.
Figure 87B:
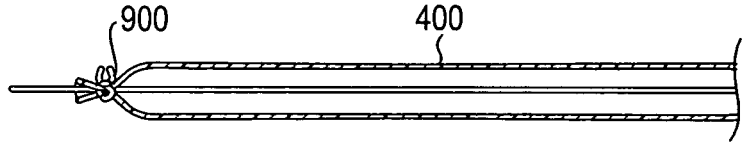
Figure 87C:
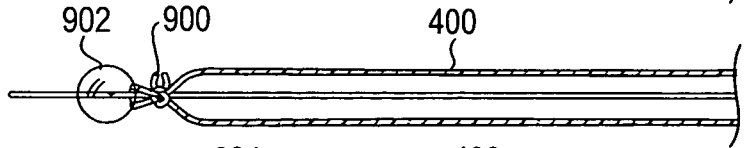
Figure 87D:
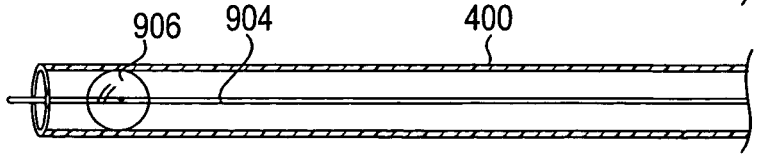

The gastrointestinal sleeve device 400 in FIGS. 86B and 86C could be optionally everted using the method of internal pressurization that is well known in the everting catheter art. To maintain the internal fluid pressure used to assist in everting the inverted gastrointestinal sleeve device 400, the distal end of the device may be temporarily sealed during deployment. FIGS. 87A-87D illustrate four options for sealing the distal end of a gastrointestinal sleeve device during delivery and deployment. FIG. 87A shows the inverted distal end of the gastrointestinal sleeve device 400 sealed with a biodegradable tie 900 that is formulated to dissolve within approximately 24 hours in the intestines. Dissolution of the biodegradable tie 900 can be aided by a solvent or active agent that is ingested or placed in the optional everting fluid. FIG. 87B shows the noninverted distal end of the gastrointestinal sleeve device 400 sealed with a biodegradable tie 900 that is formulated to dissolve within approximately 24 hours in the intestines. FIG. 87C shows an inflatable balloon 902 that extends past the distal end of the gastrointestinal sleeve device 400. The gastrointestinal sleeve device 400 can be attached and/or sealed with a biodegradable tie 900 proximal to the balloon 902. The balloon 902 is carried along through the intestine by peristalsis to deploy the gastrointestinal sleeve device 400 by eversion of the inverted section. When the biodegradable tie 900 dissolves, the balloon 902 detaches and deflates and is carried harmlessly out through the intestines. The inflatable balloon 902 may also be made of a biodegradable material. FIG. 87D shows a balloon catheter 904 with an inflatable balloon 906 that is inflated within the gastrointestinal sleeve device 400 to form a seal. Once the gastrointestinal sleeve device 400 is fully deployed, the balloon 906 is deflated and the balloon catheter 904 is withdrawn. Please note that the aforementioned 24 hour dissolution time is an example and, depending on the clinical situation, this time period could range from a few hours to many weeks.

Figure 88A:
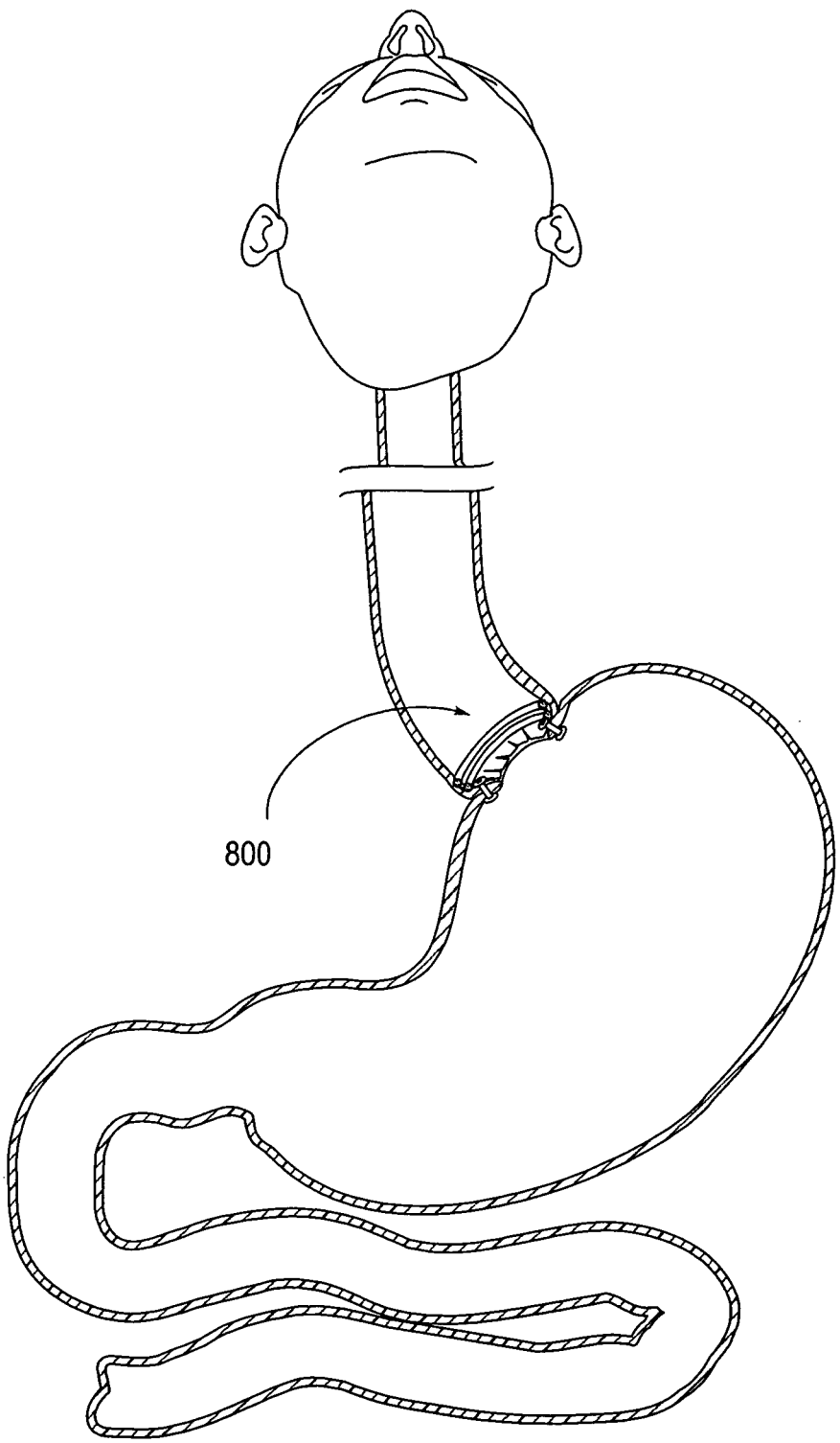
FIGS. 88A-88B illustrate a method of delivering and deploying a gastrointestinal sleeve device.
Figure 88B:
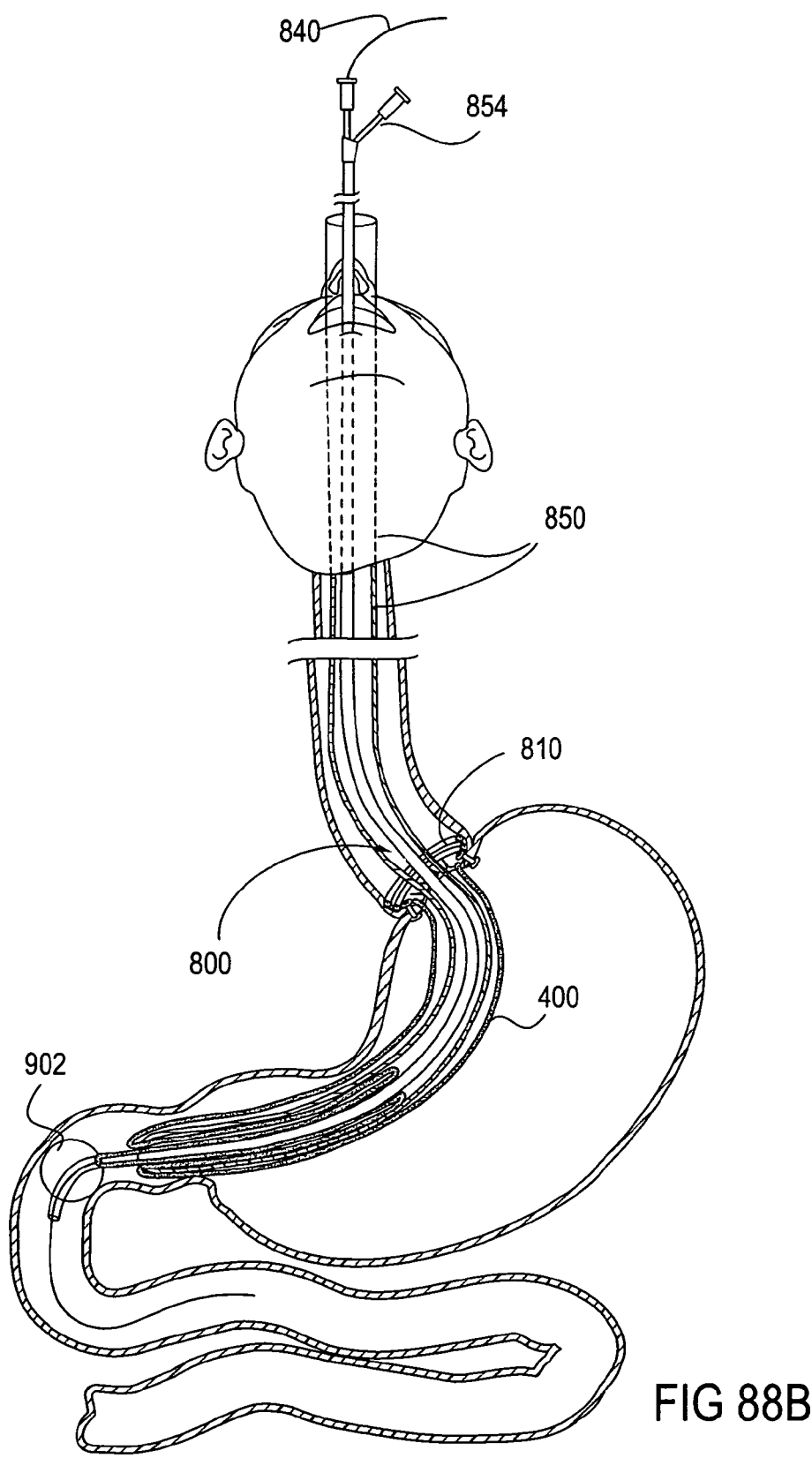

FIGS. 88A-88B illustrate a method of delivering and deploying a gastrointestinal sleeve device 400. First, an attachment ring device 800 or the like is installed in the patient's stomach using any of the devices and methods previously describe, as shown in FIG. 88A. Subsequently, the pyloric/duodenal introducer 850 with the gastrointestinal sleeve device 400 loaded into it is inserted through the patient's pylorus via a peroral route, as shown in FIG. 88B. In this example, the proximal portion of the gastrointestinal sleeve device 400 is external to the pyloric/duodenal introducer 850 and the distal portion of the sleeve is double inverted inside of the introducer 850 similar to the sleeve shown in FIG. 87C. The sleeve ring 810 is installed in the attachment ring device 800 and the pyloric/duodenal introducer 850 is withdrawn. Then, using a combination of fluid pressure, a push rod or catheter 854 inside of the gastrointestinal sleeve device 400 and/or peristalsis of the intestines, optionally assisted by an inflatable balloon on the catheter or a biodegradably attached distal peristalsis balloon 902, the gastrointestinal sleeve device 400 everts to a fully deployed position.

Figure 90A:
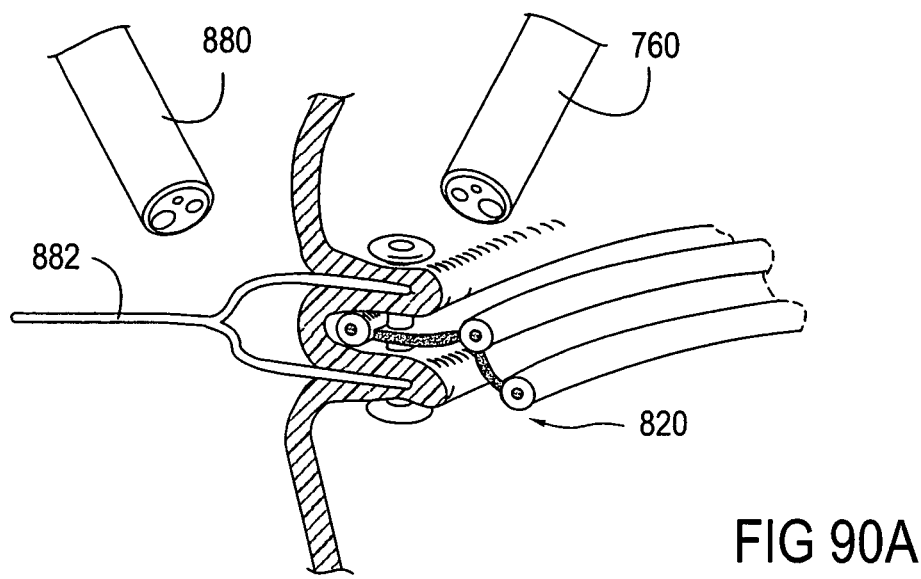
FIG. 90A illustrates a method of laparoscopically assisted formation of a double plication.
Figure 90B:
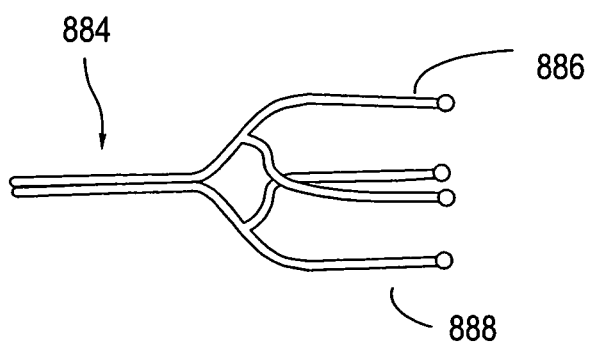
FIG. 90B illustrates a device for laparoscopically assisted formation of a double plication.

Attachment devices and fasteners are described in FIGS. 49-65, 72-76 etc. These attachment devices include means and structures to facilitate attachment using a purely peroral approach. An alternate method for employing these devices could include assistance via a laparoscopic approach. This could be indicated in certain clinical situations to facilitate location of a ring of other structure for attachment as well as invaginating tissue to form a plication and stabilizing the tissue and ring for attachment. This can be particularly useful in the case of double plications FIG. 90A illustrates an example of a laparoscopically introduced device that works from the outside of the stomach to assist in the formation of a double plication and the stabilization and attachment of a ring device 820. Laparoscope 880 is used to guide one or more laparoscopic tools. One such tool 882 is shown capturing a ring device 820 between a fold of tissue that folds mucosa-to-mucosa rather than serosa-to-serosa. Positioning of fastener delivery device 760 folds the gastric wall to form two serosa-to-serosa plications. A fastener can then follow a path through both the plications and the ring 820, which may be configured similar to the ring in FIGS. 81 and 82. FIG. 90B shows the distal structure of a tool 884 which includes an upper bifurcated fork 886 and lower bifurcated fork 888. The two forks can move relative to each other to capture tissue and/or apparatus while the use of a bifurcated fork allows their withdrawal after placement of one or more fasteners.

Figure 95:
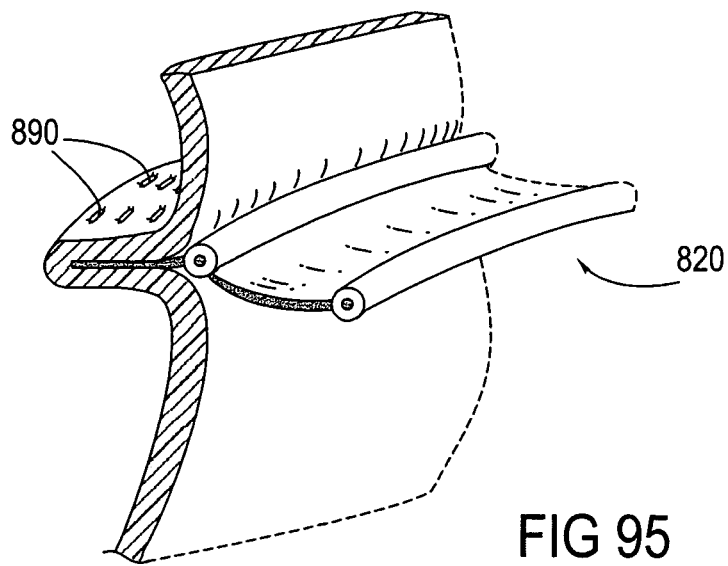
FIG. 95 illustrates extragastric laparoscopic attachment of an intragastric ring.

FIG. 95 illustrates a method for placing some configurations of attachment ring 820, such as the one illustrated in FIG. 81, using laparoscopic and standard stapling techniques. In this embodiment and method the device 820 is captured within a single plication that is formed by folding the stomach wall over the device so that mucosa is in contact with the attachment area 821 of the device. This attachment portion 821 of the device can optionally be porous or have open area to allow mucosa to mucosa contact. This area could be made from a PTFE graft material, a polyester (Marlex) mesh or other material with natural or formed openings if tissue contact is desired. In this method a laparoscope, external to the stomach, can be used to guide attachment of the device through the gastric wall. Standard laparoscopic stapling devices 890 can be used for this application, as can sutures or other attachment means. Buttressing of the attachment as described herein may be indicated in some clinical situations.

The following outline gives a more detailed description of one example of a method for delivering and deploying an embodiment of a gastrointestinal sleeve device. This procedure assumes a specific device configuration. Many other device configurations are possible and therefore some aspects of this procedure may have to be modified to accommodate other configurations. Device details are as follows:

1 Ring
    a Initially parachuted into place on stay sutures
    b Definitively attached with rivets and riveter, rivet position is not preset by holes
2 Sleeve (mating rings with or without magnet)
    a Lock sleeve into place
    b Leak shield attached to sleeve with self-expanding ring
    c A distal delivery balloon that deflates/detaches/dissolves in 2-5 days
3 Sleeve delivery using
    a Gastroscopic placement of a guide wire in the duodenum
    b An over the guidewire sleeve and duodenal introducer
    c Everting mid-sleeve deployment as it extends distally
    d A RO distal balloon to advance the distal sleeve by peristalsis
4 Sleeve removal using
    a A "swallowable" retrieval balloon catheter
    b Balloon advances to the distal sleeve by swallowing water for propulsion
    c Balloon is inflated to wedge against the walls of the sleeve
    d Balloon catheter is withdrawn as the proximal sleeve is withdrawn
5 Sleeve replacement by repeating 3
6 Ring removal by
    a Unravelling rivet heads
    b Retrieving the ring with a gastroscope and grasper Peroral Gastric Bypass Procedure:
1 Patient sees physician for referral or self-refers to an interventionist
    a. Open surgeon (present)
    b. Laparoscopic surgeon (present)
    c. Endoscopist (future)
2 Patient is referred to Surgeon/Endoscopist
3 Work up is done by support staff
4 Patient must qualify
    a. Psychologically
        i. Relaxed requirements (compared to current gastric surgery procedures)
    b. Medically
        i. Relaxed requirements (compared to current gastric surgery procedures)
            1. Marginal BMI's (e.g. <35)
            2. Super obese
    c. Financially (for reimbursement or self-pay)
        i. Should cost less that surgery
5 Patient is seen by Doc performing procedure
6 Pre-op counseling
7 Pre-op regime for weight loss prior to surgery
    a. Nothing, not needed for peroral procedure
8 Implant sleeve mounting ring
    a. Check vitals etc.
    b. Sedation
    c. IV
    d. Anesthesia
        i. May be required for ring attachment
        ii. Should not be required for most patients for sleeve procedures
    e. Prep.
    f. Place esophageal tube
    g. Place endoscope in stomach
    h. Place stay suture
        i. Identify locations by anatomical land marks
        ii. Pass suturing device through scope or tube
        iii. Take bite(s) at location 1, bring suture ends out of mouth
        iv. Repeat h (ii & iii) for locations 2, 3 & 4
    i. Position ring
        i. Attach stay sutures to ring
        ii. Fold ring for passage through sleeve
        iii. Pass ring through sleeve under direct vision using gastroscope
        iv. Secure stay sutures to position ring along gastric wall by GEJ
            1. Ring design will facilitate forming plications in the gastric wall
            2. Ring design will place gastric wall in position for riveting
            3. Stay sutures can be tied and trimmed in place
    j. Attach ring
        i. Pass riveting device through or along scope through tube
            1. Scope to include channel for grasper or other device
            2. Position riveter for attaching rivet
            3. If necessary use grasper to position gastric wall at rivet site
            4. Fire riveter
            5. Repeat j(i)2-4 as required
    k. Leak test
        i. Place mock sleeve in ring (to seal ring opening)
        ii. Pressurize to leak test
        iii. Remove mock sleeve
    l. Remove scope & instruments
    m. Remove tube 9 Wait approximately one month for the ring attachment to heal
10 Hang sleeve
   a. Check vitals etc.
   b. Sedation (no anesthesia)
   c. IV
   d. Prep. Place esophageal tube
   e. Insert gastroscope to check ring
   f. Advance gastroscope to duodenum
      i. Place guidewire in duodenum
      ii. Remove and replace scope (alongside the guidewire)
   g. Insert sleeve (sleeve comes pre-positioned on duodenal introducer)
      i. Inflate distal balloon
      ii. Thread system over guidewire
      iii. Advance through esophageal tube
      iv. Advance to system to duodenum under direct vision
      v. Pull back gastroscope proximal to ring
      vi. Advance system into duodenum (~2-5 cm) to seat sleeve in ring
         1. Manipulate sleeve to mate with ring using grasper as required
      vii. Advance distal and mid sleeves to jejunum (I)
         1. Pressurize duodenal introducer
         2. Mid-sleeve everts under pressure (maybe 20-40 cm)
         3. Advancement of mid-sleeve advances distal sleeve
         4. Remove duodenal introducer and guidewire
         5. Allow peristalsis to advance distal sleeve balloon OR
      v. Advance distal and mid sleeves to jejunum (II)
         1. Use pusher to advance distal sleeve under fluoro (balloon acts as bumper)
         2. Remove duodenal introducer, guidewire & pusher
         3. Allow peristalsis to advance distal sleeve
   h. Deploy leak shield
      i. Manipulate leak shield out of sleeve using grasper as required
      ii. Uniformly position leak shield using grasper as required
   i. Leak test
      i. Place balloon catheter in proximal sleeve
      ii. Inflate balloon to seal sleeve opening
      iii. Pressurize to leak test
      iv. Deflate and remove balloon catheter
   j. Remove scope & instruments
   k. Wait 2-4 days
      i. Balloon dissolves/detaches/deflates
   l. Wait approximately 2 weeks and observe for complication
      i. Adjust stoma by one of the methods described herein (if the device is configured to include an adjustable restrictive stoma)
11 Remove sleeve (e.g. to be performed after a therapeutic period)
   a. Check vitals etc.
   b. Sedation (no anesthesia)
   c. IV
   d. Swallow removable balloon catheter
   e. Drink copious amounts of water
   f. Check balloon position fluoroscopically
   g. Position gastroscope (with retrieval tool)
   h. Grasp sleeve at leak shield ring or mating ring
   i. Inflate removal balloon
   j. Pull out scope, sleeve and removal balloon simultaneously
13 Replace sleeve
   a. Repeat 10, 11 and 12 as required
14 Remove ring
   a. Check vitals etc.
   b. Sedation (anesthesia should not be required)
   c. IV
   d. Prep.
   e. Place esophageal tube
   f. Place endoscope in stomach
   g. Pass rivet removal tool through tube
   h. Locate rivets and remove heads
   i. Using grasper pull ring away from gastric wall
   j. Pull ring into tube (it should fold as it enters the tube)
   k. Visually examine stomach at site of ring
   l. Remove scope, instruments and tube In an alternate embodiment, all or part of the sleeve device could be constructed from a biodegradable polymer as described herein. This would obviate the need for removal of the sleeve device at the end of the treatment period. Material selection and/or selective coatings of the exterior of the biodegradable sleeve could control the rate of dissolution/degradation of the sleeve in the presence of the differing chemical environments found at different locations along the alimentary tract. For example a Parylene coating in the sleeve in the stomach, pylorus and duodenum could inhibit the effects of the stomach acids. This would be less of an issue after these acids mix with the basic secretions of bile in the duodenum an beyond in the jejunum.

Morbid obesity endoscopic transgastric diaphragmatic attachment, a.k.a. Gastropexy attachment, and apparatus are described for attaching devices and/or securing tissue at or near the gastroesophageal junction and cardia of the stomach. The method and apparatus allow attachment to include securing the tissue and/or device to the diaphragm and/or connecting the diaphragm to the esophagus via a peroral endoscopic approach. Attaching tissue to the diaphragm is common in Nissen fundoplication surgery using conventional methods.

A fastener or other attachment structure can be passed through the gastric wall and through the diaphragm while manipulating surrounding tissue, including the esophagus and the lungs, to avoid damage to these tissues.

Figure 92:
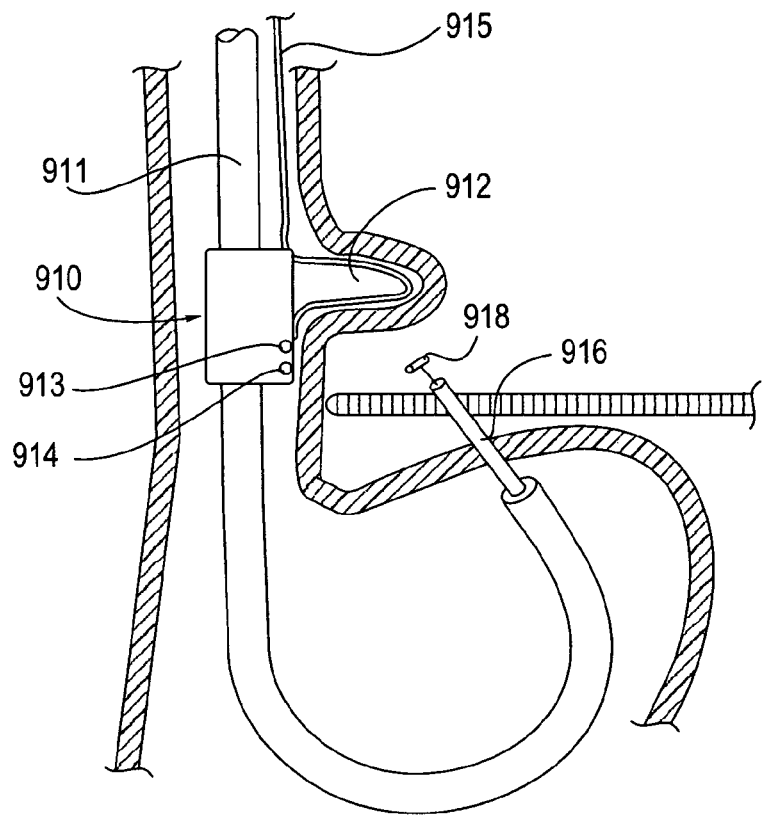
FIG. 92 illustrates a gastropexy apparatus.

FIG. 92 illustrates a gastropexy apparatus 910. The apparatus can include an endoscope 911 with a distraction means 912, transillumination means 913, and securing means 914 slidably mounted on the endoscope with a control tail 915 to control the position of these components along the endoscope 911. A fastener delivery/deployment device 916 is insertable through working channel of endoscope 911. The transillumination means 913 may be an LED or optical fiber. The optical fiber can be plastic or glass. The wavelength of light used for transillumination can be a visible wavelength selected for penetration of tissue.

The embodiment of FIG. 92 shows a balloon as the distraction means 912, suction as the securing means 914 and an LED as the transillumination means 913 for aiming the fastener delivery/deployment device 916. The combination of distraction and securing the esophageal wall creates a pocket into which a fastener 918 can be safely deployed. Transillumination through the tissue structures, i.e. the esophageal wall, diaphragm and gastric wall, is a preferred, though not required, method to aim the fastener delivery/deployment device 916. Alternatively of in addition, an ultrasound imaging or location device can be mounted on the device or externally.

A standard flexible endoscope may be used with the distraction means, securing means and optional transillumination means being incorporated into a device that can be removably attached to the endoscope. Alternatively, these features can be incorporated into a combined endoscope device.

Various types of fasteners, including those described elsewhere in this specification, can be used in this method. T-type or other expanding-head or deployable fasteners are preferable. Fasteners can include features that allow: 1) placement of the fastener, 2) removal of the delivery/deployment device, 3) positioning or actuation of a fastener attachment means, and 4) if necessary, removal of excess material from the fastener.

After delivery/deployment of the distal T of the fastener 918 in the safe zone above the diaphragm, the delivery/deployment device 916 can then be removed. An attachment means can be advanced into position over the proximal tail of the fastener 918, which extends through the endoscope 911. The fastener attachment means can screw, crimp, snap or otherwise attach to the attachment zone of the fastener. An additional device may or may not be required for delivering and attaching the fastener attachment means, depending on the attachment mechanism utilized. Excess material, including the proximal tail, can then be cut otherwise detached and removed.

The method of use could involve the steps of: 1) advancing the distal tip of the endoscope into contact with the gastric wall, 2) continuing to advance the endoscope until the gastric wall contacts the diaphragm, 3) manipulating the endoscope to visualize the transillumination means, and 4) actuating the fastener. The method may also involve the use of stay sutures to preposition a device for attachment. These stay sutures could be used optionally to parachute the device into position through the esophagus.

One possible method for gastropexy attachment would be performed as follows:
1. Position endoscope overtube
2. Attach gastropexy protector (GP) to exterior of endoscopy and attach required accessories (suction, light source, inflation syringe). Calibrate delivery device advancement stop.
3. Insert endoscope (1-channel) with mounted GP
4. Turn on transillumination (TI) light to transmit light through an optical fiber, or bundle.
5. Position scope so GP is positioned just above the diaphragm. Position scope for T-tag gastropexy. View TI light to assist in positioning.
6. Apply suction to esophagus
7. Inflate GP protection balloon
8. Confirm scope position with TI light and advance T-tag deployment device with its integrated tissue protector to the gastric wall. Continue advancing device until exterior of the gastric wall contacts the diaphragm
9. Reconfirm scope position with TI light, retract tissue protector, pass T-tag delivery cannula through the diaphragm until the advancing stop is reached and using T-tag device, deploy T-tag in safe zone above diaphragm
10. Retract T-tag deployment device out through diaphragm
11. Release vacuum
12. Deflate balloon
13. Remove scope and position tails externally
    a. Repeat steps 5-13 6 times
14. Pre-thread T-tag tails sleeve ring
15. Prepare to parachute sleeve ring through over tube and pass sleeve ring through overtube.
16. Snug T-tag tails to position device(s) and ready for final attachment
17. Using tails, guide the T-tag securement caps (crimp, snap or screw) into position and secure in place (Repeat 6 times)
18. Trim tails and remove all instrumentation Optionally, the gastropexy apparatus may also include a delivery device tip protector. The delivery device tip protector can be a removable obturator that is coaxial with an exemplary hollow needle introducer. The obdurator is removed after the delivery cannula is in place and replaced with a T-tag deployment mechanism and its associated T-tag(s)

Additionally, the gastropexy apparatus may include a delivery device advancement stop. The stop can be a structure that can be adjustably fixed to a position on the proximal portion of the T-tag delivery device that is connected to and thereby controls the position of the degree to which the T-tag delivery cannula extends from the distal end of the endoscope. This could be a collar with a thumbscrew lock Description of the calibration of the advancement stop procedure—Attach the GP to the endoscope; bend the endoscope so that the distal tip of the scope aligns with the transillumination light; extend the T-tag delivery cannula until it is a set distance from the transillumination light (on the order of 0.25" or 6 mm); position advancement stop against the working channel proximal port; then secure advancement stop. Confirm calibration of advancement stop by straightening and re-bending the scope then adjusting the position of the stop if necessary.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method of treating a patient, comprising the steps of:
providing a gastrointestinal sleeve, having a proximal end, a distal end, and a lumen extending therethrough;
providing a tubular cuff having a proximal end and a distal end, the distal end of the cuff removably attached to the proximal end of the sleeve;
transesophageally advancing the cuff to position the proximal end of the cuff adjacent an attachment site of a luminal wall in the lower esophagus;
advancing the distal end of the sleeve through the stomach and into the intestine; and
attaching the tubular cuff at the attachment site without creating a serosal to serosal bond, such that the sleeve is configured to deliver food from the esophagus directly into the intestine;
wherein the attaching the tubular cuff step comprises anchoring at least one tissue anchor having a proximal end and a distal end, said anchoring comprising changing the distal end of the tissue anchor from a transversely reduced configuration used while passing through the muscularis layer of the attachment site to a transversely enlarged configuration used after passing through the attachment site, wherein the distal end of the tissue anchor includes a proximally facing surface which rests against a distally facing surface to retain the cuff, and wherein the enlarged configuration of the tissue anchor is transversely larger than any transverse portion of the tissue anchor when the tissue anchor is passing through the attachment site.

2. A method of treating a patient as in claim 1, wherein the advancing the distal end of the sleeve step comprises advancing the distal end of the sleeve at least as far as the ligament of Treitz.

3. A method of treating a patient as in claim 1, wherein the advancing the distal end of the sleeve step comprises advancing the distal end of the sleeve distally of the duodenum.

4. A method of treating a patient as in claim 1, wherein the advancing the distal end of the sleeve step comprises advancing the distal end into the jejunum.

5. A method of treating a patient as in claim 1, wherein the attaching the tubular cuff step comprises using a suture.

6. A method of treating a patient as in claim 1, wherein the tissue anchor comprises a "T" tag.

7. A method of treating a patient as in claim 1, wherein the sleeve is at least about 50 cm in length.

8. A method of treating a patient as in claim 1, wherein the sleeve is at least about 75 cm in length.

9. A method of treating a patient as in claim 1, wherein the sleeve is at least about 125 cm in length.

10. A method of treating a patient as in claim 7, wherein the sleeve is sufficiently flexible that material traveling through the sleeve is influenced by the natural operation of the pylorus.

11. A method of treating a patient as in claim 1, wherein the transversely enlarged configuration is achieved by expanding the anchor after passing through the muscularis tissue.

12. A method of treating a patient as in claim 1, wherein the transversely enlarged configuration is achieved by flexing a portion of the anchor after passing through the muscularis tissue.

\* \* \* \* \*